United States Patent
Dong et al.

(10) Patent No.: US 10,086,013 B2
(45) Date of Patent: Oct. 2, 2018

(54) AMINO ACID-, PEPTIDE- AND POLYPEPTIDE-LIPIDS, ISOMERS, COMPOSITIONS, AND USES THEREOF

(71) Applicant: Massachusetts Institute of Technology, Cambridge, MA (US)

(72) Inventors: Yizhou Dong, Dublin, OH (US); Kevin Thomas Love, Boston, MA (US); Robert S. Langer, Newton, MA (US); Daniel Griffith Anderson, Framingham, MA (US); Delai Chen, Cambridge, MA (US); Yi Chen, Cambridge, MA (US); Arturo Jose Vegas, Belmont, MA (US); Akinleye C. Alabi, Ithaca, NY (US); Yunlong Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/340,082

(22) Filed: Nov. 1, 2016

(65) Prior Publication Data

US 2017/0165290 A1   Jun. 15, 2017
US 2018/0036333 A9   Feb. 8, 2018

Related U.S. Application Data

(62) Division of application No. 13/662,002, filed on Oct. 26, 2012, now Pat. No. 9,512,073.

(Continued)

(51) Int. Cl.
  *A61K 31/535* (2006.01)
  *A61K 31/7105* (2006.01)
  (Continued)

(52) U.S. Cl.
  CPC ........ *A61K 31/7105* (2013.01); *A61K 31/711* (2013.01); *A61K 47/22* (2013.01); *C07D 241/08* (2013.01); *A61K 2121/00* (2013.01)

(58) Field of Classification Search
  CPC ........ C07C 323/58; C12Q 1/02; C12N 15/87; G01N 33/15
  (Continued)

(56) References Cited

U.S. PATENT DOCUMENTS 2,844,629 A   7/1958   William et al.
4,022,833 A   5/1977   Diana et al.
(Continued)

FOREIGN PATENT DOCUMENTS

CA   2518132 A1   3/2006
CA   2 769 408 A1   2/2011
(Continued)

OTHER PUBLICATIONS

Moure et al., Chem. Eur. J. 2011, 17, 7927-7939.*
(Continued)

*Primary Examiner* — Clinton Brooks
*Assistant Examiner* — Kofi Adzamli
(74) *Attorney, Agent, or Firm* — Wolf, Greenfield & Sacks, P.C.

(57) ABSTRACT

Described herein are compounds and compositions characterized, in certain embodiments, by conjugation of various groups, such as lipophilic groups, to an amino or amide group of an amino acid, a linear or cyclic peptide, a linear or cyclic polypeptide, or structural isomer thereof, to provide compounds of the present invention, collectively referred to herein as "APPLs". Such APPLs are deemed useful for a variety of applications, such as, for example, improved nucleotide delivery. Exemplary APPLs include, but are not limited to, compounds of Formula (I), (II), (III), (IV), (V), and (VI), and salts thereof, as described herein:

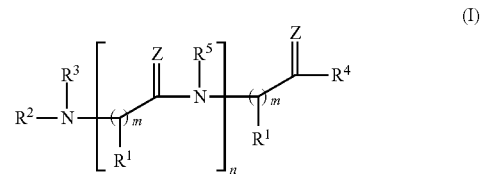

(I)

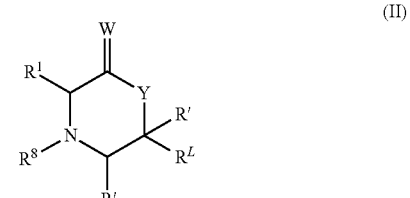

(II)

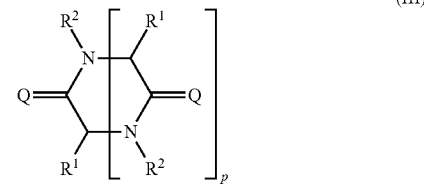

(III)

(IV)

(V)

(VI)

(Continued)

wherein m, n, p, R', $R^1$, $R^2$, $R^3$, $R^4$, $R^5$, $R^8$, Z, W, Y, and Z are as defined herein.

34 Claims, 4 Drawing Sheets

Specification includes a Sequence Listing.

Related U.S. Application Data

(60) Provisional application No. 61/552,423, filed on Oct. 27, 2011.

(51) Int. Cl.
    *A61K 31/711*     (2006.01)
    *C07D 241/08*     (2006.01)
    *A61K 47/22*     (2006.01)

(58) Field of Classification Search
    USPC .......................................... 560/169; 514/230
    See application file for complete search history.

(56) References Cited

U.S. PATENT DOCUMENTS

| | | |
|---|---|---|
| 4,308,085 A | 12/1981 | Hoerhold et al. |
| 4,762,915 A | 8/1988 | Kung et al. |
| 4,873,370 A | 10/1989 | Chiu |
| 4,897,355 A | 1/1990 | Eppstein et al. |
| 4,946,857 A | 8/1990 | Kanehira et al. |
| 4,966,945 A | 10/1990 | Drawert et al. |
| 5,171,678 A | 12/1992 | Behr et al. |
| 5,334,761 A | 8/1994 | Gebeyehu et al. |
| 5,352,461 A | 10/1994 | Feldstein et al. |
| 5,464,924 A | 11/1995 | Silvis et al. |
| 5,503,852 A | 4/1996 | Steiner et al. |
| 5,705,188 A | 1/1998 | Junichi et al. |
| 5,885,613 A | 3/1999 | Holland et al. |
| 5,976,569 A | 11/1999 | Milstein |
| 6,034,056 A | 3/2000 | Dutta |
| 6,071,497 A | 6/2000 | Steiner et al. |
| 6,331,318 B1 | 12/2001 | Milstein |
| 6,372,903 B1 | 4/2002 | Mehdi et al. |
| 6,444,226 B1 | 9/2002 | Steiner et al. |
| 6,696,424 B1 | 2/2004 | Wheeler |
| 6,998,115 B2 | 2/2006 | Langer |
| 7,427,394 B2 | 9/2008 | Anderson et al. |
| 7,507,859 B2 | 3/2009 | Grinstaff et al. |
| 8,071,082 B2 | 12/2011 | Zugates et al. |
| RE43,612 E | 8/2012 | Anderson et al. |
| 8,287,849 B2 | 10/2012 | Langer et al. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 9,006,487 B2 | 4/2015 | Anderson et al. |
| 9,101,666 B2 | 8/2015 | Langer et al. |
| 9,193,827 B2 | 11/2015 | Ma et al. |
| 9,227,197 B2 | 1/2016 | Anderson et al. |
| 9,238,716 B2 | 1/2016 | Dahlman et al. |
| 9,315,472 B2 | 4/2016 | Dong et al. |
| 9,439,968 B2 | 9/2016 | Anderson et al. |
| 9,512,073 B2 | 12/2016 | Dong et al. |
| 9,556,110 B2 | 1/2017 | Mahon et al. |
| 9,629,804 B2 | 4/2017 | Heartlein et al. |
| 9,700,627 B2 | 7/2017 | Langer et al. |
| 2002/0131951 A1 | 9/2002 | Langer et al. |
| 2003/0215395 A1 | 11/2003 | Yu et al. |
| 2004/0071654 A1 | 4/2004 | Anderson et al. |
| 2004/0181077 A1 | 9/2004 | Raymond et al. |
| 2005/0123596 A1 | 6/2005 | Kohane et al. |
| 2005/0143332 A1 | 6/2005 | Monahan et al. |
| 2006/0223939 A1 | 10/2006 | Lange et al. |
| 2007/0059373 A1 | 3/2007 | Oberg |
| 2007/0185128 A1 | 8/2007 | Conde-Frieboes et al. |
| 2007/0196503 A1 | 8/2007 | Wilson et al. |
| 2007/0275923 A1 | 11/2007 | Chen et al. |
| 2009/0221684 A1 | 9/2009 | Grinstaff et al. |
| 2010/0178699 A1 | 7/2010 | Gao et al. |
| 2010/0240072 A1 | 9/2010 | Wester et al. |
| 2011/0009641 A1 | 1/2011 | Anderson et al. |
| 2011/0158935 A1 | 6/2011 | Kraft |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0196923 A1 | 8/2012 | Rege et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0161830 A1 | 6/2014 | Anderson et al. |
| 2014/0329884 A1 | 11/2014 | Dong et al. |
| 2015/0140070 A1 | 5/2015 | Heartlein et al. |
| 2015/0203439 A1 | 7/2015 | Mahon et al. |
| 2016/0002178 A1 | 1/2016 | Fenton et al. |
| 2016/0009657 A1 | 1/2016 | Anderson et al. |
| 2016/0022821 A1 | 1/2016 | Langer et al. |
| 2016/0114042 A1 | 4/2016 | Anderson et al. |
| 2016/0137785 A1 | 5/2016 | Ma et al. |
| 2016/0158363 A1 | 6/2016 | Alabi et al. |
| 2016/0206740 A1 | 7/2016 | Dahlman et al. |
| 2016/0367686 A1 | 12/2016 | Anderson et al. |
| 2017/0152213 A1 | 6/2017 | Anderson et al. |
| 2017/0204075 A1 | 7/2017 | Mahon et al. |

FOREIGN PATENT DOCUMENTS

| | | |
|---|---|---|
| CN | 101506196 A | 8/2009 |
| CN | 100 569 877 C | 12/2009 |
| CN | 101 863 544 B | 9/2011 |
| DE | 25 20 814 A1 | 11/1976 |
| EP | 0 211 305 A2 | 2/1987 |
| EP | 0673637 A1 | 9/1995 |
| EP | 0 959 092 A1 | 11/1999 |
| EP | 1 277 829 A2 | 1/2003 |
| EP | 2 045 251 A1 | 4/2009 |
| EP | 2 532 649 A1 | 12/2012 |
| GB | 1602085 A | 11/1981 |
| JP | S49-127908 A | 12/1974 |
| JP | S51-023537 A | 2/1976 |
| JP | 51-125144 | 11/1976 |
| JP | H06-200073 A | 7/1994 |
| JP | H06-211978 A | 8/1994 |
| JP | H09-505593 A | 6/1997 |
| JP | H10-197978 A | 7/1998 |
| JP | 11-005786 A | 1/1999 |
| JP | 11-080142 A | 3/1999 |
| JP | 2003-519199 A | 6/2003 |
| JP | 2008-510824 A | 4/2008 |
| JP | 2008-247749 A | 10/2008 |
| JP | 2014172827 A | 9/2014 |
| WO | WO 93/18754 A1 | 9/1993 |
| WO | WO 95/14651 A1 | 6/1995 |
| WO | WO 1996/26179 A1 | 8/1996 |
| WO | WO 96/36314 A2 | 11/1996 |
| WO | WO 97/23457 A1 | 7/1997 |
| WO | WO 1998/16202 A2 | 4/1998 |
| WO | WO 2001/010845 A1 | 2/2001 |
| WO | WO 02/22709 A1 | 3/2002 |
| WO | WO 2002/031025 A2 | 4/2002 |
| WO | WO 2003/070735 A2 | 8/2003 |
| WO | WO 2004/048345 A2 | 6/2004 |
| WO | WO 2004/106411 A2 | 12/2004 |
| WO | WO 2005/055979 A2 | 6/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/096662 A2 | 8/2007 |
| WO | WO 2007/143659 A2 | 12/2007 |
| WO | WO 2008/011561 A2 | 1/2008 |

(56) References Cited

FOREIGN PATENT DOCUMENTS

| WO | WO 2008/113364 A2 | 9/2008 |
|---|---|---|
| WO | WO 2009/046220 A2 | 4/2009 |
| WO | WO 2009/086547 A1 | 7/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/078373 A1 | 7/2010 |
| WO | WO 2010/099387 A1 | 9/2010 |
| WO | WO 2010/114789 A1 | 10/2010 |
| WO | WO 2010/129709 A1 | 11/2010 |
| WO | WO 2010/144789 A2 | 12/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/179562 A1 | 11/2014 |
| WO | WO 2014/210356 A1 | 12/2014 |
| WO | WO 2015/061467 A1 | 4/2015 |

OTHER PUBLICATIONS

STN-CAS database Registry No. 103745-33-1. Entered STN-CAS database on Aug. 18, 1986.
STN-CAS database Registry No. 1100276-71-8. Entered STN-CAS database on Feb. 3, 2009.
STN-CAS database Registry No. 128351-30-4. Entered STN-CAS database on Jul. 20, 1990.
STN-CAS database Registry No. 129257-51-8. Entered STN-CAS database on Sep. 7, 1990.
STN-CAS database Registry No. 129257-52-9. Entered STN-CAS database on Sep. 7, 1990.
STN-CAS database Registry No. 21282-28-0. Entered STN-CAS database on Nov. 16, 1984.
STN-CAS database Registry No. 28549-91-9. Entered STN-CAS database on Nov. 16, 1984.
STN-CAS database Registry No. 3768-41-0. Entered STN-CAS database on Nov. 16, 1984.
STN-CAS database Registry No. 53731-96-7. Entered STN-CAS database on Nov. 16, 1984.
STN-CAS database Registry No. 53731-98-9. Entered STN-CAS database on Nov. 16, 1984.
STN-CAS database Registry No. 54736-47-9. Entered STN-CAS database on Nov. 16, 1984.
STN-CAS database Registry No. 57018-25-4. Entered STN-CAS database on Nov. 16, 1984.
STN-CAS database Registry No. 57273-30-0. Entered STN-CAS database on Nov. 16, 1984.
STN-CAS database Registry No. 6302-30-3. Entered STN-CAS database on Nov. 16, 1984.
STN-CAS database Registry No. 635749-38-1. Entered STN-CAS database on Jan. 9, 2004.
STN-CAS database Registry No. 68310-64-5. Entered STN-CAS database on Nov. 16, 1984.
STN-CAS database Registry No. 785789-76-6. Entered STN-CAS database on Nov. 22, 2004.
STN-CAS database Registry No. 883453-96-1. Entered STN-CAS database on May 9, 2006.
STN-CAS database Registry No. 89038-30-2. Entered STN-CAS database on Nov. 16, 1984.
STN-CAS database Registry No. 956464-55-4. Entered STN-CAS database on Dec. 3, 2007.
STN-CAS database Registry No. 956465-28-4. Entered STN-CAS database on Dec. 3, 2007.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Amirouche et al., Activation of p38 signaling increases utrophin A expression in skeletal muscle via the RNA-binding protein KSRP and inhibition of AU-rich element-mediated mRNA decay: implications for novel DMD therapeutics. Hum Mol Genet. Aug. 1, 2013;22(15):3093-111. doi: 10.1093/hmg/ddt165. Epub Apr. 10, 2013.
Cazzola et al., Use of recombinant human erythropoietin outside the setting of uremia. Blood. Jun. 15, 1997;89(12):4248-67.
Davis et al., The firrst targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.
Fenske et al., Liposomal nanomedicines. Expert Opin Drug Deliv. Jan. 2008;5(1):25-44.
Kanasty et al., Delivery materials for siRNA therapeutics. Nat Mater. Nov. 2013;12(11):967-77. doi: 10.1038/nmat3765.
Kariko et al., Increased erythropoiesis in mice injected with submicrogram quantities of pseudouridine-containing mRNA encoding erythropoietin. Mol Ther. May 2012;20(5):948-53. doi: 10.1038/mt.2012.7. Epub Feb. 14, 2012.
Kormann et al., Expression of therapeutic proteins after delivery of chemically modified mRNA in mice. Nat Biotechnol. Feb. 2011;29(2):154-7. doi: 10.1038/nbt.1733. Epub Jan. 9, 2011.
Love et al., Lipid-like materials for low-dose, in vivo gene silencing. Proc Natl Acad Sci U S A. Feb. 2, 2010;107(5):1864-9. doi: 10.1073/pnas.0910603106. Epub Jan. 11, 2010.
McClellan et al., Genetic Heterogeneity in Human Disease. Cell. Apr. 2010;141(2):210-7.
McClellan et al., Response: Why It Is Time to Sequence. Cell. Aug. 2010;142(3):353-55.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Semple et al., Rational design of cationic lipids for siRNA delivery. Nat Biotechnol. Feb. 2010;28(2):172-6. doi: 10.1038/nbt.1602. Epub Jan. 17, 2010.
Whitehead et al., Degradable lipid nanoparticles with predictable in vivo siRNA delivery activity. Nat Commun. Jun. 27, 2014;5:4277. doi: 10.1038/ncomms5277.
U.S. Appl. No. 13/662,022, filed Oct. 26, 2012, Dong et al.
U.S. Appl. No. 11/453,222, filed Jul. 14, 2006, Anderson et al.
U.S. Appl. No. 14/643,845, filed Mar. 10, 2015, Anderson et al.
U.S. Appl. No. 10/446,444, filed May 28, 2003, Anderson et al.
U.S. Appl. No. 12/568,481, filed Sep. 28, 2009, Anderson et al.
U.S. Appl. No. 09/969,431, filed Oct. 2, 2001, Langer et al.
U.S. Appl. No. 11/099,886, filed Apr. 6, 2005, Langer et al.
U.S. Appl. No. 12/507,999, filed Jul. 23, 2009, Langer et al.
U.S. Appl. No. 13/301,315, filed Nov. 21, 2011, Langer et al.
U.S. Appl. No. 14/029,552, filed Sep. 17, 2013, Langer et al.
U.S. Appl. No. 14/811,613, filed Jul. 28, 2015, Langer et al.
U.S. Appl. No. 11/780,754, filed Jul. 20, 2007, Zugates et al.
U.S. Appl. No. 13/312,224, filed Dec. 6, 2011, Zugates et al.
U.S. Appl. No. 14/051,313, filed Oct. 10, 2013, Zugates et al.
U.S. Appl. No. 11/758,078, filed Jun. 5, 2007, Anderson et al.
U.S. Appl. No. 12/613,968, filed Nov. 6, 2009, Mahon et al.
U.S. Appl. No. 12/716,732, filed Mar. 3, 2010, Mahon et al.
U.S. Appl. No. 13/128,020, filed Aug. 16, 2011, Mahon et al.
U.S. Appl. No. 14/599,004, filed Jan. 16, 2015, Mahon et al.
U.S. Appl. No. 15/417,530, filed Jan. 27, 2017, Mahon et al.
U.S. Appl. No. 13/126,260, filed Apr. 27, 2011, Nguyen et al.
U.S. Appl. No. 13/819,280, filed Feb. 26, 2013, Ma et al.
U.S. Appl. No. 14/941,384, filed Nov. 13, 2015, Ma et al.
U.S. Appl. No. 13/428,695, filed Mar. 23, 2012, Dahlman et al.
U.S. Appl. No. 14/995,842, filed Jan. 14, 2016, Dahlman et al.
U.S. Appl. No. 14/089,603, filed Aug. 13, 2013, Anderson et al.
U.S. Appl. No. 14/089,603, filed Nov. 25, 2013, Anderson et al.
U.S. Appl. No. 14/987,717, filed Jan. 4, 2016, Anderson et al.
U.S. Appl. No. 15/264,315, filed Sep. 13, 2016, Anderson et al.
U.S. Appl. No. 14/267,530, filed May 1, 2014, Dong et al.
U.S. Appl. No. 14/900,869, filed Dec. 22, 2015, Alibi et al.
U.S. Appl. No. 14/789,227, filed Jul. 1, 2015, Fenton et al.
U.S. Appl. No. 15/186,361, filed Jun. 17, 2016, Anderson et al.

(56) References Cited

OTHER PUBLICATIONS

PCT/US2012/062222, Dec. 14, 2012, Invitation to Pay Additional Fees.
PCT/US2012/062222, Mar. 27, 2013, International Search Report and Written Opinion.
PCT/US2012/062222, May 8, 2014, International Preliminary Report on Patentability.
EP06784878.8, Jun. 29, 2009, Extended European Search Report.
EP 11186795.8, Jun. 19, 2012, Extended European Search Report.
PCT/US2006/023171, May 29, 2008, International Search Report and Written Opinion.
PCT/US2006/023171, Jul. 3, 2008, International Preliminary Report on Patentability.
EP 07013193.3, Jan. 28, 2008, Extended European Search Report.
PCT/US2004/016521, Sep. 29, 2004, Invitation to Pay Additional Fees.
PCT/US2004/016521, Dec. 8, 2004, International Search Report and Written Opinion.
PCT/US2004/016521, Dec. 15, 2005, International Preliminary Report on Patentability.
PCT/US2001/031270, May 22, 2002, International Search Report.
PCT/US2001/031270, Jan. 2, 2003, Written Opinion.
PCT/US2001/031270, Aug. 19, 2003, International Preliminary Examination Report.
EP 07813156.2, Oct. 5, 2009, Extended European Search Report.
PCT/US2007/073976, Sep. 29, 2008, International Search Report and Written Opinion.
PCT/US2007/073976, Feb. 5, 2009, International Preliminary Report on Patentability.
EP 07798132.2, Jul. 18, 2011, Extended European Search Report.
PCT/US2007/070430, Dec. 13, 2007, International Search Report and Written Opinion.
PCT/US2007/070430, Dec. 24, 2008, International Preliminary Report on Patentability.
EP 09825132.5, Jul. 16, 2013, Extended European Search Report.
PCT/US2009/006018, May 25, 2010, International Search Report and Written Opinion.
PCT/US2009/006018, May 19, 2011, International Preliminary Report on Patentability.
EP11830727.3, Nov. 26, 2014, Partial European Search Report.
EP 11820727.3, Apr. 25, 2015, Extended European Search Report.
PCT/US2011/049360, Mar. 20, 2012, International Search Report and Written Opinion.
PCT/US2011/049360, Mar. 7, 2013, International Preliminary Report on Patentability.
PCT/US2012/030349, Jul. 24, 2012, Invitation to Pay Additional Fees.
PCT/US2012/030349, Oct. 5, 2012, International Search Report and Written Opinion.
PCT/US2012/030349, Oct. 10, 2013, International Preliminary Report on Patentability.
PCT/US2013/054726, Oct. 31, 2013, Invitation to Pay Additional Fees.
PCT/US2013/054726, Jan. 7, 2014, International Search Report and Written Opinion.
PCT/US2013/054726, Feb. 26, 2015, International Preliminary Report on Patentability.
PCT/US2014/036355, Aug. 5, 2014, International Search Report and Written Opinion.
PCT/US2014/044408, Oct. 24, 2014, International Search Report and Written Opinion.
PCT/US2016/038141, Sep. 20, 2016, Invitation to Pay Additional Fees.
PCT/US2016/038141, Nov. 22, 2016, International Search Report and Written Opinion.
Invitation to Pay Additional Fees for PCT/US2012/062222 dated Dec. 14, 2012.
International Search Report and Written Opinion for PCT/US2012/062222 dated Mar. 27, 2013.
International Preliminary Report on Patentability for PCT/US2012/062222, dated May 8, 2014.
Extended European Search Report for EP 06784878.8 dated Jun. 29, 2009.
Extended European Search Report for EP 11186795.8 dated Jun. 19, 2012.
International Search Report and Written Opinion for PCT/US2006/023171 dated May 29, 2008.
International Preliminary Report on Patentability for PCT/US2006/023171 dated Jul. 3, 2008.
Extended European Search Report, dated Jan. 28, 2008, for EP 07013193.3.
Invitation to Pay Additional Fees for PCT/US2004/016521 dated Sep. 29, 2004.
International Search Report and Written Opinion for PCT/US2004/016521 dated Dec. 8, 2004.
International Preliminary Report on Patentability for PCT/US2004/016521 dated Dec. 15, 2005.
International Search Report for PCT/US2001/031270 dated May 22, 2002.
Written Opinion for PCT/US2001/031270 dated Jan. 2, 2003.
International Preliminary Examination Report for PCT/US2001/031270 dated Aug. 19, 2003.
Extended European Search Report, dated Oct. 5, 2009, for EP 07813156.2.
International Search Report and Written Opinion for PCT/US2007/073976 dated Sep. 29, 2008.
International Preliminary Report on Patentability for PCT/US2007/073976 dated Feb. 5, 2009.
Extended European Search Report for EP 07798132.2 dated Jul. 18, 2011.
International Search Report and Written Opinion for PCT/US2007/070430 dated Dec. 13, 2007.
International Preliminary Report on Patentability for PCT/US2007/070430 dated Dec. 24, 2008.
Extended European Search Report for European Application No. 09825132.5 dated Jul. 16, 2013.
International Search Report and Written Opinion for PCT/US2009/006018 dated May 25, 2010.
International Preliminary Report on Patentability for PCT/US2009/006018 dated May 19, 2011.
Partial European Search Report for European Application No. 11820727.3 dated Nov. 26, 2014.
Extended European Search Report for European Application No. 11820727.3, dated Apr. 22, 2015.
International Search Report and Written Opinion for PCT/US2011/049360, dated Mar. 20, 2012.
International Preliminary Report on Patentability for PCT/US2011/049360, dated Mar. 7, 2013.
Invitation to Pay Additional Fees for PCT/US2012/030349, dated Jul. 24, 2012.
International Search Report and Written Opinion for PCT/US2012/030349, dated Oct. 5, 2012.
International Preliminary Report on Patentability for PCT/US2012/030349 dated Oct. 10, 2013.
Invitation to Pay Additional Fees for PCT/US2013/054726, dated Oct. 31, 2013.
International Search Report and Written Opinion for PCT/US2013/054726, dated Jan. 7, 2014.
International Search Report and Written Opinion for PCT/US2014/036355, dated Aug. 5, 2014.
International Search Report and Written Opinion for PCT/US2014/044408 dated Oct. 24, 2014.
International Preliminary Report on Patentability for PCT/US2013/054726, dated Feb. 26, 2015.
Invitation to Pay Additional Fees for PCT/US2016/038141, dated Sep. 20, 2016.
International Search Report and Written Opinion for PCT/US2016/038141, dated Nov. 22, 2016.
Adami et al., An amino acid-based amphoteric liposomal delivery system for systemic administration of siRNA. Mol Ther. Jun. 2011;19(6):1141-51. doi: 10.1038/mt.2011.56. Epub Apr. 19, 2011.

(56) References Cited

OTHER PUBLICATIONS

Adami et al., An amino acid-based amphoteric liposomal delivery system for systemic administration of siRNA. Mol Ther. Jun. 2011;19(6):1141-51.

Akinc et al., A combinatorial library of lipid-like materials for delivery of RNAi therapeutics. Nat Biotech. 2008;26(5):561-69.

Akinc et al., Development of lipidoid-siRNA formulations for systemic delivery to the liver. Mol Ther. May 2009;17(5):872-9. doi: 10.1038/mt.2009.36. Epub Mar. 3, 2009.

Akinc et al., Parallel synthesis and biophysical characterization of a degradable polymer library for gene delivery. J Am Chem Soc. May 7, 2003;125(18):5316-23.

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.

Anderson et al., Structure/property studies of polymeric gene delivery using a library of poly(beta-amino esters). Mol Ther. Mar. 2005;11(3):426-34.

Asokan et al., Cytosolic delivery of macromolecules. 3. Synthesis and characterization of acid-sensitive bis-detergents. Bioconjug Chem. Nov.-Dec. 2004;15(6):1166-73.

Behr et al., Efficient gene transfer into mammalian primary endocrine cells with lipopolyamine-coated DNA. Proc Natl Acad Sci U S A. Sep. 1989;86(18):6982-6.

Bourque et al., Hydroformylation Reactions Using Recyclable Rhodium-Complexed Dendrimers on Silica. J Am Chem Soc. 2000;122(5):956-957.

Braun et al., Structure/function relationships of polyamidoamine/DNA dendrimers as gene delivery vehicles. J Pharm Sci. Feb. 2005;94(2):423-36.

Brey et al., Controlling poly(beta-amino ester) network properties through macromer branching. Acta Biomater. Mar. 2008;4(2):207-17. Epub Oct. 22, 2007.

Brey et al., Influence of macromer molecular weight and chemistry on poly(beta-amino ester) network properties and initial cell interactions. J Biomed Mater Res A. Jun. 1, 2008;85(3):731-41.

Burnett et al., Current progress of siRNA/shRNA therapeutics in clinical trials. Biotechnol J. Sep. 2011;6(9):1130-46. doi: 10.1002/biot.201100054. Epub Jul. 11, 2011.

Byk et al., Synthesis, activity, and structure—activity relationship studies of novel cationic lipids for DNA transfer. J Med Chem. 1998;41(2):224-235.

Castanotto et al., The promises and pitfalls of RNA-interference-based therapeutics. Nature. Jan. 22, 2009;457(7228):426-33. doi: 10.1038/nature07758.

Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.

Chen et al., Tumor-targeted delivery of siRNA by non-viral vector: safe and effective cancer therapy. Expert Opin Drug Deliv. Dec. 2008;5(12):1301-11. doi: 10.1517/17425240802568505.

Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.

Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.

Davis et al., The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.

Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.

Felgner et al., Lipofection: a highly efficient, lipid-mediated DNA-transfection procedure. Proc Natl Acad Sci U S A. Nov. 1987;84(21):7413-7.

Fenton et al., Bioinspired Alkenyl Amino Alcohol Ionizable Lipid Materials for Highly Potent In Vivo mRNA Delivery. Adv Mater. Apr. 20, 2016;28(15):2939-43. doi: 10.1002/adma.201505822. Epub Feb. 18, 2016. With Supporting Information.

Perruti et al., A novel modification of poly(l-lysine) leading to a soluble cationic polymer with reduced toxicity and with potential as a transfection agent. Macromol Chem Phys 1998;199:2565-75.

Ferruti et al., Linear amino polymers: Synthesis, protonation and complex formation. Advances in Polymer Science. 1984;58:55-92.

Fourneau et al., Two new series of local anesthetics derived from piperazine. Bulletin de la Societe Chimique de France. 1930;47:1003-16. French.

Giuliana et al., Beyond natural antimicrobial peptides: multimeric peptides and other peptidomimetic approaches. Cell Mol Life Sci. Jul. 2011;68(13):2255-66. doi: 10.1007/s00018-011-0717-3. Epub May 20, 2011.

Gonzalez et al., New class of polymers for the delivery of macromolecular therapeutics. Bioconjug Chem. Nov.-Dec. 1999;10(6):1068-74.

Gupta et al., A review of in vitro-in vivo investigations on dendrimers: the novel nanoscopic drug carriers. Nanomedicine. Jun. 2006;2(2):66-73.

Heyes et al., Cationic lipid saturation influences intracellular delivery of encapsulated nucleic acids. J Control Release. Oct. 3, 2005;107(2):276-87.

Hill et al., In vitro cytotoxicity of poly(amidoamine)s: relevance to DNA delivery. Biochim Biophys Acta. Apr. 19, 1999;1427(2):161-74.

Hofland et al., Formation of stable cationic lipid/DNA complexes for gene transfer. Proc Natl Acad Sci USA. Jul. 9, 1996;93(14):7305-9.

Hsu et al., Diethanolamine (DEA) degradation under gas-treating conditions. Industrial and Engineering Chemistry Product Research and Development. 1985;24(4):630-35.

Ichimaru et al., Synthesis and characterization of new piperazine-type inhibitors for mitochondrial NADH-ubiquinone oxidoreductase (complex I). Biochemistry. Oct. 7, 2008;47(40):10816-26.

Ikeda et al., Role of micafungin in the antifungal armamentarium. Curr Med Chem. 2007;14(11):1263-75.

Incani et al., Lipid and hydrophobic modification of cationic carriers on route to superior gene vectors. Soft Matter. 2010; 6(10):2124-38.

Jolck et al., Solid-phase synthesis of PEGylated lipopeptides using click chemistry. Bioconjug Chem. May 19, 2010;21(5):807-10.

Jon et al., Degradable poly(amino alcohol esters) as potential DNA vectors with low cytotoxicity. Biomacromolecules. Nov.-Dec. 2003;4(6):1759-62.

Juliano et al., Biological barriers to therapy with antisense and siRNA oligonucleotides. Mol Pharm. May-Jun. 2009;6(3):686-95. doi: 10.1021/mp900093r.

Kanetani et al., Synthesis, and physicochemical and antimicrobial properties of 3-(3-alkyl-1-piperazinyl)-1-propanesulfonic acids and some related compounds. Nippon Kagaku Kaishi. 1983(12):1783-91.

Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.

Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.

Klibanov et al., Amphipathic polyethyleneglycols effectively prolong the circulation time of liposomes. FEBS Lett. Jul. 30, 1990;268(1):235-7.

Leuschner et al., Therapeutic siRNA silencing in inflammatory monocytes in mice. Nat Biotechnol. Oct. 9, 2011;29(11):1005-10. doi: 10.1038/nbt.1989.

Lukyanov et al., Micelles from lipid derivatives of water-soluble polymers as delivery systems for poorly soluble drugs. Adv Drug Deliv Rev. May 7, 2004;56(9):1273-89.

Lynn et al., Accelerated discovery of synthetic transfection vectors: parallel synthesis and screening of a degradable polymer library. J Am Chem Soc. Aug. 22, 2001;123(33):8155-6.

(56) References Cited

OTHER PUBLICATIONS

Lynn et al., Degradable Poly(β-amino esters): Synthesis, Characterization, and Self-Assembly with Plasmid DNA. J. Am. Chem. Soc. 2000;122 (44): 10761-8.

Lynn et al., pH-Responsive Polymer Microspheres: Rapid Release of Encapsulated Material within the Range of Intracellular pH. Angew Chem Int Ed Engl. May 4, 2001;40(9):1707-10.

Ma et al., Development of Cationic Polymer Coatings to Regulate Foreign Body Responses. Adv Mater. 2011;23:H189-94.

Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.

Mintzer et al., Nonviral vectors for gene delivery. Chem Rev. Feb. 2009;109(2):259-302.

Morrissey et al., Potent and persistent in vivo anti-HBV activity of chemically modified siRNAs. Nat Biotechnol. Aug. 2005;23(8):1002-7. Epub Jul. 24, 2005.

Moure et al. Chemical modulation of peptoids: synthesis and conformational studies on partially constrained derivatives. Chemistry. Jul. 4, 2011;17(28):7927-39. doi: 10.1002/chem.201100216. Epub May 24, 2011.

Narang et al., Cationic lipids with increased DNA binding affinity for nonviral gene transfer in dividing and nondividing cells. Bioconjug Chem. Jan.-Feb. 2005;16(1):156-68.

Parrish et al., Five- and six-membered ring opening of pyroglutamic diketopiperazine. J Org Chem. Mar. 22, 2002;67(6):1820-6.

Peer et al., Nanocarriers as an emerging platform for cancer therapy. Nat Nanotechnol. Dec. 2007;2(12):751-60. doi: 10.1038/nnano.2007.387.

Prata et al., Lipophilic peptides for gene delivery. Bioconjug Chem. Feb. 2008;19(2):418-20. doi: 10.1021/bc700451b. Epub Jan. 11, 2008.

Prata et al., Lipophilic peptides for gene delivery. Bioconjug Chem. Feb. 2008;19(2):418-20.

Reichmutch et al., mRNA vaccine delivery using lipid nanoparticles. Ther Deliv. 2016;7(5):319-34. doi: 10.4155/tde-2016-0006.

Rogers et al., Synthetic Experiments in the Ferrichrome Series. Biochemistry. Dec. 1964;3:1850-5.

Scheel et al., Therapeutic anti-tumor immunity triggered by injections of immunostimulating single-stranded RNA. Eur J Immunol. Oct. 2006;36(10):2807-16.

Sen et al., Surfactin: biosynthesis, genetics and potential applications. Adv Exp Med Biol. 2010;672:316-23.

Shchori, Poly(secondary Amine)s from Diacrylates and Diamines. J Polym Sci Polymer. Jun. 1983;21(6):413-15.

Siegwart et al., Combinatorial synthesis of chemically diverse core-shell nanoparticles for intracellular delivery. Proc Natl Acad Sci U S A. Aug. 9, 2011;108(32):12996-3001. doi: 10.1073/pnas.1106379108. Epub Jul. 22, 2011.

STN-CAS database Registry No. 1067642-37-8. Entered STN-CAS database on Oct. 29, 2008.

Swali et al., Solid-Phase Dendrimer Synthesis and the Generation of Super-High-Loading Resin Beads for Combinatorial Chemistry. J Org Chem Am Chem Soc. 1997;62:4902-03.

Tan et al., Engineering Nanocarriers for siRNA Delivery. Small. Apr. 4, 2011;7(7):841-56. doi: 10.1002/smll.201001389. Epub Feb. 25, 2011.

Thiel et al., Therapeutic applications of DNA and RNA aptamers. Oligonucleotides. Sep. 2009;19(3):209-22. doi: 10.1089/oli.2009.0199.

Tranchant et al., Physicochemical optimisation of plasmid delivery by cationic lipids. J Gene Med. Feb. 2004;6 Suppl 1:S24-35.

Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.

Van Balen et al., Liposome/water lipophilicity: methods, information content, and pharmaceutical applications. Med Res Rev. May 2004;24(3):299-324.

Van De Wetering et al., Structure-activity relationships of water-soluble cationic methacrylate/methacrylamide polymers for nonviral gene delivery. Bioconjug Chem. Jul.-Aug. 1999;10(4):589-97.

Vandenbroucke et al., Prolonged gene silencing in hepatoma cells and primary hepatocytes after small interfering RNA delivery with biodegradable poly(beta-amino esters). J Gene Med. Jul. 2008;10(7):783-94.

Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.

Whitehead et al., Knocking down barriers: advances in siRNA delivery. Nat Rev Drug Discov. Feb. 2009;8(2):129-38.

Winter et al., Transforming terpene-derived aldehydes into 1,2-epoxides via asymmetric α-chlorination: subsequent epoxide opening with carbon nucleophiles. Chem Commun (Camb). Nov. 28, 2011;47(44):12200-2. doi: 10.1039/c1cc15173h. Epub Oct. 10, 2011.

Wu et al., Cationic lipid polymerization as a novel approach for constructing new DNA delivery agents. Bioconjug Chem. Mar.-Apr. 2001;12(2):251-7.

Zagridullin et al., Monobasic amines. II. Cycloalkylation and hydroxyalkylation of cyclic and acyclic di- and polyamines . . . Zhurnal Organicheskoi Khimii. 1990;26(1):184-88. Russian.

Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.

Zaugg et al., 3-Carboxy-2,5-piperazinedione and Derivatives. J Amer Chem Soc. Jun. 5, 1956;78(11):2626-2631.

Liu et al., Efficacy of Erythropoietin Combined With Enteral Nutrition for the Treatment of Anemia in Crohn's Disease. Nutrition in Clinical Practice. Oct. 2012;28(1):120-7.

Ramakrisha et al., Synthesis of RGD peptidomimetic analogues of 2,5-diketopiperazine. Indian Journal of Chemistry, Dec. 1999;38B:1331-7.

Shen et al., Synthesis of Novel Amphiphilic Poly (ester-amine) Dendrimers and Their Recognition of Hg2+ at the Air/Water Interface. Chinese Journal of Chemistry, 2003;21(8):1011-4.

Siedler et al., Synthesis of neo-glycosylated L-alanyl-D-isoglutamine derivatives as potential immunoadjuvants. Pept Res. Jan.-Feb. 1992;5(1):39-47.

\* cited by examiner

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
ggaucaucuc aagucuuact t                                               21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide
```

<400> SEQUENCE: 2
guaagacuug agaugaucct t                                      21

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 3

Lys Lys Lys Lys
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Lys Lys Lys Lys Lys
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(13)
<223> OTHER INFORMATION: Lysine may be absent

<400> SEQUENCE: 5

Lys Lys Lys Lys Lys Lys Lys Lys Lys Lys Lys Lys Lys Lys
1               5                   10

<210> SEQ ID NO 6
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(34)
<223> OTHER INFORMATION: Lysine may be absent

<400> SEQUENCE: 6

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys
        35

<210> SEQ ID NO 7
<211> LENGTH: 104
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: misc_feature
<222> LOCATION: (28)..(103)
<223> OTHER INFORMATION: Lysine may be absent

<400> SEQUENCE: 7

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Lys
            100

<210> SEQ ID NO 8
<211> LENGTH: 206
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (104)..(205)
<223> OTHER INFORMATION: Lysine may be absent

<400> SEQUENCE: 8

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys
            115                 120                 125

Lys Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
            165                 170                 175
```

Lys Lys Lys Lys Lys Lys Lys Lys Lys Lys Lys Lys
            180                 185                 190

Lys Lys Lys Lys Lys Lys Lys Lys Lys Lys Lys Lys
        195                 200                 205

<210> SEQ ID NO 9
<211> LENGTH: 482
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (206)..(481)
<223> OTHER INFORMATION: Lysine may be absent

<400> SEQUENCE: 9

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys Lys Lys Lys Lys Lys Lys Lys Lys Lys Lys Lys Lys
            100                 105                 110

Lys Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys Lys
                165                 170                 175

Lys Lys Lys Lys Lys Lys Lys Lys Lys Lys Lys Lys Lys Lys Lys Lys
            180                 185                 190

Lys Lys Lys Lys Lys Lys Lys Lys Lys Lys Lys Lys Lys Lys Lys Lys
        195                 200                 205

Lys Lys Lys Lys Lys Lys Lys Lys Lys Lys Lys Lys Lys Lys Lys Lys
210                 215                 220

Lys Lys Lys Lys Lys Lys Lys Lys Lys Lys Lys Lys Lys Lys Lys Lys
225                 230                 235                 240

Lys Lys Lys Lys Lys Lys Lys Lys Lys Lys Lys Lys Lys Lys Lys Lys
                245                 250                 255

Lys Lys Lys Lys Lys Lys Lys Lys Lys Lys Lys Lys Lys Lys Lys Lys
            260                 265                 270

Lys Lys Lys Lys Lys Lys Lys Lys Lys Lys Lys Lys Lys Lys Lys Lys
        275                 280                 285

Lys Lys Lys Lys Lys Lys Lys Lys Lys Lys Lys Lys Lys Lys Lys Lys
290                 295                 300

Lys Lys Lys Lys Lys Lys Lys Lys Lys Lys Lys Lys Lys Lys Lys Lys
305                 310                 315                 320

```
Lys Lys Lys Lys Lys Lys Lys Lys Lys Lys Lys Lys Lys
            325                 330                 335

Lys Lys Lys Lys Lys Lys Lys Lys Lys Lys Lys Lys
            340                 345                 350

Lys Lys Lys Lys Lys Lys Lys Lys Lys Lys Lys Lys
            355                 360                 365

Lys Lys Lys Lys Lys Lys Lys Lys Lys Lys Lys Lys
            370                 375                 380

Lys Lys Lys Lys Lys Lys Lys Lys Lys Lys Lys Lys
385                 390                 395                 400

Lys Lys Lys Lys Lys Lys Lys Lys Lys Lys Lys Lys
            405                 410                 415

Lys Lys Lys Lys Lys Lys Lys Lys Lys Lys Lys Lys
            420                 425                 430

Lys Lys Lys Lys Lys Lys Lys Lys Lys Lys Lys Lys
            435                 440                 445

Lys Lys Lys Lys Lys Lys Lys Lys Lys Lys Lys Lys
            450                 455                 460

Lys Lys Lys Lys Lys Lys Lys Lys Lys Lys Lys Lys
465                 470                 475                 480

Lys Lys

<210> SEQ ID NO 10
<211> LENGTH: 87
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (29)..(86)
<223> OTHER INFORMATION: Arginine may be absent

<400> SEQUENCE: 10

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg
            20                  25                  30

Arg Arg Arg Arg Arg Arg Arg Arg Arg Arg Arg Arg Arg Arg Arg
            35                  40                  45

Arg Arg Arg Arg Arg Arg Arg Arg Arg Arg Arg Arg Arg Arg Arg
            50                  55                  60

Arg Arg Arg Arg Arg Arg Arg Arg Arg Arg Arg Arg Arg Arg Arg Arg
65                  70                  75                  80

Arg Arg Arg Arg Arg Arg Arg
                85

<210> SEQ ID NO 11
<211> LENGTH: 163
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (34)..(162)
<223> OTHER INFORMATION: Histidine may be absent
```

```
<400> SEQUENCE: 11

His His His His His His His His His His His His His His His
1               5                       10                      15
His His His His His His His His His His His His His His His
                20                      25                      30
His His His His His His His His His His His His His His His
        35                      40                      45
His His His His His His His His His His His His His His His
    50                      55                      60
His His His His His His His His His His His His His His His
65                      70                      75                      80
His His His His His His His His His His His His His His His
                85                      90                      95
His His His His His His His His His His His His His His His
                100                     105                     110
His His His His His His His His His His His His His His His
            115                     120                     125
His His His His His His His His His His His His His His His
        130                     135                     140
His His His His His His His His His His His His His His His
145                     150                     155                     160
His His His
```

AMINO ACID-, PEPTIDE- AND POLYPEPTIDE-LIPIDS, ISOMERS, COMPOSITIONS, AND USES THEREOF

RELATED APPLICATIONS

The present application is a division of and claims priority under 35 U.S.C. § 120 to U.S. application, U.S. Ser. No. 13/662,002, filed Oct. 26, 2012, now U.S. Pat. No. 9,512,073, which claims priority under 35 U.S.C. § 119(e) to U.S. provisional patent application, U.S. Ser. No. 61/552,423, filed Oct. 27, 2011, each of which is incorporated herein by reference.

GOVERNMENT SUPPORT

This invention was made with government support under Grant No. R37 EB000244 awarded by the National Institutes of Health. The government has certain rights in this invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464:1067-1070. It is well understood that development of genetic drugs is slowed by the inability to deliver nucleic acids effectively in vivo. When unprotected, genetic material injected into the bloodstream can be degraded by DNAases and RNAases, or, if not degraded, the genetic material can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead supra). The RISC associates with and degrades complementary mRNA sequences, thereby preventing translation of the target mRNA into protein, i.e., "silencing" the gene.

To overcome difficulties in delivery, nucleotides have been complexed with a wide variety of delivery systems, including polymers, lipids, inorganic nanoparticles and viruses. See, e.g., Peer et al. *Nature Nanotechnology*, (2007) 2:751-760. However, despite promising data from ongoing clinical trials for the treatment of respiratory syncytial virus and liver cancers (see, e.g., Zamora et al., *Am. J. Respir. Crit. Care Med*. (2011) 183:531-538), the clinical use of siRNA continues to require development of safer and more effective delivery systems. Toward this end, numerous lipid-like molecules have been developed including poly β-amino esters and amino alcohol lipids. See, e.g., PCT Application Publication Nos. WO 2002/031025; WO 2004/106411; WO 2008/011561; WO 2007/143659; WO 2006/138380; and WO 2010/053572. Amino acid, peptide, polypeptide-lipids (APPL) have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; and Damen et al., *Journal of Controlled Release* (2010) 145:33-39. However, there continues to remain a need to investigate and develop new APPL systems with improved properties, such as new and improved APPL nucleotide delivery systems.

SUMMARY OF THE INVENTION

Described herein are inventive compounds and compositions characterized, in certain embodiments, by conjugation of various groups, such as lipophilic groups, to an amino or amide group of an amino acid, a linear or cyclic peptide, a linear or cyclic polypeptide, or structural isomer thereof, to provide compounds of the present invention, collectively referred to herein as "APPLs". Such APPLs are deemed useful for a variety of applications, such as, for example, improved nucleotide delivery.

Exemplary APPLs include, but are not limited to, compounds of Formula (I), (II), (III), (IV), (V), and (VI), and salts thereof, as described herein:

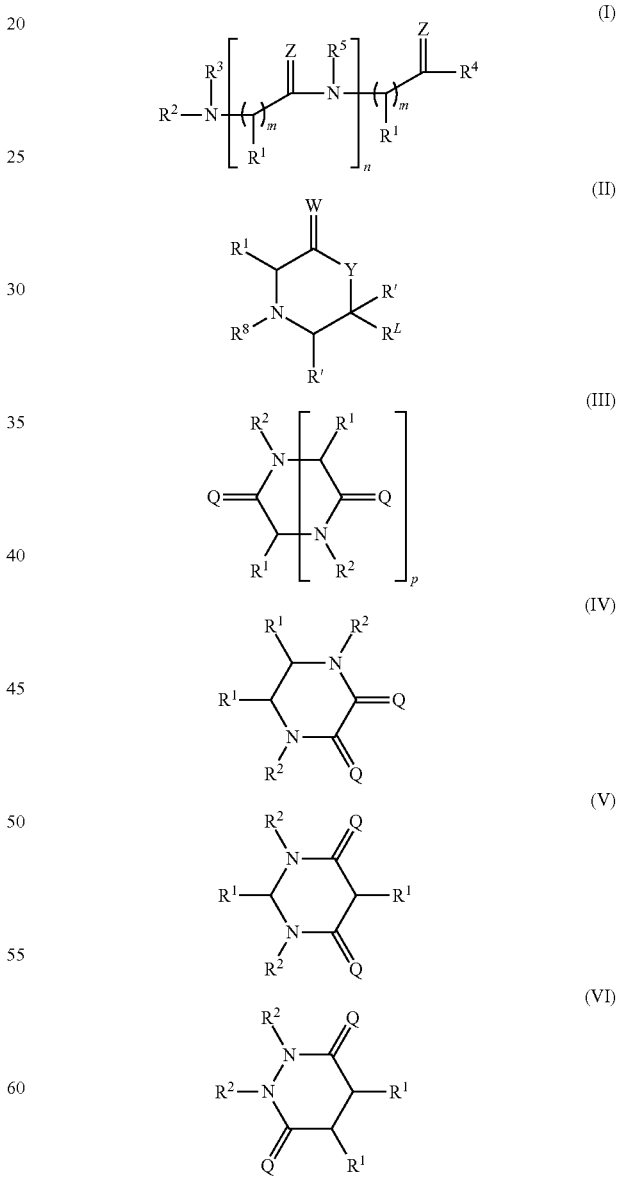

wherein m, n, p, R', $R^1$, $R^2$, $R^3$, $R^4$, $R^5$, $R^8$, Z, W, Y, and Z are as defined herein, provided that the APPL comprises at least one instance of a group of formula (i), (ii), or (iii):

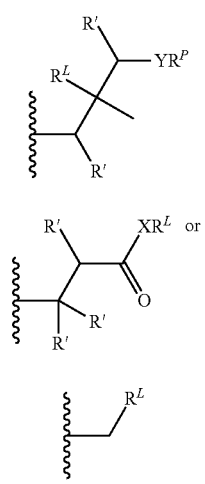

(i)

(ii)

(iii)

wherein:

each instance of R' is independently hydrogen or optionally substituted alkyl;

X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

In certain embodiments, the group of formula (i) represents a group of formula (i-a) or a group of formula (i-b):

(i-a)

(i-b)

In certain embodiments, the group of formula (i-a) is a group of formula (i-a1) or a group of formula (i-a2):

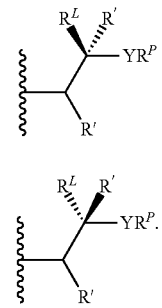

(i-a1)

(i-a2)

In certain embodiments, the group of formula (i-b) is a group of formula (i-b1) or a group of formula (i-b2):

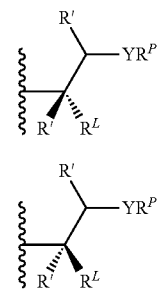

(i-b1)

(i-b2)

In certain embodiments, at least one instance of $R^1$ is a group of formula:

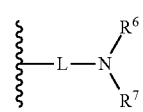

(iv)

wherein L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, and $R^6$ and $R^7$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

provided at least one instance of $R^6$ and $R^7$ is a group of formula:

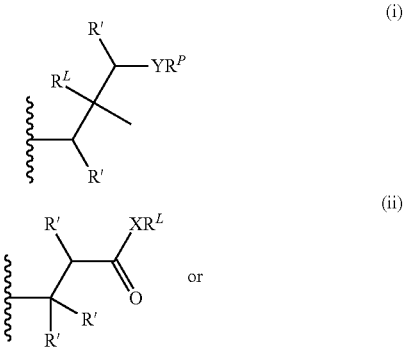

(i)

(ii)

-continued

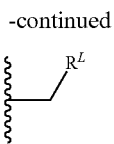

(iii)

wherein:
each instance of R' is independently hydrogen or optionally substituted alkyl;
X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and
$R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

In certain embodiments, each instance of R' is hydrogen.
In certain embodiments, L is an optionally substituted alkylene.
In certain embodiments, the group of formula (iv) is of formula:

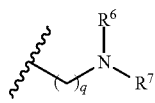

wherein q is an integer between 1 and 50, inclusive.
In certain embodiments, each instance of $R^1$ is a group of formula (iv).
An exemplary APPL of the present invention is compound (cKK-E12):

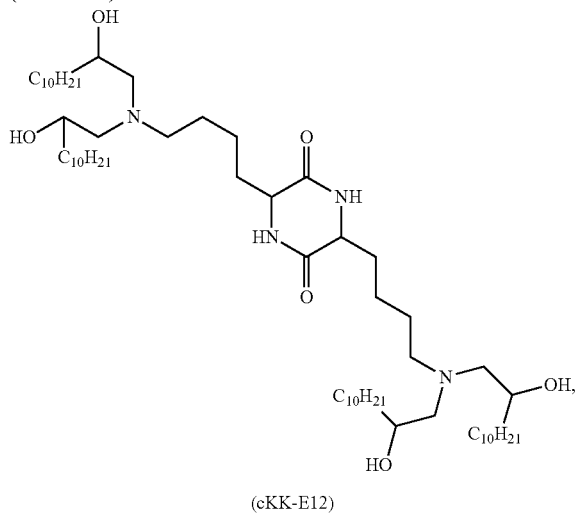

(cKK-E12)

or a salt thereof.

In another aspect, provided are compositions comprising an APPL or a salt thereof.
For example, in certain embodiments, provided is a composition comprising an APPL or salt thereof and, optionally, an excipient, wherein the APPL is an amino acid, a linear or cyclic peptide, a linear or cyclic polypeptide, or structural isomer thereof, and wherein an amino or amide group of the APPL is conjugated to a group of formula (i), (ii), or (iii). In certain embodiments, the group of formula (i), (ii), or (iii) is attached to an amino group present on the APPL scaffold. In certain embodiments, the composition is a pharmaceutical composition, a cosmetic composition, a nutraceutical composition, or a composition with non-medical application. In certain embodiments, the composition with non-medical application is an emulsion or emulsifier useful as a food component, for extinguishing fires, for disinfecting surfaces, or for oil cleanup.

In certain embodiments, the composition further comprises an agent. In certain embodiments, the agent is an organic molecule, inorganic molecule, nucleic acid, protein, peptide, polynucleotide, targeting agent, an isotopically labeled chemical compound, vaccine, an immunological agent, or an agent useful bioprocessing, e.g., in the intracellular manufacturing of proteins. In certain embodiments, the agent is a polynucleotide, and the polynucleotide is DNA or RNA. In certain embodiments, the RNA is RNAi, dsRNA, siRNA, shRNA, miRNA, or antisense RNA. In certain embodiments, the agent and the APPL are not covalently attached, e.g., for example, the agent and the APPL are non-covalently complexed to each other. However, in certain embodiments, the agent and the APPL are covalently attached.

In certain embodiments, the composition is in the form of a particle. In certain embodiments, the particle is a nanoparticle or microparticle. In certain embodiments, the particle is a micelle, liposome, or lipoplex. In certain embodiments, the particle encapsulates an agent, e.g., an agent to be delivered.

In another aspect, provided is a method of delivering a polynucleotide to a biological cell, comprising providing a composition comprising an APPL, or salt thereof, and a polynucleotide, and exposing the composition to the biological cell under conditions sufficient to facilitate delivery of the polynucleotide into the interior of the biological cell; wherein the APPL is an amino acid, a linear or cyclic peptide, or a linear or cyclic polypeptide, or structural isomer thereof, wherein an amino or amide group of the APPL is conjugated to a group of formula (i), (ii), or (iii). In certain embodiments, the polynucleotide is DNA or RNA. In certain embodiments, the RNA is RNAi, dsRNA, siRNA, shRNA, miRNA, or antisense RNA. In certain embodiments, upon delivery of the RNA into the cell, the RNA is able to interfere with the expression of a specific gene in the biological cell.

In yet another aspect, provided are screening methods. For example, in one embodiment, provided is a method of screening a compound library, the method comprising providing a plurality of different APPLs, or salts thereof, and performing at least one assay with the compound library to determine the presence or absence of a desired property; wherein the APPL is an amino acid, a linear or cyclic peptide, or a linear or cyclic polypeptide, or structural isomer thereof, wherein an amino or amide group of the APPL is conjugated to a group of formula (i), (ii), or (iii). In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support cell growth, ability to support cell attachment, ability to support tissue growth, and/or intracellular delivery of the APPL and/or an agent complexed or attached thereto to aid in bioprocessing.

In still yet another aspect, provided are methods of use of the inventive APPLs for the treatment of various diseases, disorders, or conditions. For example, in certain embodiments, provided is a method of treating a disease, disorder, or condition from which the subject suffers, comprising administering to a subject in need thereof an effective amount of an APPL, or salt thereof, wherein the APPL is an amino acid, a linear or cyclic peptide, or a linear or cyclic polypeptide, or structural isomer thereof, wherein an amino or amide group of the APPL is conjugated to a group of formula (i), (ii), or (iii).

The details of one or more embodiments of the invention are set forth herein. Other features, objects, and advantages of the invention will be apparent from the Detailed Description, the Figures, the Examples, and the Claims.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 50 carbon atoms ("$C_{1-50}$ alkyl"). In some embodiments, an alkyl group has 1 to 40 carbon atoms ("$C_{1-40}$ alkyl"). In some embodiments, an alkyl group has 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-50}$ alkyl. In certain embodiments, the alkyl group is a substituted $C_{1-50}$ alkyl.

As used herein, "heteroalkyl" refers to an alkyl group as defined herein which further includes at least one heteroatom (e.g., 1 to 25, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkyl group refers to a saturated group having from 1 to 50 carbon atoms and 1 or more heteroatoms within the parent chain ("hetero$C_{1-50}$ alkyl"). In certain embodiments, a heteroalkyl group refers to a saturated group having from 1 to 40 carbon atoms and 1 or more heteroatoms within the parent chain ("hetero$C_{1-50}$ alkyl"). In certain embodiments, a heteroalkyl group refers to a saturated group having from 1 to 30 carbon atoms and 1 or more heteroatoms within the parent chain ("hetero$C_{1-30}$ alkyl"). In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-50}$ alkyl. In certain embodiments, the heteroalkyl group is a substituted heteroC$_{1-50}$ alkyl.

As used herein, "alkenyl" refers to a radical of a straight-chain or branched hydrocarbon group having from 2 to 50 carbon atoms and one or more carbon-carbon double bonds (e.g., 1, 2, 3, or 4 double bonds) ("C$_{2-50}$ alkenyl"). In some embodiments, an alkenyl group has 2 to 40 carbon atoms ("C$_{2-40}$ alkenyl"). In some embodiments, an alkenyl group has 2 to 30 carbon atoms ("C$_{2-30}$ alkenyl"). In some embodiments, an alkenyl group has 2 to 20 carbon atoms ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-50}$ alkenyl. In certain embodiments, the alkenyl group is a substituted C$_{2-50}$ alkenyl.

As used herein, "heteroalkenyl" refers to an alkenyl group as defined herein which further includes at least one heteroatom (e.g., 1 to 25, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkenyl group refers to a group having from 2 to 50 carbon atoms, at least one double bond, and 1 or more heteroatoms within the parent chain ("heteroC$_{2-50}$ alkenyl"). In certain embodiments, a heteroalkenyl group refers to a group having from 2 to 40 carbon atoms, at least one double bond, and 1 or more heteroatoms within the parent chain ("heteroC$_{2-40}$ alkenyl"). In certain embodiments, a heteroalkenyl group refers to a group having from 2 to 30 carbon atoms, at least one double bond, and 1 or more heteroatoms within the parent chain ("heteroC$_{2-30}$ alkenyl"). In certain embodiments, a heteroalkenyl group refers to a group having from 2 to 20 carbon atoms, at least one double bond, and 1 or more heteroatoms within the parent chain ("heteroC$_{2-20}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-50}$ alkenyl. In certain embodiments, the heteroalkenyl group is a substituted heteroC$_{2-50}$ alkenyl.

As used herein, "alkynyl" refers to a radical of a straight-chain or branched hydrocarbon group having from 2 to 50 carbon atoms and one or more carbon-carbon triple bonds (e.g., 1, 2, 3, or 4 triple bonds) and optionally one or more double bonds (e.g., 1, 2, 3, or 4 double bonds) ("C$_{2-50}$ alkynyl"). An alkynyl group that has one or more triple bonds and one or more double bonds is also referred to as an "ene-yene". In some embodiments, an alkynyl group has 2 to 40 carbon atoms ("C$_{2-40}$ alkynyl"). In some embodiments, an alkynyl group has 2 to 30 carbon atoms ("C$_{2-30}$ alkynyl"). In some embodiments, an alkynyl group has 2 to 20 carbon atoms ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-50}$ alkynyl. In certain embodiments, the alkynyl group is a substituted $C_{2-50}$ alkynyl.

As used herein, "heteroalkynyl" refers to an alkynyl group as defined herein which further includes at least one heteroatom (e.g., 1 to 25, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkynyl group refers to a group having from 2 to 50 carbon atoms, at least one triple bond, and 1 or more heteroatoms within the parent chain ("heteroC$_{2-50}$ alkynyl"). In certain embodiments, a heteroalkynyl group refers to a group having from 2 to 40 carbon atoms, at least one triple bond, and 1 or more heteroatoms within the parent chain ("heteroC$_{2-40}$ alkynyl"). In certain embodiments, a heteroalkynyl group refers to a group having from 2 to 30 carbon atoms, at least one triple bond, and 1 or more heteroatoms within the parent chain ("heteroC$_{2-30}$ alkynyl"). In certain embodiments, a heteroalkynyl group refers to a group having from 2 to 20 carbon atoms, at least one triple bond, and 1 or more heteroatoms within the parent chain ("heteroC$_{2-20}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-50}$ alkynyl. In certain embodiments, the heteroalkynyl group is a substituted heteroC$_{2-50}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary C$_{3-8}$ carbocyclyl groups include, without limitation, the aforementioned C$_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary C$_{3-10}$ carbocyclyl groups include, without limitation, the aforementioned C$_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-10}$ cycloalkyl"). In some embodiments, a cycloalkyl group has 4 to 6 ring carbon atoms ("C$_{4-10}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl ($C_5$) and cyclohexyl ($C_5$). Examples of C$_{3-6}$ cycloalkyl groups include the aforementioned C$_{5-6}$ cycloalkyl groups as well as cyclopropyl ($C_3$) and cyclobutyl ($C_4$). Examples of C$_{3-8}$ cycloalkyl groups include the aforementioned C$_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, or phosphorus. In some embodiments, the 5-6 membered heterocyclyl has 1 or 2 ring heteroatoms selected from oxygen, sulfur, nitrogen, boron, silicon, or phosphorus. In some embodiments, the 5-6 membered heterocyclyl has 1 ring heteroatom selected from oxygen, sulfur, nitrogen, boron, silicon, or phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic or tricyclic) 4n+2 aromatic ring system (e.g., having 6, 10, or 14π electrons shared in a cyclic array) having ring carbon atoms and 1 or more (e.g., 1, 2, 3, or 4 ring heteroatoms) ring heteroatoms provided in the aromatic ring system, wherein each heteroatom is independently selected from oxygen, sulfur, nitrogen, boron, silicon, or phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, or phosphorus. In some embodiments, the 5-6 membered heteroaryl has 1 or 2 ring heteroatoms selected from oxygen, sulfur, nitrogen, boron, silicon, or phosphorus. In some embodiments, the 5-6 membered heteroaryl has 1 ring heteroatom selected from oxygen, sulfur, nitrogen, boron, silicon, or phosphorus. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SeH, —SeR$^{aa}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-50}$ alkyl, C$_{2-50}$ alkenyl, C$_{2-50}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-50}$ alkyl, C$_{2-50}$ alkenyl, C$_{2-50}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-50}$ alkyl, C$_{2-50}$ alkenyl, C$_{2-50}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-50}$ alkyl, C$_{2-50}$ alkenyl, C$_{2-50}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-50}$ alkyl, —ON(C$_{1-50}$ alkyl)$_2$, —N(C$_{1-50}$ alkyl)$_2$, —N(C$_{1-50}$ alkyl)$_3$$^+$X$^-$, —NH(C$_{1-50}$ alkyl)$_2$$^+$X$^-$, —NH$_2$(C$_{1-50}$ alkyl)$^+$X$^-$, —NH$_3$$^+$X$^-$, —N(OC$_{1-50}$ alkyl)(C$_{1-50}$ alkyl), —N(OH)(C$_{1-50}$ alkyl), —NH(OH), —SH, —SC$_{1-50}$ alkyl, —SS(C$_{1-50}$ alkyl), —C(=O)(C$_{1-50}$ alkyl), —CO$_2$H, —CO$_2$(C$_{1-50}$ alkyl), —OC(=O)(C$_{1-50}$ alkyl), —OCO$_2$(C$_{1-50}$ alkyl), —C(=O)NH$_2$, —C(=O)N(C$_{1-50}$ alkyl)$_2$, —OC(=O)NH(C$_{1-50}$ alkyl), —NHC(=O)(C$_{1-50}$ alkyl), —N(C$_{1-50}$ alkyl)C(=O)(C$_{1-50}$ alkyl), —NHCO$_2$(C$_{1-50}$ alkyl), —NHC(=O)N(C$_{1-50}$ alkyl)$_2$, —NHC(=O)NH(C$_{1-50}$ alkyl), —NHC(=O)NH$_2$, —C(=NH)O(C$_{1-50}$ alkyl), —OC(=NH)(C$_{1-50}$ alkyl), —OC(=NH)OC$_{1-50}$ alkyl, —C(=NH)N(C$_{1-50}$ alkyl)$_2$, —C(=NH)NH(C$_{1-50}$ alkyl), —C(=NH)NH$_2$, —OC(=NH)N(C$_{1-50}$ alkyl)$_2$, —OC(NH)NH(C$_{1-50}$ alkyl), —OC(NH)NH$_2$, —NHC(NH)N(C$_{1-50}$ alkyl)$_2$, —NHC(=NH)NH$_2$, —NHSO$_2$(C$_{1-50}$ alkyl), —SO$_2$N(C$_{1-50}$ alkyl)$_2$, —SO$_2$NH(C$_{1-50}$ alkyl), —SO$_2$NH$_2$, —SO$_2$C$_{1-50}$ alkyl, —SO$_2$OC$_{1-50}$ alkyl, —OSO$_2$C$_{1-6}$ alkyl, —SOC$_{1-6}$ alkyl, —Si(C$_{1-50}$ alkyl)$_3$, —OSi(C$_{1-6}$ alkyl)$_3$-C(=S)N(C$_{1-50}$ alkyl)$_2$, C(=S)NH(C$_{1-50}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-50}$ alkyl), —P(=O)(C$_{1-50}$ alkyl)$_2$, —OP(=O)(C$_{1-50}$ alkyl)$_2$, —OP(=O)(OC$_{1-50}$ alkyl)$_2$, C$_{1-50}$ alkyl, C$_{2-50}$ alkenyl, C$_{2-50}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, o-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1, 3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" is an art-understood term referring to a molecular fragment that departs with a pair of electrons in heterolytic bond cleavage, wherein the molecular fragment is an anion or neutral molecule. See, for example, Smith, *March Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

These and other exemplary substituents are described in more detail in the Detailed Description, Examples, Figures, and Claims. The invention is not intended to be limited in any manner by the above exemplary listing of substituents.

Other Definitions

As used herein, use of the phrase "at least one instance" refers to one instance, but also encompasses more than one instance, e.g., for example, 1, 2, 3, 4, 5, 6, 7, 8, 9, or 10 instances, and up to 100 instances.

An "amino acid" refers to natural and unnatural D/L alpha-amino acids, as well as natural and unnatural beta- and gamma-amino acids. A "peptide" refers to two amino acids joined by a peptide bond. A "polypeptide" refers to three or more amino acids joined by peptide bonds. An "amino acid side chain" refers to the group(s) pended to the alpha carbon (if an alpha amino acid), alpha and beta carbon (if a beta amino acid), or the alpha, beta, and gamma carbon (if a gamma amino acid). Exemplary amino acid side chains are depicted herein; see, e.g., Table 1 of the Examples.

As used herein, a "polymer" refers to a compound comprised of at least 3 (e.g., at least 10, 20, 30, 40, 50, 60, 70, 80, 90, 100, etc.) repeating covalently bound structural units.

"Conjugated" and "attached" refer to the covalent attachment of a group, and are used interchangeably herein.

As used herein, "lipophilic" refers to the ability of a group to dissolve in fats, oils, lipids, and lipophilic non-polar solvents such as hexane or toluene. In general, a lipophilic group refers to an unsubstituted n-alkyl or unsubstituted n-alkenyl group having 6 to 50 carbon atoms, e.g., 6 to 40, 6 to 30, 6 to 20, 8 to 20, 8 to 19, 8 to 18, 8 to 17, 8 to 16, or 8 to 15 carbon atoms.

Use of the terms "structural isomer," "organic molecule," and "inorganic molecule" are meant to encompass the common meaning of each term as known in the art.

As used herein, a "small organic molecule" or "small molecule" refers to an organic molecule with a molecular weight of 800 g/mol or less (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small organic molecule is a therapeutically active agent such as a drug (e.g., a small organic molecule approved by the U.S. Food and Drug Administration as provided in the Code of Federal Regulations (CFR)). The small organic molecule may also be complexed with a metal. In this instance, the small organic molecule is also referred to as an "small organometallic molecule."

As used herein, a "large organic molecule" or "large molecule" refers to an organic compound with a molecular weight of greater than 800 g/mol (e.g., greater than 800 g/mol, greater than 900 g/mol, greater than 1000 g/mol, greater than 2000 g/mol, between 801 to 2000 g/mol, inclusive, between 900 to 2000 g/mol, inclusive, between 1000 to 2000 g/mol, inclusive, or between 801 to 1000 g/mol, inclusive). In certain embodiments, the large organic molecule is a therapeutically active agent such as a drug (e.g., a large organic molecule approved by the U.S. Food and Drug Administration as provided in the Code of Federal Regulations (CFR)). The large organic molecule may also be complexed with a metal. In this instance, the large organic molecule is also referred to as an "large organometallic compound."

As used herein, a "small inorganic molecule" refers to an inorganic compound with a molecular weight of 800 g/mol or less (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small inorganic molecule is a therapeutically active agent such as a drug (e.g., a small inorganic molecule approved by the U.S. Food and Drug Administration as provided in the Code of Federal Regulations (CFR)).

As used herein, a "large inorganic molecule" refers to an inorganic compound with a molecular weight of greater than 800 g/mol (e.g., greater than 800 g/mol, greater than 900 g/mol, greater than 1000 g/mol, greater than 2000 g/mol, between 801 to 2000 g/mol, inclusive, between 900 to 2000 g/mol, inclusive, between 1000 to 2000 g/mol, inclusive, or between 801 to 1000 g/mol, inclusive). In certain embodiments, the large inorganic molecule is a therapeutically active agent such as a drug (e.g., a large inorganic molecule approved by the U.S. Food and Drug Administration as provided in the Code of Federal Regulations (CFR)).

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

DETAILED DESCRIPTION OF CERTAIN EMBODIMENTS OF THE INVENTION

Figure 1:
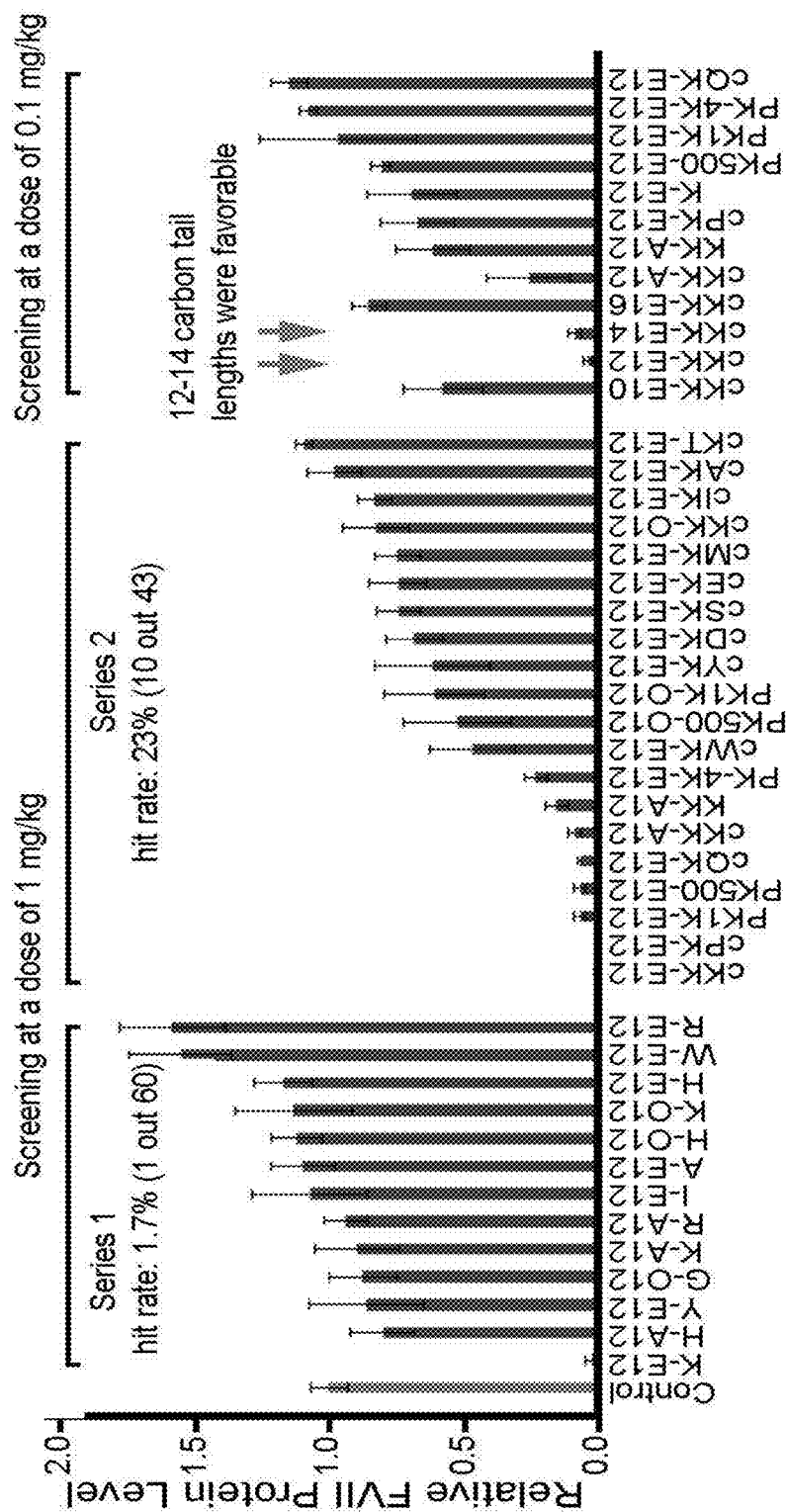
FIG. 1 depicts the structural design and optimization through in vivo evaluation in mice. Single amino acid-based lipid derivatives were tested at a dose of 1 mg/kg in mice, which indicated that lysine was a favorable amino acid. Lysine-based peptide and polypeptide-lipid derivatives were then investigated at the same dose. The hit rate was improved from 1.7% to 23% (including those compounds not screened due to particle instability or no entrapment of siRNA). The top hits and their analogs were explored at a lower dose of 0.1 mg/kg, which led to selection of cKK-E12 as the lead compound. K-E12; K: abbreviation of lysine, E: epoxide, A: aldehyde, O: acrylate, 12: carbon tail length. cKK-E12; c: cyclic; Control, phosphate-buffered saline.

Described herein are inventive compounds and compositions, certain embodiments of which involve conjugation of various groups, such as lipophilic groups, to an amino or amide group of an amino acid, a linear or cyclic peptide, a linear or cyclic polypeptide, or structural isomer thereof, to provide compounds of the present invention, collectively referred to herein as "APPLs". Such APPLs are deemed useful for a variety of applications, such as, for example, improved nucleotide delivery.

Exemplary APPLs include, but are not limited to, compounds of Formula (I), (II), (III), (IV), (V), and (VI), and salts thereof, as described herein:

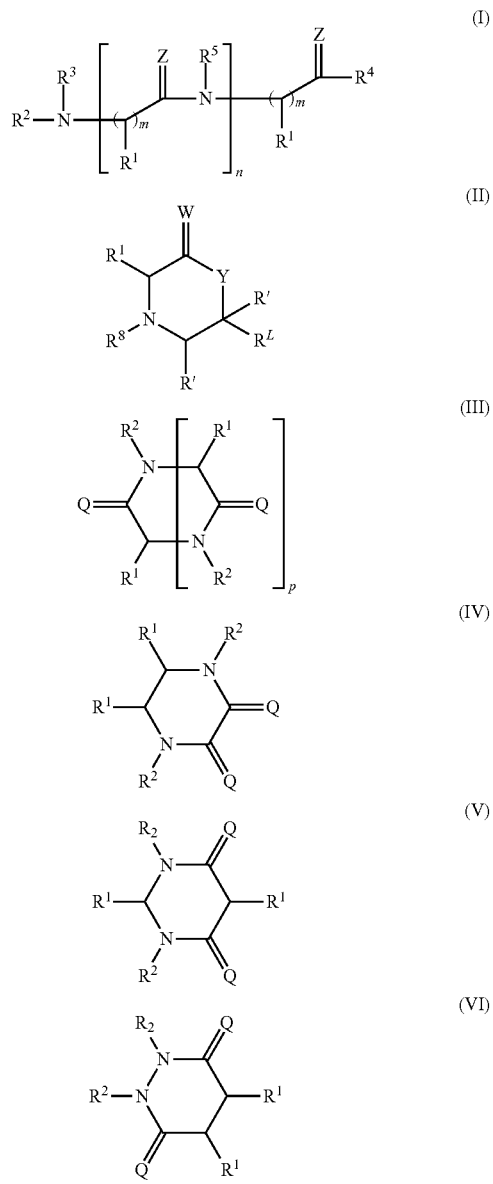

wherein m, n, p, $R^1$, $R^2$, $R^3$, $R^4$, $R^5$, $R^8$, Z, W, Y, and Z are as defined herein.

Various $R^L$ groups, e.g., lipophilic groups, may be attached to the APPL via conjugation of a primary or secondary amino group or amide of the amino acid, peptide, or polypeptide precursor, or structural isomer thereof, with an epoxide, thiirane, or aziridine of formula (i-x), Michael addition to an α,β-unsaturated ester, thioester, or amide of formula (ii-x), or reductive amination to an aldehyde of formula (iii-x) (Scheme 1).

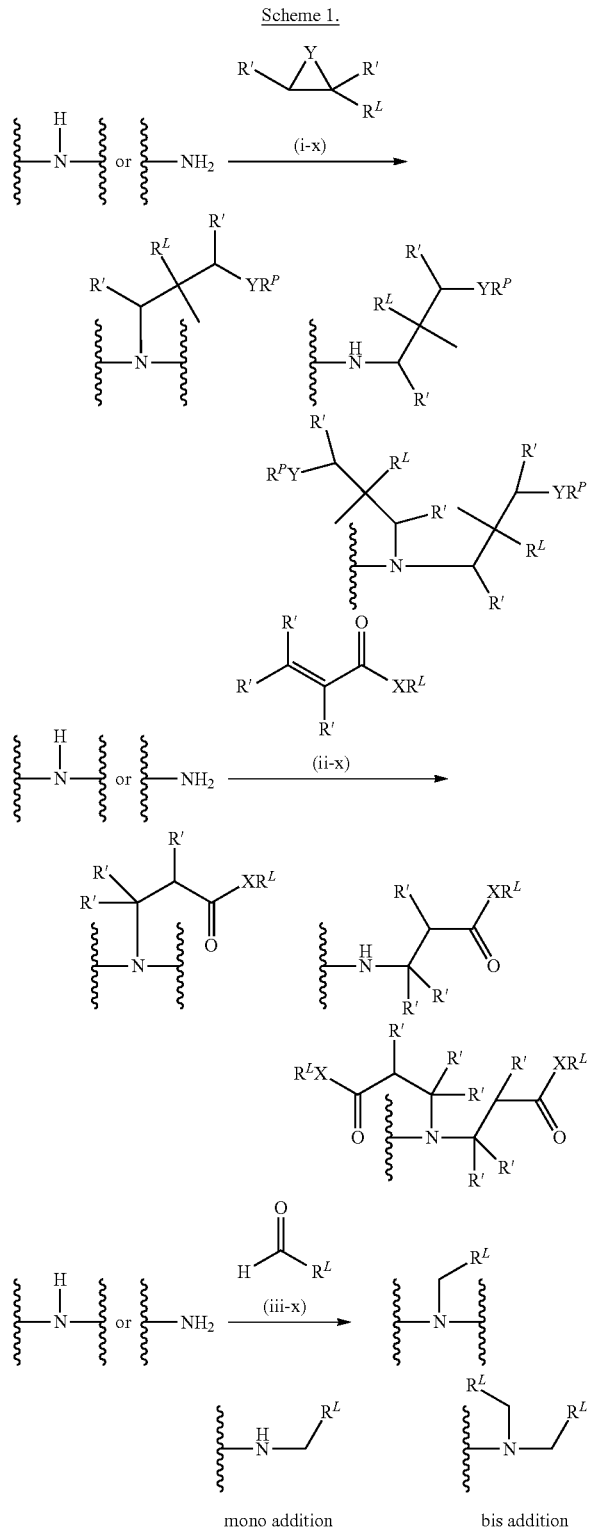

Thus, in the broadest aspect, the present invention provides APPLs, and in certain embodiments, compounds of Formula (I), (II), (III), (IV), (V), and (VI), comprising at least one instance of a group attached thereto of the formula:

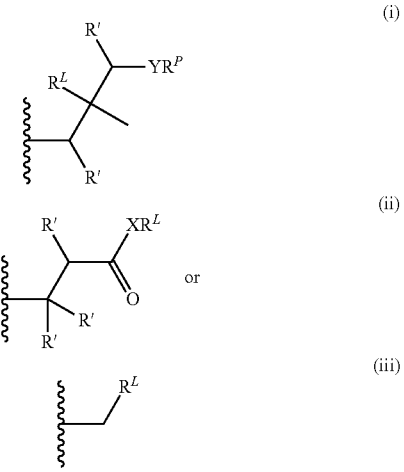

wherein:

each instance of R' is independently hydrogen or optionally substituted alkyl;

X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and $R^L$ is optionally substituted $C_{1-50}$ alkyl, optionally substituted $C_{2-50}$ alkenyl, optionally substituted $C_{2-50}$ alkynyl, optionally substituted $C_{1-50}$ heteroalkyl, optionally substituted $C_{2-50}$ heteroalkenyl, optionally substituted $C_{2-50}$ heteroalkynyl, or a polymer.

Various embodiments of formula (i), (ii), and (iii), and variables $R^L$, $R^P$, X, and Y are described in greater detail herein.

Compounds of Formula (I)

Compounds of Formula (I) encompasses amino acids, linear peptides, and linear polypeptides which comprise one or more sites of conjugation, e.g., to the terminal amino group, to an amino substituent, and/or to an imino nitrogen, of a group of formula (i), (ii), or (iii).

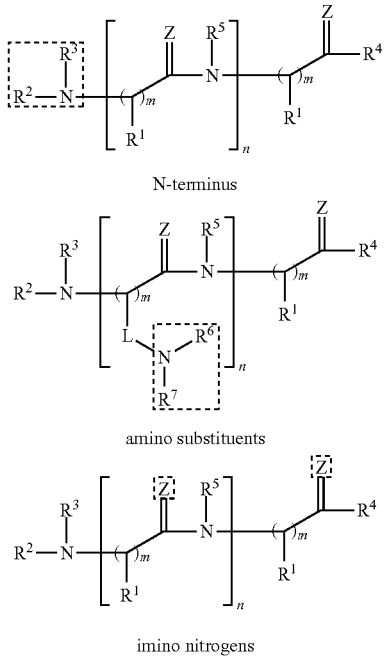

N-terminus amino substituents

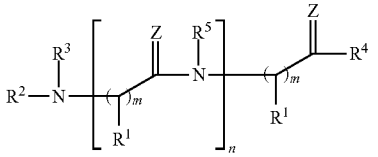

imino nitrogens

Thus, in one aspect, provided is a compound of Formula (I):

(I)

or salt thereof;
wherein:
n is 0 or is an integer between 1 and 100,000, inclusive;
each instance of m is independently 1, 2, or 3;
each instance of Z is independently O, S, or $NR^Z$, wherein $R^Z$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii);
each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{A1}$, $-N(R^{A1})_2$, or $-SR^{A1}$; wherein each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A1}$ groups are joined to form an optionally substituted heterocyclic or optionally substituted heteroaryl ring;
$R^2$ is a group of formula (i), (ii), or (iii);
$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii);
or $R^3$ and an $R^1$ group are joined to form an optionally substituted 5-6 membered heterocyclic ring;
$R^4$ is $-OR^{A4}$, $-N(R^{A4})_2$, or $-SR^{A4}$; wherein each occurrence of $R^{A4}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A4}$ groups are joined to form an optionally substituted heterocyclic or optionally substituted heteroaryl ring;
$R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; and
Formulae (i), (ii), and (iii) are:

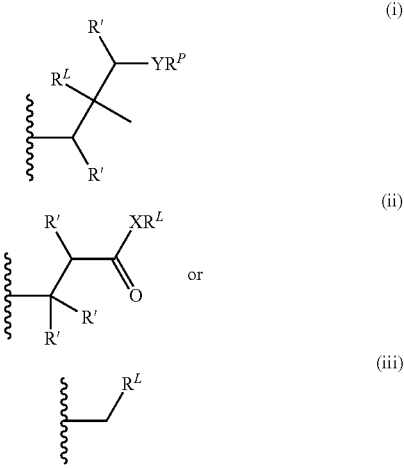

wherein:
each instance of R' is independently hydrogen or optionally substituted alkyl;
X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and $R^L$ is optionally substituted $C_{1-50}$ alkyl, optionally substituted $C_{2-50}$ alkenyl, optionally substituted $C_{2-50}$ alkynyl, optionally substituted heteroC$_{1-50}$ alkyl, optionally substituted heteroC$_{2-50}$ alkenyl, or optionally substituted heteroC$_{2-50}$ alkynyl, or a polymer.

In certain embodiments, when n is greater than 10, then neither $R^2$ nor $R^3$ is a group of the formula (iii). In certain embodiments, when n is greater than 9, then neither $R^2$ nor $R^3$ is a group of the formula (iii). In certain embodiments, when n is greater than 8, then neither $R^2$ nor $R^3$ is a group of the formula (iii). In certain embodiments, when n is greater than 7, then neither $R^2$ nor $R^3$ is a group of the formula (iii). In certain embodiments, when n is greater than 6, then neither $R^2$ nor $R^3$ is a group of the formula (iii). In certain embodiments, when n is greater than 5, then neither $R^2$ nor $R^3$ is a group of the formula (iii). In certain embodiments, when n is greater than 4, then neither $R^2$ nor $R^3$ is a group of the formula (iii). In certain embodiments, when n is greater than 3, then neither $R^2$ nor $R^3$ is a group of the formula (iii). In certain embodiments, when n is greater than 2, then neither $R^2$ nor $R^3$ is a group of the formula (iii). In certain embodiments, when n is greater than 1, then neither $R^2$ nor $R^3$ is a group of the formula (iii). In certain embodiments, neither $R^2$ nor $R^3$ is a group of the formula (iii).

In certain embodiments, wherein n is 0 and Z is O, one or more of the following compounds are excluded:

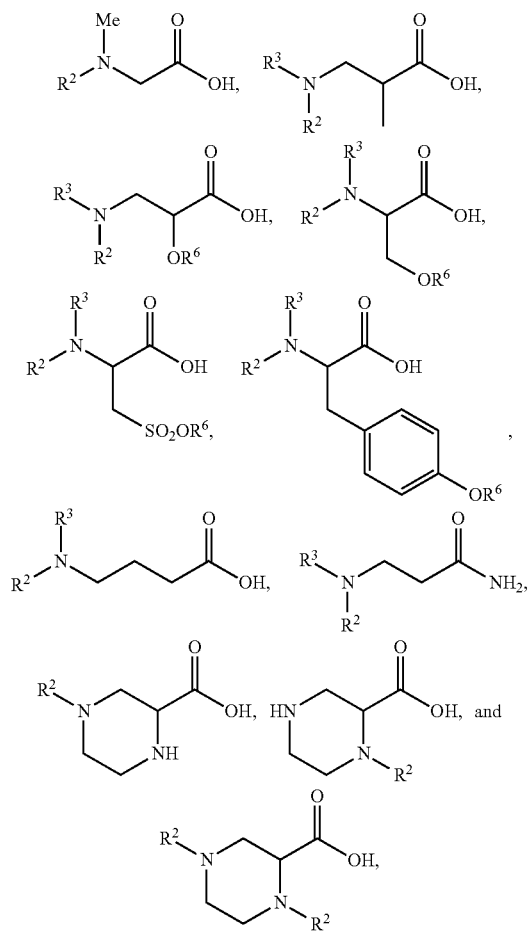

and salts thereof; wherein $R^2$ is a group of the formula (i), $R^3$ and $R^6$ are independently hydrogen or a group of formula (i), and Y is O.

As generally defined above, n is 0 or is an integer between 1 and 100,000, inclusive. It is thus understood that Formula (I) encompasses amino acids conjugated to a lipid group, as well as linear peptides and linear polypeptides conjugated to lipid groups.

In certain embodiments, n is 0 or is an integer between 1 and 90,000, inclusive. In certain embodiments, n is 0 or is an integer between 1 and 80,000, inclusive. In certain embodiments, n is 0 or is an integer between 1 and 70,000, inclusive. In certain embodiments, n is 0 or is an integer between 1 and 50,000, inclusive. In certain embodiments, n is 0 or is an integer between 1 and 40,000, inclusive. In certain embodiments, n is 0 or is an integer between 1 and 30,000, inclusive. In certain embodiments, n is 0 or is an integer between 1 and 20,000, inclusive. In certain embodiments, n is 0 or is an integer between 1 and 10,000, inclusive. In certain embodiments, n is 0 or is an integer between 1 and 9,000, inclusive. In certain embodiments, n is 0 or is an integer between 1 and 8,000, inclusive. In certain embodiments, n is 0 or is an integer between 1 and 7,000, inclusive. In certain embodiments, n is 0 or is an integer between 1 and 6,000, inclusive. In certain embodiments, n is 0 or is an integer between 1 and 5,000, inclusive. In certain embodiments, n is 0 or is an integer between 1 and 4,000, inclusive. In certain embodiments, n is 0 or is an integer between 1 and 3,000, inclusive. In certain embodiments, n is 0 or is an integer between 1 and 2,000, inclusive. In certain embodiments, n is 0 or is an integer between 1 and 1,000, inclusive. In certain embodiments, n is 0 or is an integer between 1 and 900, inclusive. In certain embodiments, n is 0 or is an integer between 1 and 800, inclusive. In certain embodiments, n is 0 or is an integer between 1 and 700, inclusive. In certain embodiments, n is 0 or is an integer between 1 and 600, inclusive. In certain embodiments, n is 0 or is an integer between 1 and 500, inclusive. In certain embodiments, n is 0 or is an integer between 100 and 80,000, inclusive. In certain embodiments, n is 0 or is an integer between 200 and 80,000, inclusive. In certain embodiments, n is 0 or is an integer between 300 and 80,000, inclusive. In certain embodiments, n is 0 or is an integer between 400 and 80,000, inclusive. In certain embodiments, n is 0 or is an integer between 500 and 80,000, inclusive. In certain embodiments, n is 0 or is an integer between 500 and 40,000, inclusive. In certain embodiments, n is 0 or is an integer between 500 and 30,000, inclusive. In certain embodiments, n is 0 or is an integer between 1 and 400, inclusive. In certain embodiments, n is 0 or is an integer between 1 and 300, inclusive. In certain embodiments, n is 0 or is an integer between 1 and 200, inclusive. In certain embodiments, n is 0 or is an integer between 1 and 100, inclusive. In certain embodiments, n is 0 or is an integer between 1 and 75, inclusive. In certain embodiments, n is 0 or is an integer between 1 and 50, inclusive. In certain embodiments, n is 0 or is an integer between 1 and 25, inclusive. In certain embodiments, n is 0 or is an integer between 1 and 15, inclusive. In certain embodiments, n is 0 or is an integer between 1 and 10, Inclusive. In certain embodiments, n is 0, 1, 2, 3, 4, 5, 6, 7, 8, 9, or 10.

For example, when n is 0, the compound of Formula (I) is a compound of the Formula (I-a):

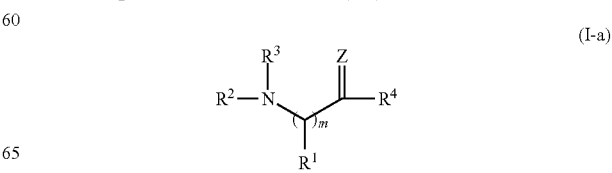

(I-a)

or salt thereof.

In certain embodiments, when n is 1, the compound of Formula (I) is a compound of the Formula (I-b):

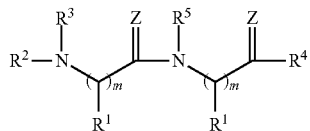

(I-b)

or salt thereof.

In certain embodiments, when n is 2, the compound of Formula (I) is a compound of the Formula (I-c):

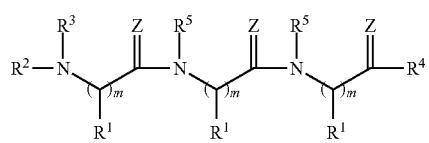

(I-c)

or salt thereof.

In certain embodiments, when n is 3, the compound of Formula (I) is a compound of the Formula (I-d):

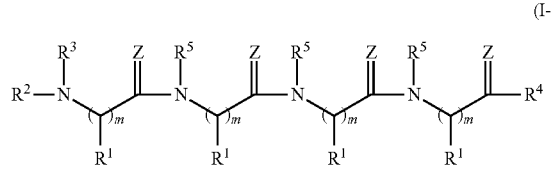

(I-d)

or salt thereof.

In certain embodiments, when n is 4, the compound of Formula (I) is a compound of the Formula (I-e):

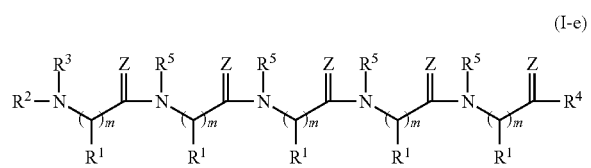

(I-e)

or salt thereof.

As generally defined above, each instance of m is independently 1, 2, or 3. In certain embodiments, at least one instance of m is 1. In certain embodiments, each instance of m is 1. In certain embodiments, at least one instance of m is 2. In certain embodiments, at least one instance of m is 3.

As generally defined above, each instance of R' is independently hydrogen or optionally substituted alkyl. In certain embodiments, at least one instance of R' is hydrogen. In certain embodiments, at least two instances of R' is hydrogen. In certain embodiments, each instance of R' is hydrogen. In certain embodiments, at least one instance of R' is optionally substituted alkyl, e.g., methyl. In certain embodiments, at least two instances of R' is optionally substituted alkyl, e.g., methyl. In certain embodiments, one instance of R' is optionally substituted alkyl, and the rest are hydrogen.

As generally defined above, each instance of Z is independently O, S, or $NR^Z$, wherein $R^Z$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii). In certain embodiments, at least one instance of Z is O. In certain embodiments, each instance of Z is O. In certain embodiments, at least one instance of Z is S. In certain embodiments, each instance of Z is S. In certain embodiments, at least one instance of Z is $NR^Z$. In certain embodiments, each instance of Z is $NR^Z$. In certain embodiments, each instance of $R^Z$ is independently hydrogen or a group of the formula (i), (ii), or (iii).

As generally defined above, each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{41}$, $-N(R^{41})_2$, or $-SR^{41}$.

In certain embodiments, at least one instance of $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, at least one instance of $R^1$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, at least one instance of $R^1$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, at least one instance of $R^1$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, at least one instance of $R^1$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In certain embodiments, at least one instance of $R^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of $R^1$ is optionally substituted aryl, e.g., optionally substituted phenyl.

In certain embodiments, at least one instance of $R^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In any of the above embodiments, the $R^1$ alkyl, alkenyl, alkynyl, carbocyclyl, heterocyclyl, aryl, or heteroaryl group may be substituted, for example, with an optionally substituted amino group (e.g., $-NR^6R^7$), an optionally substituted hydroxyl group (e.g., —OR$^6$), an optionally substituted thiol group (e.g., —SR$^6$), or with a group of formula (i), (ii), or (iii), wherein each instance of R$^6$ and R$^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

For example, in certain embodiments, at least one instance of R$^1$ is an alkyl, alkenyl, alkynyl, carbocyclyl, heterocyclyl, aryl, or heteroaryl group substituted with an amino group of the formula —N(R$^6$)(R$^7$). In that instance, in certain embodiments, at least one instance of R$^1$ is a group of formula:

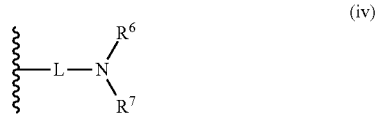
(iv)

wherein:
L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and R$^6$ and R$^7$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

provided at least one instance of R$^6$ and R$^7$ is a group of the formula (i), (ii), or (iii):

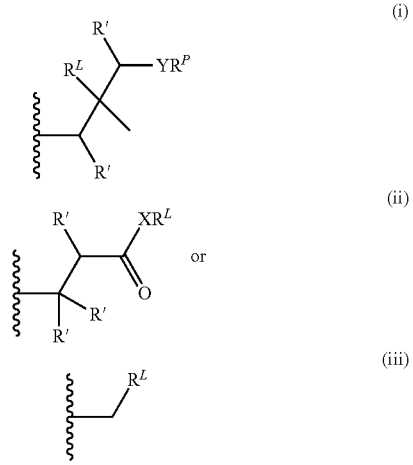

wherein R', X, Y, R$^L$, and R$^P$ are as defined herein.

In certain embodiments, at least two instances of R$^1$ is a group of formula (iv). In certain embodiments, at least three instances of R$^1$ is a group of formula (iv). In certain embodiments, at least four instances of R$^1$ is a group of formula (iv). In certain embodiments, at least five instances of R$^1$ is a group of formula (iv). In certain embodiments, each instance of R$^1$ is a group of formula (iv).

In certain embodiments, L is an optionally substituted alkylene; e.g., optionally substituted $C_{1-50}$ alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{8-20}$alkenylene, optionally substituted $C_{10-20}$alkenylene, optionally substituted $C_{2-6}$alkenylene, optionally substituted $C_{3-6}$alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted $C_{8-20}$alkynylene, optionally substituted $C_{10-20}$alkynylene, optionally substituted $C_{2-6}$alkynylene, optionally substituted $C_{3-6}$alkynylene, optionally substituted $C_{4-6}$alkynylene, optionally substituted $C_{4-5}$alkynylene, or optionally substituted $C_{3-4}$alkynylene.

In certain embodiments, L is an optionally substituted heteroalkylene; e.g., optionally substituted heteroC$_{1-50}$alkylene, optionally substituted heteroC$_{1-40}$alkylene, optionally substituted heteroC$_{1-30}$alkylene, optionally substituted heteroC$_{1-20}$alkylene, optionally substituted heteroC$_{4-20}$alkylene, optionally substituted heteroC$_{6-20}$alkylene, optionally substituted heteroC$_{8-20}$alkylene, optionally substituted heteroC$_{10-20}$alkylene, optionally substituted heteroC$_{1-6}$alkylene, optionally substituted heteroC$_{2-6}$alkylene, optionally substituted heteroC$_{3-6}$alkylene, optionally substituted heteroC$_{4-6}$alkylene, optionally substituted heteroC$_{4-5}$alkylene, or optionally substituted heteroC$_{3-4}$alkylene.

In certain embodiments, L is an optionally substituted heteroalkenylene, e.g., optionally substituted heteroC$_{2-50}$alkenylene, optionally substituted heteroC$_{2-40}$alkenylene, optionally substituted heteroC$_{2-30}$alkenylene, optionally substituted heteroC$_{2-20}$alkenylene, optionally substituted heteroC$_{4-20}$alkenylene, optionally substituted heteroC$_{6-20}$alkenylene, optionally substituted heteroC$_{8-20}$alkenylene, optionally substituted heteroC$_{10-20}$alkenylene, optionally substituted heteroC$_{2-6}$alkenylene, optionally substituted heteroC$_{3-6}$alkenylene, optionally substituted heteroC$_{4-6}$alkenylene, optionally substituted heteroC$_{4-5}$alkenylene, or optionally substituted heteroC$_{3-4}$alkenylene.

In certain embodiments, L is an optionally substituted alkynylene, e.g., optionally substituted heteroC$_{2-50}$alkynylene, optionally substituted heteroC$_{2-40}$alkynylene, optionally substituted heteroC$_{2-30}$alkynylene, optionally substituted heteroC$_{2-20}$alkynylene, optionally substituted heteroC$_{4-20}$alkynylene, optionally substituted heteroC$_{6-20}$ alkynylene, optionally substituted heteroC$_{8-20}$alkynylene, optionally substituted heteroC$_{10-20}$alkynylene, optionally substituted heteroC$_{2-6}$alkynylene, optionally substituted C$_{3-6}$alkynylene, optionally substituted heteroC$_{4-6}$alkynylene, optionally substituted heteroC$_{4-5}$alkynylene, or optionally substituted heteroC$_{3-4}$alkynylene.

In certain embodiments, L is an optionally substituted carbocyclylene, e.g., optionally substituted C$_{3-10}$ carbocyclylene, optionally substituted C$_{5-8}$ carbocyclylene, optionally substituted C$_{5-6}$ carbocyclylene, optionally substituted C$_5$ carbocyclylene, or optionally substituted C$_6$ carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5 membered heterocyclylene, or optionally substituted 6 membered heterocyclylene.

In certain embodiments, L is an optionally substituted arylene, e.g., optionally substituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5 membered heteroarylene, or optionally substituted 6 membered heteroarylene.

For example, in certain embodiments, wherein L is an optionally substituted alkylene group, the group of formula (iv) is a group of the formula:

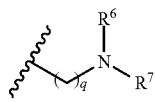

wherein q is an integer between 1 and 50, inclusive.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 4 and 20, inclusive. In certain embodiments, q is an integer between 6 and 20, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, both R$^6$ and R$^7$ are hydrogen. In certain embodiments, R$^6$ is hydrogen and R$^7$ is a group of the formula (i), (ii), or (iii). In certain embodiments, R$^6$ is hydrogen and R$^7$ is a group of the formula (i). In certain embodiments, R$^6$ is hydrogen and R$^7$ is a group of the formula (ii). In certain embodiments, R$^6$ is hydrogen and R$^7$ is a group of the formula (iii). In certain embodiments, both R$^6$ and R$^7$ are independently a group of the formula (i), (ii), or (iii). In certain embodiments, both R$^6$ and R$^7$ are independently a group of the formula (i). In certain embodiments, both R$^6$ and R$^7$ are independently a group of the formula (ii). In certain embodiments, both R$^6$ and R$^7$ are independently a group of the formula (iii). In certain embodiments, both R$^6$ and R$^7$ are the same group, selected from a group of the formula (i), (ii), or (iii).

It is understood that R$^1$ encompasses amino acid side chains such as exemplified in Table 1 of the Examples. In certain embodiments, R$^1$ is a group selected from any one of the amino acid side chain groups listed therein.

In certain embodiments, each instance of R$^1$ is the same. In certain embodiments, at least one R$^1$ group is different. In certain embodiments, each R$^1$ group is different.

As generally defined above, R$^2$ is a group of the formula (i), (ii), or (iii):

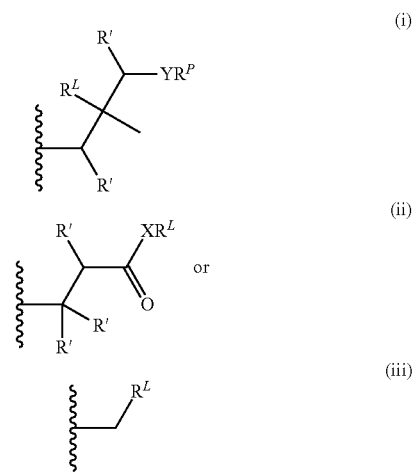

wherein R', X, Y, R$^L$, and R$^P$ are as defined herein.

In certain embodiments, R$^2$ is a group of the formula (i). In certain embodiments, R$^2$ is a group of the formula (ii). In certain embodiments, R$^2$ is a group of the formula (iii).

As generally defined above, R$^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); optionally wherein R$^3$ and an R$^1$ group are joined to form an optionally substituted 5-6 membered heterocyclic ring;

In certain embodiments, R$^3$ is hydrogen. In certain embodiments, R$^3$ is optionally substituted alkyl; e.g., optionally substituted C$_{1-6}$alkyl, optionally substituted C$_{2-6}$alkyl, optionally substituted C$_{3-6}$alkyl, optionally substituted C$_{4-6}$alkyl, optionally substituted C$_{4-5}$alkyl, or optionally substituted C$_{3-4}$alkyl.

In certain embodiments, R$^3$ is optionally substituted alkenyl, e.g., optionally substituted C$_{2-6}$alkenyl, optionally substituted C$_{3-6}$alkenyl, optionally substituted C$_{4-6}$alkenyl, optionally substituted C$_{4-5}$alkenyl, or optionally substituted C$_{3-4}$alkenyl.

In certain embodiments, R$^3$ is optionally substituted alkynyl, e.g., optionally substituted C$_{2-6}$alkynyl, optionally substituted C$_{3-6}$alkynyl, optionally substituted C$_{4-6}$alkynyl, optionally substituted C$_{4-5}$alkynyl, or optionally substituted C$_{3-4}$alkynyl.

In certain embodiments, R$^3$ is optionally substituted carbocyclyl, e.g., optionally substituted C$_{3-10}$ carbocyclyl, optionally substituted C$_{5-8}$ carbocyclyl, optionally substituted C$_{5-6}$ carbocyclyl, optionally substituted C$_5$ carbocyclyl, or optionally substituted C$_6$ carbocyclyl.

In certain embodiments, $R^3$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, $R^3$ is optionally substituted aryl, e.g., optionally substituted phenyl.

In certain embodiments, $R^3$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In certain embodiments, $R^3$ is a nitrogen protecting group.

In certain embodiments, $R^3$ is group of the formula (i), (ii), or (iii). In certain embodiments, $R^3$ is group of the formula (i). In certain embodiments, $R^3$ is group of the formula (ii). In certain embodiments, $R^3$ is group of the formula (iii).

In certain embodiments, $R^3$ and an adjacent $R^1$ group are joined to form an optionally substituted 5-6 membered heterocyclic ring, e.g., a 5-membered heterocyclic ring, e.g., an optionally substituted pyrrolidinyl ring.

In certain embodiments, $R^3$ is hydrogen and $R^2$ is a group of the formula (i), (ii), or (iii). In certain embodiments, $R^3$ is hydrogen and $R^2$ is a group of the formula (i). In certain embodiments, $R^3$ is hydrogen and $R^2$ is a group of the formula (ii). In certain embodiments, $R^3$ is hydrogen and $R^2$ is a group of the formula (iii). In certain embodiments, both $R^2$ and $R^3$ independently a group of the formula (i), (ii), or (iii). In certain embodiments, both $R^2$ and $R^3$ are independently a group of the formula (i). In certain embodiments, both $R^2$ and $R^3$ are independently a group of the formula (ii). In certain embodiments, both $R^2$ and $R^3$ are independently a group of the formula (iii). In certain embodiments, both $R^2$ and $R^3$ are the same group, selected from a group of the formula (i), (ii), or (iii).

As generally defined above, $R^4$ is $-OR^{44}$, $-N(R^{44})_2$, or $-SR^{44}$; wherein each occurrence of $R^{44}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{44}$ groups are joined to form an optionally substituted heterocyclic or optionally substituted heteroaryl ring.

In certain embodiments, $R^4$ is $-OR^{44}$, wherein $R^{44}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{44}$ is hydrogen or optionally substituted alkyl. In certain embodiments, $R^{44}$ is hydrogen.

In certain embodiments, $R^4$ is $-N(R^{44})_2$, wherein each occurrence of $R^{44}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or two $R^{44}$ groups are joined to form an optionally substituted heterocyclic or optionally substituted heteroaryl ring. In certain embodiments, at least one instance of $R^{44}$ is hydrogen or optionally substituted alkyl. In certain embodiments, at least one instance of $R^{44}$ is hydrogen.

In certain embodiments, $R^4$ is $-SR^{44}$, wherein $R^{44}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or sulfur protecting group. In certain embodiments, $R^{44}$ is hydrogen or optionally substituted alkyl. In certain embodiments, $R^{44}$ is hydrogen.

As generally defined above, $R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, at least one instance of $R^5$ is hydrogen. In certain embodiments, each instance of $R^5$ is hydrogen.

Various combinations of the above embodiments of Formula (I) are contemplated herein.

For example, in certain embodiments, wherein each instance of m is 1 and each instance of Z is O, the compound of Formula (I) is a compound of Formula (I-f):

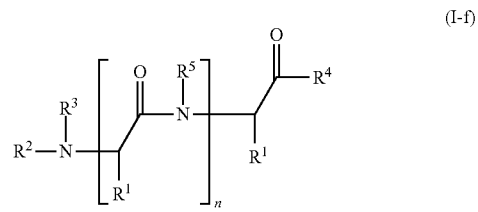

(I-f)

or salt thereof. In certain embodiments, at least one $R^1$ is a group of formula (iv). In certain embodiments, $R^2$ is a group of formula (i). In certain embodiments, $R^2$ is a group of formula (ii). In certain embodiments, $R^2$ is a group of formula (iii). In certain embodiments, $R^3$ is a group of formula (i). In certain embodiments, $R^3$ is a group of formula (ii). In certain embodiments, $R^3$ is a group of formula (iii). In certain embodiments, $R^4$ is $-OR^{44}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f), wherein each instance of $R^1$ is a group of the formula (iv), provided is a compound of Formula (I-f1):

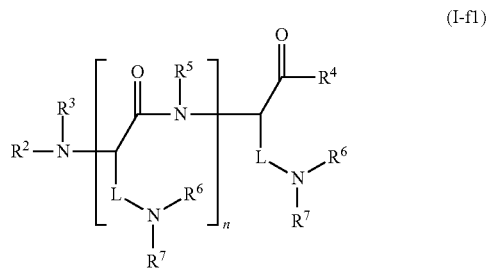

(I-f1)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ is a group of formula (i), the compound is of Formula (I-f2):

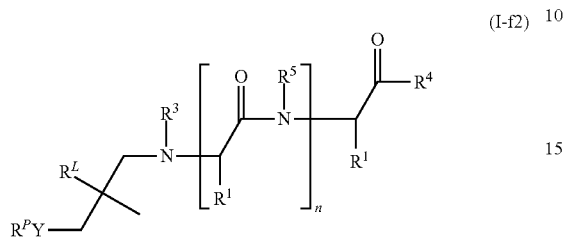

or salt thereof. In certain embodiments, at least one $R^1$ is a group of formula (iv). In certain embodiments, $R^3$ is a group of formula (i). In certain embodiments, $R^3$ is a group of formula (ii). In certain embodiments, $R^3$ is a group of formula (iii). In certain embodiments, $R^4$ is $-OR^{A4}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f2), wherein each instance of $R^1$ is a group of the formula (iv), provided is a compound of Formula (I-f3):

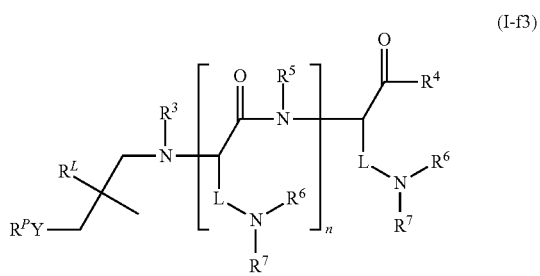

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ and $R^3$ are each independently a group of formula (i), the compound is of Formula (I-f4):

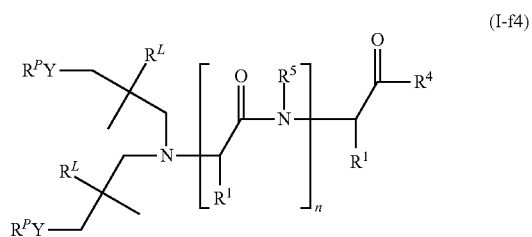

or salt thereof. In certain embodiments, at least one $R^1$ is a group of formula (iv). In certain embodiments, $R^4$ is $-OR^{A4}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f4), wherein each instance of $R^1$ is a group of the formula (iv), provided is a compound of Formula (I-f5):

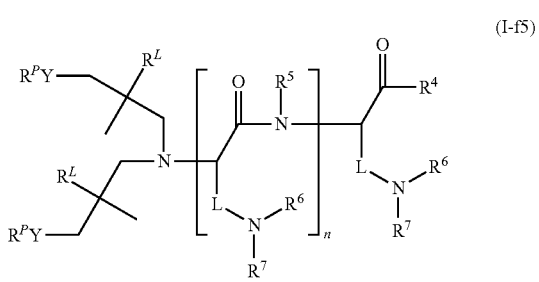

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ is a group of formula (ii), the compound is of Formula (I-f6):

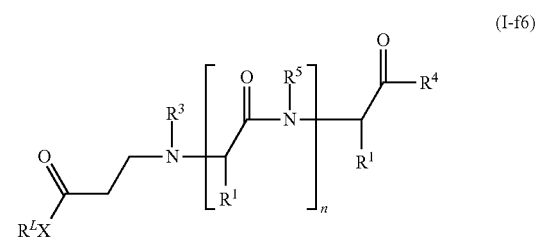

or salt thereof. In certain embodiments, at least one $R^1$ is a group of formula (iv). In certain embodiments, $R^3$ is a group of formula (i). In certain embodiments, $R^3$ is a group of formula (ii). In certain embodiments, $R^3$ is a group of formula (iii). In certain embodiments, $R^4$ is $-OR^{A4}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f6), wherein each instance of $R^1$ is a group of the formula (iv), provided is a compound of Formula (I-f7):

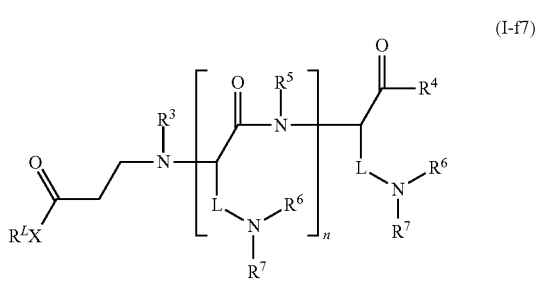

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ and $R^3$ are independently a group of formula (ii), the compound is of Formula (I-f8):

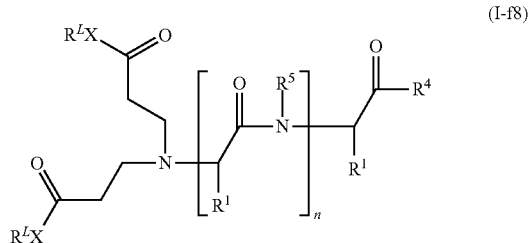

(I-f8)

or salt thereof. In certain embodiments, at least one $R^1$ is a group of formula (iv). In certain embodiments, $R^4$ is $-OR^{44}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f8), wherein each instance of $R^1$ is a group of the formula (iv), provided is a compound of Formula (I-f9):

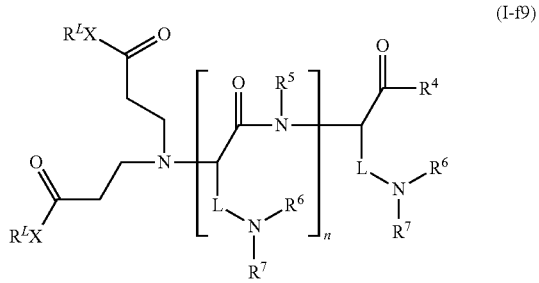

(I-f9)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ is a group of formula (iii), the compound is of Formula (I-f10):

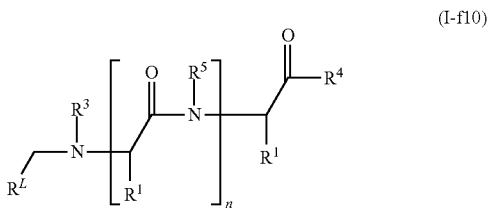

(I-f10)

or salt thereof. In certain embodiments, at least one $R^1$ is a group of formula (iv). In certain embodiments, $R^3$ is a group of formula (i). In certain embodiments, $R^3$ is a group of formula (ii). In certain embodiments, $R^3$ is a group of formula (iii). In certain embodiments, $R^4$ is $-OR^{44}$. In certain embodiments, $R^5$ is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f10), wherein each instance of $R^1$ is a group of the formula (iv), provided is a compound of Formula (I-f11):

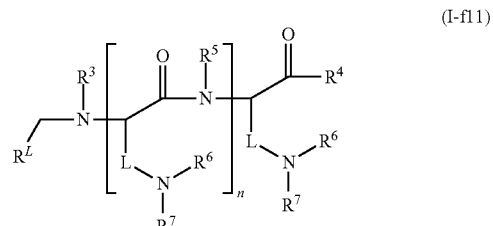

(I-f11)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

In certain embodiments of Formula (I-f), wherein $R^2$ and $R^3$ are independently a group of formula (iii), the compound is of Formula (I-f12):

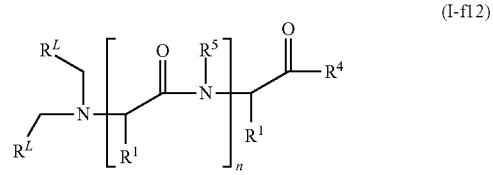

(I-f12)

or salt thereof. In certain embodiments, at least one $R^1$ is a group of formula (iv). In certain embodiments, $R^4$ is $-OR^{44}$. In certain embodiments, R is hydrogen. In certain embodiments, n is 0. In certain embodiments, n is 1. In certain embodiments, n is 2. In certain embodiments, n is 3. In certain embodiments, n is 4. In certain embodiments, n is 5.

For example, in certain embodiments of Formula (I-f12), wherein each instance of $R^1$ is a group of the formula (iv), provided is a compound of Formula (I-f13):

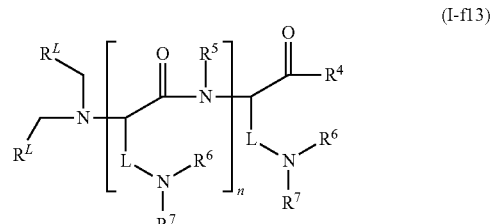

(I-f13)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii).

Compounds of Formula (II)

Compounds of Formula (II) may be prepared via internal cyclization of the addition product of a primary or secondary amine or amide of an amino acid, peptide, or polypeptide, and an epoxide, thiirane, or aziridine of formula (i-x) (Scheme 2).

Scheme 2.

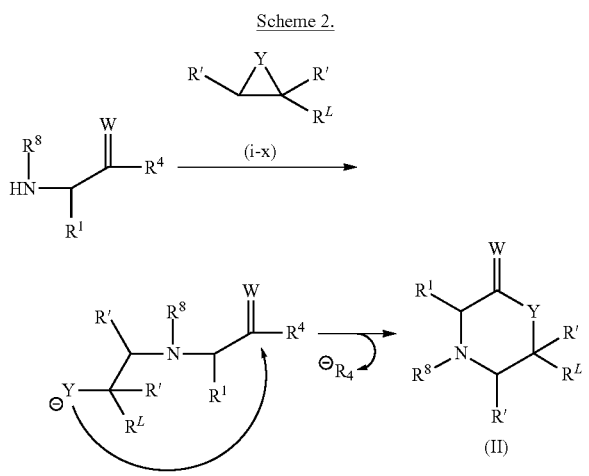

Compounds of Formula (II) may encompass additional sites of conjugation, e.g., the secondary amino group, appended to a group attached to the secondary amino group, an amino substituent, and/or an imino nitrogen, to a group of formula (i), (ii), or (iii):

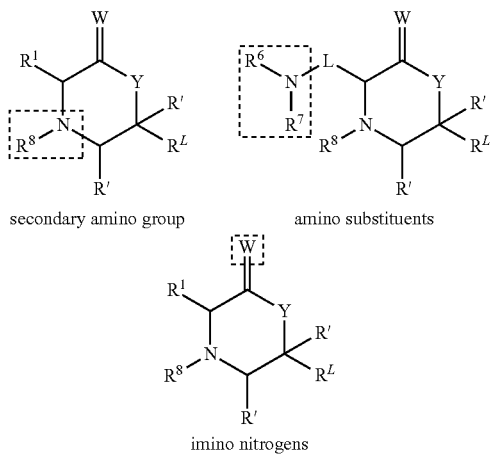

secondary amino group    amino substituents

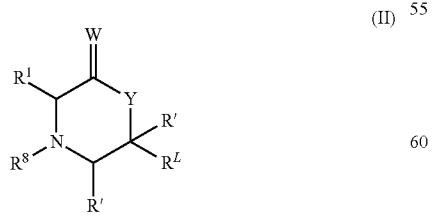

imino nitrogens

Thus, in a second aspect, provided is a compound of Formula (II):

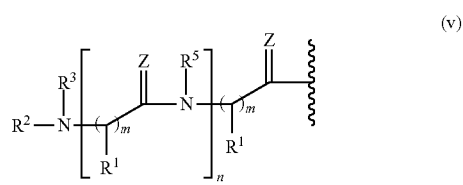

or salt thereof;
wherein:
each instance of R' is independently hydrogen or optionally substituted alkyl;

each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{A1}$, —$N(R^{A1})_2$, or —$SR^{A1}$; wherein each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A1}$ groups are joined to form an optionally substituted heterocyclic or optionally substituted heteroaryl ring;

$R^8$ is hydrogen, a group of the formula (i), (ii), or (iii), or a group of the formula (v):

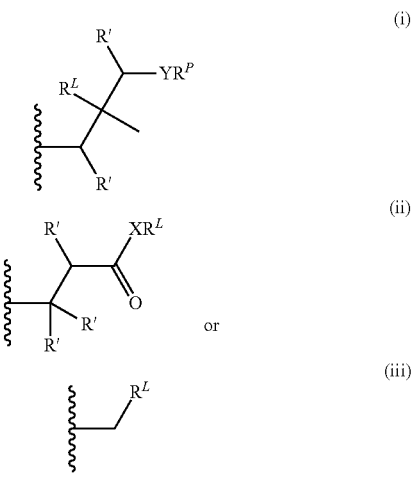

wherein Z, $R^2$, $R^3$, $R^5$, m, and n are as defined for Formula (I);

or $R^8$ and an $R^1$ group are joined to form an optionally substituted 5-6 membered heterocyclic ring;

each instance of W is independently O, S, or $NR^W$, wherein $R^W$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); and each instance of Y is independently O, S, or $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Formulae (i), (ii), and (iii) are:

wherein:
X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, NR$^Y$, wherein R$^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R$^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and R$^L$ is optionally substituted C$_{1-50}$ alkyl, optionally substituted C$_{2-50}$ alkenyl, optionally substituted C$_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer.

In certain embodiments, wherein Y is O and W is O, the following compounds are specifically excluded:

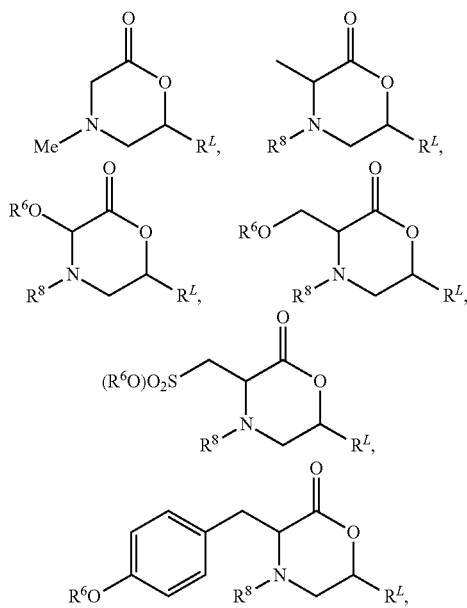

wherein R$^8$ and R$^6$ are independently hydrogen or a group of formula (i), and salts thereof.

In certain embodiments, at least one instance of R$^W$, R$^2$, R$^3$, R$^6$, R$^7$, or R$^8$ is a group of the formula (i), (ii), or (iii).

As generally defined above, each instance of R' is independently hydrogen or optionally substituted alkyl. In certain embodiments, at least one instance of R' is hydrogen. In certain embodiments, at least two instances of R' is hydrogen. In certain embodiments, each instance of R' is hydrogen. In certain embodiments, at least one instance of R' is optionally substituted alkyl, e.g., methyl. In certain embodiments, at least two instances of R' is optionally substituted alkyl, e.g., methyl. In certain embodiments, one instance of R' is optionally substituted alkyl, and the rest are hydrogen.

As generally defined above, each instance of R$^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —OR$^{41}$, —N(R$^{41}$)$_2$, or —SR$^{41}$.

In certain embodiments, at least one instance of R$^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, at least one instance of R$^1$ is optionally substituted alkyl; e.g., optionally substituted C$_{1-6}$alkyl, optionally substituted C$_{2-6}$alkyl, optionally substituted C$_{3-6}$alkyl, optionally substituted C$_{4-6}$alkyl, optionally substituted C$_{4-5}$alkyl, or optionally substituted C$_{3-4}$alkyl.

In certain embodiments, at least one instance of R$^1$ is optionally substituted alkenyl, e.g., optionally substituted C$_{2-6}$alkenyl, optionally substituted C$_{3-6}$alkenyl, optionally substituted C$_{4-6}$alkenyl, optionally substituted C$_{4-5}$alkenyl, or optionally substituted C$_{3-4}$alkenyl.

In certain embodiments, at least one instance of R$^1$ is optionally substituted alkynyl, e.g., optionally substituted C$_{2-6}$alkynyl, optionally substituted C$_{3-6}$alkynyl, optionally substituted C$_{4-6}$alkynyl, optionally substituted C$_{4-5}$alkynyl, or optionally substituted C$_{3-4}$alkynyl.

In certain embodiments, at least one instance of R$^1$ is optionally substituted carbocyclyl, e.g., optionally substituted C$_{3-10}$ carbocyclyl, optionally substituted C$_{5-8}$ carbocyclyl, optionally substituted C$_{5-6}$ carbocyclyl, optionally substituted C$_5$ carbocyclyl, or optionally substituted C$_6$ carbocyclyl.

In certain embodiments, at least one instance of R$^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of R$^1$ is optionally substituted aryl, e.g., optionally substituted phenyl.

In certain embodiments, at least one instance of R$^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In any of the above embodiments, the R$^1$ alkyl, alkenyl, alkynyl, carbocyclyl, heterocyclyl, aryl, or heteroaryl group may be substituted, for example, with an optionally substituted amino group (e.g., —NR$^6$R$^7$), an optionally substituted hydroxyl group (e.g., —OR$^6$), an optionally substituted thiol group (e.g., —SR$^6$), or with a group of formula (i), (ii), or (iii), wherein each instance of R$^6$ and R$^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

For example, in certain embodiments, at least one instance of $R^1$ is an alkyl, alkenyl, alkynyl, carbocyclyl, heterocyclyl, aryl, or heteroaryl group substituted with an amino group of the formula $-N(R^6)(R^7)$. In that instance, in certain embodiments, at least one instance of $R^1$ is a group of formula:

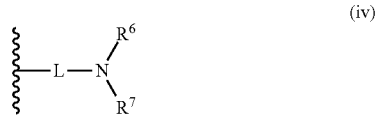

(iv)

wherein:

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and $R^6$ and $R^7$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

provided at least one instance of $R^6$ and $R^7$ is a group of the formula (i), (ii), or (iii):

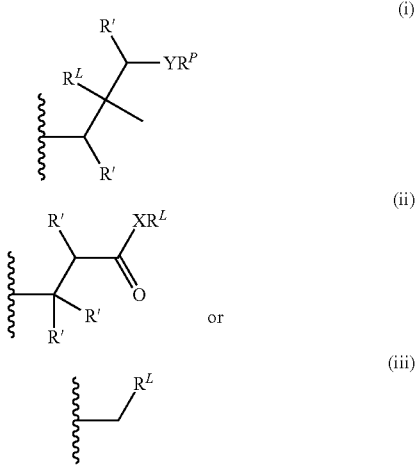

wherein R', X, Y, $R^L$, and $R^P$ are as defined herein.

In certain embodiments, at least two instances of $R^1$ is a group of formula (iv). In certain embodiments, at least three instances of $R^1$ is a group of formula (iv). In certain embodiments, at least four instances of $R^1$ is a group of formula (iv). In certain embodiments, at least five instances of $R^1$ is a group of formula (iv). In certain embodiments, each instance of $R^1$ is a group of formula (iv).

In certain embodiments, $R^1$ alpha to the group $-C(=W)-Y-$ is a group of formula (iv).

In certain embodiments, at least one instance of $R^1$ provided in group $R^8$ is a group of formula (iv). In certain embodiments, at least two instances of $R^1$ provided in group $R^8$ is a group of formula (iv). In certain embodiments, at least three instances of $R^1$ provided in group $R^8$ is a group of formula (iv). In certain embodiments, at least four instances of $R^1$ provided in group $R^8$ is a group of formula (iv). In certain embodiments, at least five instances of $R^1$ provided in group $R^8$ is a group of formula (iv). In certain embodiments, each instance of $R^1$ provided in group $R^8$ is a group of formula (iv).

In certain embodiments, L is an optionally substituted alkylene; e.g., optionally substituted $C_{1-50}$ alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{8-20}$alkenylene, optionally substituted $C_{10-20}$alkenylene, optionally substituted $C_{2-6}$alkenylene, optionally substituted $C_{3-6}$alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted $C_{8-20}$alkynylene, optionally substituted $C_{10-20}$alkynylene, optionally substituted $C_{2-6}$alkynylene, optionally substituted $C_{3-6}$alkynylene, optionally substituted $C_{4-6}$alkynylene, optionally substituted $C_{4-5}$alkynylene, or optionally substituted $C_{3-4}$alkynylene.

In certain embodiments, L is an optionally substituted heteroalkylene; e.g., optionally substituted heteroC$_{1-50}$ alkylene, optionally substituted heteroC$_{1-40}$alkylene, optionally substituted heteroC$_{1-30}$alkylene, optionally substituted heteroC$_{1-20}$alkylene, optionally substituted heteroC$_{4-20}$alkylene, optionally substituted heteroC$_{6-20}$alkylene, optionally substituted heteroC$_{8-20}$alkylene, optionally substituted heteroC$_{10-20}$alkylene, optionally substituted heteroC$_{1-6}$alkylene, optionally substituted heteroC$_{2-6}$alkylene, optionally substituted heteroC$_{3-6}$alkylene, optionally substituted heteroC$_{4-6}$alkylene, optionally substituted heteroC$_{4-5}$alkylene, or optionally substituted heteroC$_{3-4}$alkylene.

In certain embodiments, L is an optionally substituted heteroalkenylene, e.g., optionally substituted heteroC$_{2-50}$ alkenylene, optionally substituted heteroC$_{2-40}$alkenylene, optionally substituted heteroC$_{2-30}$alkenylene, optionally substituted heteroC$_{2-20}$alkenylene, optionally substituted heteroC$_{4-20}$alkenylene, optionally substituted heteroC$_{6-20}$ alkenylene, optionally substituted heteroC$_{8-20}$alkenylene, optionally substituted heteroC$_{10-20}$alkenylene, optionally substituted heteroC$_{2-6}$alkenylene, optionally substituted heteroC$_{3-6}$alkenylene, optionally substituted heteroC$_{4-6}$alkenylene, optionally substituted heteroC$_{4-5}$alkenylene, or optionally substituted heteroC$_{3-4}$alkenylene.

In certain embodiments, L is an optionally substituted alkynylene, e.g., optionally substituted heteroC$_{2-50}$alkynylene, optionally substituted heteroC$_{2-40}$alkynylene, optionally substituted heteroC$_{2-30}$alkynylene, optionally substituted heteroC$_{2\text{-}20}$alkynylene, optionally substituted heteroC$_{4\text{-}20}$alkynylene, optionally substituted heteroC$_{6\text{-}20}$alkynylene, optionally substituted heteroC$_{8\text{-}20}$alkynylene, optionally substituted heteroC$_{10\text{-}20}$alkynylene, optionally substituted heteroC$_{2\text{-}6}$alkynylene, optionally substituted C$_{3\text{-}6}$alkynylene, optionally substituted heteroC$_{4\text{-}6}$alkynylene, optionally substituted heteroC$_{4\text{-}5}$alkynylene, or optionally substituted heteroC$_{3\text{-}4}$alkynylene.

In certain embodiments, L is an optionally substituted carbocyclylene, e.g., optionally substituted C$_{3\text{-}10}$ carbocyclylene, optionally substituted C$_{5\text{-}8}$ carbocyclylene, optionally substituted C$_{5\text{-}6}$ carbocyclylene, optionally substituted C$_5$ carbocyclylene, or optionally substituted C$_6$ carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5 membered heterocyclylene, or optionally substituted 6 membered heterocyclylene.

In certain embodiments, L is an optionally substituted arylene, e.g., optionally substituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5 membered heteroarylene, or optionally substituted 6 membered heteroarylene.

For example, in certain embodiments, wherein L is an optionally substituted alkylene group, the group of formula (iv) is a group of the formula:

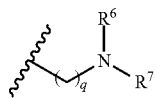

wherein q is an integer between 1 and 50, inclusive.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 4 and 20, inclusive. In certain embodiments, q is an integer between 6 and 20, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, both $R^6$ and $R^7$ are hydrogen. In certain embodiments, $R^6$ is hydrogen and $R^7$ is a group of the formula (i), (ii), or (iii). In certain embodiments, $R^6$ is hydrogen and $R^7$ is a group of the formula (i). In certain embodiments, $R^6$ is hydrogen and $R^7$ is a group of the formula (ii). In certain embodiments, $R^6$ is hydrogen and $R^7$ is a group of the formula (iii). In certain embodiments, both $R^6$ and $R^7$ are independently a group of the formula (i), (ii), or (iii). In certain embodiments, both $R^6$ and $R^7$ are independently a group of the formula (i). In certain embodiments, both $R^6$ and $R^7$ are independently a group of the formula (ii). In certain embodiments, both $R^6$ and $R^7$ are independently a group of the formula (iii). In certain embodiments, both $R^6$ and $R^7$ are the same group, selected from a group of the formula (i), (ii), or (iii).

It is understood that $R^1$ encompasses amino acid side chains such as exemplified in Table 1 of the Examples. In certain embodiments, $R^1$ is a group selected from any one of the amino acid side chain groups listed therein.

In certain embodiments, each instance of $R^1$ is the same. In certain embodiments, at least one $R^1$ group is different. In certain embodiments, each $R^1$ group is different.

As generally defined above, each instance of W is independently O, S, or NR$^W$, wherein R$^W$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii). In certain embodiments, W is O. In certain embodiments, W is S. In certain embodiments, W is NR$^W$. In certain embodiments, R$^W$ is hydrogen or a group of the formula (i), (ii), or (iii).

As generally defined above, each instance of Y is independently O, S, or NR$^Y$, wherein R$^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, Y is O. In certain embodiments, each instance of Y is S. In certain embodiments, Y is NR$^Y$. In certain embodiments, R$^Y$ is hydrogen or a nitrogen protecting group.

In certain embodiments, W is O and Y is O. In certain embodiments, W is O and Y is S. In certain embodiments, W is O and Y is NR$^Y$. In certain embodiments, W is S and Y is O. In certain embodiments, W is S and Y is S. In certain embodiments, W is S and Y is NR$^Y$. In certain embodiments, W is NR$^W$ and Y is O. In certain embodiments, W is NR$^W$ and Y is S. In certain embodiments, W is NR$^W$ and Y is NR$^Y$.

As generally defined above, $R^8$ is hydrogen, a group of the formula (i), (ii), or (iii), or a group of the formula (v):

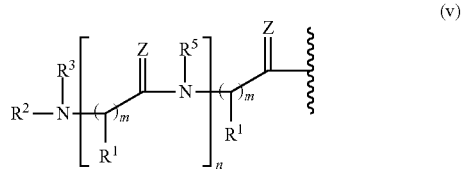

wherein $R^2$, $R^3$, $R^5$, Z, m, and n are as defined in Formula (I), provided at least one instance of $R^W$, $R^2$, $R^3$, $R^8$, $R^6$, $R^7$, or $R^8$ is a group of the formula (i), (ii), or (iii).

In certain embodiments, $R^8$ is hydrogen.

In certain embodiments, $R^8$ is a group of the formula (i), (ii), or (iii). In certain embodiments, $R^8$ is a group of the formula (i). In certain embodiments, $R^8$ is a group of the formula (ii). In certain embodiments, $R^8$ is a group of the formula (iii).

In certain embodiments, $R^8$ is a group of the formula (v). In certain embodiments, $R^8$ is a group of the formula (v) and $R^8$ is a group of the formula (i), (ii), or (iii). In certain embodiments, $R^2$ is a group of the formula (v) and $R^3$ is a group of the formula (i), (ii), or (iii).

In certain embodiments, at least one $R^1$ is a group of formula (iv) and $R^6$ is a group of the formula (i), (ii), or (iii). In certain embodiments, at least one $R^1$ is a group of formula (iv) and $R^7$ is a group of the formula (i), (ii), or (iii). In certain embodiments, at least one $R^1$ is a group of formula (iv), and both $R^6$ and $R^7$ are independently groups of the formula (i), (ii), or (iii).

Alternatively, in certain embodiments, $R^8$ and the adjacent $R^1$ group are joined to form an optionally substituted 5-6 membered heterocyclic ring, e.g., a 5-membered heterocyclic ring, e.g., an optionally substituted pyrrolidinyl ring.

Various combinations of the above embodiments of Formula (II) are contemplated herein.

For example, in certain embodiments, wherein each instance of R' is hydrogen, W is O and Y is O, the compound of Formula (II) is a compound of Formula (II-a):

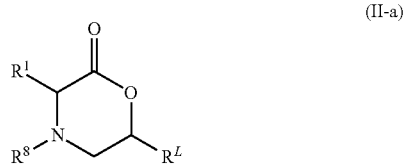

(II-a)

or salt thereof. In certain embodiments, $R^8$ is a group of the formula (i), (ii), or (iii). In certain embodiments, $R^8$ is a group of the formula (v) and $R^2$ is a group of the formula (i), (ii), or (iii). In certain embodiments, $R^8$ is a group of the formula (v) and $R^3$ is a group of the formula (i), (ii), or (iii). In certain embodiments, at least one $R^1$ is a group of formula (iv). In certain embodiments, $R^1$ is a group of formula (iv) and $R^6$ is a group of the formula (i), (ii), or (iii). In certain embodiments, $R^1$ is a group of formula (iv) and $R^7$ is a group of the formula (i), (ii), or (iii). In certain embodiments, both $R^6$ and $R^7$ are independently groups of the formula (i), (ii), or (iii).

In certain embodiments of Formula (II-a), wherein $R^1$ alpha to the group —C(=O)—O— is a group of formula (iv), provided is a compound of Formula (II-b):

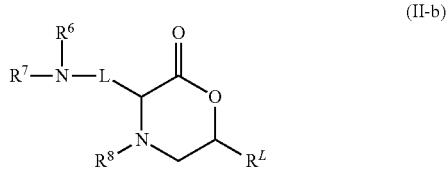

(II-b)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-a), wherein $R^8$ is a group of formula (v), provided is a compound of Formula (II-c):

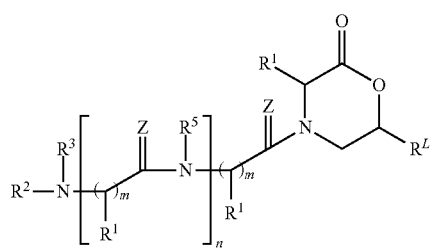

(II-c)

or salt thereof. In certain embodiments, at least one $R^1$ is a group of formula (iv). In certain embodiments, $R^2$ is a group of formula (i). In certain embodiments, $R^2$ is a group of formula (ii). In certain embodiments, $R^2$ is a group of formula (iii). In certain embodiments, $R^3$ is a group of formula (i). In certain embodiments, $R^3$ is a group of formula (ii). In certain embodiments, $R^3$ is a group of formula (iii). In certain embodiments, $R^5$ is hydrogen. In certain embodiments, Z is O. In certain embodiments, n is 0. In certain embodiments, n is 1. In certain embodiments, n is 2. In certain embodiments, n is 3. In certain embodiments, n is 4. In certain embodiments, n is 5. In certain embodiments, m is 1.

In certain embodiments of Formula (II-c), wherein $R^1$ alpha to the group —C(=O)—O— is a group of formula (iv), provided is a compound of Formula (II-c1):

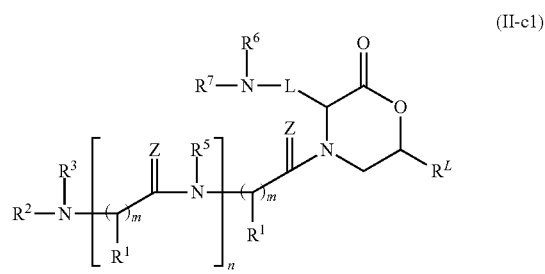

(II-c1)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-c), wherein each instance of $R^1$ provided in group $R^8$ is a group of formula (iv), provided is a compound of Formula (II-c2):

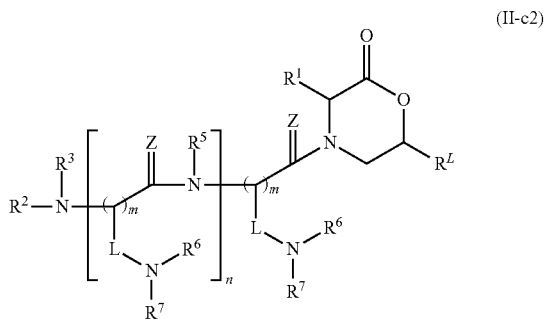

(II-c2)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-c), wherein each instance of $R^1$ is a group of formula (iv), provided is a compound of Formula (II-c3):

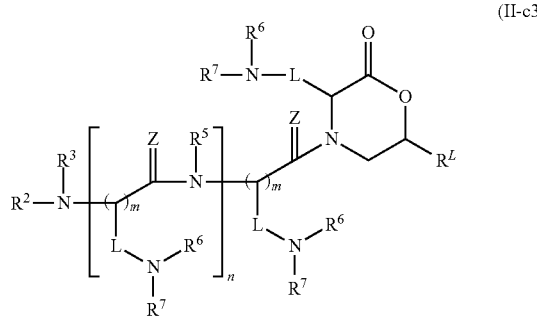

(II-c3)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-a), wherein $R^8$ is a group of formula (i), provided is a compound of Formula (II-d):

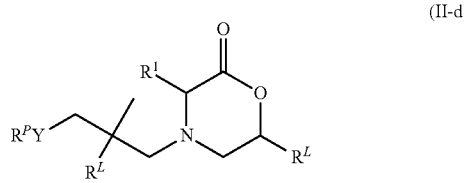

(II-d)

or salt thereof. In certain embodiments, $R^1$ is hydrogen. In certain embodiments, $R^1$ is a group of formula (iv). In certain embodiments, $R^1$ is a group of formula (iv) and $R^6$ is a group of the formula (i), (ii), or (iii). In certain embodiments, $R^1$ is a group of formula (iv) and both $R^6$ and $R^7$ are independently groups of the formula (i), (ii), or (iii).

In certain embodiments of Formula (II-d), wherein $R^1$ alpha to the group —C(=O)—O— is a group of formula (iv), provided is a compound of Formula (II-d1):

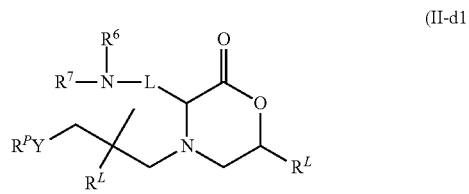

(II-d1)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-a), wherein $R^8$ is a group of formula (ii), provided is a compound of Formula (II-e):

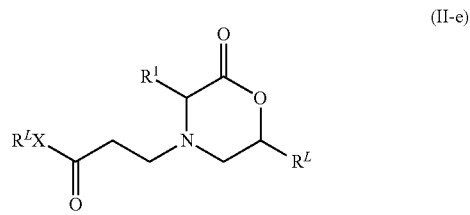

(II-e)

or salt thereof. In certain embodiments, $R^1$ is hydrogen. In certain embodiments, $R^1$ is a group of formula (iv). In certain embodiments, $R^1$ is a group of formula (iv) and $R^6$ is a group of the formula (i), (ii), or (iii). In certain embodiments, $R^1$ is a group of formula (iv) and both $R^6$ and $R^7$ are independently groups of the formula (i), (ii), or (iii).

In certain embodiments of Formula (II-e), wherein $R^1$ alpha to the group —C(=O)—O— is a group of formula (iv), provided is a compound of Formula (II-e1):

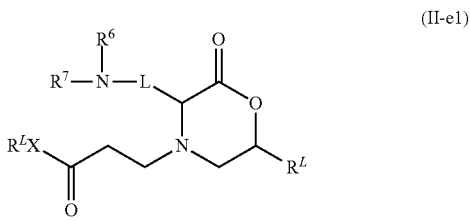

(II-e1)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-a), wherein $R^8$ is a group of formula (iii), provided is a compound of Formula (II-f):

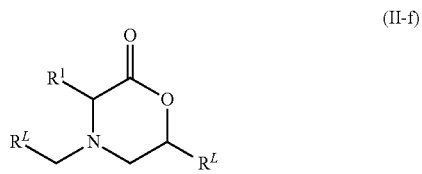

(II-f)

or salt thereof. In certain embodiments, $R^1$ is hydrogen. In certain embodiments, $R^1$ is a group of formula (iv). In certain embodiments, $R^1$ is a group of formula (iv) and $R^6$ is a group of the formula (i), (ii), or (iii). In certain embodiments, $R^1$ is a group of formula (iv) and both $R^6$ and $R^7$ are independently groups of the formula (i), (ii), or (iii).

In certain embodiments of Formula (II-f), wherein $R^1$ alpha to the group —C(=O)—O— is a group of formula (iv), provided is a compound of Formula (II-f1):

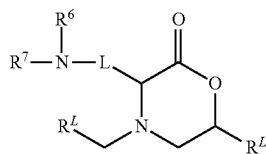

(II-f1)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of the formula (i), (ii), or (iii).

In certain embodiments of Formula (II-a), wherein $R^1$ and $R^8$ are joined to form an optionally substituted 5-6 membered heterocyclic ring, provided is a compound of Formula (II-g):

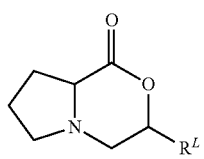

(II-g)

or salt thereof. In certain embodiments, L is an optionally substituted alkylene.

Compounds of Formula (III)

Compounds of Formula (III) are the cyclic condensation product of the same or different two, three, four, five, six, seven, eight, nine, or ten amino acids, and which further comprise one or more sites of conjugation attached thereto, e.g., to an internal amide nitrogen, to an amino substituent, and/or to an imino nitrogen, of a group of formula (i), (iii), or (iii). Such groups may be conjugated before cyclization, i.e., to the amino acid precursors of the cyclization product, or after cyclization.

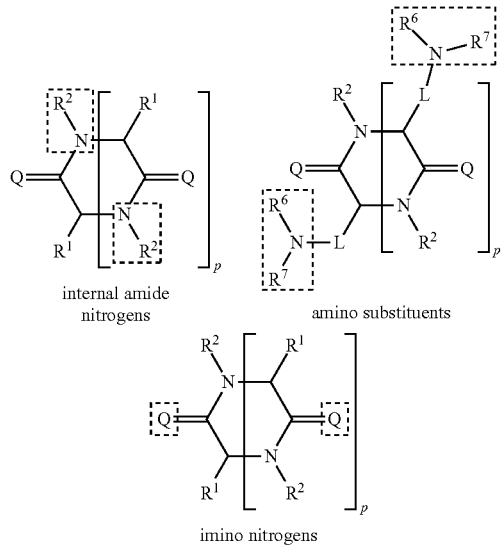

internal amide nitrogens amino substituents imino nitrogens

Thus, in a third aspect, provided is a compound of Formula (III):

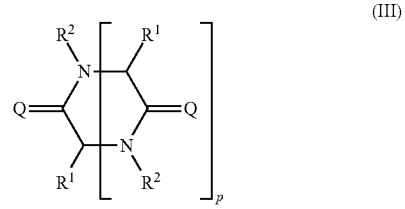

(III)

or salt thereof;
wherein:
p is an integer of between 1 and 9, inclusive;
each instance of Q is independently O, S, or $NR^Q$, wherein $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), (iii);
each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{41}$, —$N(R^{41})_2$, or —$SR^{41}$; wherein each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups are joined to form an optionally substituted heterocyclic or optionally substituted heteroaryl ring; and
each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); and
Formulae (i), (ii), and (iii) are:

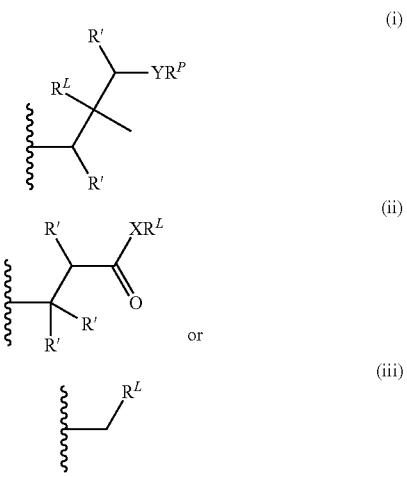

(i)

(ii)

or (iii)

wherein:
each instance of R' is independently hydrogen or optionally substituted alkyl;

X is O, S, NR$^X$, wherein R$^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, NR$^Y$, wherein R$^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R$^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and R$^L$ is optionally substituted C$_{1-50}$ alkyl, optionally substituted C$_{2-50}$ alkenyl, optionally substituted C$_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer;

provided that at least one instance of R$^Q$, R$^2$, R$^6$, or R$^7$ is a group of the formula (i), (ii), or (iii).

As generally defined above, p is an integer of between 1 and 9, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9.

For example, in certain embodiments, wherein p is 1, the compound of Formula (III) is a compound of Formula (III-a):

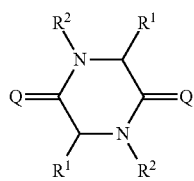

(III-a)

or salt thereof.

In certain embodiments, wherein p is 2, the compound of Formula (III) is a compound of Formula (III-b):

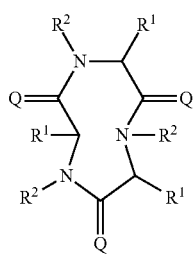

(III-b)

or salt thereof.

In certain embodiments, wherein p is 3, the compound of Formula (III) is a compound of Formula (III-c):

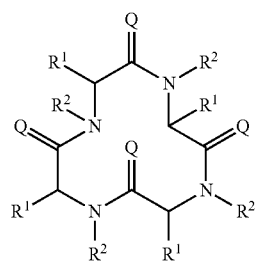

(III-c)

or salt thereof.

In certain embodiments, wherein p is 4, the compound of Formula (III) is a compound of Formula (III-d):

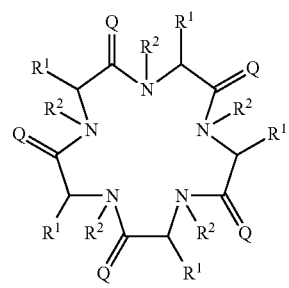

(III-d)

or salt thereof.

In certain embodiments, wherein p is 5, the compound of Formula (III) is a compound of Formula (III-e):

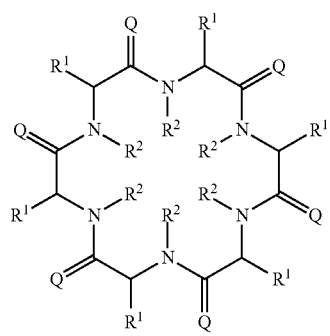

(III-e)

or salt thereof.

In certain embodiments, wherein p is 6, the compound of Formula (III) is a compound of Formula (III-f):

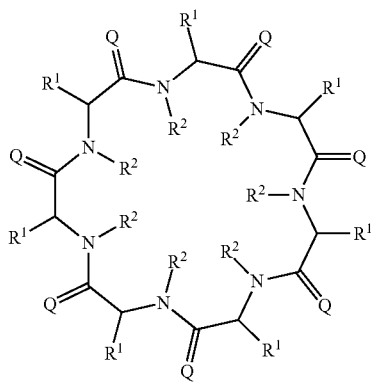

(III-f)

or salt thereof.

In certain embodiments, wherein p is 7, the compound of Formula (III) is a compound of Formula (III-g):

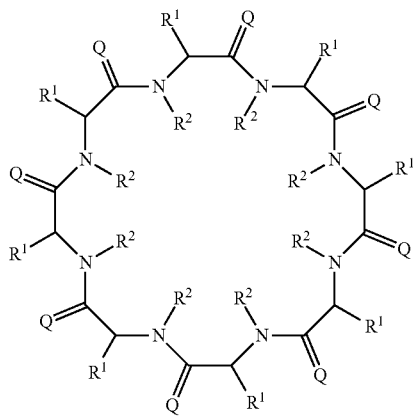

(III-g)

or salt thereof.

In certain embodiments, wherein p is 8, the compound of Formula (III) is a compound of Formula (III-h):

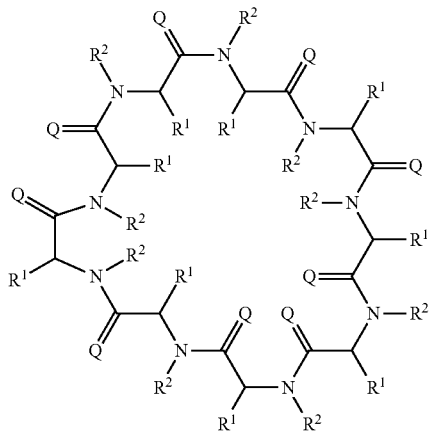

(III-h)

or salt thereof.

In certain embodiments, wherein p is 9, the compound of Formula (III) is a compound of Formula (III-i):

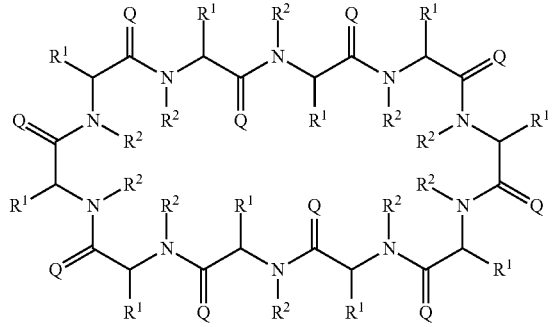

(III-i)

or salt thereof.

As generally defined above, each instance of $R^P$ is independently hydrogen or optionally substituted alkyl. In certain embodiments, at least one instance of $R^P$ is hydrogen. In certain embodiments, at least two instances of $R^P$ is hydrogen. In certain embodiments, each instance of $R^P$ is hydrogen. In certain embodiments, at least one instance of $R^P$ is optionally substituted alkyl, e.g., methyl. In certain embodiments, at least two instances of $R^P$ is optionally substituted alkyl, e.g., methyl. In certain embodiments, one instance of $R^P$ is optionally substituted alkyl, and the rest are hydrogen.

As generally defined above, each instance of Q is independently O, S, or $NR^Q$, wherein $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii). In certain embodiments, at least one instance of Q is O. In certain embodiments, each instance of Q is O. In certain embodiments, at least one instance of Q is S. In certain embodiments, each instance of Q is S. In certain embodiments, at least one instance of Q is $NR^Z$. In certain embodiments, each instance of Q is $NR^Z$. In certain embodiments, each instance of $R^Q$ is independently hydrogen or a group of the formula (i), (ii), or (iii).

As generally defined above, each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{A1}$, —$N(R^{A1})_2$, or —$SR^{A1}$.

In certain embodiments, at least one instance of $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, at least one instance of $R^1$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, at least one instance of $R^1$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, at least one instance of $R^1$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, at least one instance of $R^1$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In certain embodiments, at least one instance of $R^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of $R^1$ is optionally substituted aryl, e.g., optionally substituted phenyl.

In certain embodiments, at least one instance of $R^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In any of the above embodiments, the $R^1$ alkyl, alkenyl, alkynyl, carbocyclyl, heterocyclyl, aryl, or heteroaryl group may be substituted, for example, with an optionally substituted amino group (e.g., —$NR^6R^7$), an optionally substituted hydroxyl group (e.g., —$OR^6$), an optionally substituted thiol group (e.g., —$SR^6$), or with a group of formula (i), (ii), or (iii), wherein each instance of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

For example, in certain embodiments, at least one instance of $R^1$ is an alkyl, alkenyl, alkynyl, carbocyclyl, heterocyclyl, aryl, or heteroaryl group substituted with an amino group of the formula —$N(R^6)(R^7)$. In that instance, in certain embodiments, at least one instance of $R^1$ is a group of formula:

(iv)

wherein:

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and $R^6$ and $R^7$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

provided at least one instance of $R^6$ and $R^7$ is a group of the formula (i), (ii), or (iii):

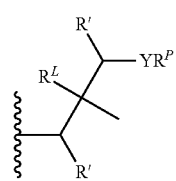
(i)

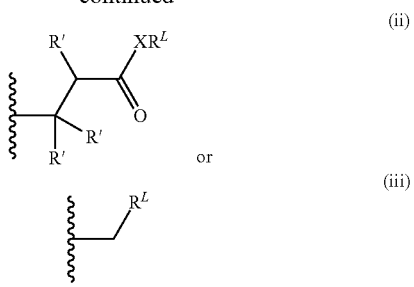

wherein R', X, Y, $R^L$, and $R^P$ are as defined herein.

In certain embodiments, at least two instances of $R^1$ is a group of formula (iv). In certain embodiments, at least three instances of $R^1$ is a group of formula (iv). In certain embodiments, at least four instances of $R^1$ is a group of formula (iv). In certain embodiments, at least five instances of $R^1$ is a group of formula (iv). In certain embodiments, at least six instances of $R^1$ is a group of formula (iv). In certain embodiments, at least seven instances of $R^1$ is a group of formula (iv). In certain embodiments, at least eight instances of $R^1$ is a group of formula (iv). In certain embodiments, at least nine instances of $R^1$ is a group of formula (iv). In certain embodiments, each instance of $R^1$ is a group of formula (iv).

In certain embodiments, L is an optionally substituted alkylene; e.g., optionally substituted $C_{1-50}$ alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{4-20}$alkenylene, optionally substituted $C_{10-20}$alkenylene, optionally substituted $C_{2-6}$alkenylene, optionally substituted $C_{3-6}$alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted $C_{8-20}$alkynylene, optionally substituted $C_{10-20}$alkynylene, optionally substituted $C_{2-6}$alkynylene, optionally substituted $C_{3-6}$alkynylene, optionally substituted $C_{4-6}$alkynylene, optionally substituted $C_{4-5}$alkynylene, or optionally substituted $C_{3-4}$alkynylene.

In certain embodiments, L is an optionally substituted heteroalkylene; e.g., optionally substituted hetero$C_{1-50}$alkylene, optionally substituted hetero$C_{1-40}$alkylene, optionally substituted hetero$C_{1-30}$alkylene, optionally substituted hetero$C_{1-20}$alkylene, optionally substituted hetero$C_{4-20}$alkylene, optionally substituted hetero$C_{6-20}$alkylene, optionally substituted heteroC$_{8-20}$alkylene, optionally substituted heteroC$_{10-20}$alkylene, optionally substituted heteroC$_{1-6}$alkylene, optionally substituted heteroC$_{2-6}$alkylene, optionally substituted heteroC$_{3-6}$alkylene, optionally substituted heteroC$_{4-6}$alkylene, optionally substituted heteroC$_{4-5}$alkylene, or optionally substituted heteroC$_{3-4}$alkylene.

In certain embodiments, L is an optionally substituted heteroalkenylene, e.g., optionally substituted heteroC$_{2-50}$alkenylene, optionally substituted heteroC$_{2-40}$alkenylene, optionally substituted heteroC$_{2-30}$alkenylene, optionally substituted heteroC$_{2-20}$alkenylene, optionally substituted heteroC$_{4-20}$alkenylene, optionally substituted heteroC$_{6-20}$alkenylene, optionally substituted heteroC$_{8-20}$alkenylene, optionally substituted heteroC$_{10-20}$alkenylene, optionally substituted heteroC$_{2-6}$alkenylene, optionally substituted heteroC$_{3-6}$alkenylene, optionally substituted heteroC$_{4-6}$alkenylene, optionally substituted heteroC$_{4-5}$alkenylene, or optionally substituted heteroC$_{3-4}$alkenylene.

In certain embodiments, L is an optionally substituted heteroalkynylene, e.g., optionally substituted heteroC$_{2-50}$alkynylene, optionally substituted heteroC$_{2-40}$alkynylene, optionally substituted heteroC$_{2-30}$alkynylene, optionally substituted heteroC$_{2-20}$alkynylene, optionally substituted heteroC$_{4-20}$alkynylene, optionally substituted heteroC$_{6-20}$alkynylene, optionally substituted heteroC$_{8-20}$alkynylene, optionally substituted heteroC$_{10-20}$alkynylene, optionally substituted heteroC$_{2-6}$alkynylene, optionally substituted heteroC$_{3-6}$alkynylene, optionally substituted heteroC$_{4-6}$alkynylene, optionally substituted heteroC$_{4-5}$alkynylene, or optionally substituted heteroC$_{3-4}$alkynylene.

In certain embodiments, L is an optionally substituted carbocyclylene, e.g., optionally substituted C$_{3-10}$ carbocyclylene, optionally substituted C$_{5-8}$ carbocyclylene, optionally substituted C$_{5-6}$ carbocyclylene, optionally substituted C$_5$ carbocyclylene, or optionally substituted C$_6$ carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5 membered heterocyclylene, or optionally substituted 6 membered heterocyclylene.

In certain embodiments, L is an optionally substituted arylene, e.g., optionally substituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5 membered heteroarylene, or optionally substituted 6 membered heteroarylene.

For example, in certain embodiments, wherein L is an optionally substituted alkylene group, the group of formula (iv) is a group of the formula:

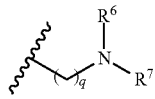

wherein q is an integer between 1 and 50, inclusive.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 4 and 20, inclusive. In certain embodiments, q is an integer between 6 and 20, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, both R$^6$ and R$^7$ are hydrogen. In certain embodiments, R$^6$ is hydrogen and R$^7$ is a group of the formula (i), (ii), or (iii). In certain embodiments, R$^6$ is hydrogen and R$^7$ is a group of the formula (i). In certain embodiments, R$^6$ is hydrogen and R$^7$ is a group of the formula (ii). In certain embodiments, R$^6$ is hydrogen and R$^7$ is a group of the formula (iii). In certain embodiments, both R$^6$ and R$^7$ are independently a group of the formula (i), (ii), or (iii). In certain embodiments, both R$^6$ and R$^7$ are independently a group of the formula (i). In certain embodiments, both R$^6$ and R$^7$ are independently a group of the formula (ii). In certain embodiments, both R$^6$ and R$^7$ are independently a group of the formula (iii). In certain embodiments, both R$^6$ and R$^7$ are the same group, selected from a group of the formula (i), (ii), or (iii).

It is understood that R$^1$ encompasses amino acid side chains such as exemplified in Table 1 of the Examples. In certain embodiments, R$^1$ is a group selected from any one of the amino acid side chain groups listed therein.

In certain embodiments, each instance of R$^1$ is the same. In certain embodiments, at least one R$^1$ group is different. In certain embodiments, each R$^1$ group is different.

As generally defined above, each instance of R$^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii):

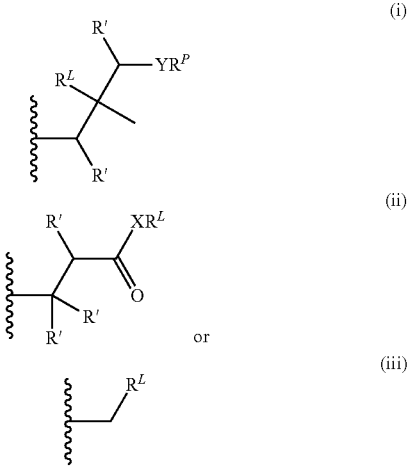

wherein R', X, Y, R$^L$, and R$^P$ are as defined herein.

In certain embodiments, at least one instance of R$^2$ is optionally substituted alkyl; e.g., optionally substituted C$_{1-6}$alkyl, optionally substituted C$_{2-6}$alkyl, optionally substituted C$_{3-6}$alkyl, optionally substituted C$_{4-6}$alkyl, optionally substituted C$_{4-5}$alkyl, or optionally substituted C$_{3-4}$alkyl.

In certain embodiments, at least one instance of $R^2$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, at least one instance of $R^2$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, at least one instance of $R^2$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In certain embodiments, at least one instance of $R^2$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of $R^2$ is optionally substituted aryl, e.g., optionally substituted phenyl.

In certain embodiments, at least one instance of $R^2$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In certain embodiments, at least one instance of $R^2$ is a nitrogen protecting group.

In certain embodiments, at least one instance of $R^2$ is a group of the formula (i). In certain embodiments, at least one instance of $R^2$ is a group of the formula (ii). In certain embodiments, at least one instance of $R^2$ is a group of the formula (iii).

In certain embodiments, each instance of $R^2$ is a group other than formula (i), (ii), or (iii); in that instance, it follows that at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii). For example, in certain embodiments, both instances of $R^2$ are hydrogen, and thus at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii).

Various combinations of the above embodiments of Formula (III) are contemplated herein.

For example, in certain embodiments, wherein each instance of Q is O, the compound of Formula (III) is a compound of Formula (III-a):

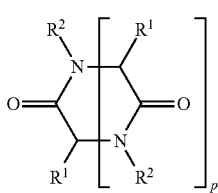

(III-a)

or salt thereof. In certain embodiments, at least one $R^1$ is a group of formula (iv). In certain embodiments, each instance of $R^1$ is a group of formula (iv). In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3.

In certain embodiments of Formula (III-a), wherein at least one $R^1$ is a group the formula (iv), provided is a compound of Formula (III-b):

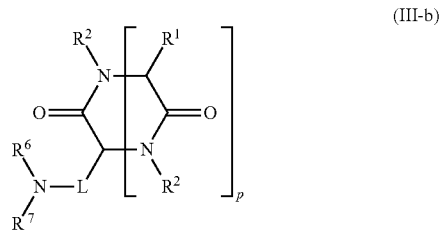

(III-b)

or salt thereof. In certain embodiments, each instance of $R^1$ is a group of formula (iv). In certain embodiments, $R^2$ is hydrogen. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formula (III-a), wherein each instance of $R^1$ is a group the formula (iv), provided is a compound of Formula (III-c):

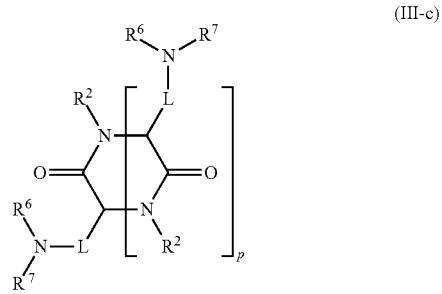

(III-c)

or salt thereof. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3. In certain embodiments, L is an optionally substituted alkylene.

In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formula (III-c), wherein p is 1, provided is a compound of Formula (III-c1):

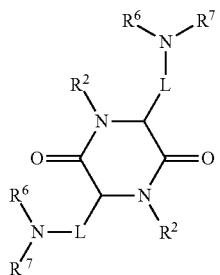

(III-c1)

or salt thereof. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formula (III-c1), wherein each instance of $R^2$ is hydrogen, provided is a compound of Formula (III-c2):

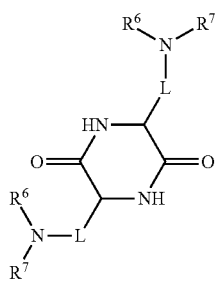

(III-c2)

or salt thereof. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are groups of formula (i), (ii), or (iii).

In certain embodiments of Formula (III-c1), wherein L is an optionally substituted alkylene, provided is a compound of Formula (III-c3):

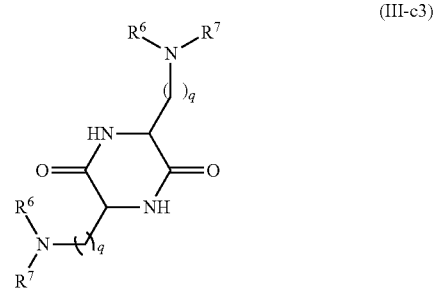

(III-c3)

or salt thereof, wherein q is an integer between 1 and 10, inclusive. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formula (III-a), wherein at least one instance of $R^2$ is a group of formula (i) and each instance of R' is hydrogen, provided is a compound of Formula (III-d):

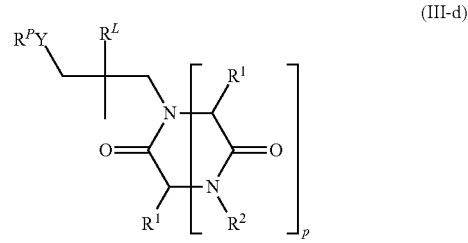

(III-d)

or salt thereof. In certain embodiments, at least one $R^1$ is a group of formula (iv). In certain embodiments, each instance of $R^1$ is a group of formula (iv). In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, $R^2$ is a group of formula (iii). In certain embodiments, p is 1. In certain embodiments, p is 2. In certain embodiments, p is 3.

In certain embodiments of Formula (III-a), wherein at least one instance of $R^2$ is a group of formula (ii) and each instance of R' is hydrogen, provided is a compound of Formula (III-e):

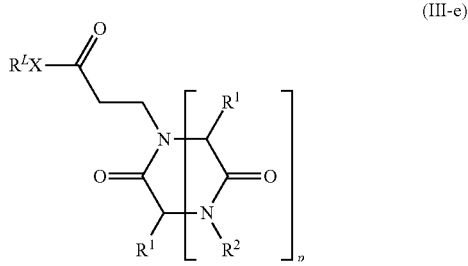

(III-e)

or salt thereof. In certain embodiments, at least one $R^1$ is a group of formula (iv). In certain embodiments, each instance of $R^1$ is a group of formula (iv). In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3.

In certain embodiments of Formula (III-a), wherein at least one instance of $R^2$ is a group of formula (iii), provided is a compound of Formula (III-f):

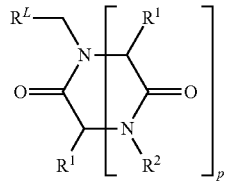

or salt thereof. In certain embodiments, at least one $R^1$ is a group of formula (iv). In certain embodiments, each instance of $R^1$ is a group of formula (iv). In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3.

Compounds of Formula (IV), (V), and (VI)

Compounds of Formula (IV), (V), and (VI), while not constructed from amino acid starting materials, share the same molecular formula and cyclic motif, and are thus structural isomers of compounds of Formula (III-a). The present invention embraces each as exemplary APPL structural isomers of the present invention.

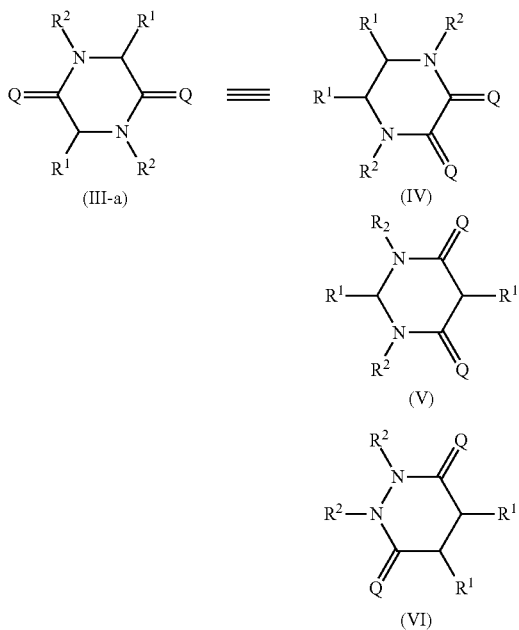

Thus, in yet another aspect, provided is a compound of Formula (IV), (V), or (VI):

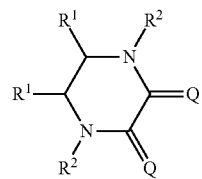

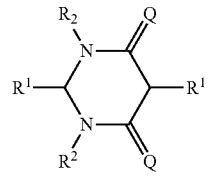

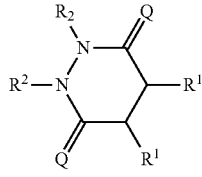

or salt thereof;
wherein:
each instance of Q is independently O, S, or $NR^Q$, wherein $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii), (iii);

each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{41}$, $-N(R^{41})_2$, or $-SR^{41}$; wherein each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups are joined to form an optionally substituted heterocyclic or optionally substituted heteroaryl ring;

each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii), or (iii); and Formulae (i), (ii), and (iii) are:

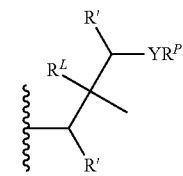

-continued

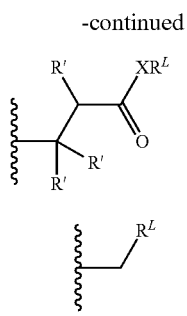

wherein:
each instance of R' is independently hydrogen or optionally substituted alkyl;
X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and
$R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer;
provided that at least one instance of $R^Q$, $R^2$, $R^6$, or $R^7$ is a group of the formula (i), (ii), or (iii).

As generally defined above, each instance of Q is independently O, S, or $NR^Q$, wherein $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii). In certain embodiments, at least one instance of Q is O. In certain embodiments, each instance of Q is O. In certain embodiments, at least one instance of Q is S. In certain embodiments, each instance of Q is S. In certain embodiments, at least one instance of Q is $NR^Z$. In certain embodiments, each instance of Q is $NR^Z$. In certain embodiments, each instance of $R^Q$ is independently hydrogen or a group of the formula (i), (ii), or (iii).

As generally defined above, each instance of R' is independently hydrogen or optionally substituted alkyl. In certain embodiments, at least one instance of $R^P$ is hydrogen. In certain embodiments, at least two instances of $R^P$ is hydrogen. In certain embodiments, each instance of $R^P$ is hydrogen. In certain embodiments, at least one instance of $R^P$ is optionally substituted alkyl, e.g., methyl. In certain embodiments, at least two instances of $R^P$ is optionally substituted alkyl, e.g., methyl. In certain embodiments, one instance of $R^P$ is optionally substituted alkyl, and the rest are hydrogen.

As generally defined above, each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{A1}$, $-N(R^{A1})_2$, or $-SR^{A1}$.

In certain embodiments, at least one instance of $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, at least one instance of $R^1$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, at least one instance of $R^1$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, at least one instance of $R^1$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, at least one instance of $R^1$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In certain embodiments, at least one instance of $R^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of $R^1$ is optionally substituted aryl, e.g., optionally substituted phenyl.

In certain embodiments, at least one instance of $R^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In any of the above embodiments, the $R^1$ alkyl, alkenyl, alkynyl, carbocyclyl, heterocyclyl, aryl, or heteroaryl group may be substituted, for example, with an optionally substituted amino group (e.g., $-NR^6R^7$), an optionally substituted hydroxyl group (e.g., $-OR^6$), an optionally substituted thiol group (e.g., $-SR^6$), or with a group of formula (i), (ii), or (iii), wherein each instance of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

For example, in certain embodiments, at least one instance of $R^1$ is an alkyl, alkenyl, alkynyl, carbocyclyl, heterocyclyl, aryl, or heteroaryl group substituted with an amino group of the formula —$N(R^6)(R^7)$. In that instance, in certain embodiments, at least one instance of $R^1$ is a group of formula:

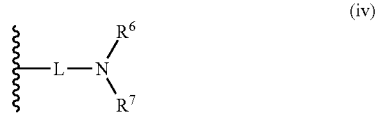

(iv)

wherein:

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and $R^6$ and $R^7$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

provided at least one instance of $R^6$ and $R^7$ is a group of the formula (i), (ii), or (iii):

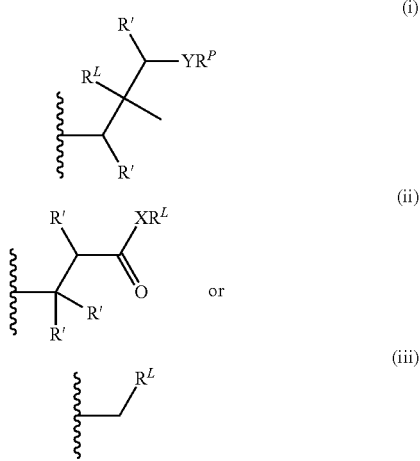

wherein R', X, Y, $R^L$, and $R^P$ are as defined herein.

In certain embodiments, both instances of $R^1$ are groups of formula (iv).

In certain embodiments, L is an optionally substituted alkylene; e.g., optionally substituted $C_{1-50}$alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{8-20}$alkenylene, optionally substituted $C_{10-20}$alkenylene, optionally substituted $C_{2-6}$alkenylene, optionally substituted $C_{3-6}$alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted $C_{8-20}$alkynylene, optionally substituted $C_{10-20}$alkynylene, optionally substituted $C_{2-6}$alkynylene, optionally substituted $C_{3-6}$alkynylene, optionally substituted $C_{4-6}$alkynylene, optionally substituted $C_{4-5}$alkynylene, or optionally substituted $C_{3-4}$alkynylene.

In certain embodiments, L is an optionally substituted heteroalkylene; e.g., optionally substituted hetero$C_{1-50}$alkylene, optionally substituted hetero$C_{1-40}$alkylene, optionally substituted hetero$C_{1-30}$alkylene, optionally substituted hetero$C_{1-20}$alkylene, optionally substituted hetero$C_{4-20}$alkylene, optionally substituted hetero$C_{6-20}$alkylene, optionally substituted hetero$C_{8-20}$alkylene, optionally substituted hetero$C_{10-20}$alkylene, optionally substituted hetero$C_{1-6}$alkylene, optionally substituted hetero$C_{2-6}$alkylene, optionally substituted hetero$C_{3-6}$alkylene, optionally substituted hetero$C_{4-6}$alkylene, optionally substituted hetero$C_{4-5}$alkylene, or optionally substituted hetero$C_{3-4}$alkylene.

In certain embodiments, L is an optionally substituted heteroalkenylene, e.g., optionally substituted hetero$C_{2-50}$alkenylene, optionally substituted hetero$C_{2-40}$alkenylene, optionally substituted hetero$C_{2-30}$alkenylene, optionally substituted hetero$C_{2-20}$alkenylene, optionally substituted hetero$C_{4-20}$alkenylene, optionally substituted hetero$C_{6-20}$alkenylene, optionally substituted hetero$C_{8-20}$alkenylene, optionally substituted hetero$C_{10-20}$alkenylene, optionally substituted hetero$C_{2-6}$alkenylene, optionally substituted hetero$C_{3-6}$alkenylene, optionally substituted hetero$C_{4-6}$alkenylene, optionally substituted hetero$C_{4-5}$alkenylene, or optionally substituted hetero$C_{3-4}$alkenylene.

In certain embodiments, L is an optionally substituted heteroalkynylene, e.g., optionally substituted hetero$C_{2-50}$alkynylene, optionally substituted hetero$C_{2-40}$alkynylene, optionally substituted hetero$C_{2-30}$alkynylene, optionally substituted hetero$C_{2-20}$alkynylene, optionally substituted hetero$C_{4-20}$alkynylene, optionally substituted hetero$C_{6-20}$alkynylene, optionally substituted hetero$C_{8-20}$alkynylene, optionally substituted hetero$C_{10-20}$alkynylene, optionally substituted hetero$C_{2-6}$alkynylene, optionally substituted hetero$C_{3-6}$alkynylene, optionally substituted hetero$C_{4-6}$alkynylene, optionally substituted hetero$C_{4-5}$alkynylene, or optionally substituted hetero$C_{3-4}$alkynylene.

In certain embodiments, L is an optionally substituted carbocyclylene, e.g., optionally substituted $C_{3-10}$ carbocyclylene, optionally substituted $C_{5-8}$ carbocyclylene, optionally substituted $C_{5-6}$ carbocyclylene, optionally substituted $C_5$ carbocyclylene, or optionally substituted $C_6$ carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5 membered heterocyclylene, or optionally substituted 6 membered heterocyclylene.

In certain embodiments, L is an optionally substituted arylene, e.g., optionally substituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5 membered heteroarylene, or optionally substituted 6 membered heteroarylene.

For example, in certain embodiments, wherein L is an optionally substituted alkylene group, the group of formula (iv) is a group of the formula:

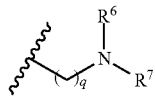

wherein q is an integer between 1 and 50, inclusive.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 4 and 20, inclusive. In certain embodiments, q is an integer between 6 and 20, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, both $R^6$ and $R^7$ are hydrogen. In certain embodiments, $R^6$ is hydrogen and $R^7$ is a group of the formula (i), (ii), or (iii). In certain embodiments, $R^6$ is hydrogen and $R^7$ is a group of the formula (i). In certain embodiments, $R^6$ is hydrogen and $R^7$ is a group of the formula (ii). In certain embodiments, $R^6$ is hydrogen and $R^7$ is a group of the formula (iii). In certain embodiments, both $R^6$ and $R^7$ are independently a group of the formula (i), (ii), or (iii). In certain embodiments, both $R^6$ and $R^7$ are independently a group of the formula (i). In certain embodiments, both $R^6$ and $R^7$ are independently a group of the formula (ii). In certain embodiments, both $R^6$ and $R^7$ are independently a group of the formula (iii). In certain embodiments, both $R^6$ and $R^7$ are the same group, selected from a group of the formula (i), (ii), or (iii).

It is understood that $R^1$ encompasses amino acid side chains such as exemplified in Table 1 of the Examples. In certain embodiments, $R^1$ is a group selected from any one of the amino acid side chain groups listed therein.

In certain embodiments, each instance of $R^1$ is the same. In certain embodiments, at least one $R^1$ group is different. In certain embodiments, each $R^1$ group is different.

As generally defined above, each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii):

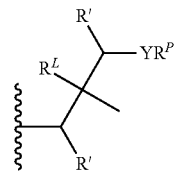

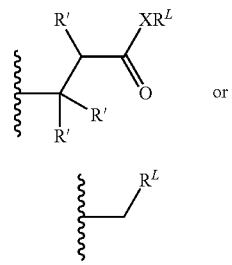

wherein R', X, Y, $R^L$, and $R^P$ are as defined herein.

In certain embodiments, at least one instance of $R^2$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, at least one instance of $R^2$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, at least one instance of $R^2$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, at least one instance of $R^2$ is optionally substituted carbocyclyl, e.g., optionally substituted $C_{3-10}$ carbocyclyl, optionally substituted $C_{5-8}$ carbocyclyl, optionally substituted $C_{5-6}$ carbocyclyl, optionally substituted $C_5$ carbocyclyl, or optionally substituted $C_6$ carbocyclyl.

In certain embodiments, at least one instance of $R^2$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5 membered heterocyclyl, or optionally substituted 6 membered heterocyclyl.

In certain embodiments, at least one instance of $R^2$ is optionally substituted aryl, e.g., optionally substituted phenyl.

In certain embodiments, at least one instance of $R^2$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In certain embodiments, at least one instance of $R^2$ is a nitrogen protecting group.

In certain embodiments, at least one instance of $R^2$ is a group of the formula (i). In certain embodiments, at least one instance of $R^2$ is a group of the formula (ii). In certain embodiments, at least one instance of $R^2$ is a group of the formula (iii).

In certain embodiments, each instance of $R^2$ is a group other than formula (i), (ii), or (iii); in that instance, it follows that at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii). For example, in certain embodiments, both instances of $R^2$ are hydrogen, and thus at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii).

Various combinations of the above embodiments of Formula (IV), (V), and (VI) are contemplated herein. For example, in certain embodiments, wherein each instance of Q is O, the compound of Formula (IV), (V), or (VI) is a compound of Formula (IV-a), (V-a), or (VI-a):

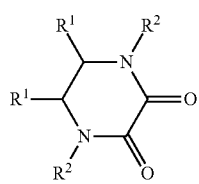
(IV-a)

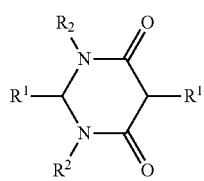
(V-a)

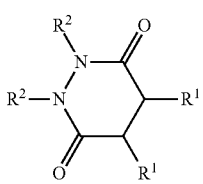
(VI-a)

or salt thereof. In certain embodiments, at least one instance of $R^1$ is a group of formula (iv). In certain embodiments, each instance of $R^1$ is a group of formula (iv). In certain embodiments, at least one instance of $R^2$ is optionally substituted alkyl, optionally substituted alkenyl, or optionally substituted alkynyl. In certain embodiments, at least one instance of $R^2$ is a group of formula (i). In certain embodiments, at least one instance of $R^2$ is a group of formula (ii). In certain embodiments, at least one instance of $R^2$ is a group of formula (iii).

In certain embodiments of Formula (IV-a), (V-a), or (VI-a), wherein at least one $R^1$ is a group the formula (iv), provided is a compound of Formula (IV-b), (V-b), or (VI-b):

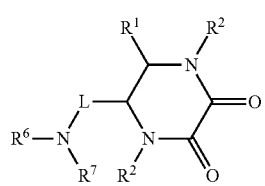
(IV-b)

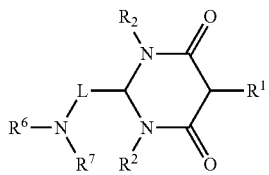
(V-b)

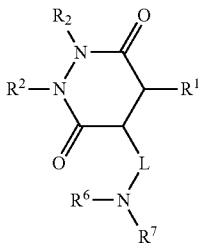
(VI-b)

or salt thereof. In certain embodiments, at least one instance of R is optionally substituted alkyl, optionally substituted alkenyl, or optionally substituted alkynyl. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formula (IV-b), (V-b), or (VI-b), wherein both $R^1$ groups are a group the formula (iv), provided is a compound of Formula (IV-c), (V-c), or (VI-c):

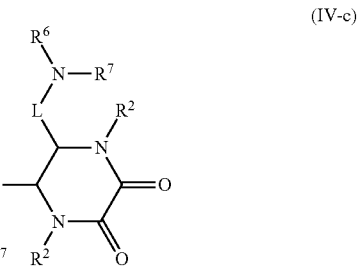
(IV-c)

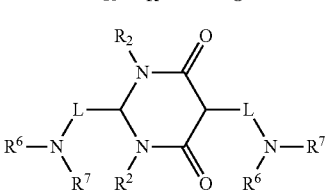
(V-c)

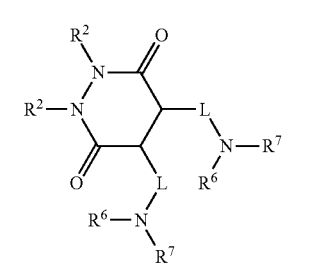
(VI-c)

or salt thereof. In certain embodiments, at least one instance of $R^2$ is optionally substituted alkyl, optionally substituted alkenyl, or optionally substituted alkynyl. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In certain embodiments of Formulae (IV-a), (V-a), and (VI-a), wherein at least one instance of $R^2$ is a group of formula (i) and each instance of R' is hydrogen, provided is a compound of Formulae (IV-d), (V-d), and (VI-d):

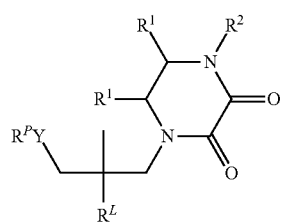
(IV-d)

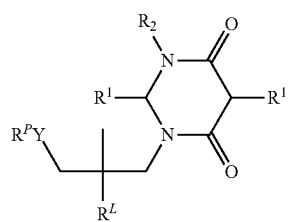
(V-d)

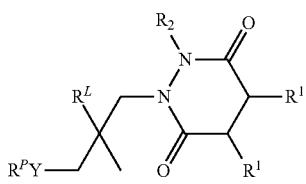
(VI-d)

or salt thereof. In certain embodiments, at least one instance of R is a group of formula (iv). In certain embodiments, each instance of $R^1$ is a group of formula (iv). In certain embodiments, $R^2$ is optionally substituted alkyl, optionally substituted alkenyl, or optionally substituted alkynyl. In certain embodiments, $R^2$ is a group of formula (i). In certain embodiments, $R^2$ is a group of formula (ii). In certain embodiments, $R^2$ is a group of formula (iii).

In certain embodiments of Formulae (IV-a), (V-a), and (VI-a), wherein both instances of $R^2$ is a group of formula (i) and each instance of R' is hydrogen, provided is a compound of Formulae (IV-e), (V-e), and (VI-e):

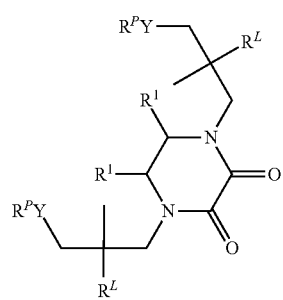
(IV-e)

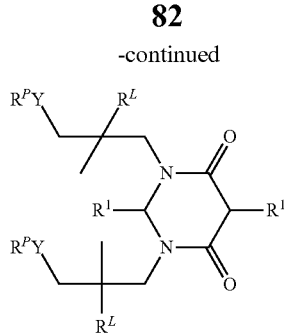
(V-e)

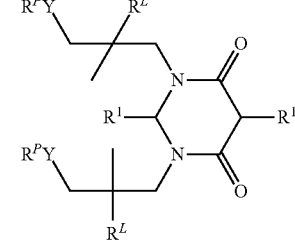
(VI-e)

or salt thereof. In certain embodiments, at least one instance of $R^1$ is a group of formula (iv). In certain embodiments, each instance of $R^1$ is a group of formula (iv).

In certain embodiments of Formulae (IV-a), (V-a), and (VI-a), wherein at least one instance of $R^2$ is a group of formula (ii) and each instance of R' is hydrogen, provided is a compound of Formulae (IV-f), (V-f), and (VI-f):

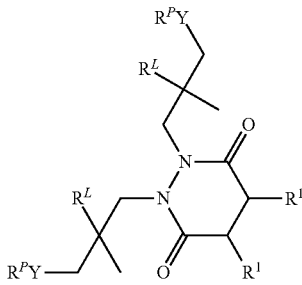
(IV-f)

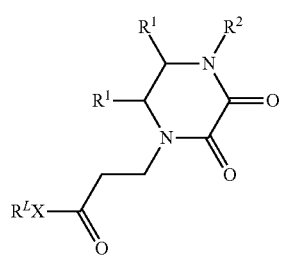
(V-f)

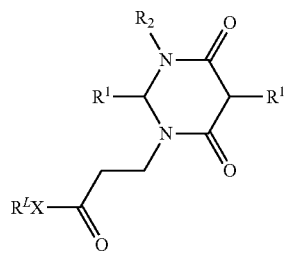
(VI-f)

or salt thereof. In certain embodiments, at least one instance of $R^1$ is a group of formula (iv). In certain embodiments, each instance of $R^1$ is a group of formula (iv). In certain embodiments, $R^2$ is optionally substituted alkyl, optionally substituted alkenyl, or optionally substituted alkynyl. In certain embodiments, $R^2$ is a group of formula (i). In certain embodiments, $R^2$ is a group of formula (ii). In certain embodiments, $R^2$ is a group of formula (iii).

In certain embodiments of Formulae (IV-a), (V-a), and (VI-a), wherein both instances of $R^2$ is a group of formula (ii) and each instance of R' is hydrogen, provided is a compound of Formulae (IV-g), (V-g), and (VI-g):

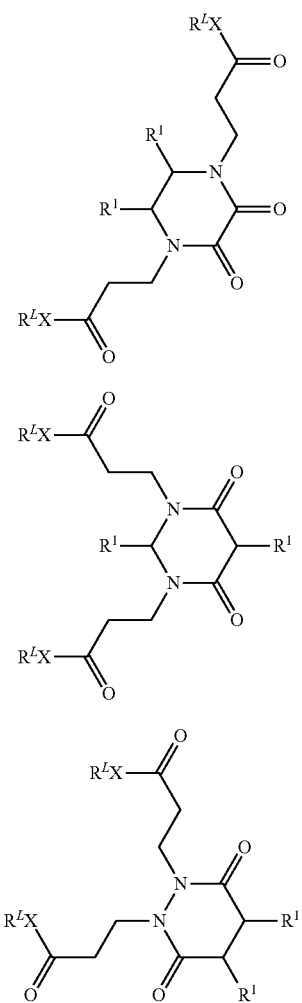

or salt thereof. In certain embodiments, at least one instance of $R^1$ is a group of formula (iv). In certain embodiments, each instance of $R^1$ is a group of formula (iv).

In certain embodiments of Formulae (IV-a), (V-a), and (VI-a), wherein at least one instance of $R^2$ is a group of formula (iii), provided is a compound of Formulae (IV-h), (V-h), and (VI-h):

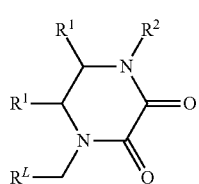

(IV-h)

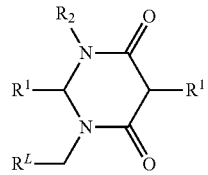

(V-h)

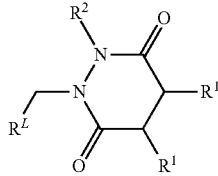

(VI-h)

or salt thereof. In certain embodiments, at least one instance of $R^1$ is a group of formula (iv). In certain embodiments, each instance of $R^1$ is a group of formula (iv). In certain embodiments, $R^2$ is optionally substituted alkyl, optionally substituted alkenyl, or optionally substituted alkynyl. In certain embodiments, $R^2$ is a group of formula (i). In certain embodiments, $R^2$ is a group of formula (ii). In certain embodiments, $R^2$ is a group of formula (iii).

In certain embodiments of Formulae (IV-a), (V-a), and (VI-a), wherein both instances of $R^2$ are a group of formula (iii), provided is a compound of Formulae (IV-e), (V-e), and (VI-e):

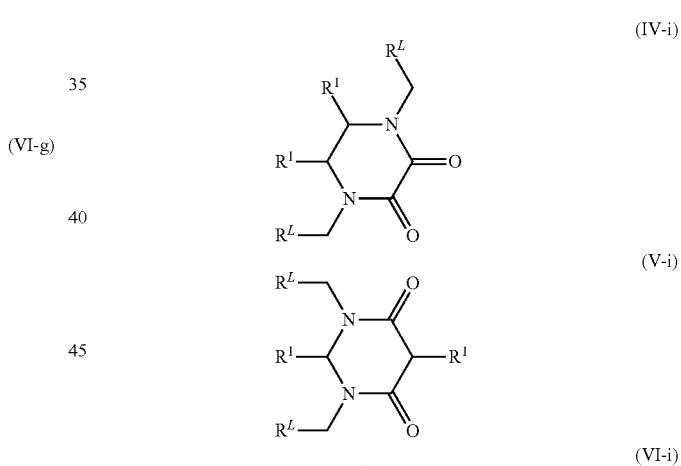

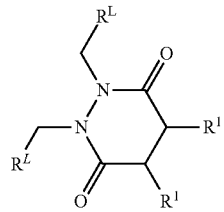

(VI-i)

or salt thereof. In certain embodiments, at least one instance of R is a group of formula (iv). In certain embodiments, each instance of $R^1$ is a group of formula (iv).

Groups of Formula (i), (ii), and (iii)

As understood from the above discussion, APPLs, and in particular, APPL compounds of Formulae (I), (III), (IV), (V), and (VI), each include at least one instance of a group of the formula (i), (ii), or (iii):

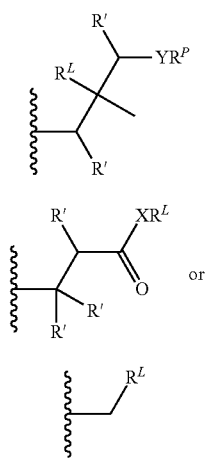

(i)

(ii)

(iii)

wherein:
each instance of R' is independently hydrogen or optionally substituted alkyl;
X is O, S, $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
Y is O, S, $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and
$R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

In the case of Formula (II), the at least one instance of group of formula (i) is incorporated as part of the scaffold, e.g., by monoaddition of a compound (i-x), followed by internal cyclization. See, e.g., Scheme 2.

In certain embodiments, an APPL, and in particular, a compound of Formulae (I), (II), (III), (IV), (V), or (VI), comprises at least one instance of a group of the formula (i) attached thereto:

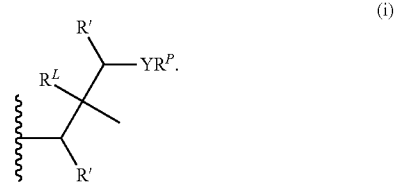

(i)

In certain embodiments of formula (i), Y is O. In certain embodiments of formula (i), Y is S. In certain embodiments of formula (i), Y is $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments of formula (i), Y is $NR^Y$, wherein $R^Y$ is hydrogen, optionally substituted alkyl, or a nitrogen protecting group. In certain embodiments of formula (i), each instance of R' is hydrogen.

As used herein, when the group $R^L$ is depicted as bisecting a carbon-carbon bond, e.g., of the group of the formula (i), it is understood that $R^L$ may be substituted at either carbon. Nucleophilic attack of an amino or amide group at the least sterically hindered carbon of the epoxide, thiirane, or aziridine of formula (i-x) provides a group of the formula (i-a1), (i-a2), or (i-a3) (route a), while nucleophilic attack at the more sterically hindered carbon of the epoxide, thiirane, or aziridine of formula (i-x) provides a group of the formula (i-b1), (i-b2), or (i-b3) (route b), wherein $R^P$ is hydrogen (Scheme 6). It is understood that compounds of the present invention may comprise a mixture of products attached thereto arising from route (a) and route (b) depending on the preference, or lack thereof, of the mode of addition. The bisecting group $R^L$ depicted in the Formulae seeks to encompasses all contemplated modes of addition.

Scheme 6.

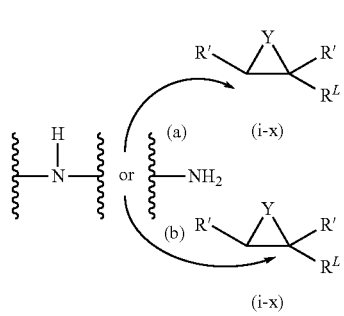
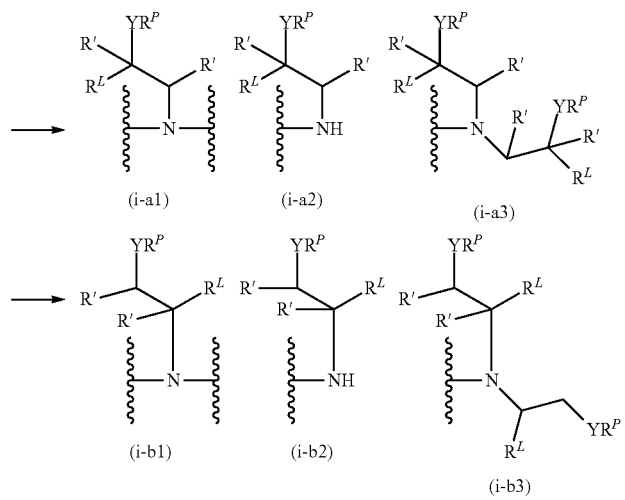

The resulting hydroxyl, thiol, or amino group —YR$^P$, wherein R$^P$ is hydrogen, may optionally be converted to a substituted group, wherein R$^P$ is a group other than hydrogen, i.e., wherein R$^P$ is independently selected from optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; using conventional methods. Alkylation, acylation, and/or protection of a hydroxyl, thiol, or amino moiety are methods well-known in the art; see, e.g., *Protecting Groups in Organic Synthesis*, T. W. Greene and P. G. M. Wuts, 3$^{rd}$ edition, John Wiley & Sons, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. For example, in certain non-limiting embodiments, the hydroxyl, thiol, or amino moiety —YR$^P$, wherein R$^P$ is hydrogen, may be reacted with an electrophile of the formula R$^P$—X$^2$ wherein R$^P$ is a group other than hydrogen, and X$^2$ is a leaving group, to provide a substituted hydroxyl, thiol, and amino group in formula (i).

In certain embodiments of formula (i), R$^P$ is hydrogen. In certain embodiments of formula (i), R$^P$ is optionally substituted alkyl. In certain embodiments of formula (i), R$^P$ is optionally substituted alkenyl. In certain embodiments of formula (i), R$^P$ is optionally substituted alkynyl. In certain embodiments of formula (i), R$^P$ is optionally substituted carbocyclyl. In certain embodiments of formula (i), R$^P$ is optionally substituted heterocyclyl. In certain embodiments of formula (i), R$^P$ is optionally substituted aryl. In certain embodiments of formula (i), R$^P$ is optionally substituted heteroaryl. In certain embodiments of formula (i), R$^P$ is an oxygen protecting group when attached to an oxygen atom. In certain embodiments of formula (i), R$^P$ is a sulfur protecting group when attached to a sulfur atom. In certain embodiments of formula (i), R$^P$ is a nitrogen protecting group when attached to a nitrogen atom.

It is understood from the present disclosure that the group of formula (i) represents a group of formula (i-a) or a group of formula (i-b):

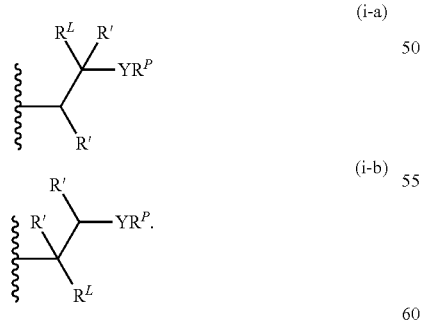

In certain embodiments, the reaction mixture provides a mixture of APPLs comprising more APPLs conjugated to a group of formula (i-a) than formula (i-b), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of an APPL attached to formula (i-a).

In certain embodiments, the epoxide, thiirane, or aziridine of formula (i-x) is chiral, i.e., having (R) or (S) stereochemistry. Chiral epoxides, thiiranes, and aziridines can be obtained from a variety of sources which are familiar to those skilled in the art of organic synthesis. In some embodiments, the chiral epoxide, thiirane, or aziridine is obtained commercially. In some embodiments, the chiral epoxide, thiirane, or aziridine is synthesized according to methods known to those of skill in the art, such as, but not limited to the Sharpless epoxidation of primary and secondary allylic alcohols into 2,3-epoxyalcohols (see, e.g., Katsuki et al., *J. Am. Chem. Soc.* 1980, 102, 5974; Hill et al., *Org. Syn.*, Coll. Vol. 7, p. 461 (1990); Vol. 63, p. 66 (1985); Katsuki et al., *Org. React.* 1996, 48, 1-300). In some embodiments, the chiral epoxide, thiirane, or aziridine is obtained from the resolution of a mixture (e.g., racemic mixture) of epoxides, thiiranes, or aziridines. In some embodiments, the chiral epoxide, thiirane, or aziridine is obtained by the separation of enantiomers or diastereoisomers using chiral chromatography. Chirality can be characterized in a variety of ways, e.g., obtaining a crystal structure of the compound containing a heavy atom attached thereto, obtaining the optical rotation of the compound, and/or NMR analysis after chemical modification of the optically active compound with a chiral derivatizing agent are some methods useful in evaluating chirality.

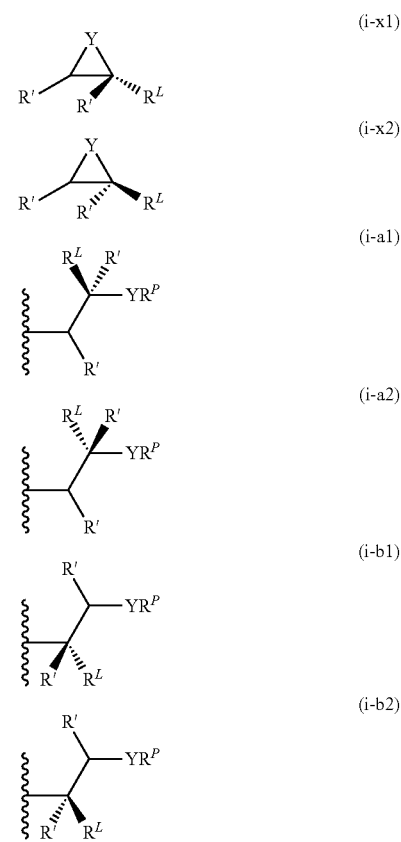

In certain embodiments, wherein the epoxide, thiirane, or aziridine of formula (i-x1) is chiral, the conjugation reaction is regioselective, and the reaction provides a chiral mixture of APPLs comprising more APPLs conjugated to a group of formula (i-a1) than formula (i-b1), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of an APPL attached to formula (i-a1).

In other embodiments, wherein the epoxide, thiirane, or aziridine of formula (i-x2) is chiral, the conjugation reaction is regioselective, and the reaction provides a chiral mixture of APPLs comprising more APPLs conjugated to a group of formula (i-a2) than formula (i-b2), e.g., the reaction mixture comprises greater than 50%, greater than 60%, greater than 70%, greater than 80%, greater than 90%, greater than 95%, greater than 99%, between about 60% to about 100%, between about 70% to about 100%, between about 80% to about 100%, between about 90% to about 100%, between about 95% to about 100%, or between about 99% to about 100%, of an APPL attached to formula (i-a2).

In certain embodiments, an APPL, and in particular, a compound of Formulae (I), (II), (III), (IV), (V), or (VI), comprises at least one instance of a group of the formula (ii) attached thereto:

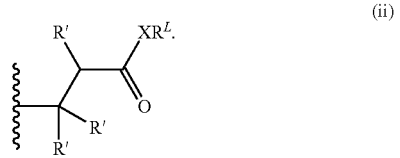

(ii)

In certain embodiments of formula (ii), X is O. In certain embodiments of formula (ii), X is S. In certain embodiments of formula (ii), X is $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments of formula (ii), X is $NR^X$, wherein $R^X$ is hydrogen, optionally substituted alkyl, or a nitrogen protecting group. In certain embodiments of formula (i), each instance of R' is hydrogen.

In certain embodiments, an APPL, and in particular, a compound of Formulae (I), (II), (III), (IV), (V), or (VI), comprises at least one instance of a group of the formula (ii) attached thereto:

(iii)

As generally defined above, $R^L$ is optionally substituted $C_{1-50}$ alkyl, optionally substituted $C_{2-50}$ alkenyl, optionally substituted $C_{2-50}$ alkynyl, optionally substituted $C_{1-50}$ heteroalkyl, optionally substituted $C_{2-50}$ heteroalkenyl, optionally substituted $C_{2-50}$ heteroalkynyl, or a polymer. The group $R^L$ seeks to encompass lipophilic, hydrophobic, and/or non-polar groups, but such terms should not limit the scope of $R^L$.

In certain embodiments, at least one instance of $R^L$ is an optionally substituted $C_{1-50}$ alkyl. In certain embodiments, $R^L$ is an optionally substituted $C_{6-50}$ alkyl. In certain embodiments, $R^L$ is an optionally substituted $C_{6-40}$ alkyl. In certain embodiments, $R^L$ is an optionally substituted $C_{6-30}$ alkyl. In certain embodiments, $R^L$ is an optionally substituted $C_{6-20}$ alkyl. In certain embodiments, $R^L$ is an optionally substituted $C_{8-20}$ alkyl. In certain embodiments, $R^L$ is an optionally substituted $C_8$ alkyl. In certain embodiments, $R^L$ is an optionally substituted $C_9$ alkyl. In certain embodiments, $R^L$ is an optionally substituted $C_{10}$ alkyl. In certain embodiments, $R^L$ is an optionally substituted $C_{11}$ alkyl. In certain embodiments, $R^L$ is an optionally substituted $C_{12}$ alkyl. In certain embodiments, $R^L$ is an optionally substituted $C_{13}$ alkyl. In certain embodiments, $R^L$ is an optionally substituted $C_{14}$ alkyl. In certain embodiments, $R^L$ is an optionally substituted $C_{15}$ alkyl. In certain embodiments, $R^L$ is an optionally substituted $C_{16}$ alkyl. In certain embodiments, $R^L$ is an optionally substituted $C_{17}$ alkyl. In certain embodiments, $R^L$ is an optionally substituted $C_{18}$ alkyl. In certain embodiments, $R^L$ is an optionally substituted $C_{19}$ alkyl. In certain embodiments, $R^L$ is an optionally substituted $C_{20}$ alkyl. In any of the above embodiments, the group $R^L$ is an unsubstituted alkyl group.

In certain embodiments, at least one instance of $R^L$ is an unsubstituted alkyl. Exemplary unsubstituted alkyl groups include, but are not limited to, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, —$C_{20}H_{41}$, —$C_{21}H_{43}$, —$C_{22}H_{45}$, —$C_{23}H_{47}$, —$C_{24}H_{49}$, and —$C_{25}H_{51}$.

In certain embodiments, at least one instance of $R^L$ is a substituted alkyl. For example, in certain embodiments, at least one instance of $R^L$ is an alkyl substituted with one or more fluorine substituents. Exemplary fluorinated alkyl groups include, but are not limited to:

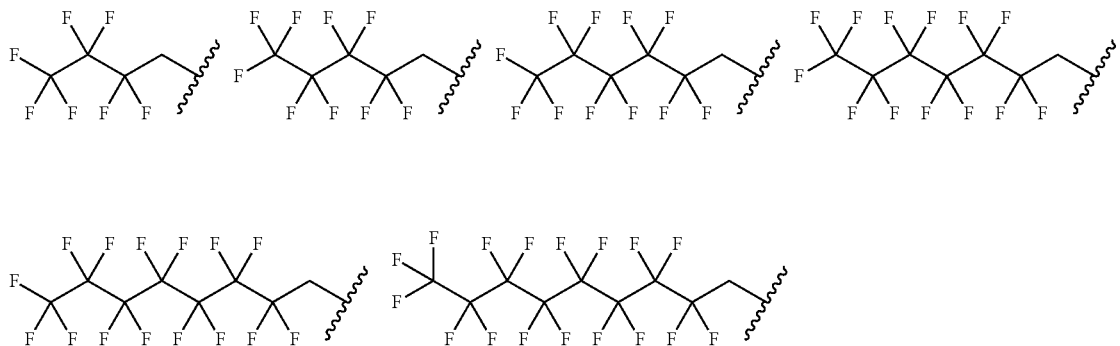

-continued

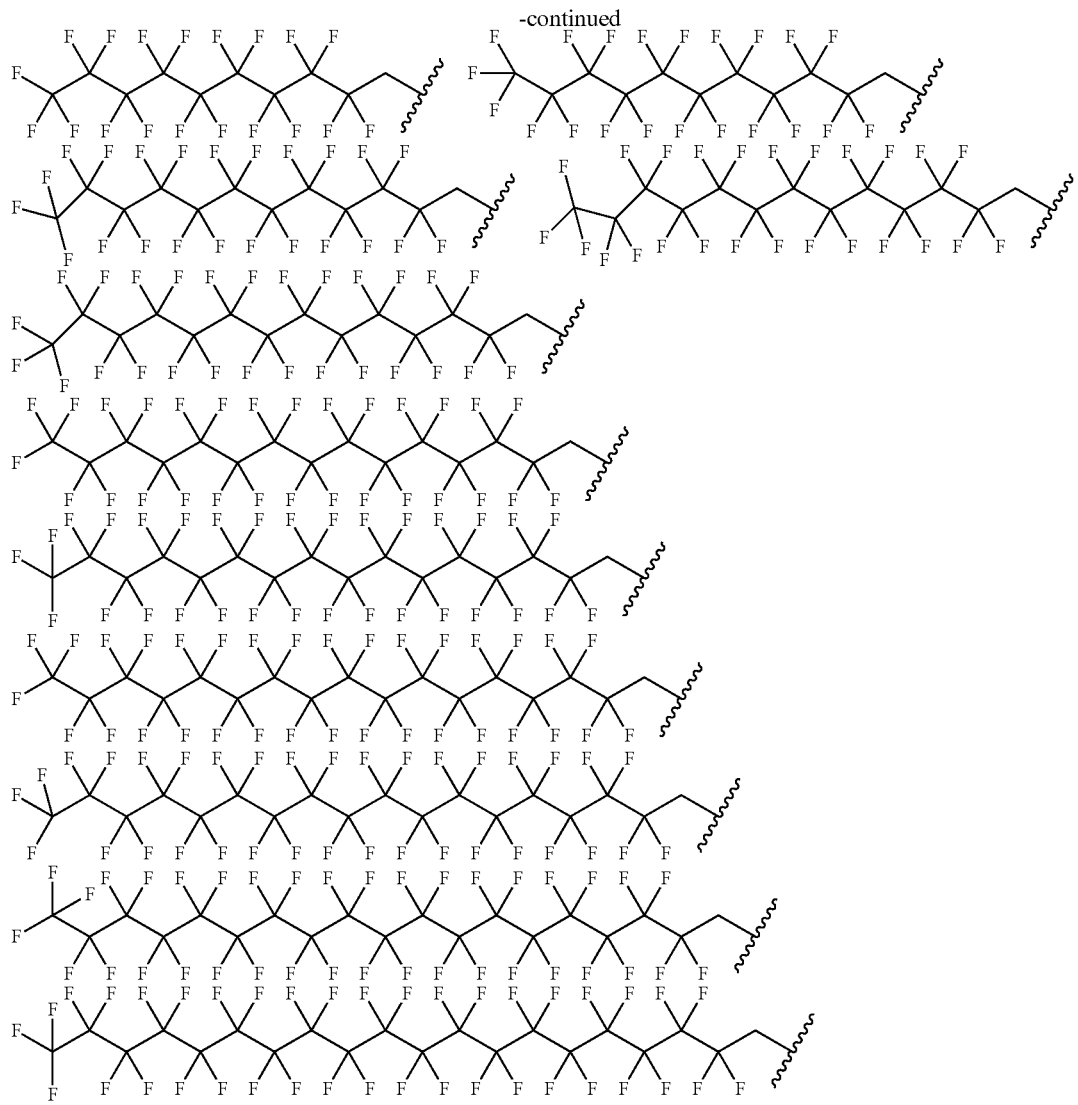

In certain embodiments, at least one instance of $R^L$ is an optionally substituted $C_{2-50}$ alkenyl. In certain embodiments, $R^L$ is an optionally substituted $C_{6-50}$alkenyl. In certain embodiments, $R^L$ is an optionally substituted $C_{6-40}$alkenyl. In certain embodiments, $R^L$ is an optionally substituted $C_{6-30}$alkenyl. In certain embodiments, $R^L$ is an optionally substituted $C_{6-20}$alkenyl. In certain embodiments, at least one instance of R is an optionally substituted $C_{8-20}$alkenyl. In certain embodiments, $R^L$ is an optionally substituted $C_8$alkenyl. In certain embodiments, $R^L$ is an optionally substituted $C_9$alkenyl. In certain embodiments, $R^L$ is an optionally substituted $C_{10}$alkenyl. In certain embodiments, $R^L$ is an optionally substituted $C_2$alkenyl. In certain embodiments, $R^L$ is an optionally substituted $C_8$alkenyl. In certain embodiments, $R^L$ is an optionally substituted $C_{13}$alkenyl. In certain embodiments, $R^L$ is an optionally substituted $C_{14}$alkenyl. In certain embodiments, $R^L$ is an optionally substituted $C_{15}$alkenyl. In certain embodiments, $R^L$ is an optionally substituted $C_{16}$alkenyl. In certain embodiments, $R^L$ is an optionally substituted $C_{17}$alkenyl. In certain embodiments, $R^L$ is an optionally substituted $C_{18}$alkenyl. In certain embodiments, $R^L$ is an optionally substituted $C_9$alkenyl. In certain embodiments, $R^L$ is an optionally substituted $C_{20}$alkenyl. In any of the above embodiments, the group $R^L$ is an unsubstituted alkenyl group.

Exemplary unsubstituted alkenyl groups include, but are not limited to:

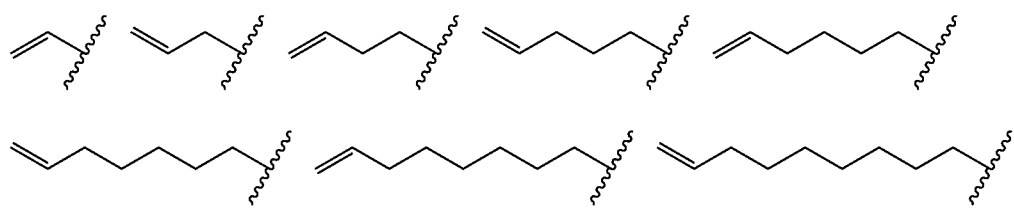

-continued

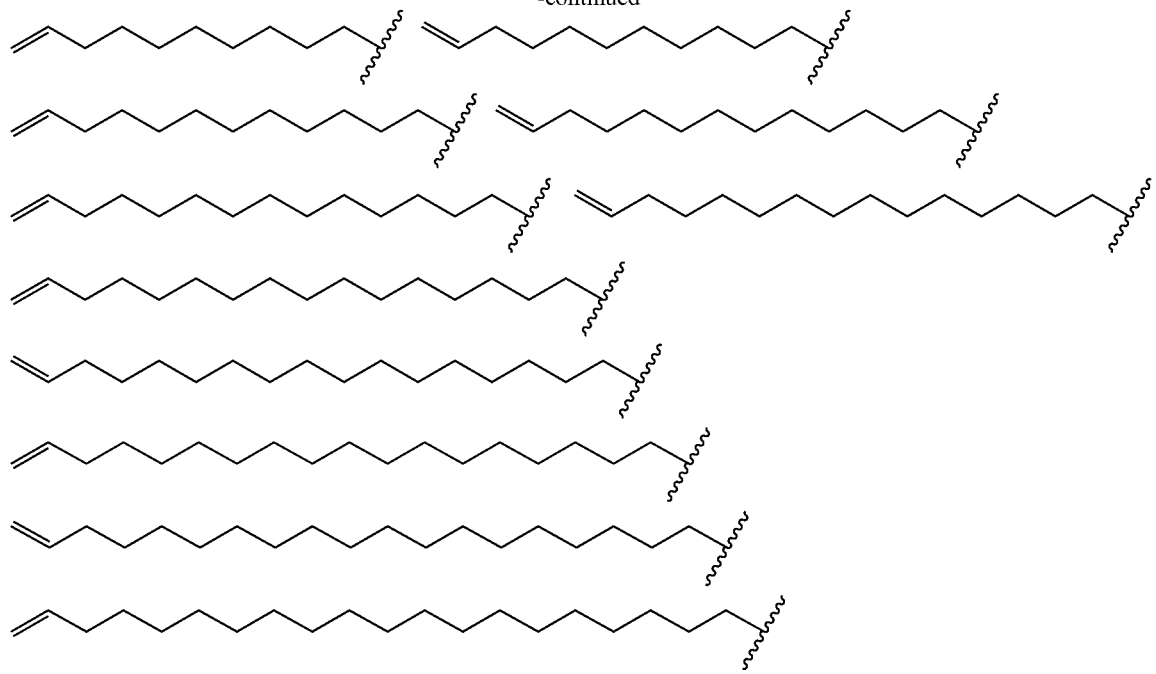

Myristoleic —(CH$_2$)$_7$CH═CH(CH$_2$)$_3$CH$_3$,
Palmitoliec —(CH$_2$)$_7$CH═CH(CH$_2$)$_5$CH$_3$,
Sapienic —(CH$_2$)$_4$CH═CH(CH$_2$)$_8$CH$_3$,
Oleic —(CH$_2$)$_7$CH═CH(CH$_2$)$_7$CH$_3$,
Linoleic —(CH$_2$)$_7$CH═CHCH$_2$CH═CH(CH$_2$)$_4$CH$_3$,
α-Linolenic —(CH$_2$)$_7$CH═CHCH$_2$CH═CHCH$_2$CH═CHCH$_2$CH$_3$,
Arachinodonic —(CH$_2$)$_3$CH═CHCH$_2$CH═CHCH$_2$CH═CHCH$_2$CH═CH(CH$_2$)$_4$CH$_3$,
Eicosapentaenoic —(CH$_2$)$_3$CH═CHCH$_2$CH═CHCH$_2$CH═CHCH$_2$CH═CHCH$_2$CH═CHCH$_2$CH$_3$,
Erucic —(CH$_2$)$_{11}$CH═CH(CH$_2$)$_7$CH$_3$, and
Docosahexaenoic —(CH$_2$)$_2$CH═CHCH$_2$CH═CHCH$_2$CH═CHCH$_2$CH═CHCH$_2$CH═CHCH$_2$CH═CH—CH$_2$CH$_3$.

In embodiments, wherein $R^L$ is defined as a $C_{6-50}$alkyl or $C_{6-50}$alkenyl groups, such groups are meant to encompass lipophilic groups (also referred to as a "lipid tail"). Lipophilic groups comprise a group of molecules that include fats, waxes, oils, fatty acids, and the like. Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

In certain embodiments, $R^L$ is an optionally substituted $C_{2-50}$ alkynyl. In certain embodiments, $R^L$ is an optionally substituted $C_{6-50}$alkynyl. In certain embodiments, $R^L$ is an optionally substituted $C_{6-40}$alkynyl. In certain embodiments, $R^L$ is an optionally substituted $C_{6-30}$alkynyl. In certain embodiments, $R^L$ is an optionally substituted $C_{6-20}$alkynyl. In certain embodiments, $R^L$ is an optionally substituted $C_{8-20}$alkynyl. In certain embodiments, $R^L$ is an optionally substituted $C_8$alkynyl. In certain embodiments, $R^L$ is an optionally substituted $C_9$alkynyl. In certain embodiments, $R^L$ is an optionally substituted $C_{10}$alkynyl. In certain embodiments, $R^L$ is an optionally substituted $C_{11}$alkynyl. In certain embodiments, $R^L$ is an optionally substituted $C_{12}$alkynyl. In certain embodiments, $R^L$ is an optionally substituted $C_{13}$alkynyl. In certain embodiments, $R^L$ is an optionally substituted $C_{14}$alkynyl. In certain embodiments, $R^L$ is an optionally substituted $C_{15}$alkynyl. In certain embodiments, $R^L$ is an optionally substituted $C_{16}$alkynyl. In certain embodiments, $R^L$ is an optionally substituted $C_{17}$alkynyl. In certain embodiments, $R^L$ is an optionally substituted $C_{18}$alkynyl. In certain embodiments, $R^L$ is an optionally substituted $C_{19}$alkynyl. In certain embodiments, $R^L$ is an optionally substituted $C_{20}$alkynyl. In any of the above embodiments, the group $R^L$ is an unsubstituted alkynyl group.

In certain embodiments, at least one instance of $R^L$ is an optionally substituted heteroC$_{1-50}$ alkyl. In certain embodiments, $R^L$ is an optionally substituted heteroC$_{6-50}$ alkyl. In certain embodiments, $R^L$ is an optionally substituted heteroC$_{6-40}$ alkyl. In certain embodiments, $R^L$ is an optionally substituted heteroC$_{6-30}$alkyl. In certain embodiments, $R^L$ is an optionally substituted heteroC$_{6-20}$alkyl. In certain embodiments, $R^L$ is an optionally substituted heteroC$_{10-20}$ alkyl. In certain embodiments, $R^L$ is an optionally substituted heteroC$_8$alkyl. In certain embodiments, $R^L$ is an optionally substituted heteroC$_9$alkyl. In certain embodiments, $R^L$ is an optionally substituted heteroC$_{10}$alkyl. In certain embodiments, $R^L$ is an optionally substituted heteroC$_{11}$alkyl. In certain embodiments, $R^L$ is an optionally substituted heteroC$_{12}$alkyl. In certain embodiments, R is an optionally substituted heteroC$_{13}$alkyl. In certain embodiments, $R^L$ is an optionally substituted heteroC$_{14}$alkyl. In certain embodiments, $R^L$ is an optionally substituted heteroC$_{15}$alkyl. In certain embodiments, $R^L$ is an optionally substituted heteroC$_{16}$alkyl. In certain embodiments, $R^L$ is an optionally substituted heteroC$_{17}$alkyl. In certain embodiments, $R^L$ is an optionally substituted heteroC$_{18}$alkyl. In certain embodiments, $R^L$ is an optionally substituted heteroC$_{19}$alkyl. In certain embodiments, R$^L$ is an optionally substituted heteroC$_{20}$alkyl. In any of the above embodiments, the group R$^L$ is an unsubstituted heteroalkyl group.

Exemplary unsubstituted heteroalkyl groups include, but are not limited to,

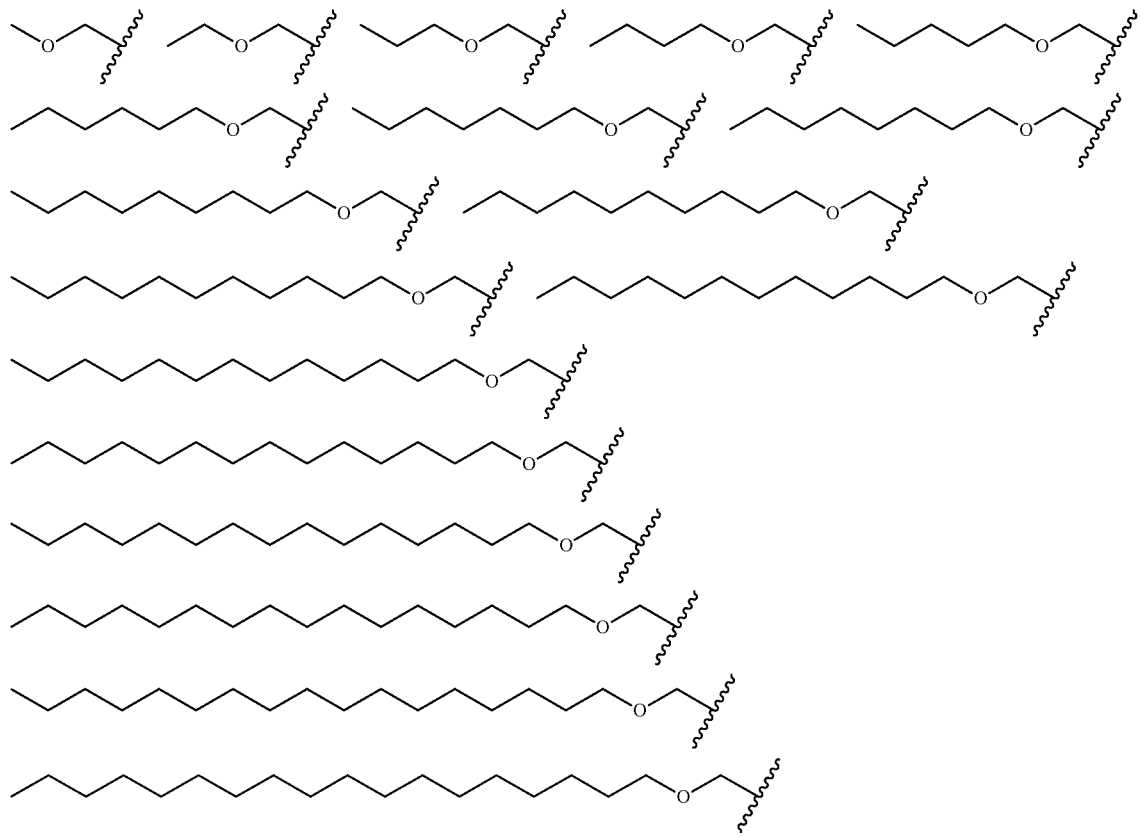

In certain embodiments, at least one instance of R$^L$ is an optionally substituted heteroC$_{2-50}$alkenyl. In certain embodiments, R$^L$ is an optionally substituted heteroC$_{6-50}$alkenyl. In certain embodiments, R$^L$ is an optionally substituted heteroC$_{6-40}$alkenyl. In certain embodiments, R$^L$ is an optionally substituted heteroC$_{6-30}$alkenyl. In certain embodiments, R$^L$ is an optionally substituted heteroC$_{6-20}$alkenyl. In certain embodiments, R$^L$ is an optionally substituted heteroC$_{8-20}$alkenyl. In certain embodiments, R$^L$ is an optionally substituted heteroC$_8$alkenyl. In certain embodiments, R$^L$ is an optionally substituted heteroC$_9$alkenyl. In certain embodiments, R$^L$ is an optionally substituted heteroC$_{10}$alkenyl. In certain embodiments, R$^L$ is an optionally substituted heteroC$_{11}$alkenyl. In certain embodiments, R$^L$ is an optionally substituted heteroC$_{12}$alkenyl. In certain embodiments, R$^L$ is an optionally substituted heteroC$_{13}$alkenyl. In certain embodiments, R$^L$ is an optionally substituted heteroC$_{14}$alkenyl. In certain embodiments, R$^L$ is an optionally substituted heteroC$_{15}$alkenyl. In certain embodiments, R$^L$ is an optionally substituted heteroC$_{16}$alkenyl. In certain embodiments, R$^L$ is an optionally substituted heteroC$_{17}$alkenyl. In certain embodiments, R$^L$ is an optionally substituted heteroC$_{18}$alkenyl. In certain embodiments, R$^L$ is an optionally substituted heteroC$_{19}$alkenyl. In certain embodiments, R$^L$ is an optionally substituted heteroC$_{20}$alkenyl. In any of the above embodiments, the group R$^L$ is an unsubstituted heteroalkenyl group.

In certain embodiments, R$^L$ is an optionally substituted heteroC$_{2-50}$alkynyl. In certain embodiments, R$^L$ is an optionally substituted heteroC$_{6-50}$alkynyl. In certain embodiments, R$^L$ is an optionally substituted heteroC$_{6-40}$alkynyl. In certain embodiments, R$^L$ is an optionally substituted heteroC$_{6-30}$alkynyl. In certain embodiments, R$^L$ is an optionally substituted heteroC$_{6-20}$alkynyl. In certain embodiments, R$^L$ is an optionally substituted heteroC$_{8-20}$alkynyl. In certain embodiments, R$^L$ is an optionally substituted heteroC$_8$alkynyl. In certain embodiments, R$^L$ is an optionally substituted heteroC$_9$alkynyl. In certain embodiments, R$^L$ is an optionally substituted heteroC$_{10}$alkynyl. In certain embodiments, R$^L$ is an optionally substituted heteroC$_1$alkynyl. In certain embodiments, R$^L$ is an optionally substituted heteroC$_{12}$alkynyl. In certain embodiments, R$^L$ is an optionally substituted heteroC$_{13}$alkynyl. In certain embodiments, R$^L$ is an optionally substituted heteroC$_{14}$alkynyl. In certain embodiments, R$^L$ is an optionally substituted heteroC$_{15}$alkynyl. In certain embodiments, R$^L$ is an optionally substituted heteroC$_{16}$alkynyl. In certain embodiments, R$^L$ is an optionally substituted heteroC$_{17}$alkynyl. In certain embodiments, R$^L$ is an optionally substituted heteroC$_{18}$alkynyl. In certain embodiments, R$^L$ is an optionally substituted heteroC$_{19}$alkynyl. In certain embodiments, R$^L$ is an optionally substituted heteroC$_{20}$alkynyl. In any of the above embodiments, the group R$^L$ is an unsubstituted heteroalkynyl group.

In certain embodiments, at least one instance of R$^L$ is a polymer. As used herein, a "polymer" refers to a compound comprised of at least 3 (e.g., at least 10, 20, 30, 40, 50, 60, 70, 80, 90, 100, etc.) repeating covalently bound structural units. The polymer is in certain embodiments biocompatible (i.e., non-toxic). Exemplary polymers include, but are not limited to, cellulose polymers (e.g., hydroxyethylcellulose, ethylcellulose, carboxymethylcellulose, methyl cellulose, hydroxypropylmethylcellulose (HPMC)), dextran polymers, polymaleic acid polymers, poly(acrylic acid) polymers, poly (vinylalcohol) polymers, polyvinylpyrrolidone (PVP) polymers, and polyethyleneglycol (PEG) polymers, and combinations thereof.

Additional Methods of Preparation

As described herein, in order to provide compounds of the present invention, an APPL precursor is treated with one or more conjugating reagents, e.g., selected from an epoxide, thiirane, or aziridine of formula (i-x), an α,β-unsaturated ester, thioester, or amide of formula (ii-x), or an aldehyde of formula (iii-x), to provide the APPL.

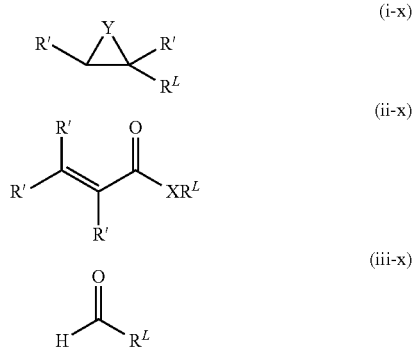

For example, in one aspect, provided is a method of preparing an APPL functionalized with a group of formula (i) comprising heating the precursor in an organic solvent (e.g., EtOH) with one or more conjugating reagents of formula (i-x) to provide the desired APPL. In certain embodiments, the mixture is heated between about 100 to about 200° C., inclusive, e.g., about 150° C.

In another aspect, provided is a method of preparing an APPL functionalized with a group of formula (ii) comprising heating the precursor in an organic solvent (e.g., EtOH) with one or more conjugating reagents of formula (ii-x) to provide the desired APPL. In certain embodiments, the mixture is heated between about 50 to about 100° C., inclusive, e.g., about 90° C.

In another aspect, provided is a method of preparing an APPL functionalized with a group of formula (iii) comprising mixing the precursor in an organic solvent (e.g., THF) with one or more conjugating reagents of formula (iii-x) and a reducing agent (e.g., NaBH(OAc)$_3$) to provide the desired APPL. In certain embodiments, the temperature of the reaction mixture is room temperature mixture.

In certain embodiments, wherein only one conjugating reagent is used, each instance of $R^L$ is the same in the APPL. For example, in certain embodiments, each instance of $R^L$ is the same wherein $R^L$ is an optionally substituted alkyl. In certain embodiments, each instance of $R^L$ is the same wherein $R^L$ is an unsubstituted alkyl. In certain embodiments, each instance of $R^L$ is the same wherein $R^L$ is selected from the group consisting of —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, and —$C_{20}H_{41}$. In certain embodiments, each instance of $R^L$ is the same wherein $R^L$ is an n-alkyl group selected from —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, and —$C_{16}H_{33}$.

Alternatively, in certain embodiments, wherein more than one conjugating reagent is used in the conjugation reaction (e.g., two, three, four, five, six, seven, eight, nine, or ten different conjugating reagents), the APPL may comprise two or more (e.g., two, three, four, five, six, seven, eight, nine, or ten) different groups of the formula (i), (ii), and/or (iii) attached thereto.

For example, in certain embodiments, two different epoxides are used in the conjugation reaction. In this instance, in certain embodiments, the APPL comprises two different $R^L$ groups. For example, in certain embodiments, the APPL comprises a mixture of two different $R^L$ groups, wherein the first $R^L$ group is an optionally substituted alkyl, and the second $R^L$ group is a polymer.

As would be appreciated by one of skill in this art, the degree of conjugation may be controlled by the reaction conditions (e.g., temperature, starting materials, concentration, solvent, etc.) used in the synthesis. The synthesized APPL may be purified by any technique known in the art including, but not limited to, precipitation, crystallization, chromatography, distillation, etc.

In certain embodiments, the APPL is isolated as a salt. For example, in certain embodiments, the APPL is reacted with an acid (e.g., an organic acid or inorganic acid) to form the corresponding salt. In other embodiments, tertiary amines are alkylated to form a quaternary ammonium salt of the APPL. The tertiary amines may be alkylated with any alkylating agent, for example, alkyl halides such as methyl iodide may be used to from the quaternary amino groups. The anion associated with the quaternary amine may be any organic or inorganic anion. In certain embodiments, the anion is a pharmaceutically acceptable anion.

The invention also provides libraries of APPLs prepared by the inventive methods. For example, in certain embodiments, provided is a method of screening a compound library, the method comprising providing a plurality of different APPLs, or salts thereof; and performing at least one assay with the compound library to determine the presence or absence of a desired property. These APPLs may be prepared and/or screened using high-throughput techniques involving liquid handlers, robots, microtiter plates, computers, etc. In certain embodiments, the APPLs are screened for their ability to transfect polynucleotides or other agents (e.g., proteins, peptides, small molecules) into the cell. For example, in one embodiment, provided is a method of screening a compound library, the method comprising providing a plurality of two or more different APPLs and screening the compound library for a desired property.

In one embodiment, a library of different APPLs is prepared in parallel. A different precursor and/or conjugating reagent is added to each vial in a set of vials or to each well of a multi-well plate used to prepare the library. The array of reaction mixtures is incubated at a temperature and length of time sufficient to allow formation of the APPL. The APPL may then be isolated and purified using techniques known in the art. The APPL may then be screened using high-throughput techniques to identify APPLs with a desired property, e.g., wherein the desired property is solubility in water, solubility at different pH, ability to bind polynucleotides, ability to bind heparin, ability to bind small molecules, ability to bind protein, ability to form microparticles, ability to increase transfection efficiency, ability to support cell growth, ability to support cell attachment, ability to support tissue growth, and/or intracellular delivery of the APPL and/or an agent complexed or attached thereto to aid in bioprocessing, e.g., for the purpose of manufacturing proteins. In certain embodiments the APPLs may be screened for properties or characteristics useful as coatings, additives, materials, and excipients in biotechnology and biomedical applications such as the coating of medical devices or implants with films or multilayer films, as non-biofouling agents, micropatterning agents, and cellular encapsulation agents. In certain embodiments the APPL may be screened for properties or characteristics useful in gene therapy (e.g., the ability to bind polynucleotides and/or increase in transfection efficiency), bioprocessing (e.g., aiding in the intracellular manufacturing of proteins), or the administration and/or delivery of a therapeutic agent (e.g., polynucleotide, small molecule, antigen, drug, protein, peptide, etc.) to a subject, tissue, organ, or cell.

Exemplary Compounds of the Present Invention

Certain compounds of the present invention are specifically contemplated herein. For example, compounds comprising unsubstituted n-alkyl $R^L$ groups containing 8, 9, 10, 11, 12, 13, and 14 carbon atoms are specifically contemplated. In certain embodiments $R^1$ of such compounds is an amino acid side chain as defined in Table 1 of the Examples.

Exemplary amino acid, peptide, and polypeptide compounds of Formula (I) include, but are not limited to:

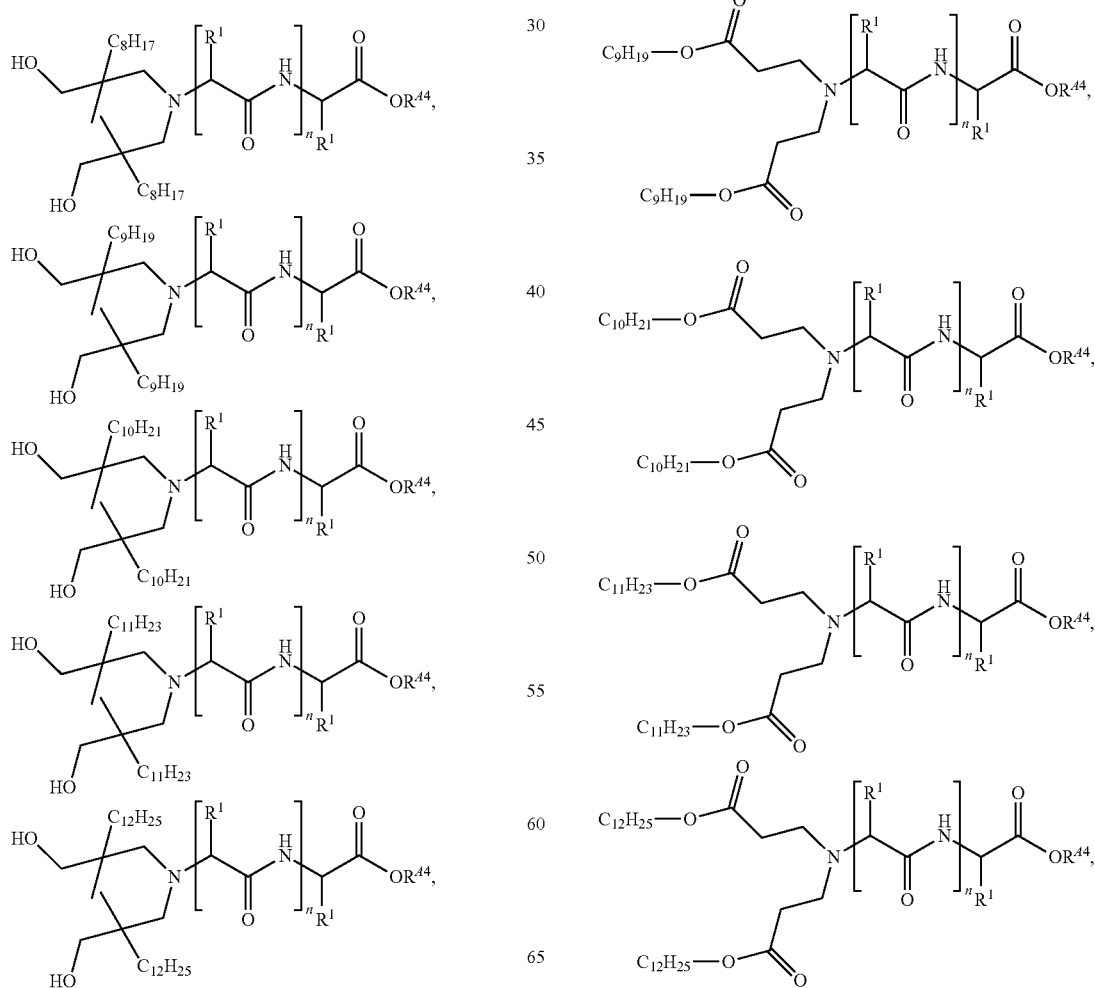

and salts thereof.

Exemplary cyclized compounds of Formula (II), include, but are not limited to:

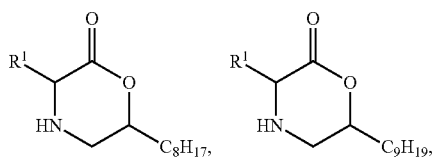
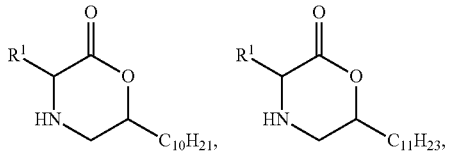
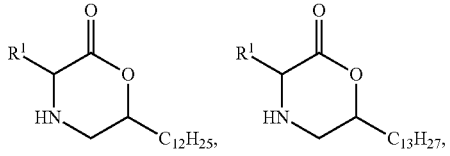
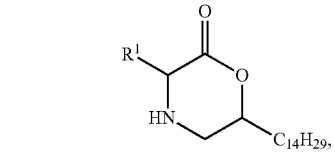
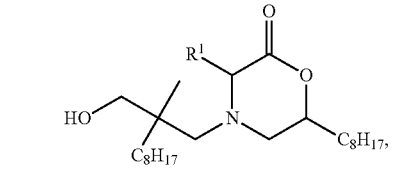
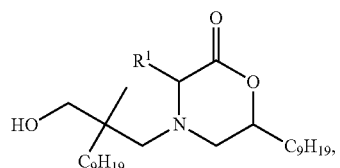
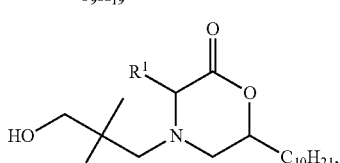
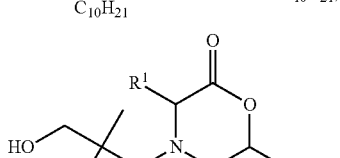
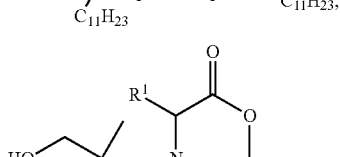
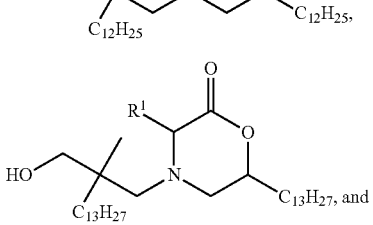
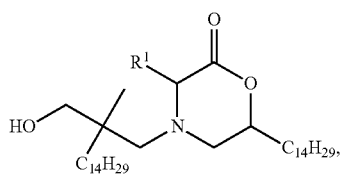
and salts thereof.
Exemplary cyclic dipeptide and cyclic polypeptide compounds of Formula (III) include, but are not limited to:
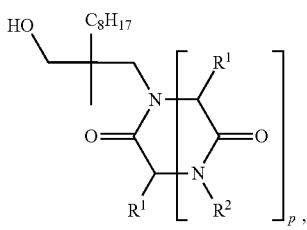
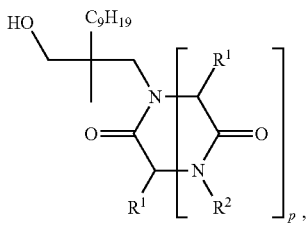
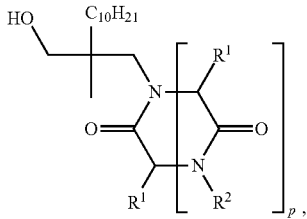
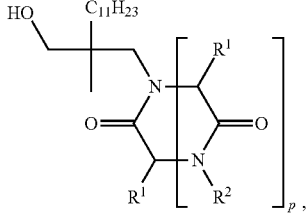
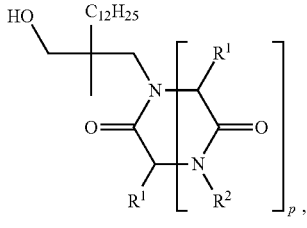
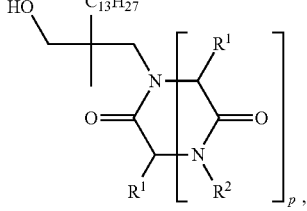

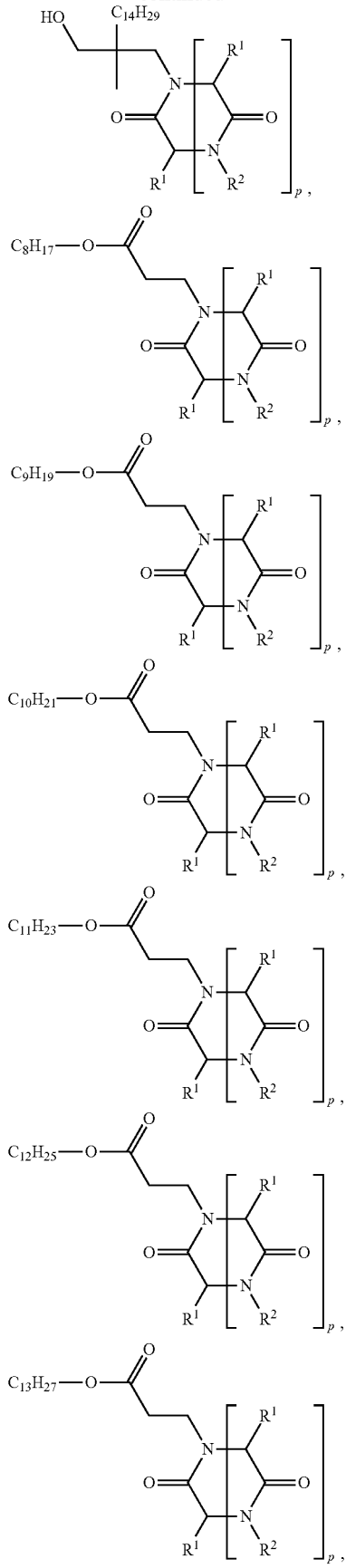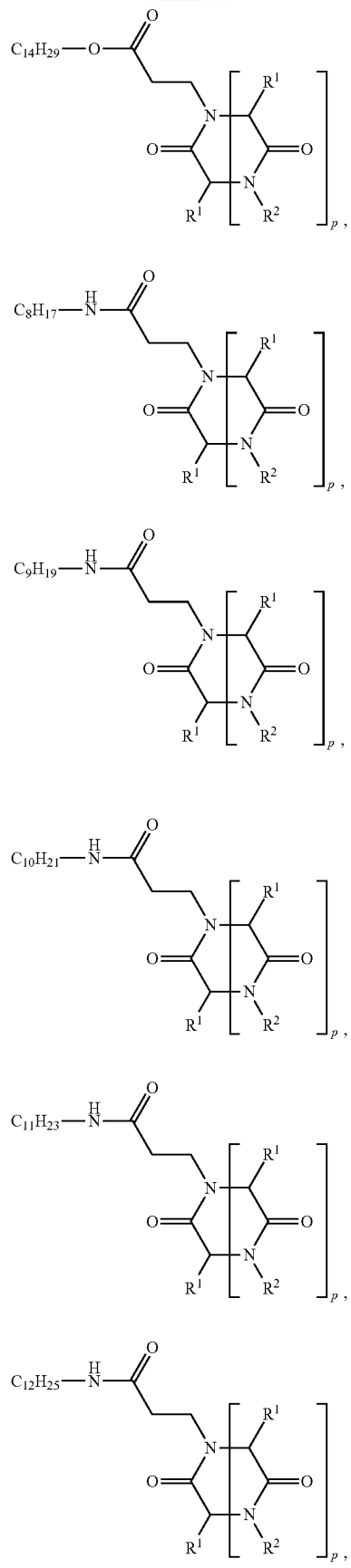

-continued
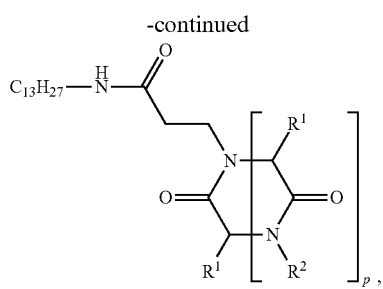
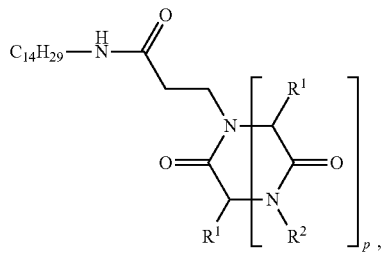
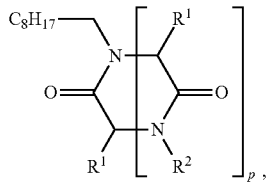
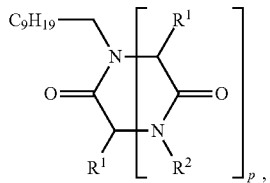
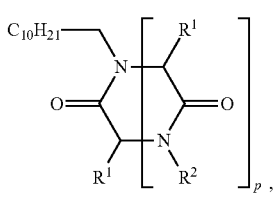
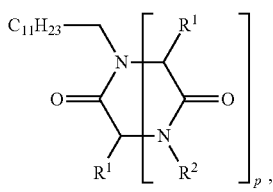
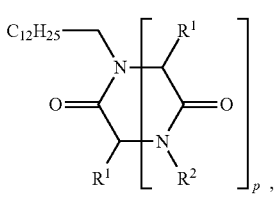
-continued
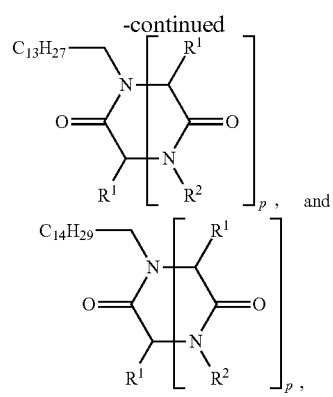
and, in particular, cyclic-KK and polycyclic lysine APPLs of the formula:
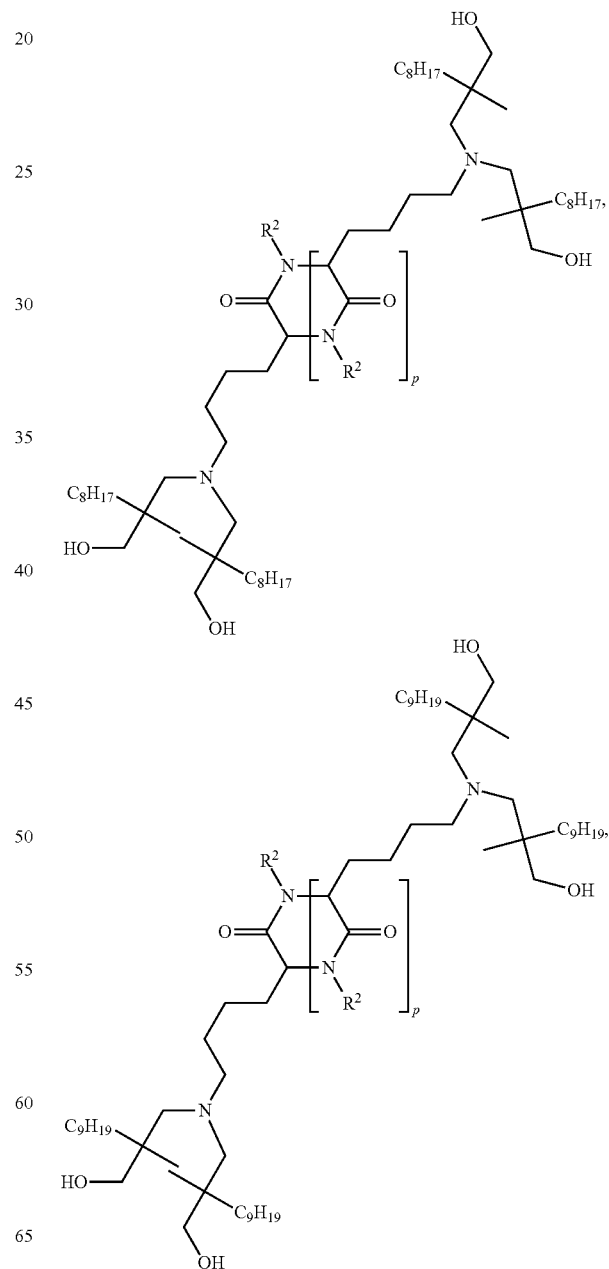

109
-continued
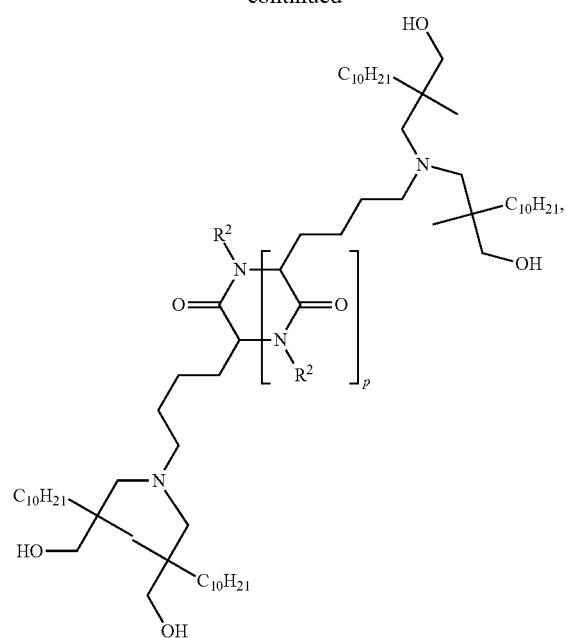
110
-continued
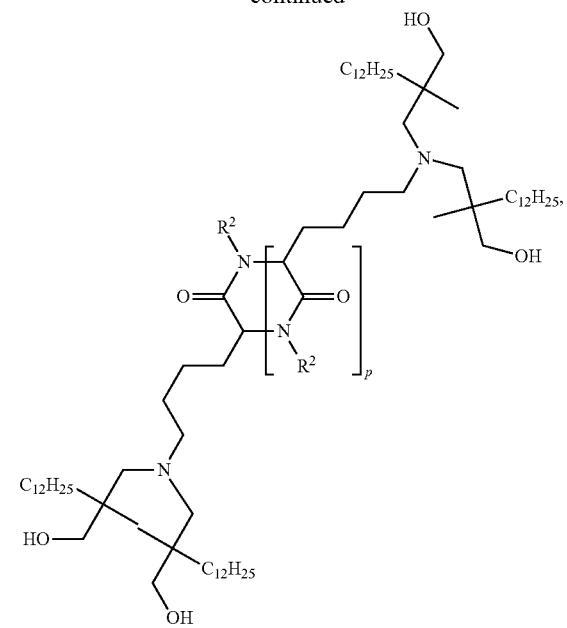

111
-continued
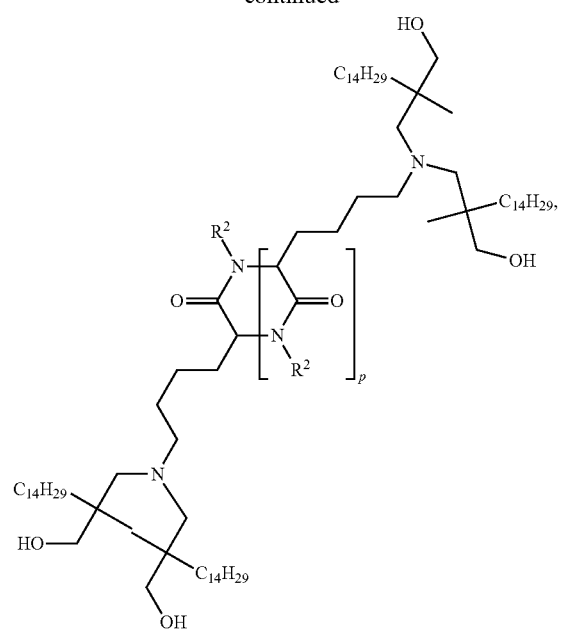
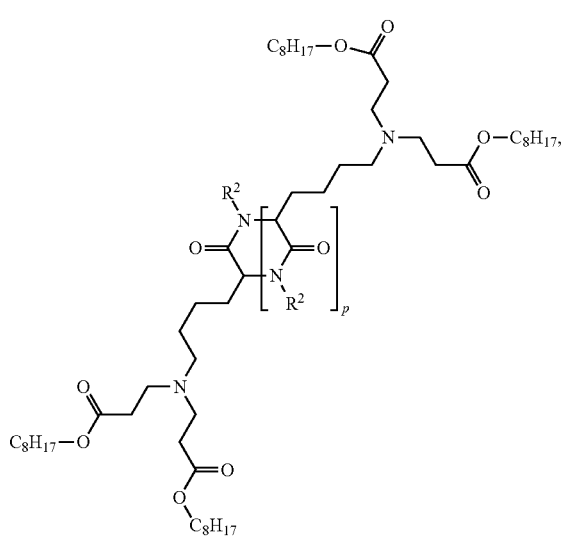
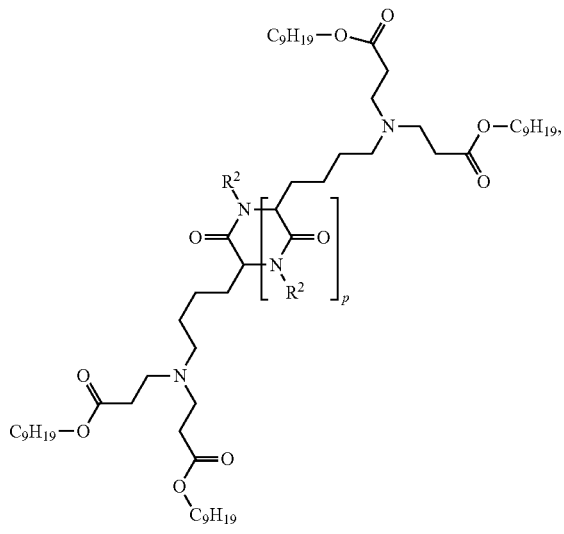
112
-continued
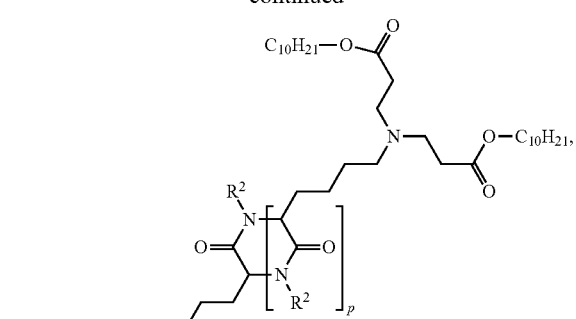
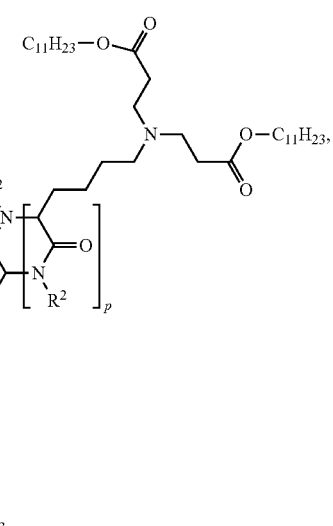
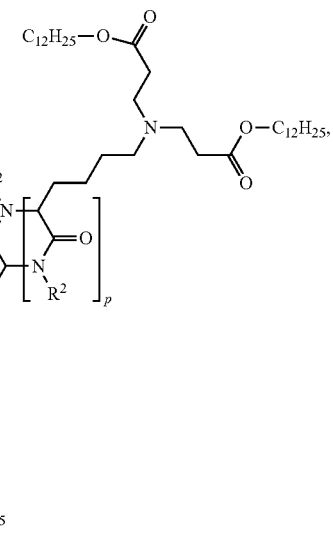

113
-continued
114
-continued
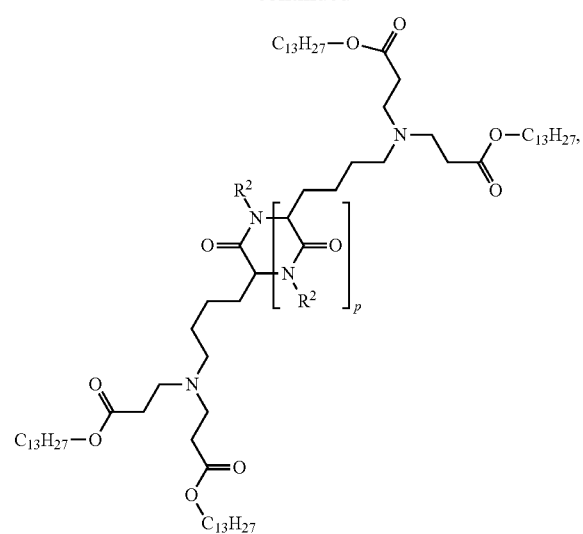
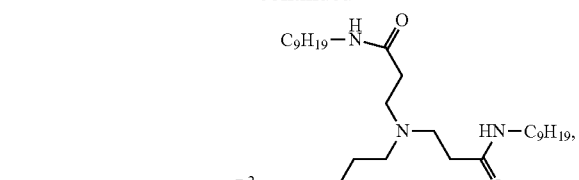
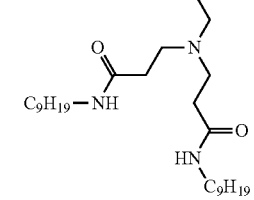
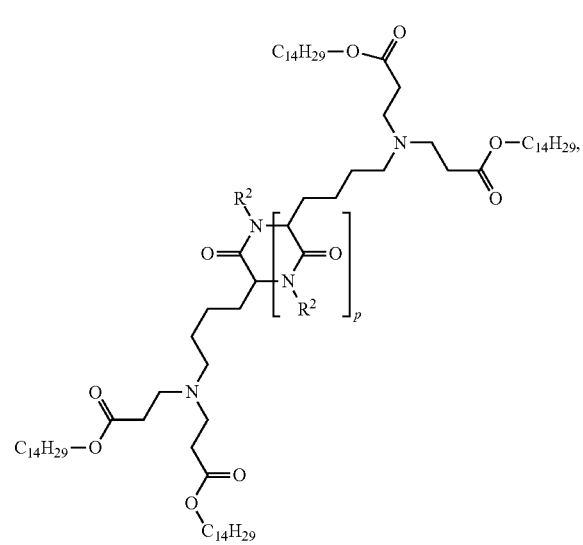
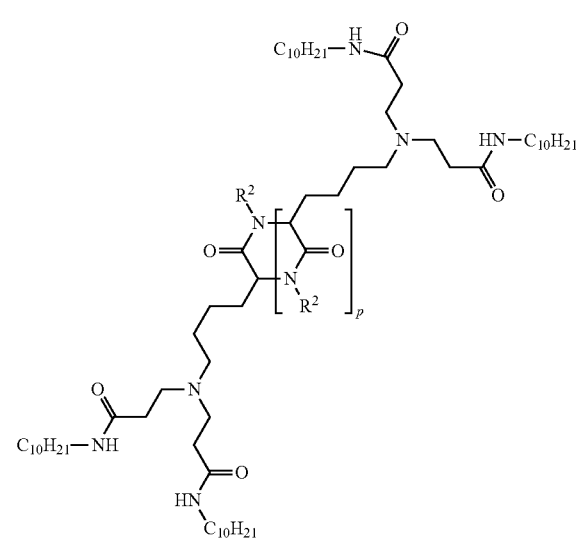
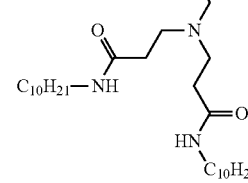
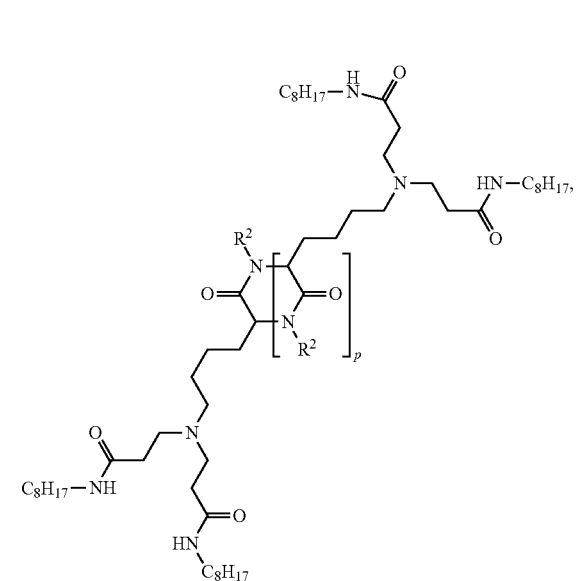
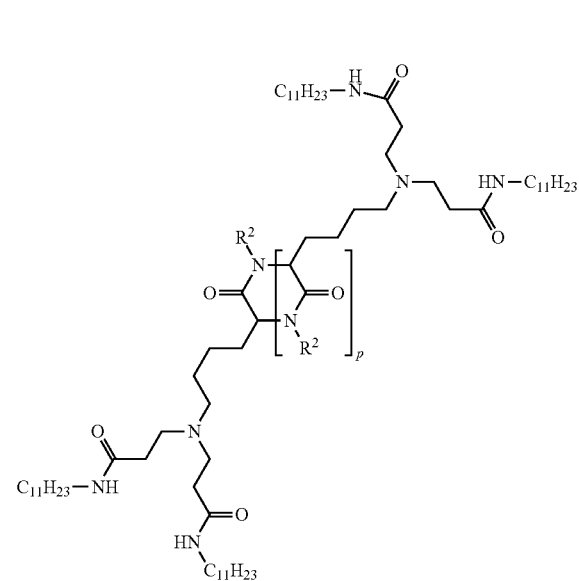
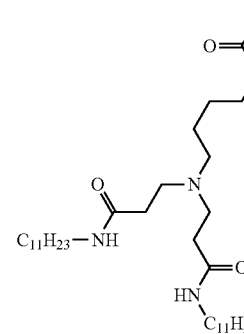

115
-continued
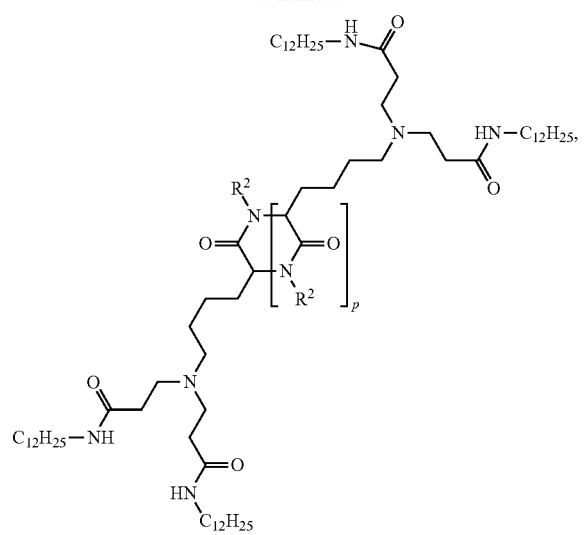
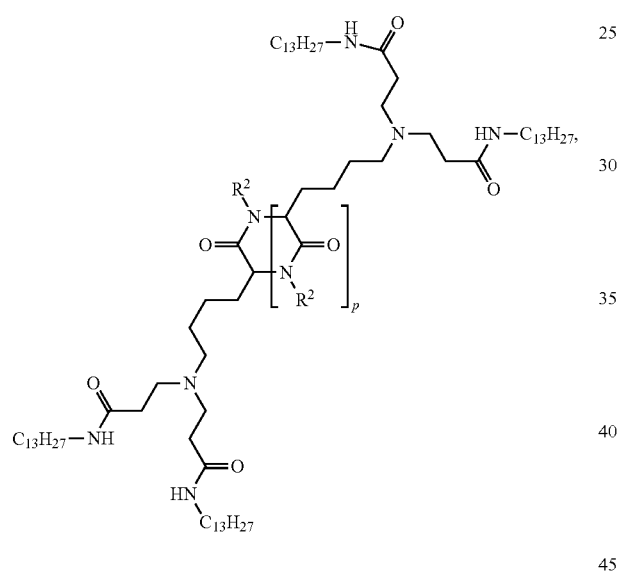
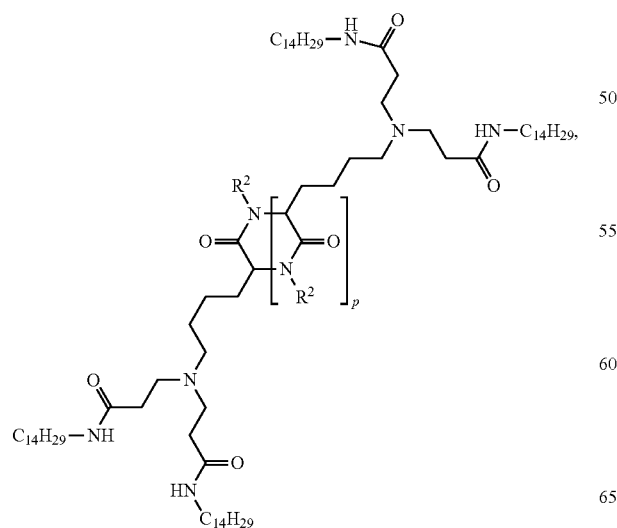
116
-continued
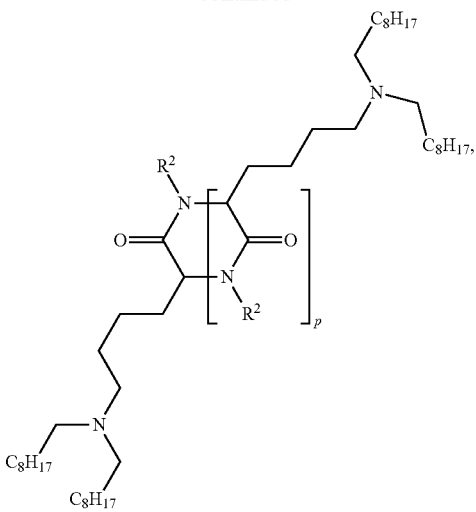
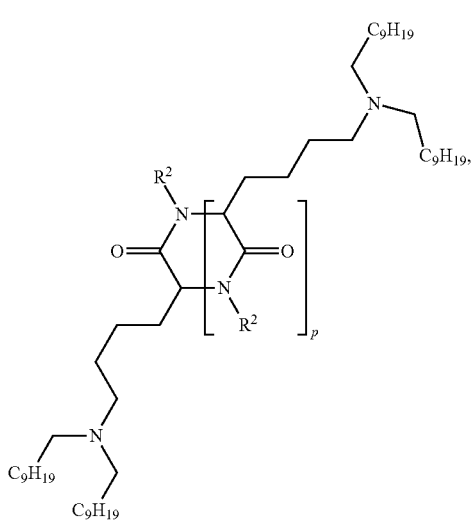
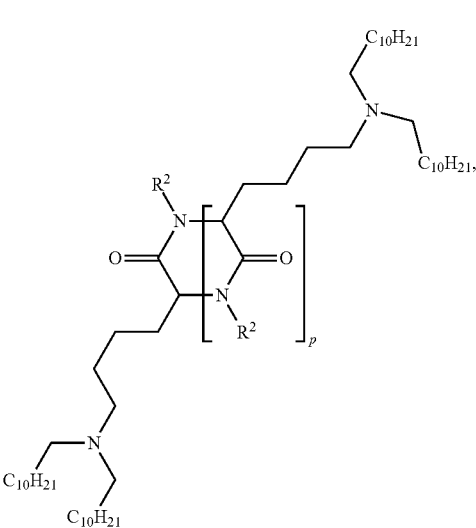

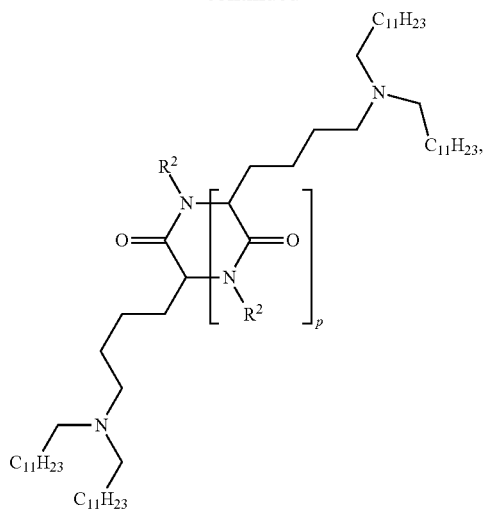

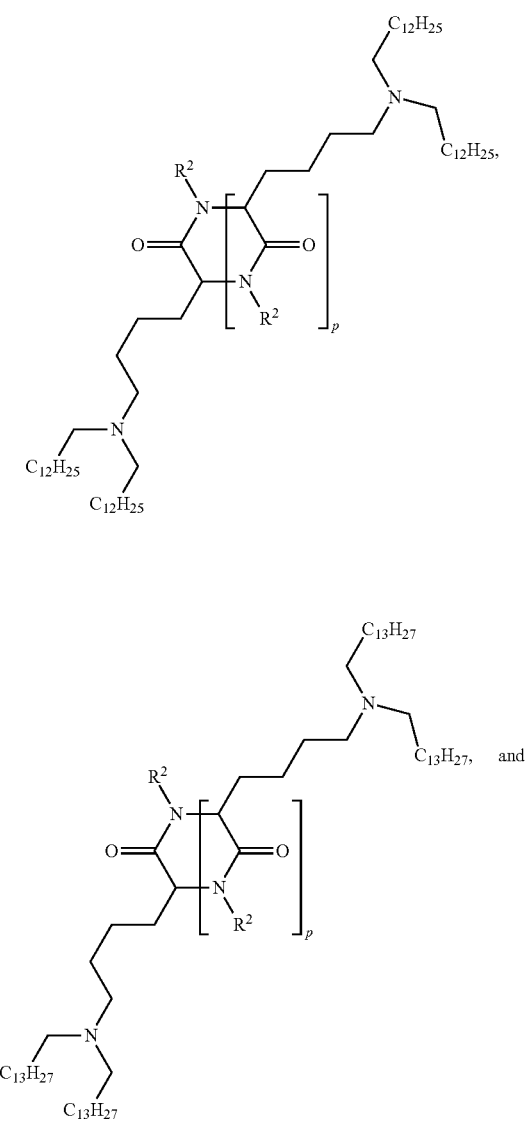

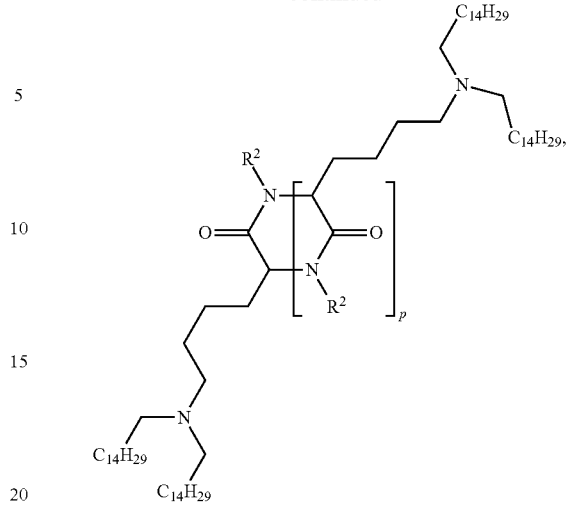

and salts thereof.

Compositions

The present invention contemplates an APPL as a component of a composition. For example, in certain embodiments, provided is a composition comprising an APPL, or salt thereof, and an excipient, wherein the APPL is an amino acid, a linear or cyclic peptide, or a linear or cyclic polypeptide, or structural isomer thereof, and wherein an amino or amide group of the APPL is conjugated to a group of formula (i), (ii), or (iii). In certain embodiments, the group of formula (i), (ii), or (iii) is attached to an amino group present on the APPL scaffold.

Compositions, as described herein, comprising an APPL and an excipient of some sort may be useful in a variety of medical and non-medical applications. For example, pharmaceutical compositions comprising an APPL and an excipient may be useful in the delivery of an effective amount of an agent to a subject in need thereof. Nutraceutical compositions comprising an APPL and an excipient may be useful in the delivery of an effective amount of a nutraceutical, e.g., a dietary supplement, to a subject in need thereof. Cosmetic compositions comprising an APPL and an excipient may be formulated as a cream, ointment, balm, paste, film, or liquid, etc., and may be useful in the application of make-up, hair products, and materials useful for personal hygiene, etc. Compositions comprising an APPL and an excipient may be useful for non-medical applications, e.g., such as an emulsion or emulsifier, useful, for example, as a food component, for extinguishing fires, for disinfecting surfaces, for oil cleanup, etc.

Peptides play significant roles in endogenous cellular signaling and trafficking pathways, and offer tremendous potential in leveraging such interactions to enhance the delivery efficiency of systems which incorporate peptide moieties. Thus, compositions comprising an APPL and an excipient may further be useful in bioprocessing, such as a cell's bioprocessing of a commercially useful chemical or fuel. For example, intracellular delivery of the APPL or an agent complexed thereto may be useful in bioprocessing by maintaining the cell's health and/or growth, e.g., in the manufacturing of proteins.

The composition may comprise one type of APPL but may also comprise any number of different types of APPLs, e.g., 1, 2, 3, 4, 5, 6, 7, 8, 9, 10 or more different types of APPLs.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA. In certain embodiments, the polynucleotide and the one or more APPLs are not covalently attached.

In certain embodiments, the one or more APPLs are in the form of a particle. In certain embodiments, the particle is a nanoparticle or microparticle. In certain embodiments, the one or more APPLs are in the form of liposomes or micelles. It is understood that, in certain embodiments, these APPLs self-assemble to provide a particle, micelle, or liposome. In certain embodiments, the particle, micelle, or liposome encapsulates an agent. The agent to be delivered by the particle, micelle, or liposome may be in the form of a gas, liquid, or solid. The APPLs may be combined with polymers (synthetic or natural), surfactants, cholesterol, carbohydrates, proteins, lipids etc. to form the particles. These particles may be further combined with an excipient to form the composition.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may comprise a phospholipid. Exemplary phospholipids include, but are not limited to, disteroylphosphatidylcholine (DSPC), dimyristoylphosphatidylcholine (DMPC), Dipalmitoylphosphatidylcholine (DPPC), and dioleoyl-sn-glycero-3-phosphocholine (DOPC), 1,2-Dilauroyl-sn-Glycero-3-Phosphocholine (dilauroylphosphatidylcholine, DLPC), 1,2-Dimyristoyl-sn-Glycero-3-Phosphocholine (dimyristoylphosphatidylcholine, DMPC), 1,2-Dipentadecanoyl-sn-Glycero-3-Phosphocholine (dipentadecanoylphosphatidylcholine, DPDPC), 1,2-dipalmitoyl-sn-Glycero-3-Phosphocholine (dipalmitoylphosphatidylcholine, DPPC), 1-Myristoyl-2-Palmitoyl-sn-Glycero-3-Phosphocholine (1-myristoyl-2-palmitoylphosphatidylcholine, MPPC), 1,2-Dimyristoyl-sn-Glycero-3-[Phospho-rac-(1-glycerol)] (DMPG), and 1,2-Dimyristoyl-3-Trimethylammonium-propane.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, poly(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms*. Mol Ther. 18(7): p. 1357-64. In certain embodiments, the apolipoprotein is ApoA, ApoB, ApoC, ApoE, or ApoH, or an isoform thereof.

Liquid compositions include emulsions, microemulsions, solutions, suspensions, syrups, and elixirs. In addition to the APPL, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The APPL is admixed with an excipient and any needed preservatives or buffers as may be required. Ophthalmic formulation, ear drops, and eye drops are also contemplated as being within the scope of this invention.

The ointments, pastes, creams, and gels may contain, in addition to the APPL, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the APPL, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

Agents

Agents to be delivered by the systems described herein may be therapeutic, diagnostic, or prophylactic agents. Any chemical compound to be administered to a subject may be delivered using the complexes, picoparticles, nanoparticles, microparticles, micelles, or liposomes, described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc.

In certain embodiments, the agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents

Since it is often desirable to target a particular cell, collection of cells, or tissue, an APPL, and the complexes, liposomes, micelles, microparticles, picoparticles and nanoparticles, prepared therefrom, may be modified to include targeting agents or targeting regions. For example, the APPL scaffold may include a targeting region. A variety of agents or regions that target particular cells are known in the art. See, e.g., Cotten et al., *Methods Enzym.* 217:618, 1993. The targeting agents may be included throughout the particle or may be only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Polynucleotide Complexes

The present invention contemplates APPLs are particularly useful in the administration of polynucleotides. For example, APPLs comprise secondary or tertiary amines, and, although these amines are hindered, they are available to non-covalently interact with a polynucleotide (e.g., DNA, RNA, synthetic analogs of DNA and/or RNA, DNA/RNA hydrids, etc.). Polynucleotides or derivatives thereof are contacted with an APPL under conditions suitable to form a polynucleotide/APPL non-covalent complex. The interaction of the APPL with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive $\zeta$-potential. In certain embodiments the $\zeta$-potential is between 0 and +30.

In one aspect, provided is a method of delivering a polynucleotide to a biological cell, comprising providing a composition comprising an APPL, or salt thereof, and a polynucleotide; and exposing the composition to the biological cell under conditions sufficient to facilitate delivery of the polynucleotide into the interior of the biological cell; wherein the APPL is an amino acid, a linear or cyclic peptide, or a linear or cyclic polypeptide, or structural isomer thereof, wherein an amino or amide group of the APPL is conjugated to a group of formula (i), (ii), or (iii). In certain embodiments, the method is an in vivo method. In certain embodiments, the method is an in vitro method.

An APPL may be at least partially provided as a salt (e.g., is protonated) so as to form a complex with the negatively charged polynucleotide. In certain embodiments, the polynucleotide/APPL complex form particles that are useful in the delivery of polynucleotides to cells. In certain embodiments, more than one APPL may be associated with a polynucleotide molecule. For example, the complex may include 1-100 APPLs, 1-1000 APPLs, 10-1000 APPLs, or 100-10,000 APPLs associated with a polynucleotide molecule.

Increasing nitrogen:phosphate ratios have been shown to positively influence delivery of genetic material by increasing nucleic acid binding and negatively influence delivery by increasing toxicity. See, e.g., Incani et al., *Soft Matter* (2010) 6:2124-2138. In certain embodiments, the nitrogen: phosphate ratio (i.e., the ratio between the amino groups present in the APPL, and the phosphate groups present in the polynucleotide) is between about 10:1 to about 50:1, inclusive. In certain embodiments, the nitrogen phosphate ratio is between about 10:1 to about 45:1, between about 15:1 to about 45:1, or between about 20:1 to about 40:1, inclusive. In certain embodiments, the APPL:polynucleotide mass ratio is between about 10:1 to about 20:1, inclusive. In certain embodiments, the APPL:polynucleotide mass ratio is about 15:1. In certain embodiments, the APPL:polynucleotide molar ratio is between about 10:1 to about 400:1, inclusive. In certain embodiments, the APPL:polynucleotide molar ratio is between about 10:1 to about 350:1, between about 15:1 to about 300:1, or between about 20:1 to about 250:1, inclusive.

In certain embodiments, the complex may form a particle. In certain embodiments, the diameter of the particles ranges from 10-500 micrometers. In certain embodiments, the diameter of the particles ranges from 10-1200 micrometers. In certain embodiments, the diameter of the particles ranges from 50-150 micrometers. In certain embodiments, the diameter of the particles ranges from 10-500 nm, in certain embodiments the diameter of the particles ranges from 10-1200 nm, and in certain embodiments from 50-150 nm. The particles may be associated with a targeting agent as described below. In certain embodiments, the diameter of the particles ranges from 10-500 pm, in certain embodiments the diameter of the particles ranges from 10-1200 pm, and in certain embodiments from 50-150 pm. The particles may be associated with a targeting agent as described below. The film architecture is precisely designed and can be controlled to 1 nm precision with a range from 1 to 150000 nm and with a definite knowledge of its molecular composition.

The polynucleotide may be complexed, encapsulated by an APPL, or included in a composition comprising an APPL. The polynucleotide may be any nucleic acid including, but not limited to, RNA and DNA. In certain embodiments, the polynucleotide is DNA. In certain embodiments, the polynucleotide is RNA. In certain embodiments, upon delivery of the RNA into a cell, the RNA is able to interfere with the expression of a specific gene in the biological cell.

In certain embodiments, the polynucleotide is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the polynucleotide is a dsRNA (double-stranded RNA). In certain embodiments, the polynucleotide is an siRNA (short interfering RNA). In certain embodiments, the polynucleotide is an shRNA (short hairpin RNA). In certain embodiments, the polynucleotide is an miRNA (micro RNA). Micro RNAs (miRNAs) are genomically encoded non-coding RNAs of about 21-23 nucleotides in length that help regulate gene expression, particularly during development. See, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189. In certain embodiments, the polynucleotide is an antisense RNA.

In certain embodiments, the polynucleotide may be provided as an antisense agent or RNA interference (RNAi). See, e.g., Fire et al., *Nature* 391:806-811, 1998. Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation. See, e.g., Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, dsRNA, siRNA, shRNA, miRNA, antisense RNA, and/or RNAi can be designed and/or predicted using one or more of a large number of available algorithms. To give but a few examples, the following resources can be utilized to design and/or predict polynucleotides: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online Gen- Script Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. In certain embodiments, the polynucleotide is greater than 50% pure, in certain embodiments greater than 75% pure, and in certain embodiments greater than 95% pure. The polynucleotide may be provided by any means known in the art. In certain embodiments, the polynucleotide has been engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides may be prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health. See, e.g., Allison *Dev. Biol. Stand.* 92:3-11, 1998; Unkeless et al., *Annu. Rev. Immunol.* 6:251-281, 1998; and Phillips et al., *Vaccine* 10:151-158, 1992.

The antigenic protein or peptides encoded by the polynucleotide may be derived from such bacterial organisms as *Streptococccus pneumoniae*, *Haemophilus influenzae*, *Staphylococcus aureus*, *Streptococcus pyrogenes*, *Corynebacterium diphtheriae*, *Listeria monocytogenes*, *Bacillus anthracis*, *Clostridium tetani*, *Clostridium botulinum*, *Clostridium perfringens*, *Neisseria meningitidis*, *Neisseria gonorrhoeae*, *Streptococcus mutans*, *Pseudomonas aeruginosa*, *Salmonella typhi*, *Haemophilus parainfluenzae*, *Bordetella pertussis*, *Francisella tularensis*, *Yersinia pestis*, *Vibrio cholerae*, *Legionella pneumophila*, *Mycobacterium tuberculosis*, *Mycobacterium leprae*, *Treponema pallidum*, *Leptospirosis interrogans*, *Borrelia burgdorferi*, *Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans*, *Histoplasma capsulatum*, *Candida albicans*, *Candida tropicalis*, *Nocardia asteroides*, *Rickettsia ricketsii*, *Rickettsia typhi*, *Mycoplasma pneumoniae*, *Chlamydial psittaci*, *Chlamydial trachomatis*, *Plasmodium falciparum*, *Trypanosoma brucei*, *Entamoeba histolytica*, *Toxoplasma gondii*, *Trichomonas vaginalis*, *Schistosoma mansoni*, and the like.

Particles

The present invention also contemplates APPLs useful as a delivery device. APPLs have several properties that make them particularly suitable for delivery, including: 1) the ability of an APPL to complex and "protect" labile agents; 2) the ability to buffer the pH in the endosome; 3) the ability to act as a "proton sponge" and cause endosomolysis; and 4) the ability to neutralize the charge on negatively charged agents.

In certain embodiments, an APPL is used to form particles containing the agent to be delivered. An APPL may be used to encapsulate agents including, but not limited to, organic molecules (e.g., cholesterol, drugs), inorganic molecules, nucleic acids, proteins, peptides, polynucleotides, targeting agents, isotopically labeled organic or inorganic molecules, vaccines, immunological agents, etc. Other exemplary agents are described in greater detail herein. These particles may include other materials such as polymers (e.g., synthetic polymers (e.g., PEG, PLGA), natural polymers (e.g., phospholipids)). In certain embodiments, the APPL is mixed with one or more agents (e.g., cholesterol) and/or one or more other materials (e.g., polymers).

In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

The particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

Micelles and Liposomes

The present invention further contemplates use of APPLs in the preparation of micelles or liposomes. Any agent may be further included in a micelle or liposome. Micelles and liposomes are particularly useful in delivering hydrophobic agents such as hydrophobic small molecules. When the micelle or liposome is complexed with (e.g., encapsulates or covers) a polynucleotide it is also referred to as a "lipoplex." Many techniques for preparing micelle and liposomes are known in the art, and any such method may be used with an APPL to make micelles and liposomes.

In certain embodiments, liposomes are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein. The preparation of liposomes involves preparing the APPL for hydration, hydrating the APPL with agitation, and sizing the vesicles to achieve a homogenous distribution of liposomes. APPLs are first dissolved in an organic solvent to assure a homogeneous mixture of the APPL. The solvent is then removed to form a polymer-derived film. This polymer-derived film is thoroughly dried to remove residual organic solvent by placing the vial or flask on a vacuum pump overnight. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm. In certain embodiments, the amount of APPL in the liposome ranges from 30-80 mol %, in certain embodiments 40-70 mol %, and in certain embodiments 60-70 mol %. In certain embodiments, the APPL employed further complexes an agent, such as DNA and RNA. In such embodiments, the application of the liposome is the delivery of polynucleotides.

The following scientific papers described other methods for preparing liposomes and micelles: Narang et al., "Cationic Lipids with Increased DNA Binding Affinity for Nonviral Gene Transfer in Dividing and Nondividing Cells" *Bioconjugate Chem.* 16:156-68, 2005; Hofland et al., "Formation of stable cationic lipid/DNA complexes for gene transfer" *Proc. Natl. Acad. Sci. USA* 93:7305-7309, July 1996; Byk et al., "Synthesis, Activity, and Structure-Activity Relationship Studies of Novel Cationic Lipids for DNA Transfer" *J. Med. Chem.* 41(2):224-235, 1998; Wu et al., "Cationic Lipid Polymerization as a Novel Approach for Constructing New DNA Delivery Agents" *Bioconjugate Chem.* 12:251-57, 2001; Lukyanov et al., "Micelles from lipid derivatives of water-soluble polymers as delivery systems for poorly soluble drugs" *Advanced Drug Delivery Reviews* 56:1273-1289, 2004; Tranchant et al., "Physicochemical optimisation of plasmid delivery by cationic lipids" *J. Gene Med.* 6:S24-S35, 2004; van Balen et al., "Liposome/Water Lipophilicity: Methods, Information Content, and Pharmaceutical Applications" *Medicinal Research Rev.* 24(3):299-324, 2004.

Treatment Methods

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A., et al., *Therapeutic siRNAs for dominant genetic skin disorders including pachyonychia congenita*. J Dermatol Sci, 2008. 51(3): p. 151-7. Many of these diseases are fatal, such as cancer, severe hypercholesterolemia, and familial amyloidotic polyneuropathy. See, e.g., Frank-Kamenetsky, M., et al., *Therapeutic RNAi targeting PCSK9 acutely lowers plasma cholesterol in rodents and LDL cholesterol in nonhuman primates*. Proc Natl Acad Sci USA, 2008. 105(33): p. 11915-20; Coelho, T., *Familial amyloid polyneuropathy: new developments in genetics and treatment*. Curr Opin Neurol, 1996. 9(5): p. 355-9. Since the discovery of gene expression silencing via RNA interference (RNAi) by Fire and Mello (Fire, A., et al., *Potent and specific genetic interference by double-stranded RNA in Caenorhabditis elegans*. Nature, 1998. 391(6669): p. 806-11), there has been extensive effort toward developing therapeutic applications for RNAi in humans. See, e.g., Davis, M. E., *The first targeted delivery of siRNA in humans via a self-assembling, cyclodextrin polymer-based nanoparticle: from concept to clinic*. Mol Pharm, 2009. 6(3): p. 659-68; Whitehead, K. A., R. Langer, and D. G. Anderson, *Knocking down barriers: advances in siRNA delivery*. Nat. Rev. Drug Discovery, 2009. 8(2): p. 129-138; Tan, S. J., et al., *Engineering Nanocarriers for siRNA Delivery*. Small. 7(7): p. 841-56; Castanotto, D. and J. J. Rossi, *The promises and pitfalls of RNA-interference-based therapeutics*. Nature, 2009. 457(7228): p. 426-33; Chen, Y. and L. Huang, *Tumor-targeted delivery of siRNA by non-viral vector: safe and effective cancer therapy*. Expert Opin Drug Deliv, 2008. 5(12): p. 1301-11; Weinstein, S. and D. Peer, *RNAi nanomedicines: challenges and opportunities within the immune system*. Nanotechnology. 21(23): p. 232001; Fenske, D. B. and P. R. Cullis, *Liposomal nanomedicines*. Expert Opin Drug Deliv, 2008. 5(1): p. 25-44; and Thiel, K. W. and P. H. Giangrande, *Therapeutic applications of DNA and RNA aptamers*. Oligonucleotides, 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Current progress of siRNA/shRNA therapeutics in clinical trials*. Biotechnol J. 6(9): p. 1130-46. However, the efficient and safe delivery of siRNA is still a key challenge in the development of siRNA therapeutics. See, e.g., Juliano, R., et al., *Biological barriers to therapy with antisense and siRNA oligonucleotides*. Mol Pharm, 2009. 6(3): p. 686-95.

Thus, in another aspect, provided are methods of using APPLs, e.g., for the treatment of a disease, disorder or condition from which a subject suffers. It is contemplated that APPLs will be useful in the treatment of a variety of diseases, disorders, or conditions, especially a system for delivering agents useful in the treatment of that particular disease, disorder, or condition. "Disease," "disorder," and "condition" are used interchangeably herein. In certain embodiments, the disease, disorder or condition from which a subject suffers is caused by an abnormality in a gene or chromosome of the subject.

For example, in one embodiment, provided is a method of treating disease, disorder, or condition from which a subject suffers, comprising administering to a subject in need thereof an effective amount of a composition comprising an APPL, or salt thereof. Exemplary disease, disorder, or conditions contemplated include, but are not limited to, proliferative disorders, inflammatory disorders, autoimmune disorders, painful conditions, liver diseases, and amyloid neuropathies.

As used herein, an "active ingredient" is any agent which elicits the desired biological response. For example, the APPL may be the active ingredient in the composition. Other agents, e.g., therapeutic agents, as described herein may also be classified as an active ingredient. In certain embodiments, the composition further comprises, in addition to the APPL, a therapeutic agent useful in treating the disease, disorder, or condition. In certain embodiments, the APPL encapsulates the other (therapeutic) agent. In certain embodiments, the APPL and the other (therapeutic) agent form a particle (e.g., a nanoparticle, a microparticle, a micelle, a liposome, a lipoplex).

In certain embodiments, the condition is a proliferative disorder and, in certain embodiments, the composition further includes an anti-cancer agent. Exemplary proliferative diseases include, but are not limited to, tumors, begnin neoplasms, pre-malignant neoplasms (carcinoma in situ), and malignanat neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/

SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemiallymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the condition is an inflammatory disorder and, in certain embodiments, the composition further includes an anti-inflammatory agent. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, sclerodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the condition is a painful condition and, in certain embodiments, the composition further includes an analgesic agent. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is inflammatory pain. In certain embodiments, the painful condition (e.g., inflammatory pain) is associated with an inflammatory disorder and/or an autoimmune disorder.

In certain embodiments, the condition is a liver disease and, in certain embodiments, the composition further includes an agent useful in treating liver disease. Exemplary liver diseases include, but are not limited to, drug-induced liver injury (e.g., acetaminophen-induced liver injury), hepatitis (e.g., chronic hepatitis, viral hepatitis, alcohol-induced hepatitis, autoimmune hepatitis, steatohepatitis), non-alcoholic fatty liver disease, alcohol-induced liver disease (e.g., alcoholic fatty liver, alcoholic hepatitis, alcohol-related cirrhosis), hypercholesterolemia (e.g., severe hypercholesterolemia), transthyretin-related hereditary amyloidosis, liver cirrhosis, liver cancer, primary biliary cirrhosis, cholestatis, cystic disease of the liver, and primary sclerosing cholangitis. In certain embodiments the liver disease is associated with inflammation.

In certain embodiments, the condition is a familial amyloid neuropathy and, in certain embodiments, the composition further includes an agent useful in a familial amyloid neuropathy.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); and commercially relevant mammals such as mice, rats, hamsters, cattle, pigs, horses, sheep, goats, cats, and/or dogs] and birds (e.g., commercially relevant birds such as chickens, ducks, geese, and/or turkeys). In certain embodiments, the subject is a non-human animal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of an active ingredient refers to an amount sufficient to elicit the desired biological response. As will be appreciated by those of ordinary skill in this art, the effective amount of a compound of the invention may vary depending on such factors as the desired biological endpoint, the pharmacokinetics of the active ingredient, the disease being treated, the mode of administration, and the age, health, and condition of the subject. An effective amount encompasses therapeutic and prophylactic treatment.

As used herein, and unless otherwise specified, a "therapeutically effective amount" of an active ingredient is an amount sufficient to provide a therapeutic benefit in the treatment of a disease, disorder or condition, or to delay or minimize one or more symptoms associated with the disease, disorder or condition. A therapeutically effective amount of an active ingredient means an amount of the active ingredient, alone or in combination with other agents or therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of an active ingredient is an amount sufficient to prevent a disease, disorder or condition, or one or more symptoms associated with the disease, disorder or condition, or prevent its recurrence. A prophylactically effective amount of an active ingredient means an amount of the active ingredient, alone or in combination with other agents or therapies, which provides a prophylactic benefit in the prevention of the disease, disorder or condition. The term "prophylactically effective amount" can encompass an amount that improves overall prophylaxis or enhances the prophylactic efficacy of another prophylactic agent.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the APPL itself, or the APPL in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

In order that the invention described herein may be more fully understood, the following examples are set forth. It should be understood that these examples are for illustrative purposes only and are not to be construed as limiting this invention in any manner.

Amino Acid-, Peptide-, and Polypeptide-Lipids (APPL) for Drug Delivery

To address the challenges associated with delivery efficiency, specificity, and toxicity of biological agents, we developed a potent and selective siRNA delivery system with a broad therapeutic window through rational design and optimization of novel amino acid-based lipid derivatives.

Previously, our group has pursued a combinatorial synthetic approach to develop new cationic lipids (lipidoids) for siRNA delivery. See, e.g., Akinc, A., et al., *A combinatorial library of lipid-like materials for delivery of RNAi therapeutics*. Nat Biotechnol, 2008. 26(5): p. 561-9; Love Kevin, T., et al., *Lipid-like materials for low-dose, in vivo gene silencing*. Proc Natl Acad Sci USA. 107(5): p. 1864-9; Siegwart, D. J., et al., *Combinatorial synthesis of chemically diverse core-shell nanoparticles for intracellular delivery*. Proc Natl Acad Sci USA. 108(32): p. 12996-3001. A number of these compounds have shown significant silencing effects in vivo. See, e.g., Leuschner, F., et al., *Therapeutic siRNA silencing in inflammatory monocytes in mice*. Nat Biotechnol. 29(11): p. 1005-10. Prior studies have identified key chemical and structural features and formulation methods for the development of new materials. See, e.g., Akinc, A., et al., *Development of lipidoid-siRNA formulations for systemic delivery to the liver*. Mol Ther, 2009. 17(5): p. 872-9; Akinc, A., et al., *Targeted delivery of RNAi therapeutics with endogenous and exogenous ligand-based mechanisms*. Mol Ther. 18(7): p. 1357-64; Semple, S. C., et al., *Rational design of cationic lipids for siRNA delivery*. Nat Biotechnol. 28(2): p. 172-6. For example, active compounds possess 12 or more carbons in tail length and multiple tails. See, e.g., Love Kevin, T., et al., *Lipid-like materials for low-dose, in vivo gene silencing*. Proc Natl Acad Sci USA. 107(5): p. 1864-9. In order to improve efficacy, tissue and cell-type selectivity, and tolerability, new chemical scaffolds need to be designed and investigated.

Amino acids are natural building blocks of peptides and proteins in nature. Amino acid derivatives can be metabolized by the human body; therefore, these materials are likely well tolerated and safe as therapeutics. Additionally, peptides play significant roles in membrane transport, endogenous cellular signaling and trafficking pathways, and offer tremendous potential in leveraging such interactions to enhance the delivery efficiency of systems which incorporate peptide moieties. Because of their significant physiological functions and safety in humans, amino acid-based materials, such as insulin and trastuzumab, have been widely applied as supplements and therapeutic medicines in the clinic for diverse diseases. Studies have shown that it is feasible to apply amino acid-derivatives for gene delivery or siRNA delivery. See, e.g., Prata, C. A., et al., *Lipophilic peptides for gene delivery*. Bioconjug Chem, 2008. 19(2): p. 418-20; Adami, R. C., et al., *An amino acid-based amphoteric liposomal delivery system for systemic administration of siRNA*. Mol Ther. 19(6): p. 1141-51; Margus, H., K. Padari, and M. Pooga, *Cell-penetrating peptides as versatile vehicles for oligonucleotide delivery*. Mol Ther. 20(3): p. 525-33. Combining the advantages of both natural properties of amino acids and structural features of lipidoids, we applied a strategy of structural optimization through an iterative screening process and rationally designed a series of amino acid-based lipid derivatives. We report the design, synthesis, and biological evaluation of this new series of amino acid-based lipid derivatives. This efficient and rational strategy yielded a lead material cKK-E12. We systematically investigated its delivery efficiency, tissue and cell-type selectivity, tolerability, and mechanism of action. Current results demonstrate that this delivery system is a novel platform for efficient, selective, and safe delivery of siRNA, which shows great potential for the treatment of various diseases.

General Methods

Method 1. Preparation of Compounds of Formula (I)-(III). Conjugation to Formula (i)

A mixture of amino acids, peptides or polypeptides and the conjugating reagent (an epoxide, thiirane, or aziridine) (a ratio of 1.5:1 to 3:1 conjugating reagent to amine) in EtOH was irradiated in the microwave oven at 150° C. for 5 h. The reaction mixture was purified by flash column chromatography. If amino acids, peptides or polypeptides were in salt form, triethylamine was added to the solution and stirred for 30 minutes at room temperature before irradiation.

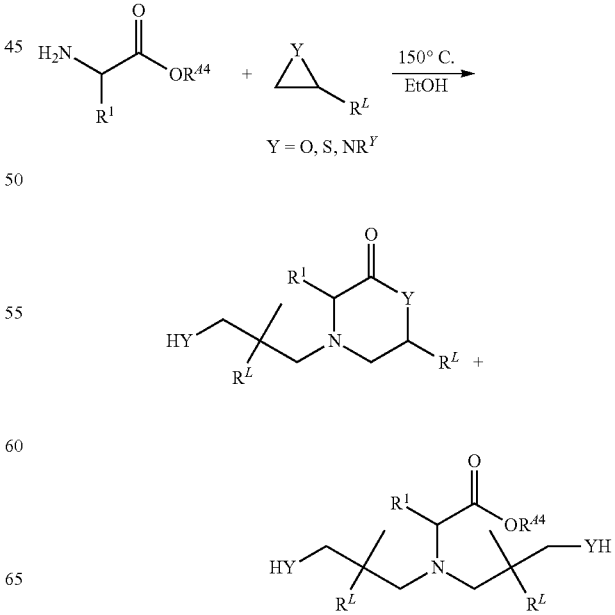

Scheme A.

Scheme B.
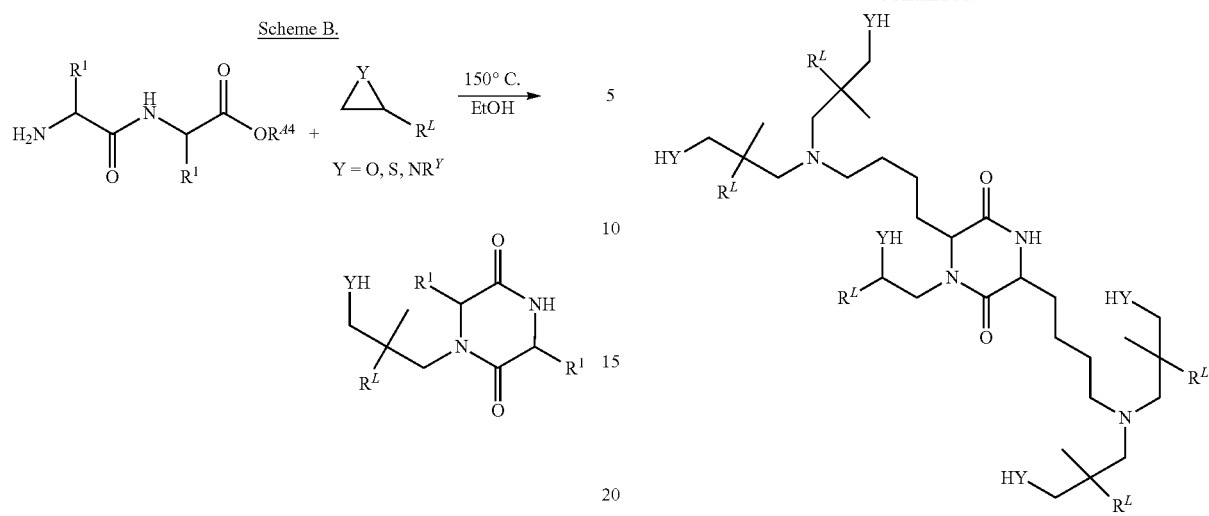
Scheme C.
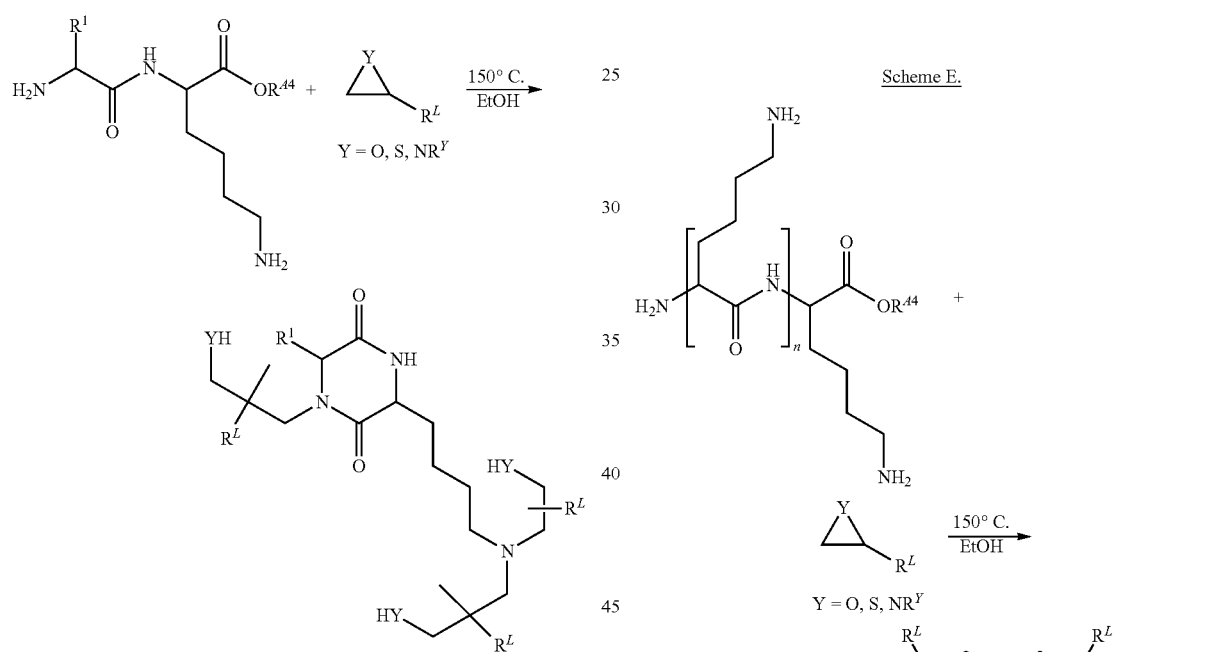
Scheme D.
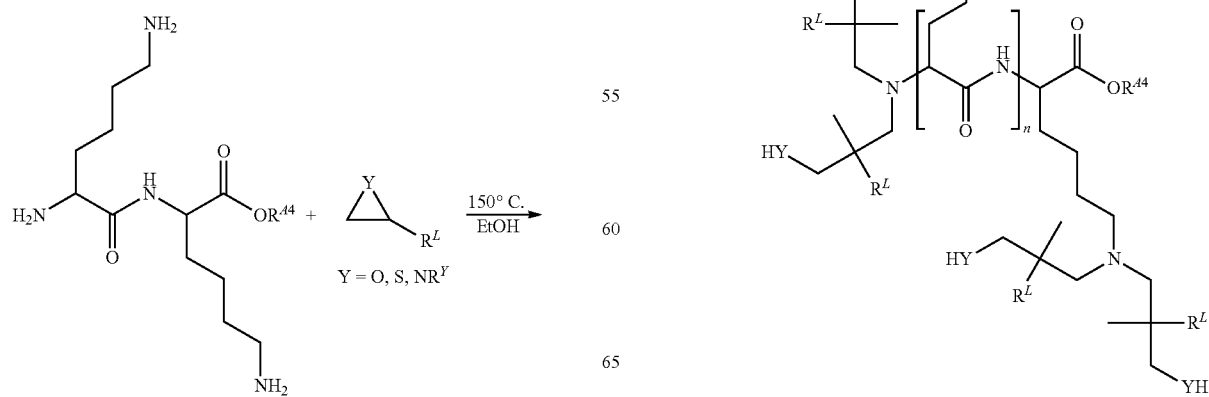
Scheme E.

Method 2. Preparation of Compounds of Formula (I)-(III). Conjugation to Formula (ii)

A mixture of amino acids, peptides or polypeptides and conjugating reagent (acrylate or acrylamide) (a ratio of 1.5:1 to 3:1 acrylates or conjugating reagent to amine) in ethanol (EtOH), isopropanol (iPrOH), or acetonitrile was heated to 90° C. and stirred for 2 hours to 2 days. The reaction solution was concentrated with silica gel and purified with flash column chromatography.

Scheme F.

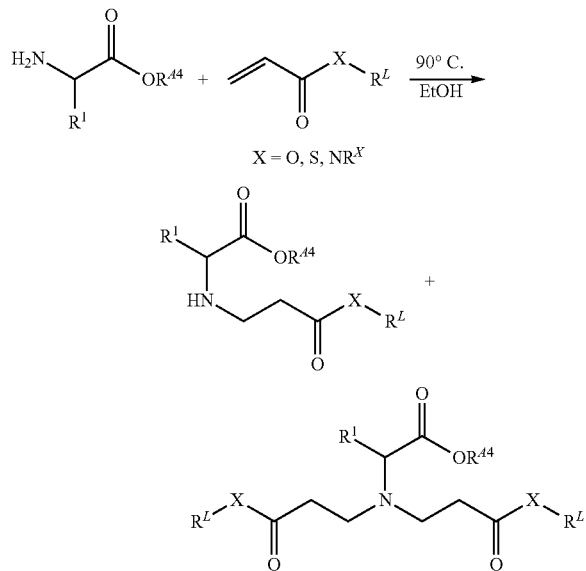

Scheme G.

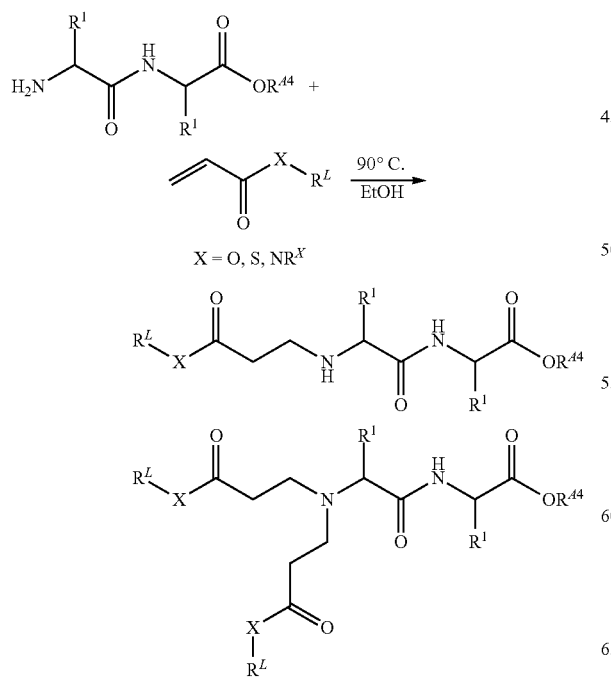

Scheme H.

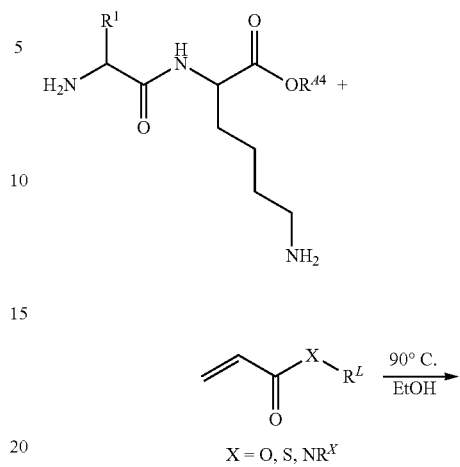

Scheme I.

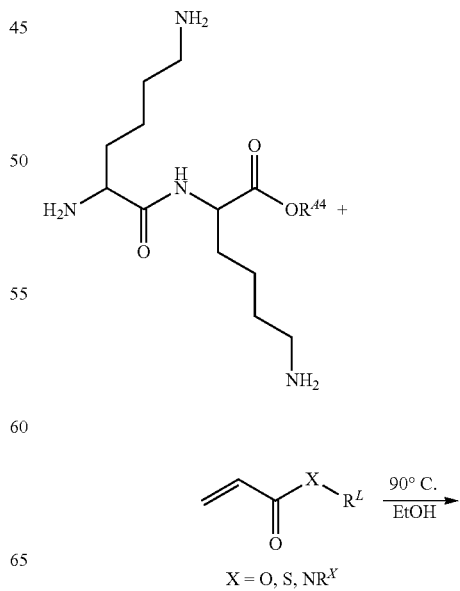

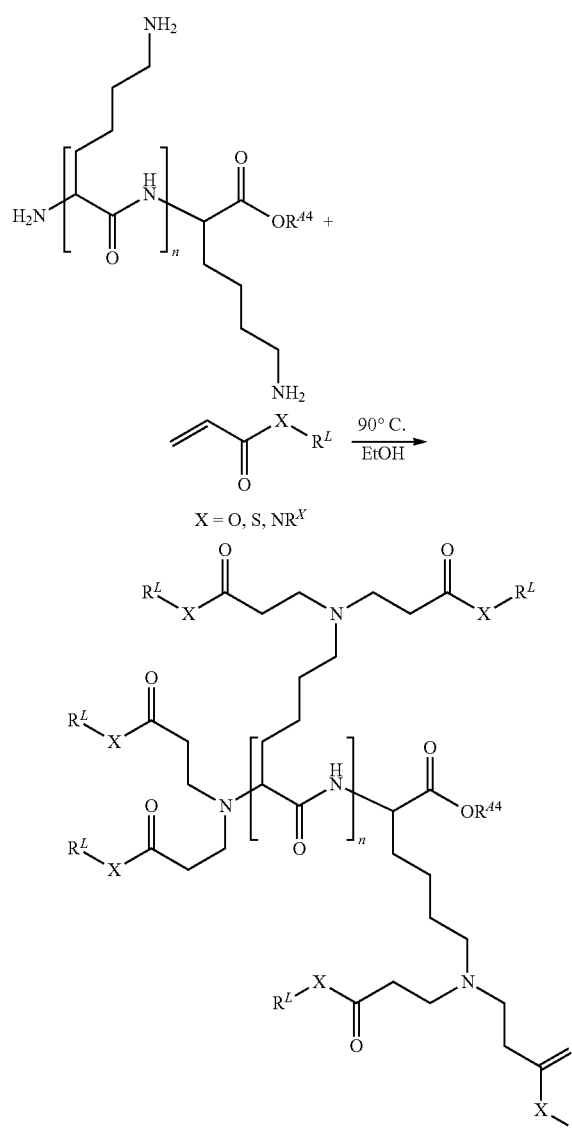

Method 3. Preparation of Compounds of Formula (I)-(III). Conjugation to Formula (iii)

To a solution of amino acids, peptides or polypeptides and conjugating reagent (aldehyde) (a ratio of 1.5:1 to 3:1 aldehydes to amine) in THF was added sodium triacetoxyborohydride (NaBH(OAc)$_3$) at rt. The reaction mixture was stirred for 3 d at rt. The reaction solution was concentrated with silica gel and purified with flash column chromatography.

Scheme K.

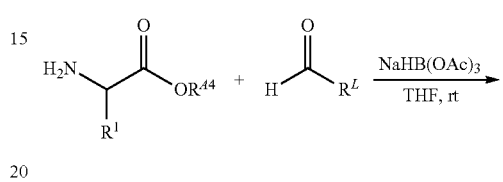

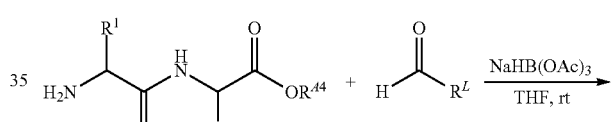

Scheme L.

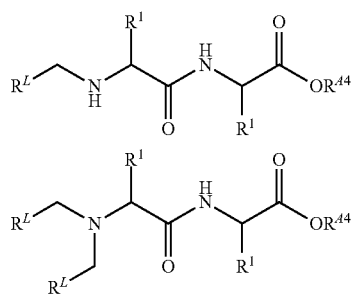

Scheme M.

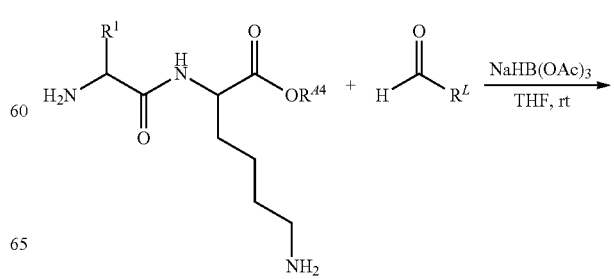

149
-continued

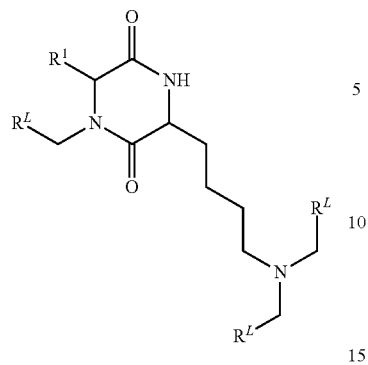

Scheme N.

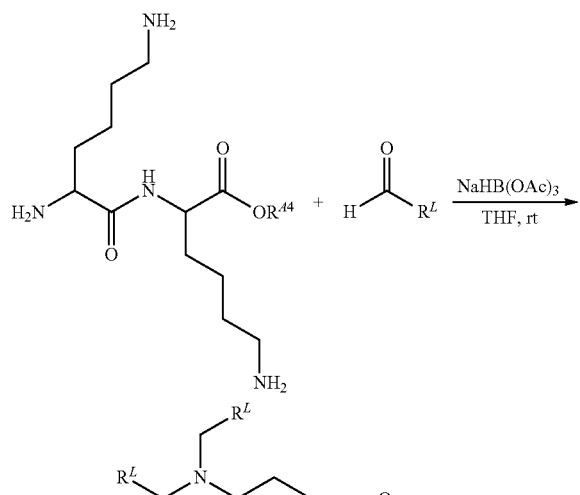

Scheme O.

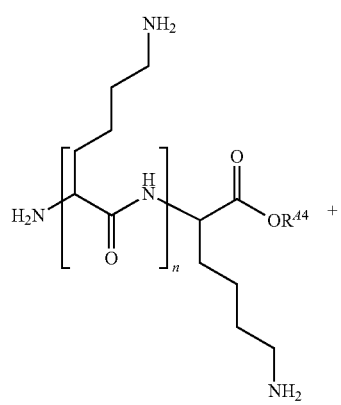

150
-continued

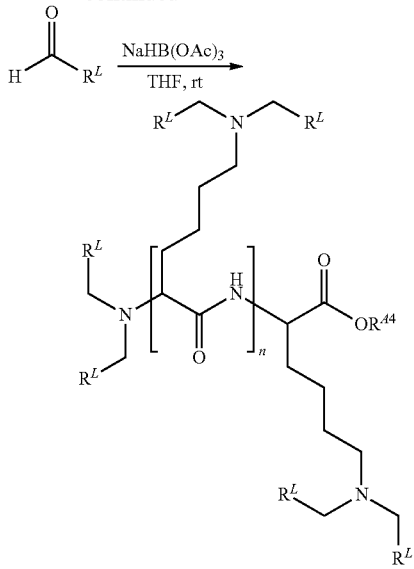

Method 4. Preparation of Compounds of Formula (IV)

Compounds of Formula (IV) may be prepared via condensation of a 1,2-diamine with an activated oxalic acid, wherein $X^1$ is a leaving group, e.g., bromo, chloro, or iodo, to provide the cyclized product. Groups of formula (i), (ii), or (iii), may be installed after cyclization, e.g., for example, via addition to an amino side chain substituent of $R^1$, or to imino nitrogen groups $R^Q$. Other groups on the scaffold, e.g., $R^2$ groups, may be installed prior to cyclization. For example, $R^2$ may be a group of the formula (i), (ii), or (iii) installed prior to cyclization.

Scheme P.

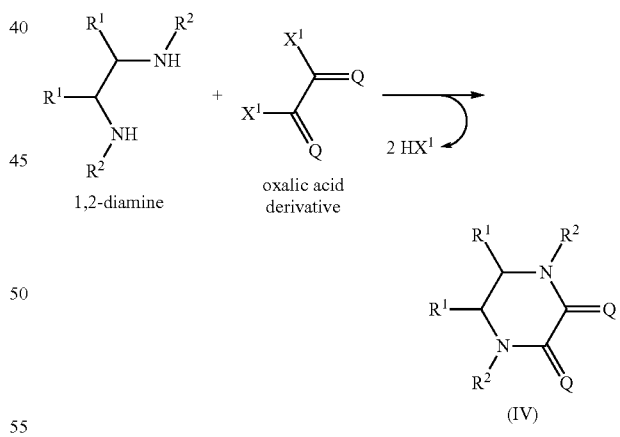

(IV)

Method 5. Preparation of Compounds of Formula (V)

Compounds of Formula (V), and (VI) may be prepared via condensation of a 1,1-diamine with an activated malonic acid, wherein $X^1$ is a leaving group, e.g., bromo, chloro, or iodo, to provide the cyclized product. Groups of formula (i), (ii), or (iii), may be installed after cyclization, e.g., for example, via addition to an amino side chain substituent of $R^1$, or to imino nitrogen groups $R^Q$. Other groups on the scaffold, e.g., $R^2$ groups, may be installed prior to cyclization. For example, $R^2$ may be a group of the formula (i), (ii), or (iii) installed prior to cyclization.

Scheme Q.

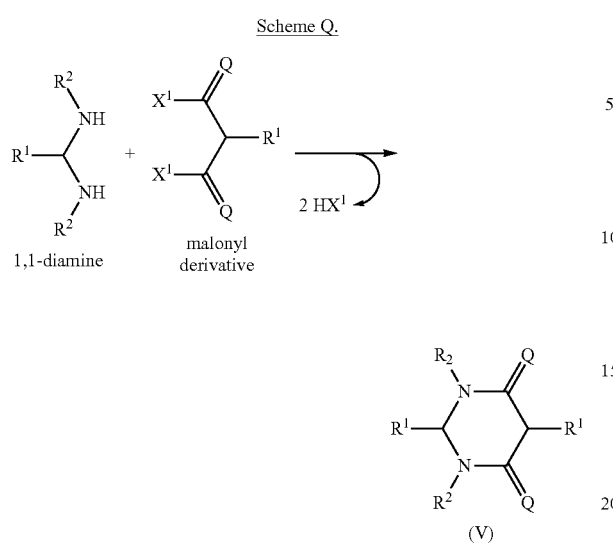

1,1-diamine + malonyl derivative → (V)

imino nitrogen groups $R^Q$. Other groups on the scaffold, e.g., $R^2$ groups, may be installed prior to cyclization. For example, $R^2$ may be a group of the formula (i), (ii), or (iii) installed prior to cyclization.

Scheme R.

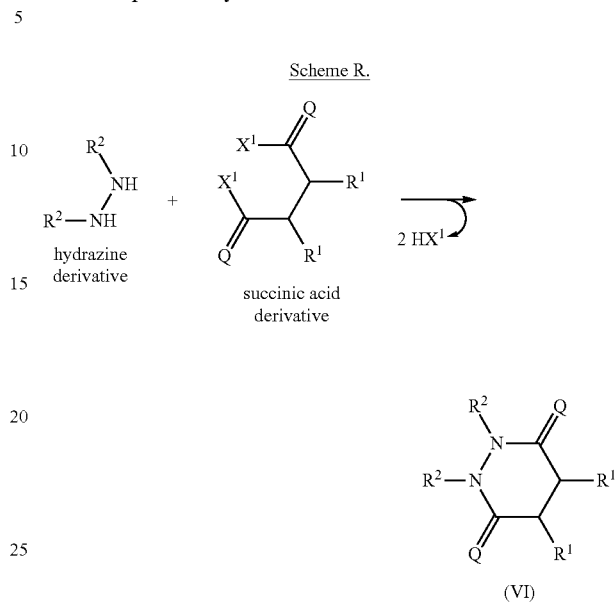

hydrazine derivative + succinic acid derivative → (VI)

Method 6. Preparation of Compounds of Formula (VI)

Compounds of Formula (VI) may be prepared via condensation of a hydrazine with an activated succinic acid, wherein $X^1$ is a leaving group, e.g., bromo, chloro, or iodo, to provide the cyclized product. Groups of formula (i), (ii), or (iii), may be installed after cyclization, e.g., for example, via addition to an amino side chain substituent of R, or to Exemplary Precursors

TABLE 1

| Amino Acids and Esters | | |
|---|---|---|
| Name, Symbol | Amino acid side chain ($R^1$)* | Amino acid or ester |
| Arginine R | 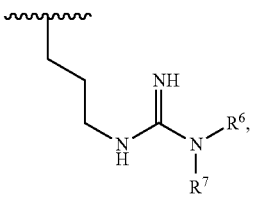 | 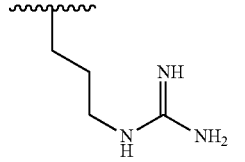 |
| Histidine H | 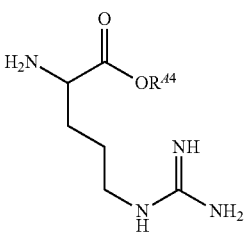 | 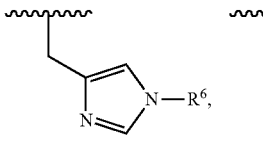 |

TABLE 1-continued
| Name, Symbol | | Amino acid side chain (R¹)* | | Amino acid or ester |
|---|---|---|---|---|
| Lysine | K | 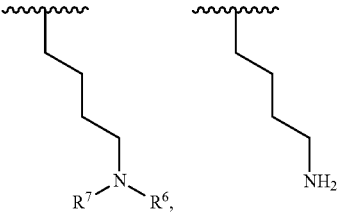 | 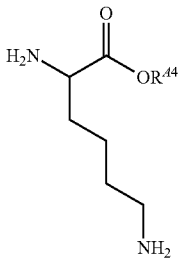 | 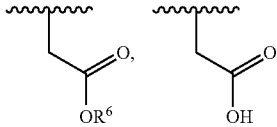 |
| Aspartic Acid | D | 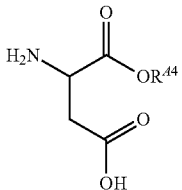 | | 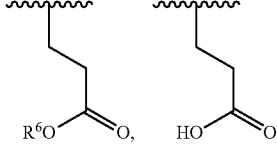 |
| Glutamic Acid | E | 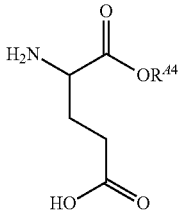 | | 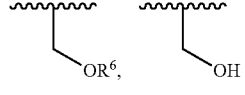 |
| Serine | S | 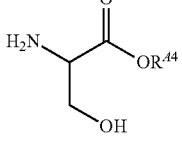 | | 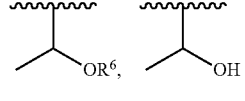 |
| Threonine | T | 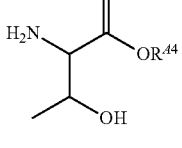 | | 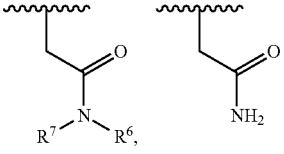 |
| Asparagine | N | 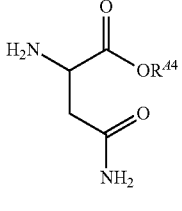 | | 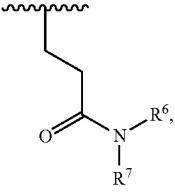 |
| Glutamine | Q | 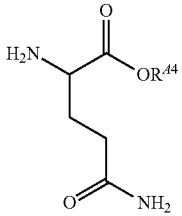 | | |

TABLE 1-continued
Amino Acids and Esters
| Name, Symbol | | Amino acid side chain (R$^1$)* | Amino acid or ester |
|---|---|---|---|
| Cysteine | C | 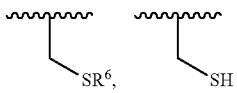 —SR$^6$, —SH | 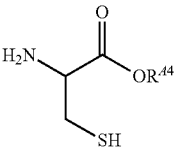 |
| Glycine | G | —H | 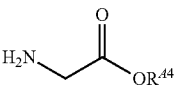 |
| Proline | P | 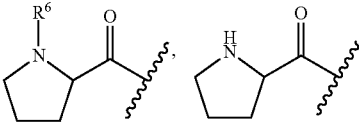<br>exemplary R$^1$-R$^3$ cyclized group | 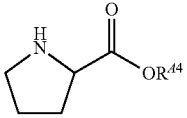 |
| Alanine | A | —CH$_3$ | 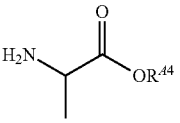 |
| Beta-alanine | | —H, H | 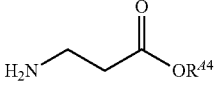 |
| Valine | V | —CH(CH$_3$)$_2$ | 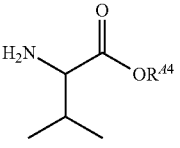 |
| Isoleucine | I | —CH(CH$_3$)(CH$_2$CH$_3$) | 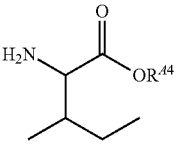 |
| Leucine | L | —CH$_2$CH(CH$_3$)$_2$ | 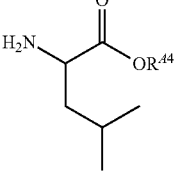 |
| Methionine | M | 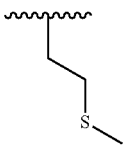 [SMILES: *CCSC] | 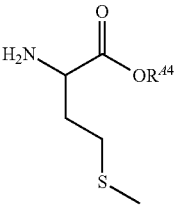 |

TABLE 1-continued

Amino Acids and Esters

| Name, Symbol | Amino acid side chain (R¹)* | Amino acid or ester |
|---|---|---|
| Phenylalanine F | 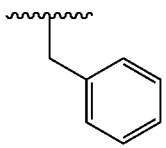 [SMILES: *Cc1ccccc1] | 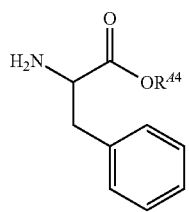 |
| Tyrosine Y | 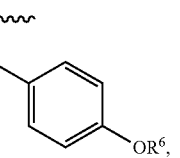 | 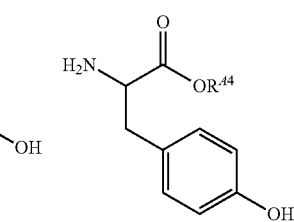 |
| Tryptophan W | 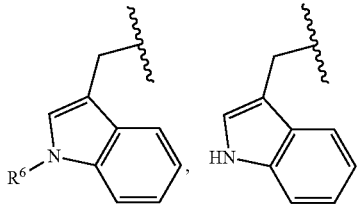 | 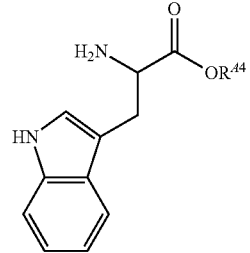 |

*$R^6$ and $R^7$ are hydrogen in the precursor, and, upon conjugation, are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

TABLE 2

Peptides and Polypeptides

| Name, Symbol | Amino acid |
|---|---|
| linear lysine-lysine | linear K-K |

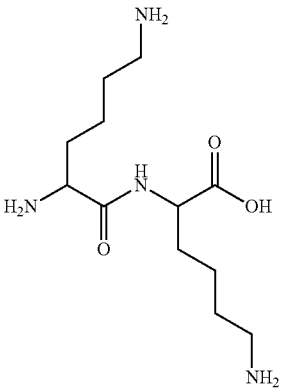

TABLE 2-continued

Peptides and Polypeptides

| Name, Symbol | | Amino acid |
|---|---|---|
| cyclic lysine-lysine | cyclic K-K | (structure of cyclic K-K diketopiperazine with two aminobutyl side chains) |
| polylysine | K-K-K | (structure of polylysine with $OR^{44}$ ester); n = 2 |
| | K-K-K-K (SEQ ID NO 3) | As above; n = 3 |
| | K-K-K-K-K (SEQ ID NO 4) | As above; n = 4 |
| polylysine (500-2000 g/mol) | K-(K)$_n$-K (SEQ ID NO 5) PK-500 | As above; n = 3-12 |
| polylysine (1000-5000 g/mol) | K-(K)$_n$-K (SEQ ID NO 6) PK-1000 | As above; n = 6-33 |
| polylysine (4000-15000 g/mol) | K-(K)$_n$-K (SEQ ID NO 7) PK4000 | As above; n = 26-102 |
| polylysine (15000-30000 g/mol) | K-(K)$_n$-K (SEQ ID NO 8) PK-15000 | As above; n = 102-204 |
| polylysine (30000-70000 g/mol) | K-(K)$_n$-K (SEQ ID NO 9) PK-30000 | As above; n = 204-480 |
| linear arginine-arginine | linear R-R | (structure of linear R-R dipeptide with $OR^{44}$ ester and two guanidino side chains) |

TABLE 2-continued
| Peptides and Polypeptides | | |
|---|---|---|
| Name, Symbol | | Amino acid |
| cyclic arginine-arginine | cyclic R-R | 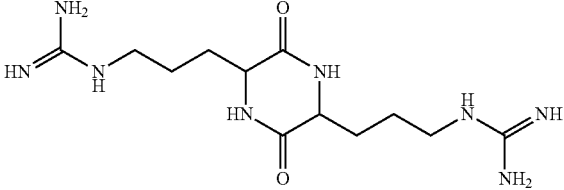 [SMILES: N=C(N)NCCCC1NC(=O)C(CCCNC(=N)N)NC1=O] |
| polyarginine (5000-15000) | R-(R)$_n$-R (SEQ ID NO 10) PR-5000 | 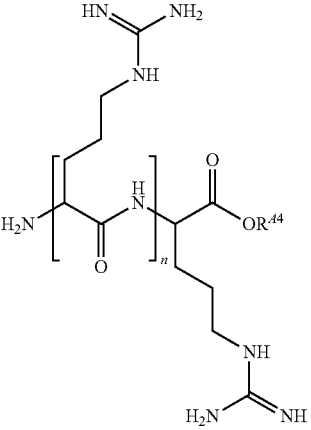<br>n = 27-85 |
| linear histidine-histidine | linear H-H | 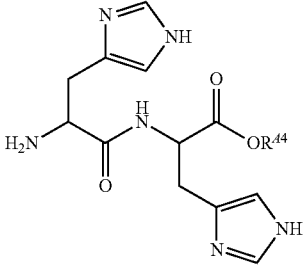 |
| cyclic histidine-histidine | cyclic H-H | 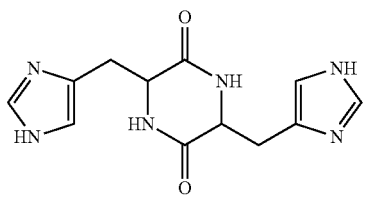 [SMILES: O=C1NC(Cc2c[nH]cn2)C(=O)NC1Cc1c[nH]cn1] |
| polyhistidine (5000-25000) | H-(H)$_n$-H (SEQ ID NO 11) PH-5000 | 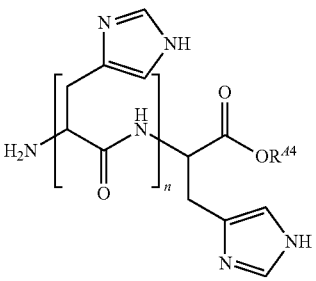<br>n = 32-161 |

TABLE 2-continued

Peptides and Polypeptides

| Name, Symbol | | Amino acid |
|---|---|---|
| linear glycine-glycine | linear G-G | (structure) |
| cyclic glycine-glycine | cyclic G-G | (structure) |
| linear arginine-lysine | linear AK | (structure) |
| linear cysteine-lysine | linear CK | (structure) |
| linear aspartic acid-lysine | linear DK | (structure) |
| linear glutamic acid-lysine | linear EK | (structure) |

TABLE 2-continued

Peptides and Polypeptides

| Name, Symbol | | Amino acid |
|---|---|---|
| linear phenylalanine-lysine | linear FK | (structure of H₂N-CH(CH₂Ph)-C(=O)-NH-CH(COOH)-(CH₂)₄-NH₂) |
| linear glycine-lysine | linear GK | (structure of H₂N-CH₂-C(=O)-NH-CH(COOH)-(CH₂)₄-NH₂) |
| linear isoleucine-lysine | linear IK | (structure of H₂N-CH(CH(CH₃)CH₂CH₃)-C(=O)-NH-CH(COOH)-(CH₂)₄-NH₂) |
| linear leucine-lysine | linear LK | (structure of H₂N-CH(CH₂CH(CH₃)₂)-C(=O)-NH-CH(COOH)-(CH₂)₄-NH₂) |
| linear methionine-lysine | linear MK | (structure of H₂N-CH(CH₂CH₂SMe)-C(=O)-NH-CH(COOH)-(CH₂)₄-NH₂) |

TABLE 2-continued
Peptides and Polypeptides
| Name, Symbol | | Amino acid |
|---|---|---|
| linear proline-lysine | linear PK | 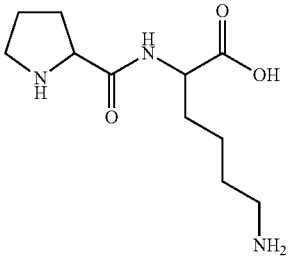 [SMILES: NCCCCC(NC(=O)C1CCCN1)C(=O)O] |
| linear glutamine-lysine | linear QK | 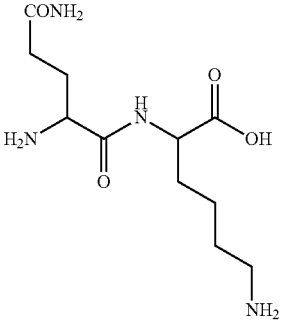 [SMILES: NCCCCC(NC(=O)C(N)CCC(N)=O)C(=O)O] |
| linear serine-lysine | linear SK | 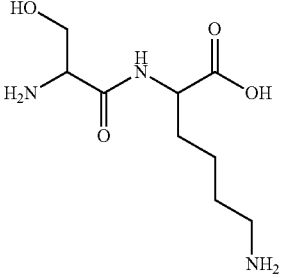 [SMILES: NCCCCC(NC(=O)C(N)CO)C(=O)O] |
| linear tryptophan-lysine | linear WK | 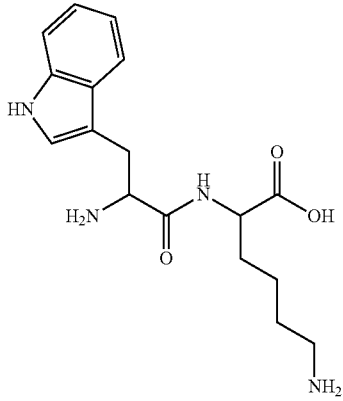 [SMILES: NCCCCC(NC(=O)C(N)Cc1c[nH]c2ccccc12)C(=O)O] |

TABLE 2-continued
Peptides and Polypeptides
| Name, Symbol | | Amino acid |
|---|---|---|
| linear tyrosine-lysine | linear YK | 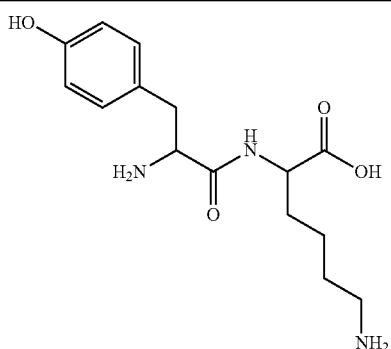 |
| linear lysine-threonine | linear KT | 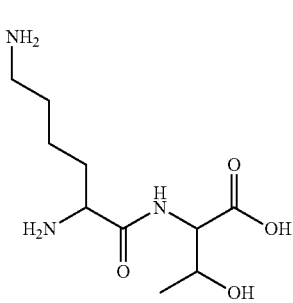 [SMILES: CC(O)C(NC(=O)C(N)CCCCN)C(=O)O] |
| linear lysine-valine | linear KV | 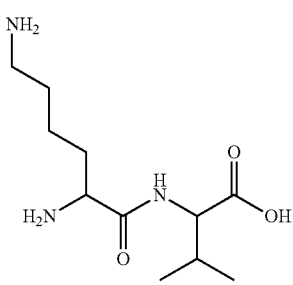 [SMILES: CC(C)C(NC(=O)C(N)CCCCN)C(=O)O] |
TABLE 3
Conjugating reagents
| Name | Structure |
|---|---|
| E10 | 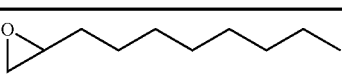 |
| E11 | 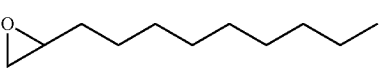 |
| E12 | 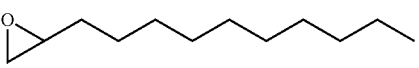 |
| E13 | 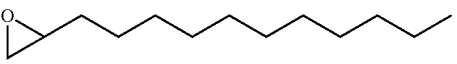 |
| E14 | 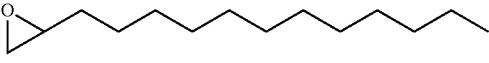 |
| E15 | 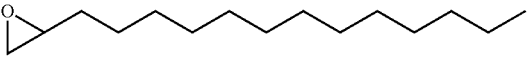 [SMILES: CCCCCCCCCCCCCC1CO1] |

TABLE 3-continued
Conjugating reagents
| Name | Structure |
|---|---|
| E16 | 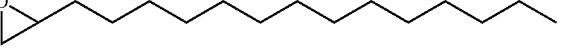 |
| A10 | 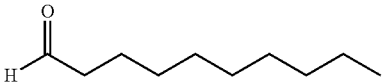 |
| A11 | 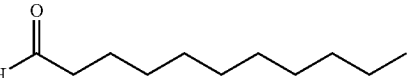 |
| A12 | 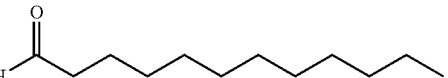 |
| A13 | 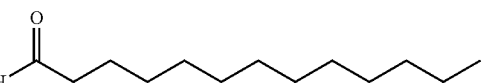 |
| A14 | 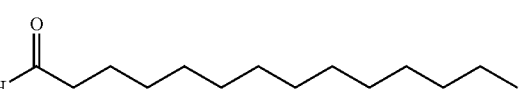 |
| O10 | 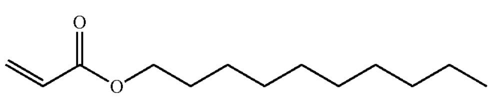 |
| O11 | 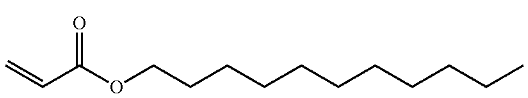 [SMILES: C=CC(=O)OCCCCCCCCCCC] |
| O12 | 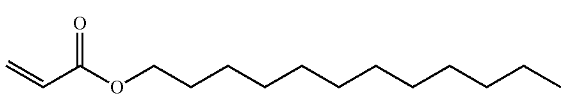 [SMILES: C=CC(=O)OCCCCCCCCCCCC] |
| O13 | 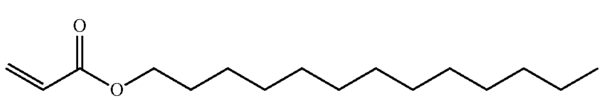 [SMILES: C=CC(=O)OCCCCCCCCCCCCC] |
| O14 | 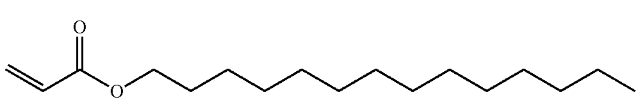 [SMILES: C=CC(=O)OCCCCCCCCCCCCCC] |

TABLE 3-continued

Conjugating reagents

| Name | Structure |
|------|-----------|
| N10 | acrylamide with C11 alkyl chain |
| N11 | acrylamide with C12 alkyl chain |
| N12 | acrylamide with C13 alkyl chain |
| N13 | acrylamide with C15 alkyl chain |
| N14 | acrylamide with C17 alkyl chain |

Synthetic Procedures

Example 1. Synthesis of APPLs

Schemes A-R show the general synthetic routes to APPLs of Formula (I) to (VI), of the present invention. Application of these methods generated a variety of APPLs, depicted in Tables 4 and 5.

Compounds were named by combination of the abbreviation of amino acids, aldehydes (A), acrylates (O), amides (N), or epoxides (E), and the length of carbon chains. For example, K-E12 represents the reaction of lysine with 1,2-epoxydodecane.

TABLE 4

| Rxn | Method | Precursor | Reagent | APPL* |
|-----|--------|-----------|---------|-------|
| 1 | 1 | E12 | R | 1A Major / 1B Minor (structures shown) |

TABLE 4-continued

| Rxn | Method | Precursor | Reagent | APPL* |
|---|---|---|---|---|
| | | | | (trace amounts, $R^{44}$ = H, Et) R-E12 |
| 2 | 1 | E12 | A | 2A Major |
| | | | | 2B Minor |
| | | | | (trace amounts, $R^{44}$ = H, Et) A-E12 |
| 3 | 1 | E12 | I | 3A Major |

TABLE 4-continued
| Rxn | Method | Precursor | Reagent | APPL* |
|---|---|---|---|---|
| | | | | 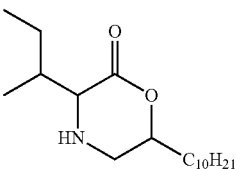
3B Minor
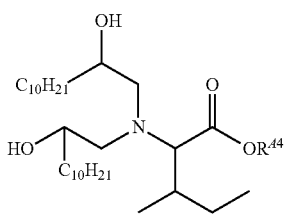
(trace amounts, $R^{44}$ = H, Et)
I-E12 |
| 4 | 1 | E12 | E | 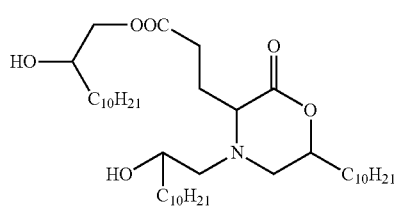
4A Major
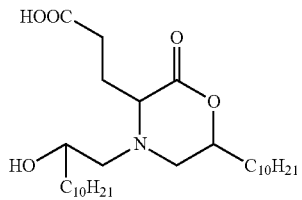
4B Minor
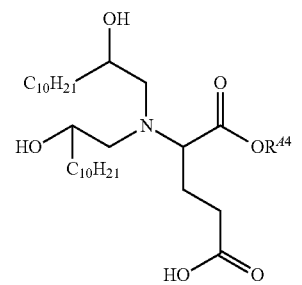
(trace amounts, $R^{44}$ = H, Et)
E-E12 |
| 5 | 1 | E12 | C | 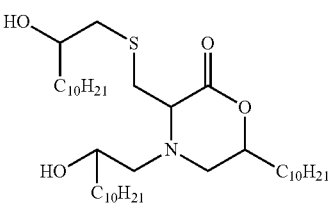
5A Major |

TABLE 4-continued
| Rxn | Method | Precursor | Reagent | APPL* |
|---|---|---|---|---|
|  |  |  |  | 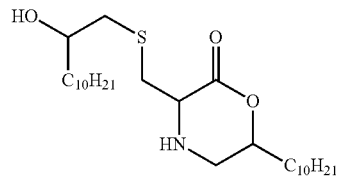 5B Minor |
|  |  |  |  | 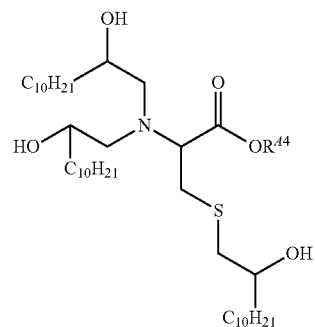 (trace amounts, $R^{44}$ = H, Et) C-E12 |
| 6 | 1 | E12 | W | 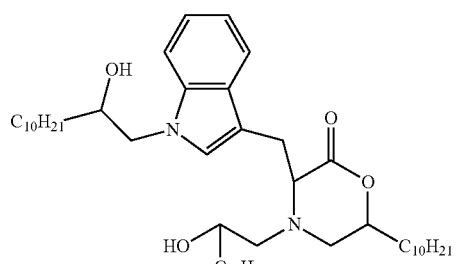 6A Major |
|  |  |  |  | 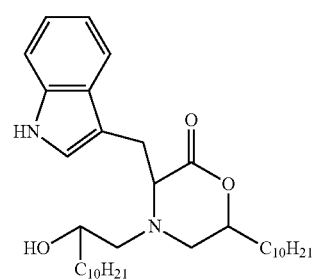 6B Minor |

TABLE 4-continued
| Rxn | Method | Precursor | Reagent | APPL* |
|---|---|---|---|---|
| | | | | 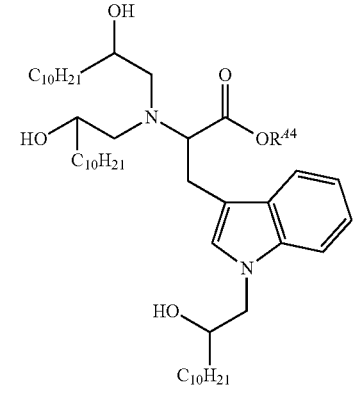
(trace amounts, R⁴⁴ = H, Et)
W-E12 |
| 7 | 1 | E12 | Y | 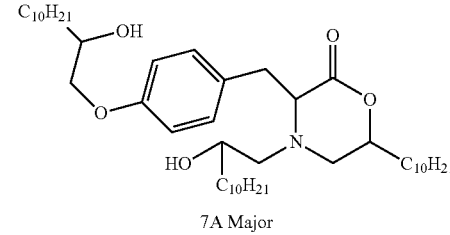
7A Major |
| | | | | 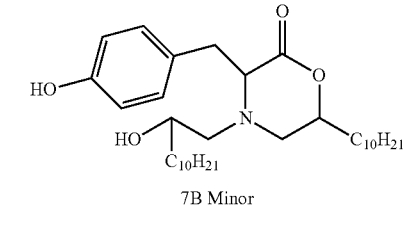
7B Minor |
| | | | | 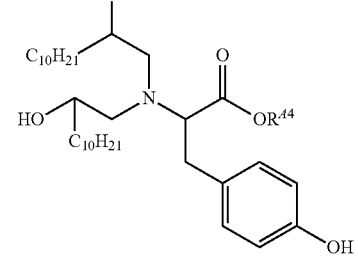
(trace amounts, R⁴⁴ = H, Et)
Y-E12 |
| 8 | 1 | E12 | G | 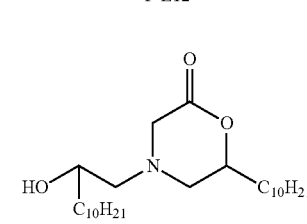
8A Major |

TABLE 4-continued
| Rxn | Method | Precursor | Reagent | APPL* |
|---|---|---|---|---|
| | | | | 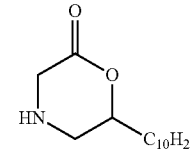<br>8B Minor |
| | | | | 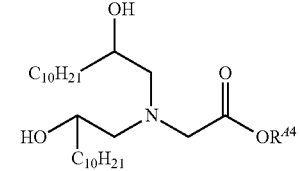<br>(trace amounts, $R^{44}$ = H, Et)<br>G-E12 |
| 9 | 1 | E12 | P | 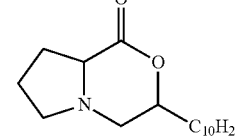<br>9 Major |
| | | | | 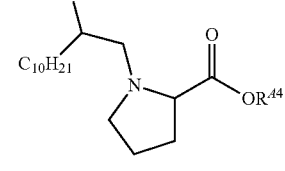<br>(trace amounts, $R^{44}$ = H, Et)<br>D-E12 |
| 10 | 1 | E12 | L | 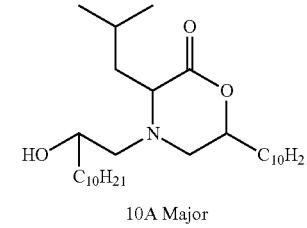<br>10A Major |
| | | | | 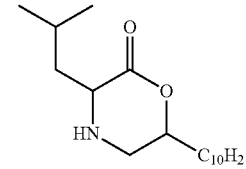<br>10B Minor |

TABLE 4-continued
| Rxn | Method | Precursor | Reagent | APPL* |
|---|---|---|---|---|
|  |  |  |  | 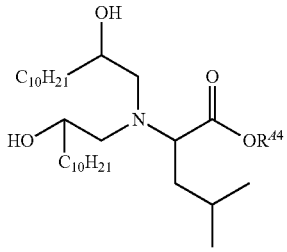 (trace amounts, $R^{44}$ = H, Et) <br> L-E12 |
| 11 | 1 | E12 | D | 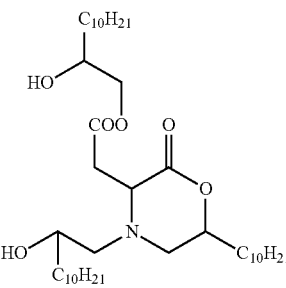 11A Major |
|  |  |  |  | 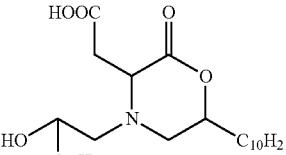 11B Minor |
|  |  |  |  | 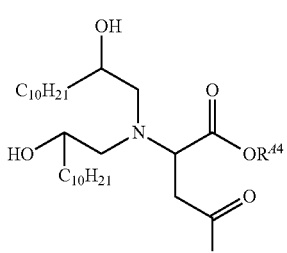 (trace amounts, $R^{44}$ = H, Et) <br> D-E12 |
| 12 | 1 | E12 | S | 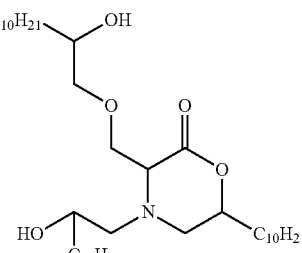 12A Major |

TABLE 4-continued
| Rxn | Method | Precursor | Reagent | APPL* |
|---|---|---|---|---|
|  |  |  |  | 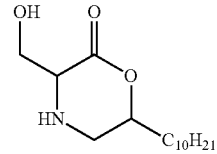 |
|  |  |  |  | 12B Minor |
|  |  |  |  | 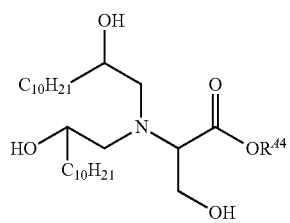 |
|  |  |  |  | (trace amounts, $R^{44}$ = H, Et) |
|  |  |  |  | S-E12 |
| 13 | 1 | E12 | T | 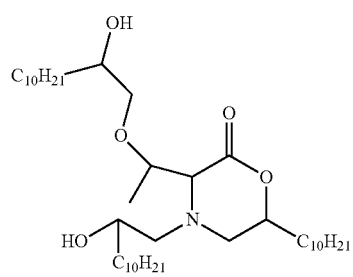 |
|  |  |  |  | 13A Major |
|  |  |  |  | 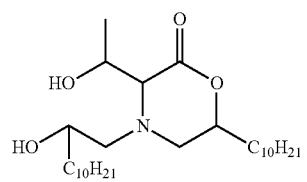 |
|  |  |  |  | 13B Minor |
|  |  |  |  | 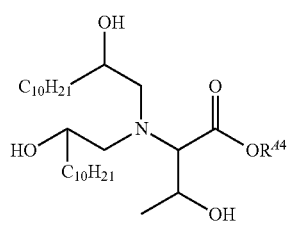 |
|  |  |  |  | (trace amounts, $R^{44}$ = H, Et) |
|  |  |  |  | T-E12 |

TABLE 4-continued
| Rxn | Method | Precursor | Reagent | APPL* |
|-----|--------|-----------|---------|-------|
| 14 | 1 | E12 | H | 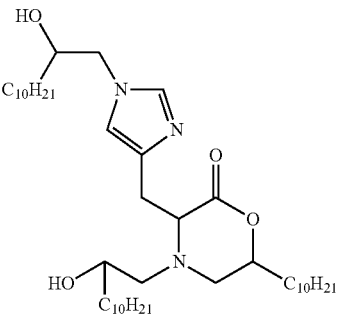 14A Major <br><br> 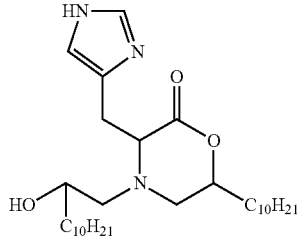 14B Minor <br><br> 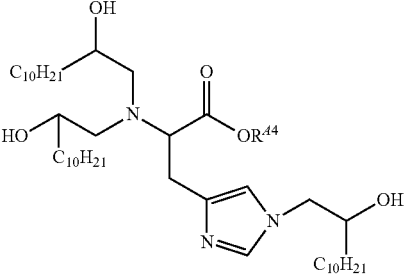 (trace amounts, $R^{44}$ = H, Et) <br> H-E12 |
| 15 | 1 | E12 | N | 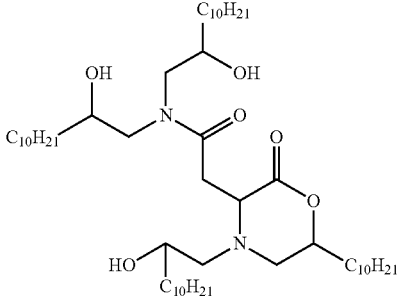 15A Major |

TABLE 4-continued
| Rxn | Method | Precursor | Reagent | APPL* |
|---|---|---|---|---|
| | | | | 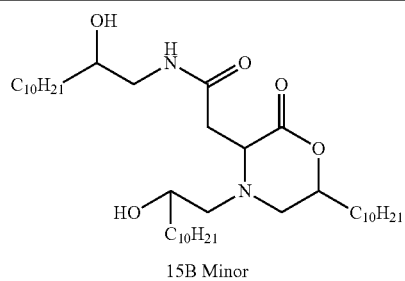 15B Minor |
| | | | | 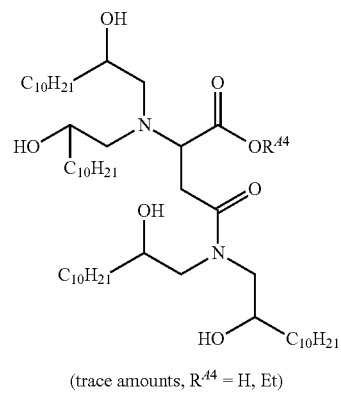 (trace amounts, $R^{44}$ = H, Et) N-E12 |
| 16 | 1 | E12 | Q | 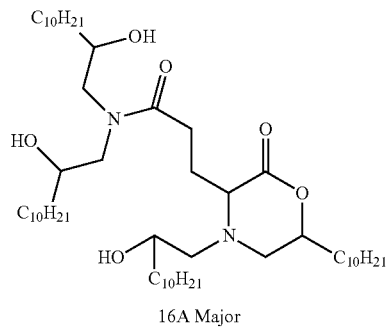 16A Major |
| | | | | 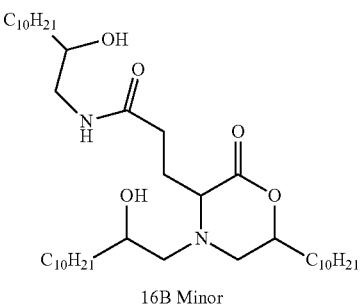 16B Minor |

TABLE 4-continued
| Rxn | Method | Precursor | Reagent | APPL* |
|---|---|---|---|---|
|  |  |  |  | 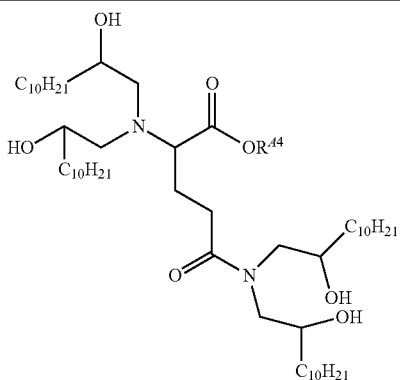<br>(trace amounts, $R^{44}$ = H, Et)<br>Q-E12 |
| 17 | 1 | E12 | F | 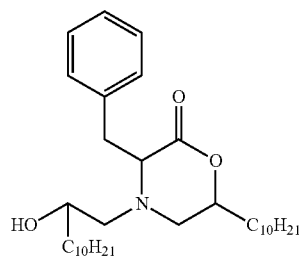<br>17A Major |
|  |  |  |  | 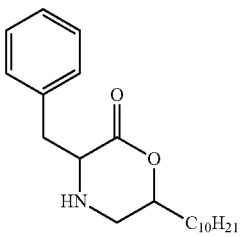<br>17B Minor |
|  |  |  |  | 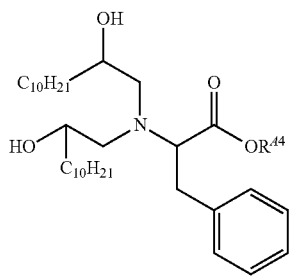<br>(trace amounts, $R^{44}$ = H, Et)<br>F-E12 |

TABLE 4-continued
| Rxn | Method | Precursor | Reagent | APPL* |
|---|---|---|---|---|
| 18 | 1 | E12 | M | |
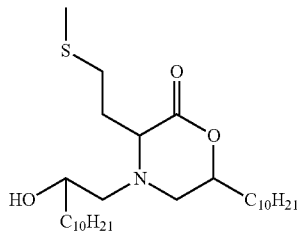
18A Major
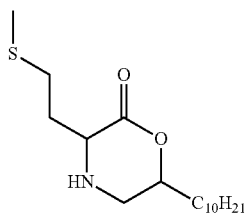
18B Minor
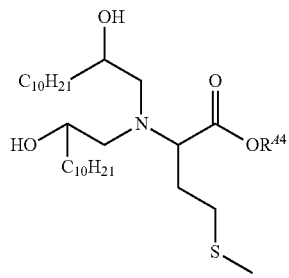
(trace amounts, R⁴⁴ = H, Et)
M-E12
| | | | | |
|---|---|---|---|---|
| 19 | 1 | E12 | V | |
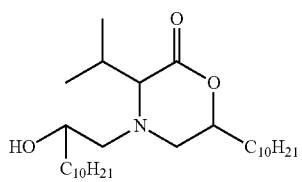
19A Major
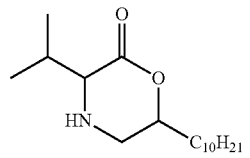
19B Minor TABLE 4-continued
| Rxn | Method | Precursor | Reagent | APPL* |
|---|---|---|---|---|
|  |  |  |  | 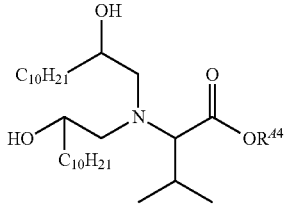<br>(trace amounts, $R^{44}$ = H, Et)<br>V-E12 |
| 20 | 3 | A12 | K | 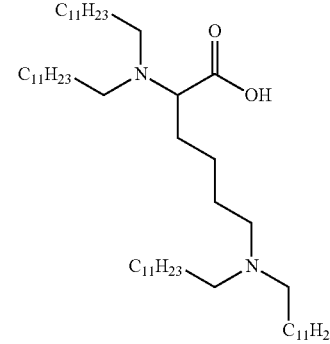<br>K-A12 |
| 21 | 3 | A12 | KK | 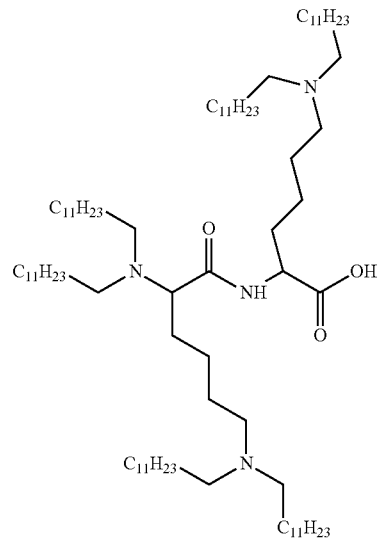<br>KK-A12 |

TABLE 4-continued
| Rxn | Method | Precursor | Reagent | APPL* |
|---|---|---|---|---|
| 22 | 1 | E12 | K | |
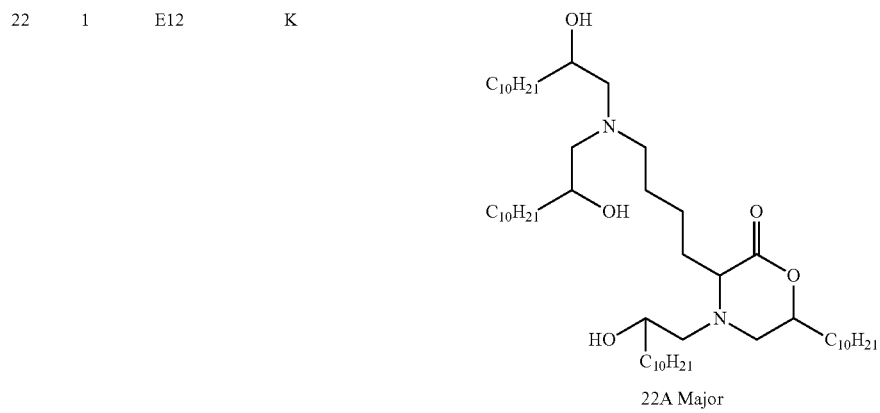
22A Major
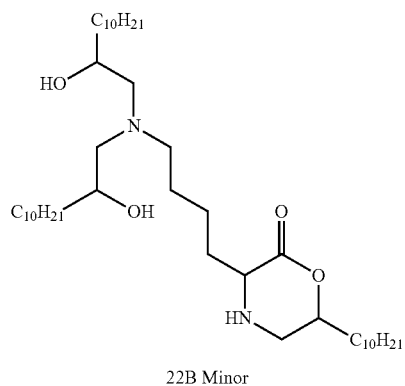
22B Minor
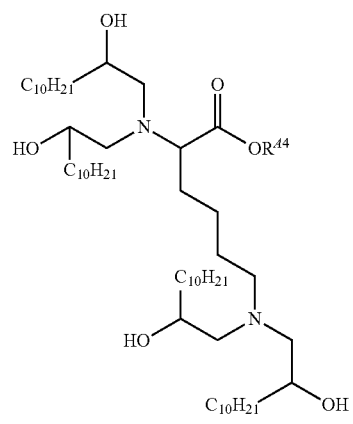
(trace amounts, $R^{44}$ = Et)
K-E12

TABLE 4-continued
| Rxn | Method | Precursor | Reagent | APPL* |
|---|---|---|---|---|
| 23 | 1 | E12 | cyclic-KK | (structures shown below) |
Major
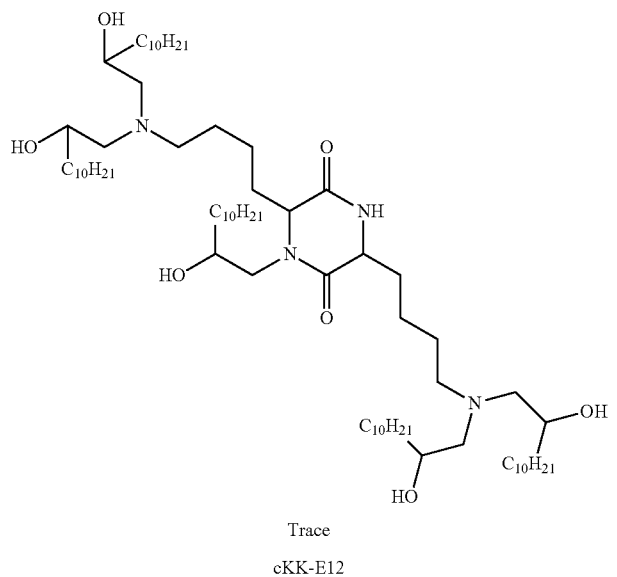
Trace
cKK-E12

TABLE 4-continued
| Rxn | Method | Precursor | Reagent | APPL* |
|---|---|---|---|---|
| 24 | 1 | E12 | PK-500 | 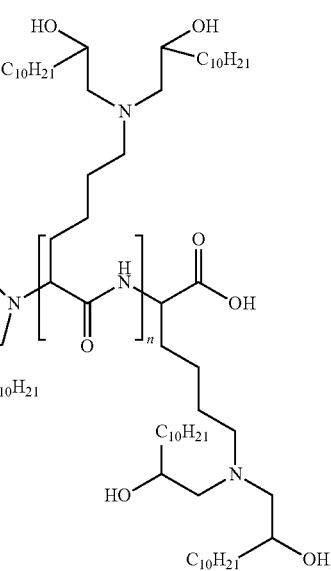 polyK$_{500}$-E12, n = 3-12 |
| 25 | 1 | E12 | PK-1000 | polyK$_{1000}$-E12 As above, n = 6-33 |
| 26 | 1 | E12 | PK-4000 | polyK$_{4000}$-E12 As above, n = 26-102 |
| 27 | 1 | E12 | PK-15000 | polyK$_{15000}$-E12 As above, n = 102-204 |
| 28 | 1 | E12 | PK-30000 | polyK$_{30000}$-E12 As above, n = 204-480 |
| 29 | 1 | E10 | cyclic-KK | 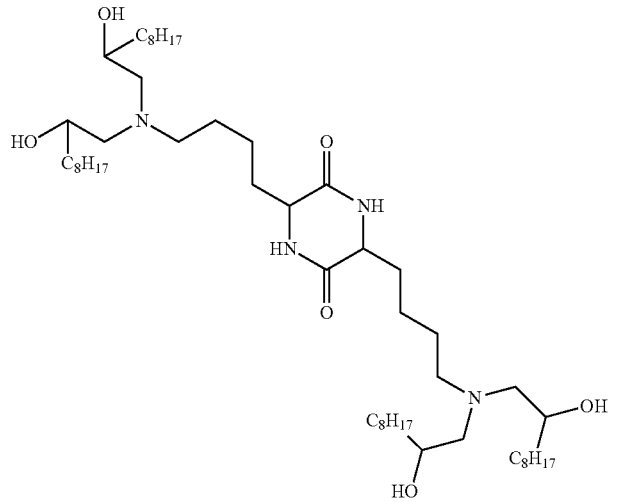 Major |

TABLE 4-continued
| Rxn | Method | Precursor | Reagent | APPL* |
|---|---|---|---|---|
|  |  |  |  | 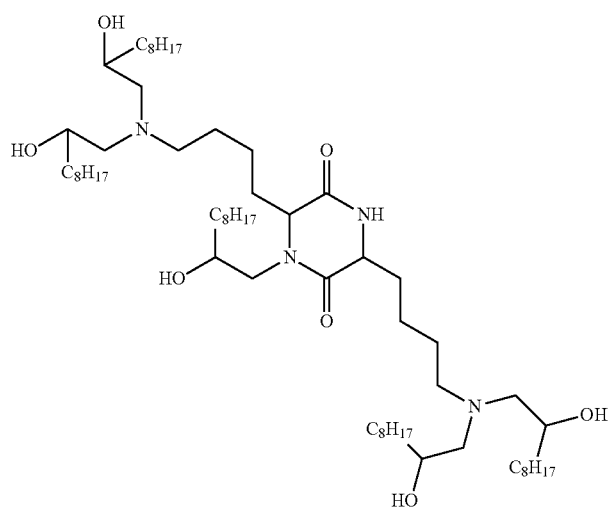<br>Trace<br>cKK-E10 |
| 30 | 1 | E14 | cyclic-KK | 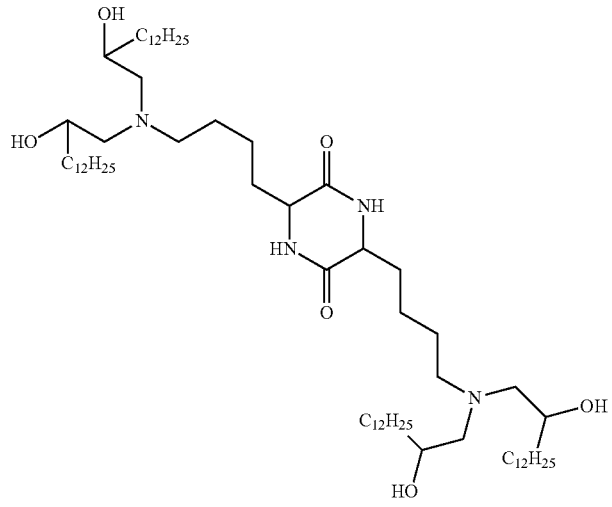<br>Major |

TABLE 4-continued
| Rxn | Method | Precursor | Reagent | APPL* |
|-----|--------|-----------|---------|-------|
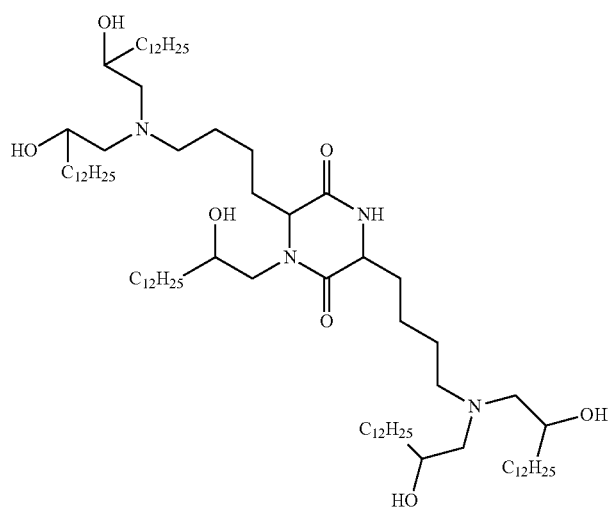
Trace
cKK-E14
| 31 | 1 | E16 | cyclic-KK | |
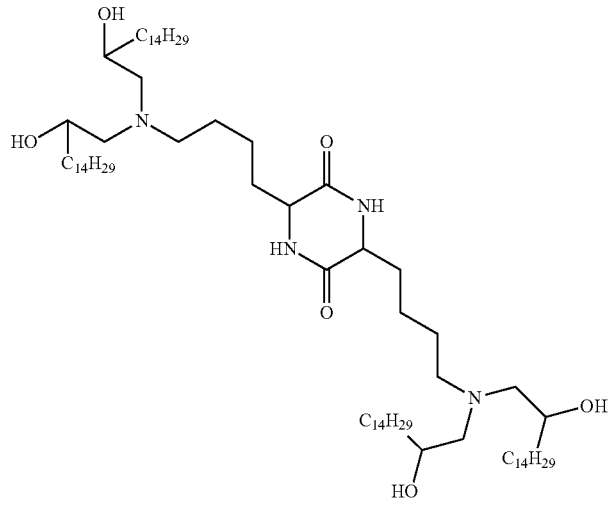
Major TABLE 4-continued
| Rxn | Method | Precursor | Reagent | APPL* |
|---|---|---|---|---|
| | | | | 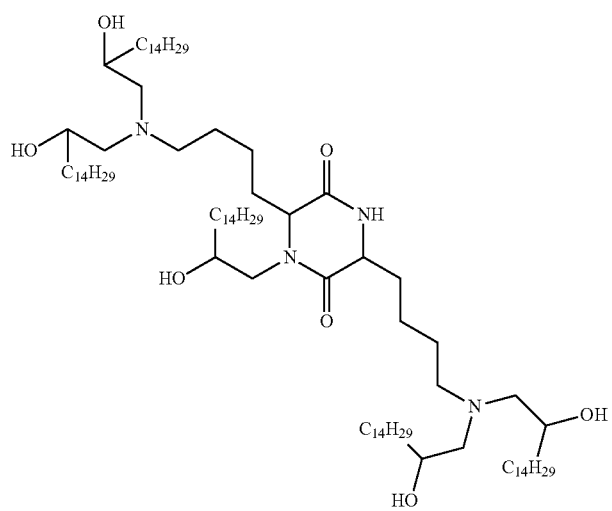 Trace cKK-E16 |
| 32 | 1 | E11 | cyclic-KK | 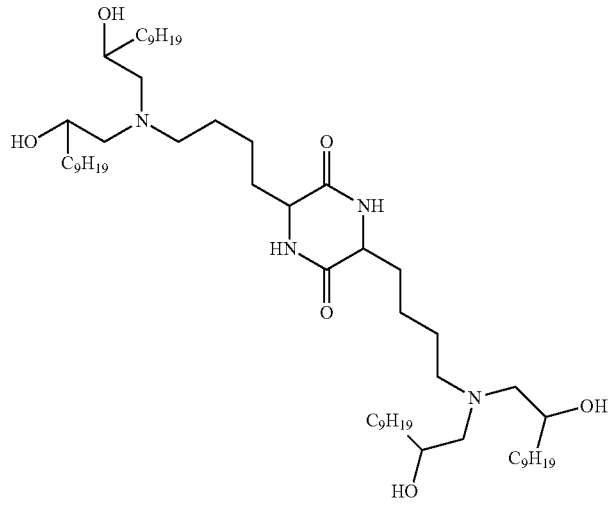 Major |

TABLE 4-continued
| Rxn | Method | Precursor | Reagent | APPL* |
|---|---|---|---|---|
|  |  |  |  | 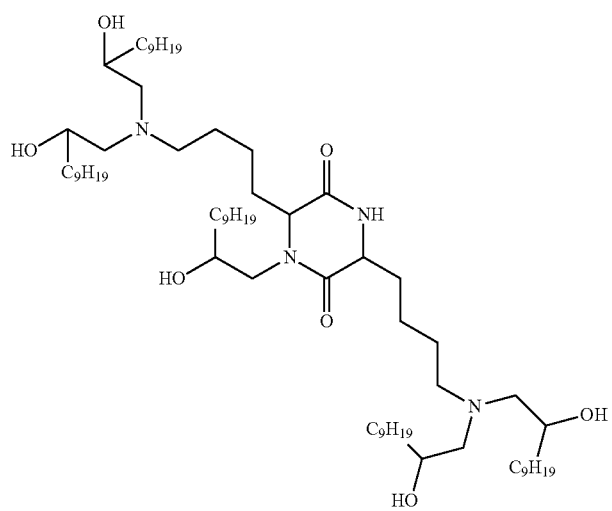 Trace cKK-E11 |
| 33 | 1 | E13 | cyclic-KK | 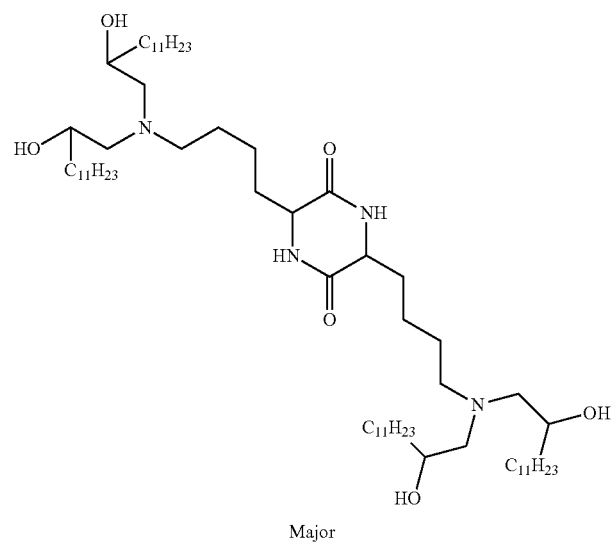 Major |

TABLE 4-continued
| Rxn | Method | Precursor | Reagent | APPL* |
|---|---|---|---|---|
| | | | | 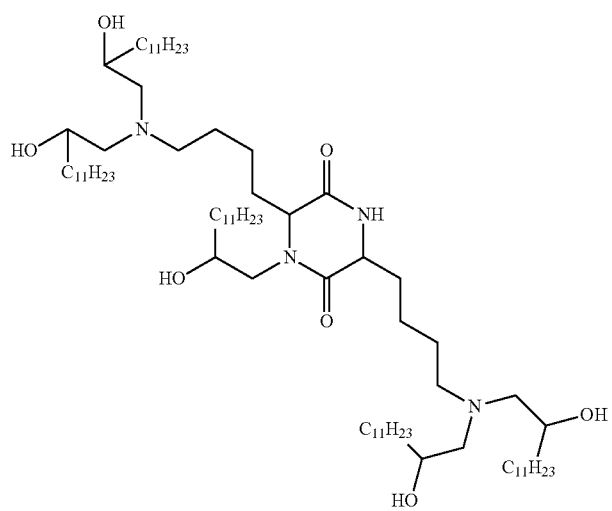<br>Trace<br>cKK-E13 |
| 34 | 1 | cyclic-KK | E15 | 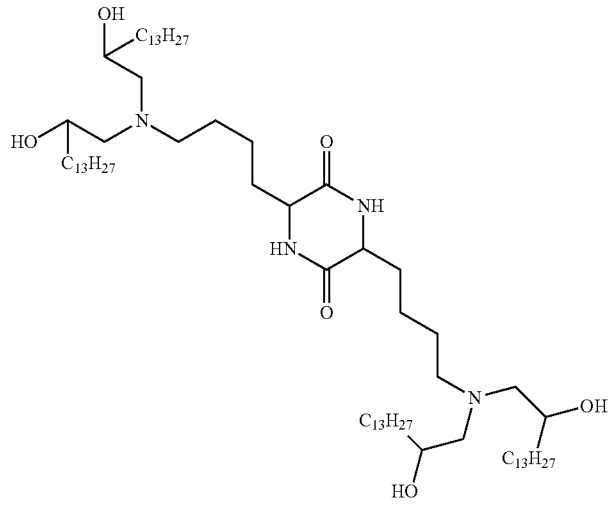<br>Major |

TABLE 4-continued

| Rxn | Method | Precursor | Reagent | APPL* |
|-----|--------|-----------|---------|-------|
|     |        |           |         | Trace<br>cKK-E15 |
| 35  | 1      | E12       | Boc-Lys-OH | 35A Major<br><br>35B Minor |

TABLE 4-continued
| Rxn | Method | Precursor | Reagent | APPL* |
|---|---|---|---|---|
| | | | | 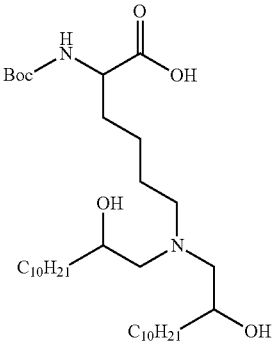
Free acid form
NBoc-K-E12 |
| 36 | 1 | E12 | H-Lys(Boc)-OMe | 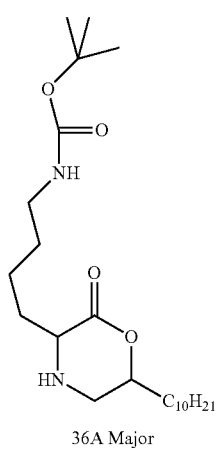
36A Major |
| | | | | 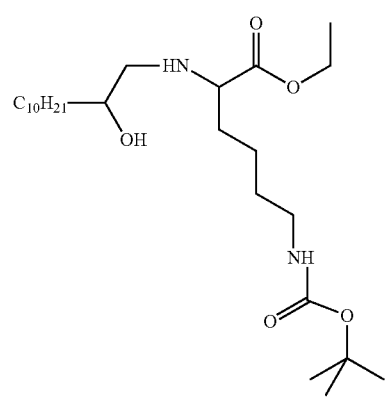
36B Minor
(side chain N-Boced)
K-E12 |

TABLE 4-continued
| Rxn | Method | Precursor | Reagent | APPL* |
|---|---|---|---|---|
| 37 | 2 | N12 | cKK | 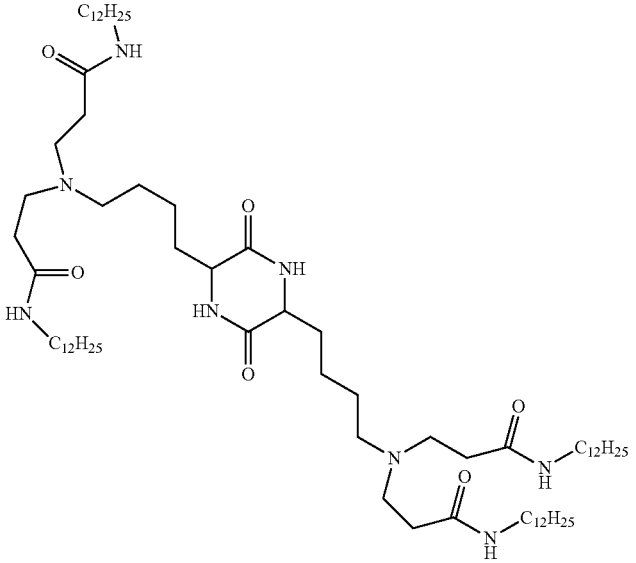 plus compounds wherein 1 tail ($R^L$) is replaced with hydrogen.<br>cKK-N12 |
| 38 | 2 | O12 | cKK | 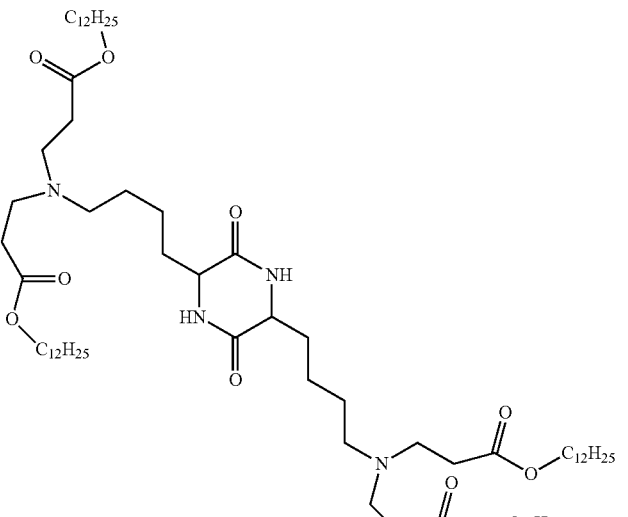<br>cKK-O12 |

TABLE 4-continued
| Rxn | Method | Precursor | Reagent | APPL* |
|---|---|---|---|---|
| 39 | 3 | A12 | cKK | 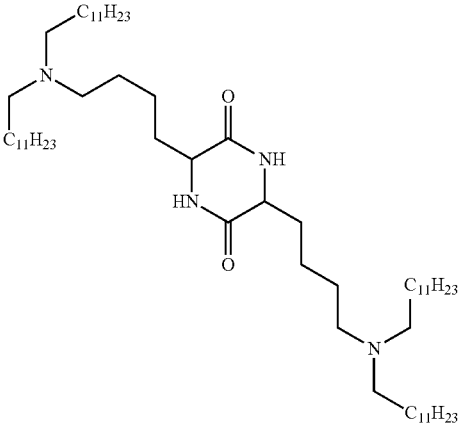<br>cKK-A12 |
| 40 | 1 | E12 | KKK | 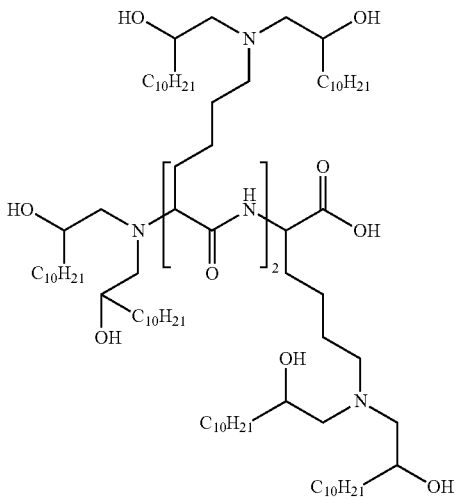<br>KKK-E12 |
| 41 | 2 | A12 | KKK | 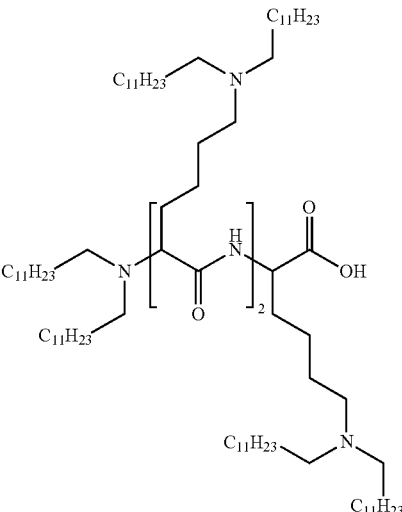<br>KKK-A12 |

TABLE 4-continued
| Rxn | Method | Precursor | Reagent | APPL* |
|-----|--------|-----------|---------|-------|
| 42 | 3 | O12 | KKK | 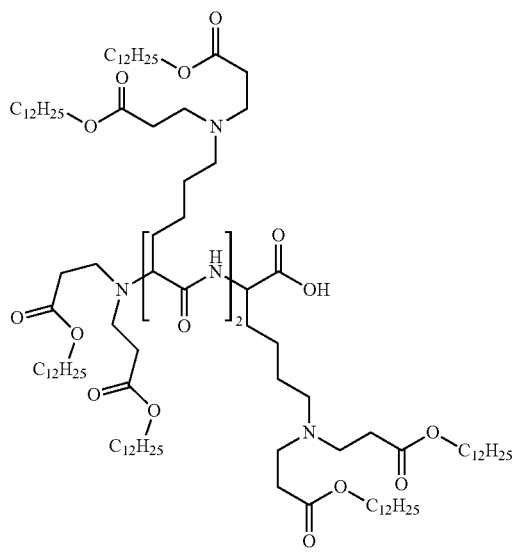<br>plus compounds wherein 1 tail ($R^L$) is replaced with hydrogen.<br>KKK-O12 |
| 43 | 3 | O12 | KK | 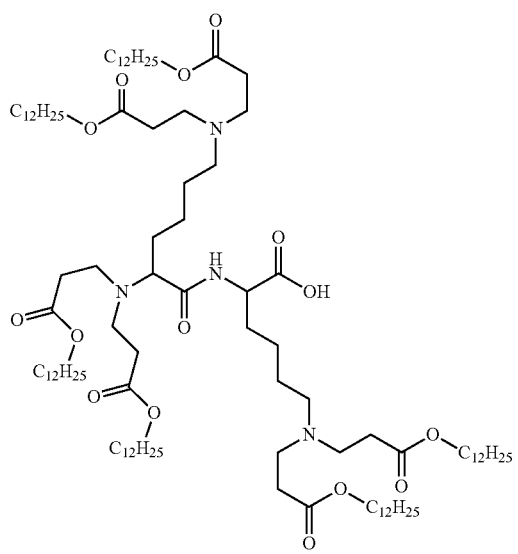<br>plus compounds wherein 1 tail ($R^L$) is replaced with hydrogen.<br>KK-O12 |

TABLE 4-continued

| Rxn | Method | Precursor | Reagent | APPL* |
|---|---|---|---|---|
| 44 | 3 | N12 | KKK | 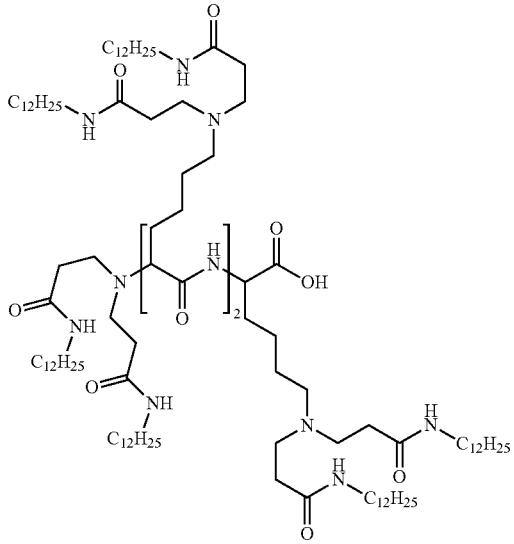 | plus compounds wherein 1 tail ($R^L$) is replaced with hydrogen.

KKK-N12

*reaction may produce a mixture of two or more APPLs; also includes compounds wherein 1 or more tails ($R^L$) are replaced with hydrogen.

TABLE 5

| Compd | Chemical formula | Calcd. | Observed | Tail # |
|---|---|---|---|---|
| A-E12 | C27H54NO3+ | 440.4098 | 440.4336 | 2 |
| C-E12 | C27H54NO3S+ | 472.3819 | 472.4303 | 2 |
| D-E12 | C28H54NO5+ | 484.3997 | 484.4327 | 2 |
| E-E12 | C29H56NO5+ | 498.4153 | 498.4117 | 2 |
| F-E12 | C33H58NO3+ | 516.4411 | 516.4332 | 2 |
| G-E12 | C26H52NO3+ | 426.3942 | 426.3772 | 2 |
| H-E12 | C42H80N3O4+ | 690.6143 | 690.6016 | 3 |
| I-E12 | C30H60NO3+ | 482.4568 | 482.4461 | 2 |
| K-E12 | C42H85N2O4+ | 681.6504 | 681.6009 | 3 |
| L-E12 | C30H60NO3+ | 482.4568 | 482.4771 | 2 |
| M-E12 | C29H58NO3S+ | 500.4132 | 500.4471 | 2 |
| N-E12 | C40H79N2O5+ | 667.5984 | 667.5894 | 3 |
| P-E12 | C17H32NO2+ | 282.2428 | 282.2585 | 1 |
| Q-E12 | C29H57N2O4+ | 497.4313 | 497.4268 | 2 |
| R-E12 | C54H109N4O5+ | 893.8392 | 893.8400 | 4 |
| S-E12 | C27H54NO4+ | 456.4047 | 456.3891 | 2 |
| T-E12 | C28H56NO4+ | 470.4204 | 470.4186 | 2 |
| V-E12 | C29H58NO3+ | 468.4411 | 468.4259 | 2 |
| W-E12 | C35H59N2O3+ | 555.4520 | 555.4510 | 2 |
| Y-E12 | C33H58NO4+ | 532.436 | 532.4149 | 2 |
| cKG-E12 | C32H64N3O4+ | 554.4891 | 554.4852 | 2 |
| cKT-E12 | C34H68N3O5+ | 598.5153 | 598.5179 | 2 |
| cYK-E12 | C39H70N3O5+ | 660.5310 | 660.5350 | 2 |
| cLK-E12 | C36H72N3O4+ | 610.5517 | 610.5556 | 2 |
| cDK-E12* | C36H70N3O6+ | 640.5259 | 640.5316 | 2 |
| cMK-E12 | C35H70N3O4S+ | 628.5082 | 628.5072 | 2 |
| cKV-E12 | C35H70N3O4+ | 596.5361 | 596.5330 | 2 |
| cAK-E12 | C33H66N3O4+ | 568.5048 | 568.4992 | 2 |
| cCK-E12 | 33H66N3O4S+ | 600.6143 | 600.6143 | 2 |
| cQK-E12 | C35H69N4O5+ | 625.5262 | 625.4733 | 2 |
| cPK-E12 | C35H68N3O4+ | 594.5204 | 594.5169 | 2 |
| cFK-E12 | C39H70N3O4+ | 644.5361 | 644.5301 | 2 |
| cWK-E12 | C41H71N4O4+ | 683.5470 | 683.5367 | 2 |
| cEK-E12 | C35H68N3O6+ | 626.5103 | 626.5053 | 2 |
| cIK-E12 | C36H72N3O4+ | 610.5517 | 610.5501 | 2 |
| cSK-E12 | C33H66N3O5+ | 584.4997 | 584.5029 | 2 |
| cKK-E10 | C52H105N4O6+ | 881.8029 | 881.8042 | 4 |
| cKK-E12 | C60H121N4O6+ | 993.9281 | 993.9224 | 4 |
| cKK-E14 | C68H137N4O6+ | 1106.0533 | 1106.0709 | 4 |
| cKK-E16 | C76H153N4O6+ | 1218.1785 | 1218.2002 | 4 |
| A-A12 | C27H56NO2+ | 426.4306 | 426.4244 | 2 |
| C-A12 | C27H56NO2S+ | 458.4026 | 458.3857 | 2 |
| D-A12 | C28H56NO4+ | 470.4204 | 470.4188 | 2 |
| E-A12 | C29H58NO4+ | 484.4360 | 484.4319 | 2 |
| F-A12 | C33H60NO2+ | 502.4619 | 502.4560 | 2 |
| G-A12 | C26H54NO2+ | 412.4149 | 412.4107 | 2 |
| H-A12 | C30H58N3O2+ | 492.4524 | 492.4503 | 2 |
| I-A12 | C30H62NO2+ | 468.4775 | 468.4714 | 2 |
| K-A12 | C54H111N2O2+ | 819.8640 | 819.8657 | 4 |
| L-A12 | C30H62NO2+ | 468.4775 | 468.4752 | 2 |
| M-A12 | C29H60NO2S+ | 486.4339 | 486.4318 | 2 |
| N-A12 | C28H57N2O3+ | 469.4364 | 469.4328 | 2 |
| P-A12 | C17H34NO2+ | 284.2584 | 284.2512 | 1 |
| Q-A12 | C29H59N2O3+ | 483.4520 | 483.4543 | 2 |
| R-A12 | C42H87N4O2+ | 679.6824 | 679.6783 | 3 |
| S-A12 | C27H56NO3+ | 442.4255 | 442.4225 | 2 |
| T-A12 | C28H58NO3+ | 456.4411 | 456.4398 | 2 |
| V-A12 | C29H60NO2+ | 454.4619 | 454.4544 | 2 |
| W-A12 | C35H61N2O2+ | 541.4728 | 541.4724 | 2 |
| Y-A12 | C33H60NO3+ | 518.4568 | 518.4543 | 2 |
| KK-A12 | C84H171N4O3+ | 1284.3346 | 1284.3458 | 6 |
| KKK-A12 | C114H231N6O4+ | 1748.8051 | 1748.8340 | 8 |
| cKK-A12 | C60H121N4O2+ | 929.9484 | 929.9445 | 4 |
| A-O12 | C18H36NO4+ | 330.2639 | 330.2582 | 1 |
| C-O12 | C33H64NO6S+ | 602.4449 | 602.4426 | 2 |
| D-O12 | C19H36NO6+ | 374.2537 | 374.2492 | 1 |
| E-O12 | C20H38NO6+ | 388.2694 | 388.2672 | 1 |
| F-O12 | C24H40NO4+ | 406.2952 | 406.2896 | 1 |
| G-O12 | C17H34NO4+ | 316.2482 | 316.2423 | 1 |
| H-O12 | C36H66N3O6+ | 636.4946 | 636.4969 | 2 |
| I-O12 | C21H42NO4+ | 372.3108 | 372.3054 | 1 |
| K-O12 | C66H127N2O10+ | 1107.9485 | 1107.9417 | 4 |
| L-O12 | C21H42NO4+ | 372.3108 | 372.3052 | 1 |
| M-O12 | C20H40NO4S+ | 390.2673 | 390.2628 | 1 |
| N-O12 | C19H37N2O5+ | 373.2697 | 373.2668 | 1 |
| P-O12 | C20H38NO4+ | 356.2795 | 356.2779 | 1 |
| Q-O12 | C20H39N2O5+ | 387.2853 | 387.2831 | 1 |
| R-O12 | C21H43N4O4+ | 415.3279 | 415.3235 | 1 |
| S-O12 | C18H36NO5+ | 346.2588 | 346.2521 | 1 |
| T-O12 | C19H38NO5+ | 360.2744 | 360.2733 | 1 |

TABLE 5-continued
| Compd | Chemical formula | Calcd. | Observed | Tail # |
|---|---|---|---|---|
| V-O12 | C20H40NO4+ | 358.2952 | 358.2905 | 1 |
| W-O12 | C26H41N2O4+ | 445.3061 | 445.3010 | 1 |
| Y-O12 | C24H40NO5+ | 422.2901 | 422.2868 | 1 |
| KK-O12 | C87H167N4O13+ | 1476.2524 | 1476.2533 | 5 |
| KKK-O12 | C123H235N6O18+ | 2084.7652 | 2084.7650 | 7 |
| cKK-O12 | C72H137N4O10+ | 1218.0329 | 1218.0880 | 4 |
*formation of ethyl ester. Compounds derived from poly-L-lysine are not included.
Exemplary Compounds of Table 5
A-E12
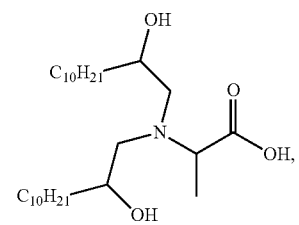
C-E12
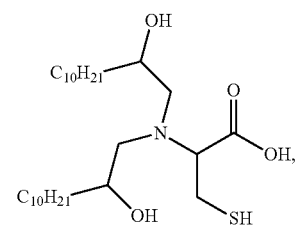
D-E12
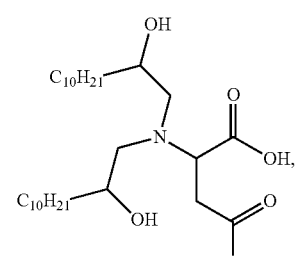
E-E12
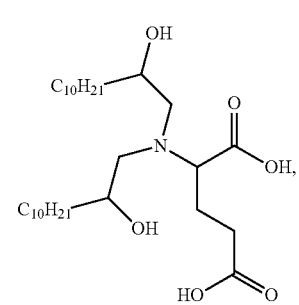
F-E12
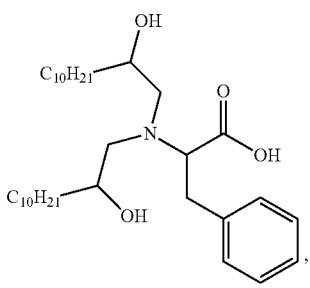
G-E12
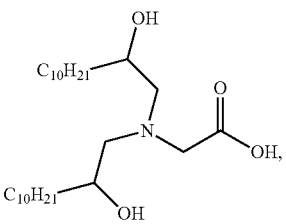
H-E12
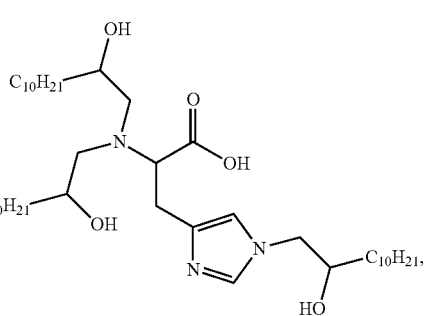
I-E12
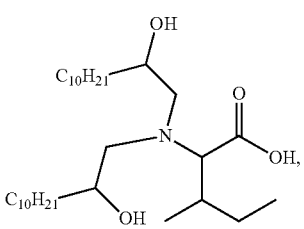
L-E12
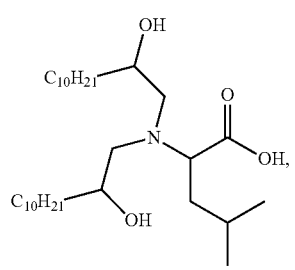
M-E12
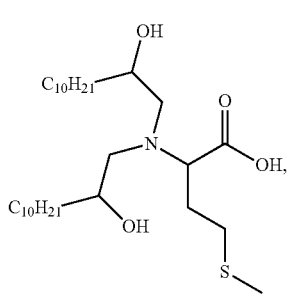

N-E12
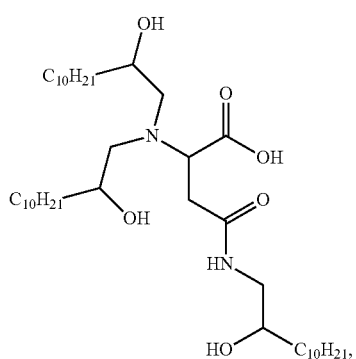
P-E12
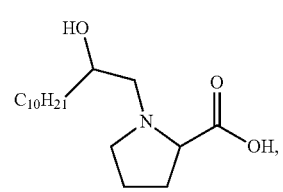
Q-E12
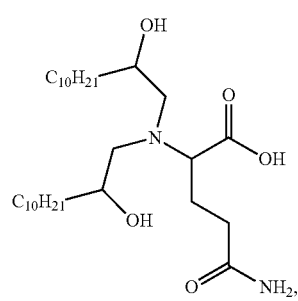
R-E12
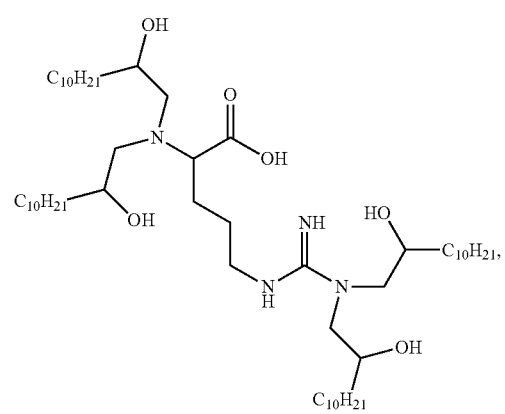
S-E12
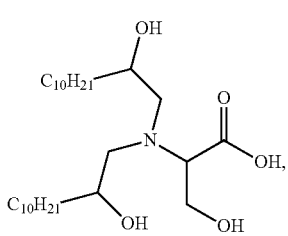
T-E12
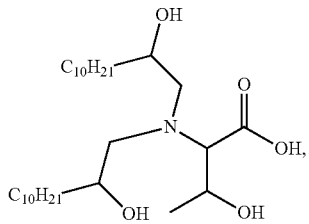
V-E12
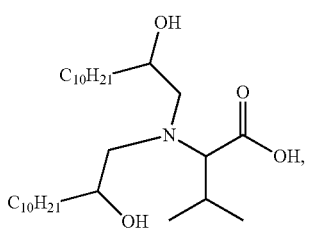
W-E12
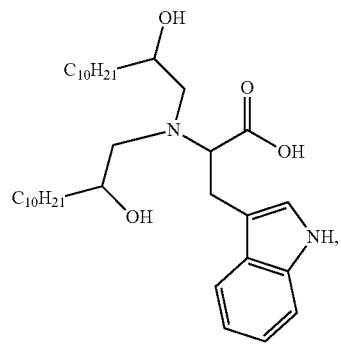
Y-E12
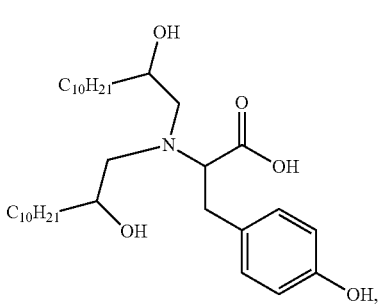
K-E12
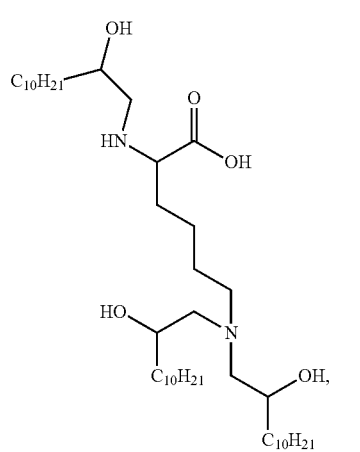

-continued
cKG-E12
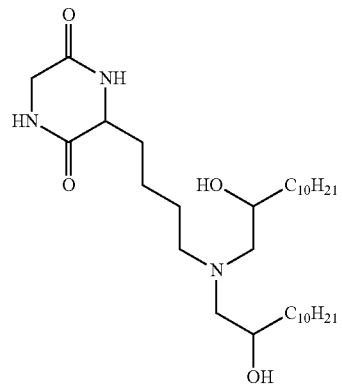
cKT-E12
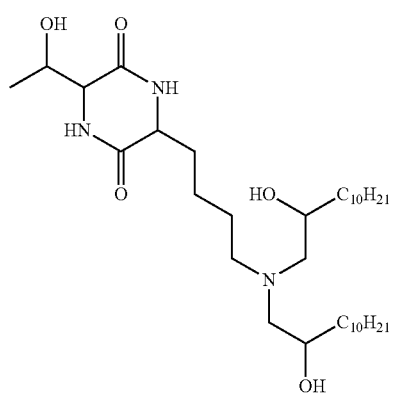
cYK-E12
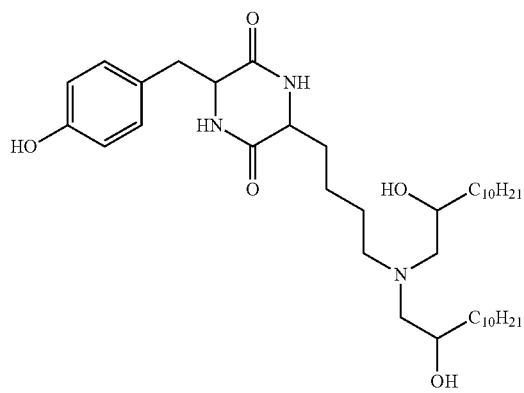
cLK-E12
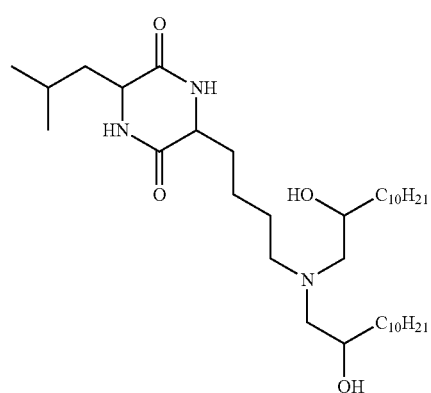
cDK-E12
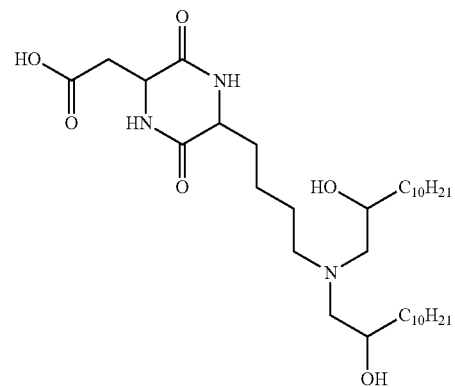
cMK-E12
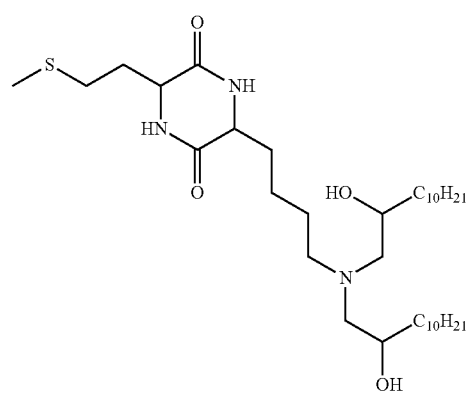
cKV-E12
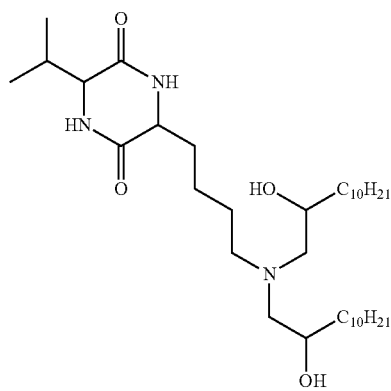
cAK-E12
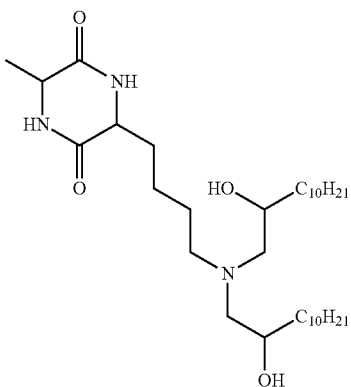

cCK-E12
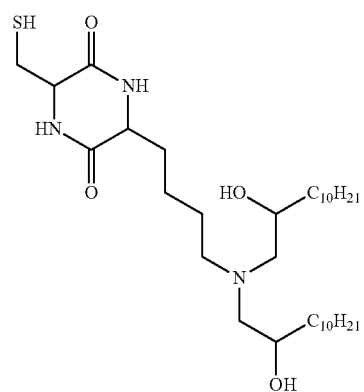
cQK-E12
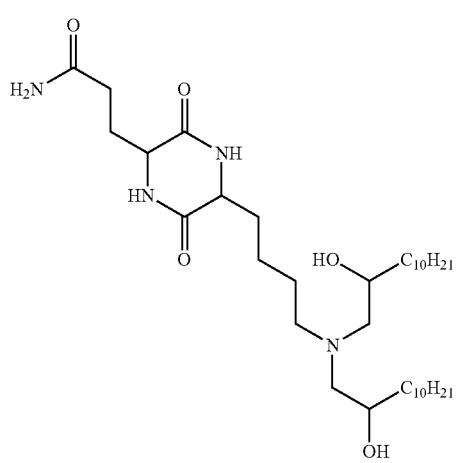
cPK-E12
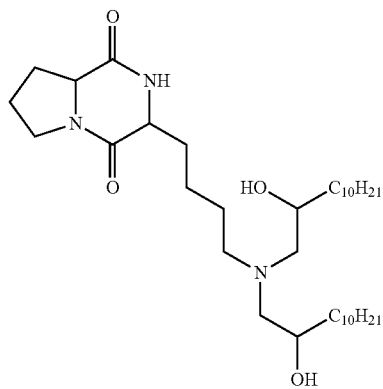
cFK-E12
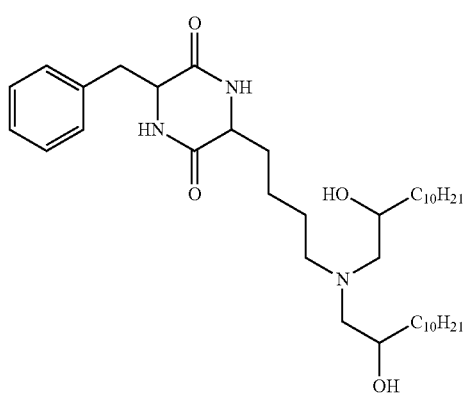
cWK-E12
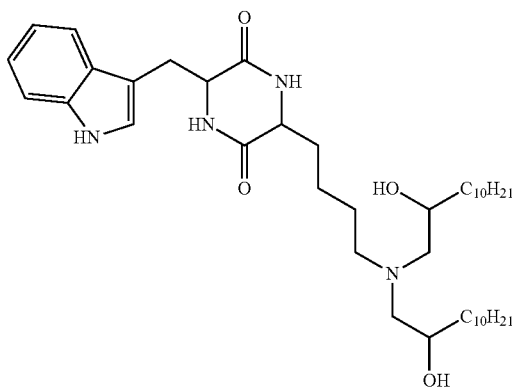
cEK-E12
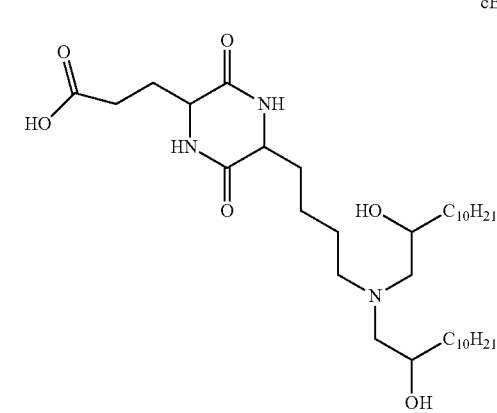
cIK-E12
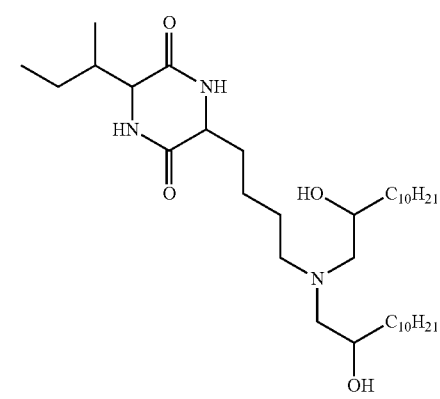
cSK-E12
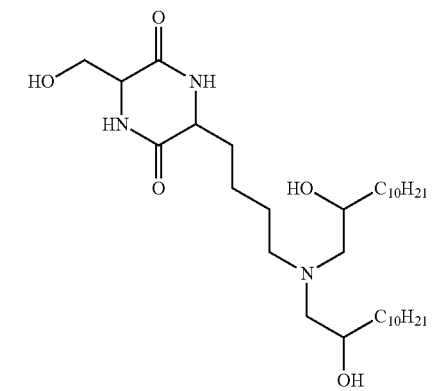

A-A12
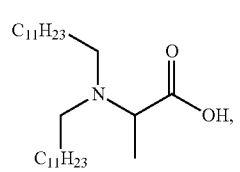

C-A12
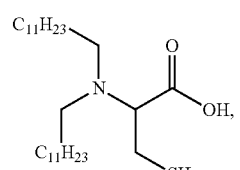

D-A12
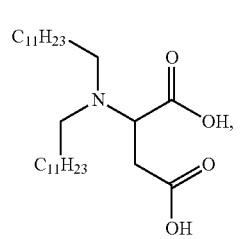

E-A12
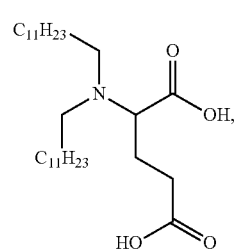

F-A12
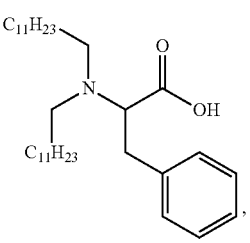

G-A12
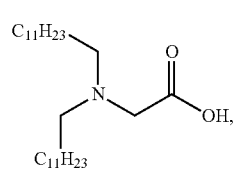

H-A12
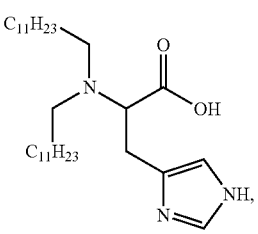

I-A12
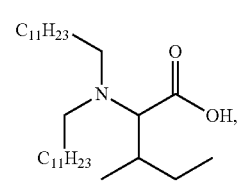

L-A12
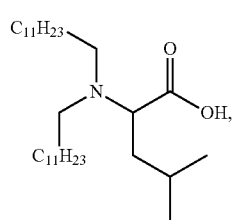

Example 2. Alternative Synthesis of Compound 23 (cKK-E12)

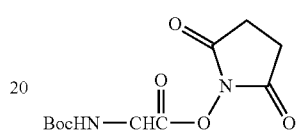

A

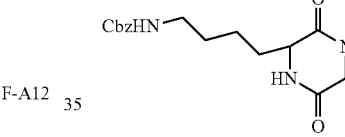

B

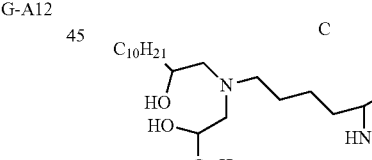

C

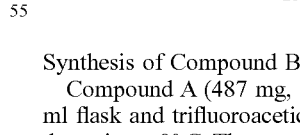

23 (cKK-E12)

Synthesis of Compound B.

Compound A (487 mg, 1.02 mmol) was charged in a 10 ml flask and trifluoroacetic acid (TFA, 1.3 mL) was added dropwise at 0° C. The reaction mixture was warmed to room temperature and stirred for 30 min. The solvents were evaporated under reduced pressure and the TFA salts in DMF (3.5 mL) were added dropwise to pyridine (100 mL) at 0° C. The reaction mixture was slowly warmed to room temperature and stirred for overnight. The solvents were evaporated under reduced pressure and the white solid was washed with EtOAc to give pure B in 69% yield. MS: m/z 525 (M+H$^+$); $^1$H NMR (500 MHz, DMSO, ppm): δ 1.29-1.40 (m, 8H, CH$_2$CH$_2$), 1.61-1.68 (m, 4H, CH$_2$), 2.97 (dd, J=6.0, 12.5 Hz, 4H, NCH$_2$), 3.79 (br, 2H, COCH), 7.22 (t, J=5.5 Hz, 2H, aromatic), 7.33-7.37 (m, 8H, aromatic), 8.10 (s, 2H, NH).

Synthesis of Compound C.

A cloudy solution of compound B (95 mg, 0.18 mmol) in 50% acetic acid/CH$_2$Cl$_2$ (6 mL) was added Pd on charcoal (10 wt %, 36.5 mg). The black suspension was degassed for 5 mins and hydrogen gas introduced. The reaction mixture stirred at rt overnight and was then filtered through a layer of Celite, which was washed several times with MeOH. The combined filtrates were concentrated to obtain a yellow viscous oil, which was solidified by adding EtOAc. The solid was washed by ethyl acetate to yield compound C in 90% yield. MS: m/z 257 (M+H$^+$); $^1$H NMR (500 MHz, D$_2$O, ppm): δ 1.39-1.52 (m, 4H, CH$_2$), 1.67-1.71 (m, 4H, CH$_2$), 1.84-1.88 (m, 4H, CH$_2$), 2.99 (t, J=7.5 Hz, 4H, NCH$_2$), 4.14 (t, J=5.0 Hz, 2H, COCH).

Synthesis of Compound 23 (cKK-E12).

A mixture of compound C (169.2 mg, 0.45 mmol) and 1,2-epoxydodecane (523 mg, 2.7 mmol) in EtOH was added triethylamine (182 mg, 1.8 mmol), which was stirred 30 mins at rt. The reaction mixture was then irradiated in the microwave oven at 150° C. for 5 h. The mixture was purified by flash column chromatography to obtain compound 23 (in 52% yield) as a light yellow oil. MS: m/z 993 (M+H$^+$); $^1$H NMR (500 MHz, DMSO, ppm): δ 0.87 (t, J=7.0 Hz, 12H, CH$_3$), 1.21-1.39 (m, 80H, CH$_2$), 1.64-1.67 (m, 4H, CH$_2$), 2.25-2.44 (m, 12H, NCH$_2$), 3.44 (br, 4H, CHOH), 3.79 (br, 2H, COCH), 4.21 (d, J=3.0 Hz, 2H, CHOH), 4.27 (d, J=3.0 Hz, 2H, CHOH), 8.11 (br, 2H, CONH).

Example 3. Synthesis of Compound D

It is envisioned compound D can be synthesized by reaction of 23 with Lawesson's reagent in dry toluene.

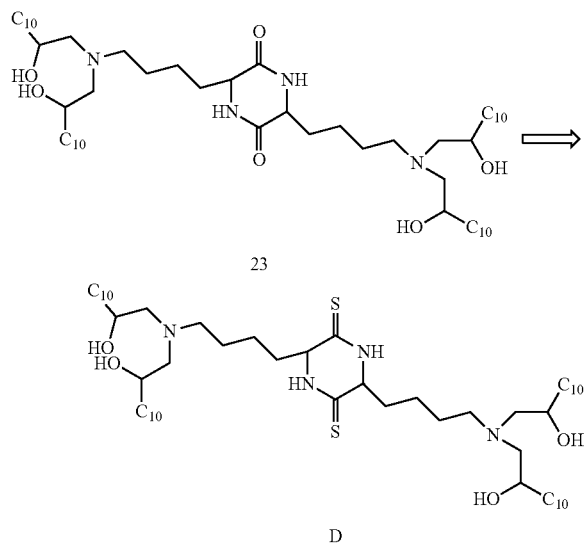

Example 4. Synthesis of Compound E

It is envisioned compound E can be synthesized by reaction of 23 with hydroxylamine hydrochloride or other substituted amines in methanol.

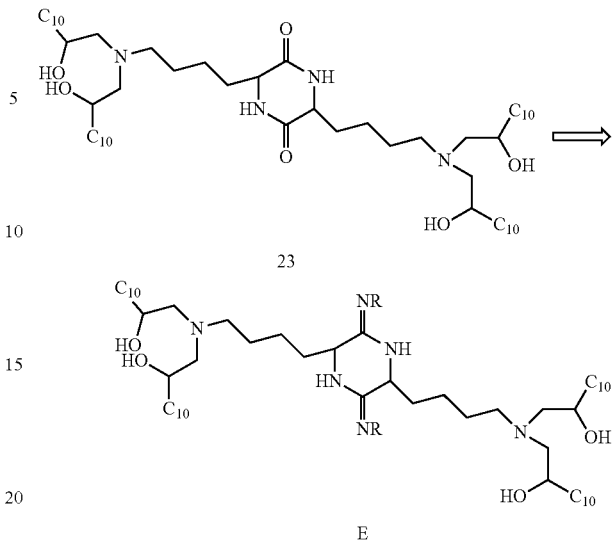

Biological Methods siRNA Formulations

Formulation A

APPL, distearoyl phosphatidylcholine (DSPC), cholesterol and mPEG2000-DMG were solubilized in 90% ethanol at a molar ratio of 50:10:38.5:1.5. The siRNA (against firefly luciferase or fVII) was solubilized in 10 mM citrate, pH 3 buffer at a concentration of 0.4 mg/mL. The ethanolic lipid solution and the aqueous siRNA solution were pumped by means of a syringe pump through a microfluidic mixing chamber to spontaneously form siRNA-containing lipid nanoparticles. Lipids were combined with siRNA at a total lipid to siRNA ratio of 7:1 (wt:wt). These formulations were dialyzed against PBS to remove ethanol and exchange buffer.

Formulation B

APPLs were formulated with cholesterol (Sigma-Aldrich), DSPC (1,2-distearoyl-sn-glycero-3-phosphocholine, Avanti), mPEG2000-DMG (synthesized by Alnylam), and siRNA via a microfluidic based mixing device See, e.g., Chen, D., et al., *Rapid Discovery of Potent siRNA-Containing Lipid Nanoparticles Enabled by Controlled Microfluidic Formulation*. J Am Chem Soc. Formulations were then dialyzed against PBS in 3,500 MWCO dialysis cassettes (Pierce) overnight. Particles were characterized with a modified Ribogreen assay (Invitrogen) for siRNA entrapment and dynamic light scattering (ZetaPALS, Brookhaven Instruments) for mean particle diameter. cKK-E12 formulations were made from cholesterol, DSPC, and mPEG2000-DMG using a similar method at a molar ratio of 50:10:38.5:1.5. This formulation afforded a particle diameter of 60-70 nm with approximately 65% siRNA entrapment.

In Vitro Luciferase Gene Silencing

HeLa cells, stably expressing firefly luciferase and *Renilla* luciferase, were seeded (14,000 cells/well) into each well of an opaque white 96-well plate (Corning-Costar) and allowed to attach overnight in growth medium. Growth medium was composed of 90% phenol red-free DMEM, 10% FBS, 100 units/ml penicillin, 100 mg/ml streptomycin (Invitrogen). Cells were transfected with LNPs formulated with anti-luciferase siRNA by addition of formulated particles to growth medium. Transfections were performed in quadruplicate. Cells were allowed to grow for 1 d at 37° C., 5% CO2 and were then analyzed for luciferase expression. Control experiments were performed with Lipofectamine 2000, as described by the vendor (Invitrogen). Firefly and *Renilla* luciferase expression was analyzed using Dual-Glo assay kits (Promega). Luminescence was measured using a Victor3 luminometer (Perkin Elmer).

In Vivo Factor VII Gene Silencing in Mice

C57BL/6 mice (Charles River Labs) were used for siRNA silencing experiments. Prior to injection, formulations were diluted in PBS at siRNA concentrations (SEQ ID NO 1 (siFVII sense): 5'-GGAucAucucAAGucuuAcT*T-3'; SEQ ID NO 2 (antisense): 5'-GuAAGAcuuGAGAuGAuccT*T-3') such that each mouse was administered a dose of 0.01 mL/g body-weight. Formulations were administered intravenously via tail vein injection. After 48 or 72 h, bodyweight gain/loss was measured and mice were anaesthetized by isofluorane inhalation for blood sample collection by retroorbital eye bleed. Serum was isolated with serum separation tubes (Falcon tubes, Becton Dickinson) and Factor VII protein levels were analyzed by chromogenic assay (Biophen FVII, Aniara Corporation). A standard curve was constructed using samples from PBS-injected mice and relative Factor VII expression was determined by comparing treated groups to untreated PBS control.

Biodistribution Cy5.5-Labeled siRNA-cKK-E12 Formulation in Mice.

The mice mentioned above were systemically injected with formulated Cy5.5-labeled siRNA at a dose of 1 mg/kg of total siRNA. The mice were sacrificed 1 hour or 24 hours post injection; the pancreas, spleen, liver, kidneys, ovaries, uterus, heart, lungs, and thymus as well as a section of the adipose tissue and muscle tissue were then removed and imaged. The organs were examined with an Ivis imaging system from Caliper using an excitation wavelength of 675 nm and an emission wavelength of 720 nm. The data were processed using the Living Image software from Caliper. Signal strength of the individual organs was normalized against the total signal strength of all organs.

In Vitro siRNA Transfection Assay and Microscopy.

Effects of apolipoproteins were evaluated through an in vitro siRNA transfection assay in HeLa cells as previously reported. HeLa cells, stably expressing firefly luciferase and *Renilla* luciferase were seeded in an opaque white 96-well plate (Corning-Costar) overnight. Cells were transfected by cKK-E12 formulated with 50 ng of firefly-specific siLuc in quadruplicate. Apolipoproteins (Fitzgerald Industries) were incubated with cKK-E12 formulations for 5 mins before adding to cells. After 24 h incubation at 37° C., 5% $CO_2$, cells were analyzed for luciferase expression using Dual-Glo assay kits (Promega). For visualization of cell uptake, cKK-E12 was formulated with an Alexa-Fluor 647-labeled siRNA and incubated with Hela cells for 3 h. Cells were then fixed in 4% paraformaldehyde, permeabilized with 0.1% saponin and stained with Hoescht. All images were acquired using an Opera spinning disc confocal system (Perkin Elmer), and the data was analyzed using Acapella Software (Perkin Elmer).

Discussion

Single amino acids were reacted with aldehydes, acrylates, and epoxides to produce APPLs. The newly-synthesized single amino acid-based lipid derivatives were evaluated for their capacity to silence hepatic genes in mice. A validated genetic target, Factor VII (a blood clotting factor), was selected as a silencing marker. See, e.g., Akinc, A., et al., *A combinatorial library of lipid-like materials for delivery of RNAi therapeutics*. Nat Biotechnol, 2008. 26(5): p. 561-9. New lipid derivatives were formulated with cholesterol, DSPC, PEG-lipid, and siRNA via a microfluidic based mixing technology. See, e.g., Chen, D., et al., *Rapid Discovery of Potent siRNA-Containing Lipid Nanoparticles Enabled by Controlled Microfluidic Formulation*. J Am Chem Soc. Formulations that were instable in solution or had no siRNA entrapment were not screened. Stable formulations were injected in mice through systemic administration at a dose of 1 mg/kg (FIG. 1). From this initial screening, we identified that K-E12 was more potent than others. The hit rate (over 50% silencing) was one out of 60 compounds (i.e. 1.7%, including those compounds not screened due to particle instability or no entrapment of siRNA).

The enhanced potency of K-E12 led to our design of a second set of lysine-based peptide and polypeptide-lipid derivatives. Lysine-based dipeptides were reacted with epoxides to give diketopiperizine APPLs. Microwave irradiation was utilized to produce these scaffolds, which dramatically reduced the reaction time from 3 days to 5 hours. In addition, to further confirm the chemical structure and improve chemical availability for large-scale synthesis, an alternative synthetic route was developed for the synthesis of cKK-E12 (Example 2). Diamine 5 was synthesized according to the method reported previously (Bergeron, R. J., et al., *Macromolecular Self-Assembly of Diketopiperazine Tetrapeptides*. J. Am. Chem. Soc., 1994. 116(19): p. 8479-84; Kaur, N., et al., *A Delineation of Diketopiperazine Self-Assembly Processes: Understanding the Molecular Events Involved in N-(Fumaroyl)diketopiperazine of L-Lys (FDKP) Interactions*. Mol. Pharmaceutics, 2008. 5(2): p. 294-315), which reacted with 1,2-epoxydodecane to afford cKK-E12. Compound (C) underwent reductive amination or Michael addition reactions with dodecanal or dodecyl acrylate to yield cKK-A12 and cKK-O12. Reactions between lysine-lysine and poly-L-lysine (molecular weight from 500-70000 g/mol) and aldehydes and acrylates were similar to those of single amino acids.

The silencing effects were next evaluated. Ten out of 43 compounds showed around 50% silencing at a dose of 1 mg/kg. The hit rate of the second set of compounds was 23%, which was over 10-fold more efficient compared to the first set of materials. The results suggested that our iterative screening process is an efficient strategy for identifying lead compounds. The results from the second set also showed that epoxide derivatives were more potent than aldehyde and acrylate derivatives (such as cKK-E12 vs cKK-A12 & cKK-O12). Hit materials were further tested at a lower dose of 0.1 mg/kg. The tail length significantly affects silencing and 12-14 carbon tail lengths appeared favorable (cKK-E10, -E12, -E14, & -E16). cKK-E12 was the most potent material and was selected for further exploration.

Biodistribution Study

Figure 2:
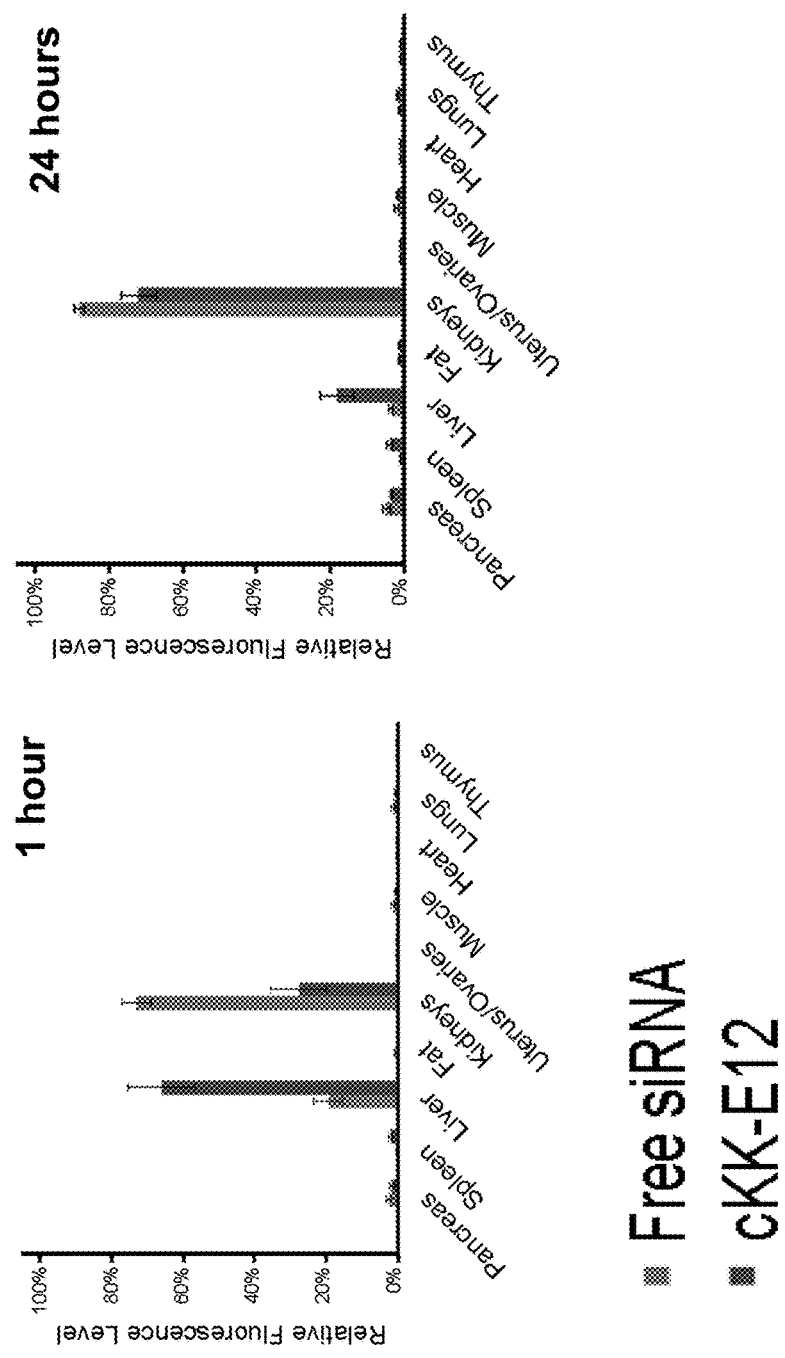
FIG. 2 depicts the bio-distribution of free Cy5.5-labeled siRNA and Cy5.5-labeled siRNA-cKK-E12 formulation in mice at 1 hr and 24 hr.

A biodistribution study was performed with naked Cy5.5 labeled siRNA and formulated cKK-E12. By subtracting the contribution of free siRNA in the formulation of cKK-E12, over 80% of particles were located in the liver at 1 hr and most residual siRNA was cleared by 24 hr through kidney (FIG. 2).

Effects of Apolipoproteins on Cell Uptake and Gene Silencing

Previous studies have reported that Apolipoprotein E (ApoE) was able to enhance cell uptake and gene silencing for a certain type of materials. Akinc, A., et al., *Targeted delivery of RNAi therapeutics with endogenous and exogenous ligand-based mechanisms*. Mol Ther. 18(7): p. 1357-

Figure 3:
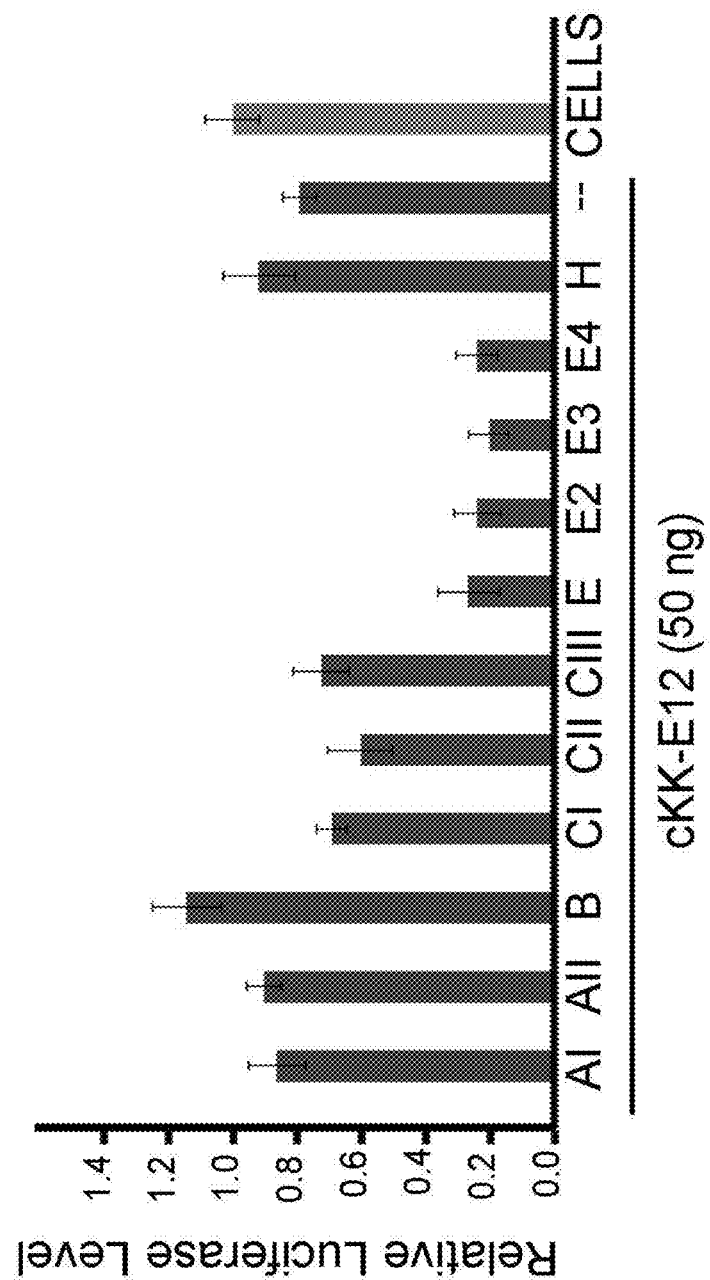
FIG. 3 depicts the silencing effects of apolipoproteins on cKK-E12 in HeLa cells. Apolipoproteins including ApoA-I (recombinant Human ApoA-I protein), ApoA-II (native Human ApoA-II protein), ApoB (native Human ApoB protein), ApoC-I (native Human ApoC-I protein), ApoC-II (native Human ApoC-II protein), ApoC-III (native Human ApoC-III protein), ApoE (native Human ApoE protein), ApoE2 (recombinant Human ApoE2 protein), ApoE3 (recombinant Human ApoE3 protein), ApoE4 (recombinant Human ApoE4 protein), ApoH (native Human ApoH protein).

64. In order to test the effects of diverse apoliproteins on cell uptake and gene silencing, and explore the mechanism of action, experiments were performed with cKK-E12 and 11 isoforms of ApoA, ApoB, ApoC, ApoE, and ApoH. Results in Hela cells showed that most apolipoproteins did not affect cell viability with the exception of ApoB. ApoA, ApoC, and ApoH did not show significant effects on silencing compared to free cKK-E12 (FIG. 3). However, four different ApoE isoforms significantly improved luciferase silencing.

Figure 4:
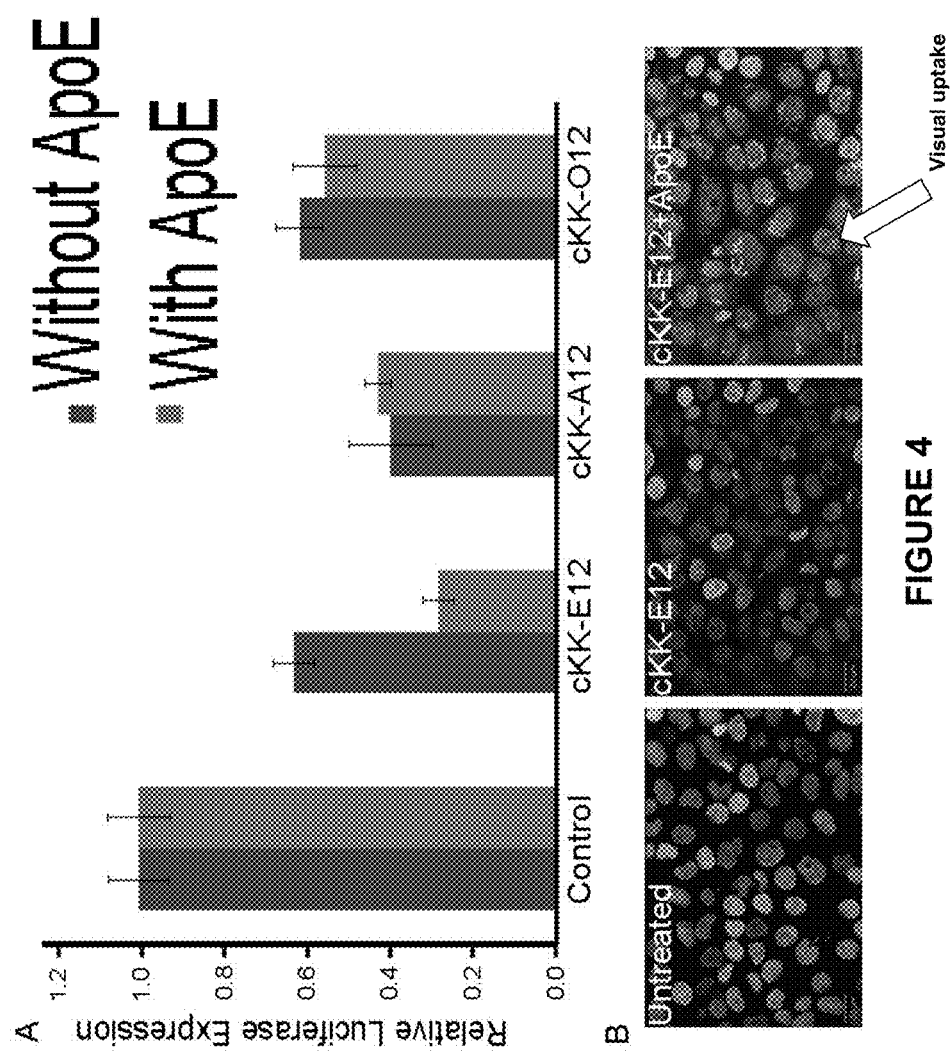
FIG. 4 depicts the effects of ApoE on gene silencing and cell uptake. A). Silencing effects of ApoE on cKK-E12, cKK-A12, and cKK-O12 in vitro (siRNA: 50 ng/well). With addition of ApoE, the order of silencing effects was cKK-E12>cKK-A12>cKK-O12, correlating well with in vivo activity. B). Cellular internalization of cKK-E12 with Alex-647 labeled siRNA after 3 hr of incubation is demonstrated by HT automated confocal microscopy. ApoE enhanced cell uptake and endosomal escape of cKK-E12; Scale bar: 20 m.

The activity of cKK-E12, cKK-A12, and cKK-O12 was compared with and without addition of apoE3 (apoE3 is the dominant isoform in humans. FIG. 4A). Without addition of ApoE3, cKK-A12 was more potent than cKK-E12 and cKK-O12. However, with addition of ApoE3, the order of silencing effects was cKK-E12>cKK-A12>cKK-O12, which correlated well with in vivo activity. The results suggested that a cell assay with addition of ApoE might be a practical and effective model for preliminary screening for liver hepatocytes silencing. In addition, the cell uptake of cKK-E12 formulated with an Alexa-Fluor 647 labeled siRNA was visualized using automated confocal microscopy (FIG. 4B).

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, books, manuals, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of delivering a polynucleotide to a cell, the method comprising contacting a composition comprising a polynucleotide and a compound of Formula (III):

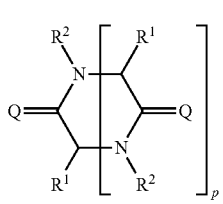

(III)

or salt thereof, with the cell under conditions sufficient to facilitate delivery of the polynucleotide into the interior of the cell;
wherein:
  p is 1;
  each instance of Q is O;
  each instance of $R^1$ is independently hydrogen, alkyl, or a group of formula (iv);
  provided at least one instance of $R^1$ is a group of formula:

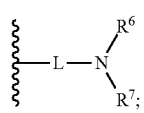

(iv)

L is alkylene;
$R^6$ and $R^7$ are each independently hydrogen, alkyl, a nitrogen protecting group, or a group of the formula (i), (ii), or (iii);

each instance of $R^2$ is independently hydrogen, alkyl, a nitrogen protecting group, or a group of the formula (i), (ii), or (iii);

Formulae (i), (ii), and (iii) are:

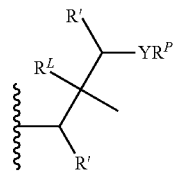

(i)

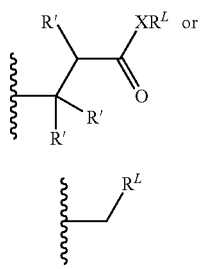

(ii)

(iii)

wherein each instance of formula (i) is independently formula (i-a) or formula (i-b):

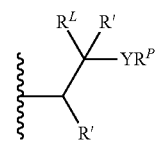

(i-a)

-continued

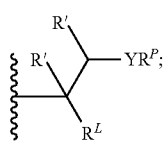
(i-b)

each instance of R' is independently hydrogen or alkyl;
X is O, S, or $NR^X$, wherein $R^X$ is hydrogen, or a nitrogen protecting group;
Y is O;
$R^P$ is hydrogen, alkyl, an oxygen protecting group when attached to an oxygen atom, a sulfur protecting group when attached to a sulfur atom, or a nitrogen protecting group when attached to a nitrogen atom; and
$R^L$ is $C_{6-50}$ alkyl,
provided that at least one instance of $R^2$, $R^6$, or $R^7$ is a group of the formula (i), (ii), or (iii);
wherein each alkyl and alkylene is independently unsubstituted or substituted at one or more positions with a group selected from halogen, —CN, —NO$_2$, —OH, —OR$^{aa}$, —N(R$^{bb}$)$_2$, —N(R$^{bb}$)$_3^+$X$^-$, —N(OR$^{cc}$)R$^{bb}$, —SH, —SR$^{aa}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, $C_{3-14}$ carbocyclyl, 3-14 membered heterocyclyl, $C_{6-14}$ aryl, and 5-14 membered heteroaryl, wherein each alkyl, carbocyclyl, heterocyclyl, aryl, and heteroaryl is independently substituted with 0, 1, 2, 3, 4, or 5 groups selected from halogen, —OH, —OR$^{ee}$, and $C_{1-50}$ alkyl; or two geminal hydrogens on a carbon atom are replaced with the group =O;
each instance of $R^{aa}$ is, independently, selected from $C_{1-50}$ alkyl;
each instance of $R^{bb}$ is, independently, selected from hydrogen, and $C_{1-50}$ alkyl;
each instance of $R^{ee}$ is, independently, selected from $C_{1-50}$ alkyl, and $C_{3-10}$ carbocyclyl;
wherein X$^-$ is a counterion.

2. The method of claim 1, wherein at least one instance of $R^2$ is hydrogen.

3. The method of claim 1, wherein each instance of $R^1$ is a group of formula (iv).

4. The method of claim 1, wherein the group of formula (iv) is of formula:

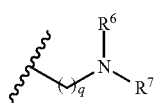

wherein q is an integer between 1 and 50, inclusive.

5. The method of claim 4, wherein the group of formula (iv) is of formula:

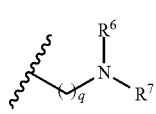

wherein q is an integer between 1 and 10, inclusive.

6. The method of claim 5, wherein q is 4.

7. The method of claim 1, wherein the compound is selected from the group consisting of:

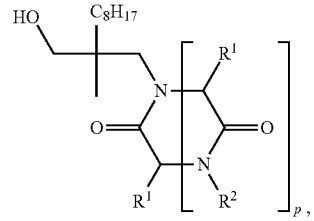

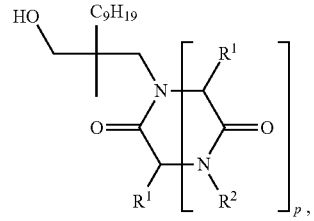

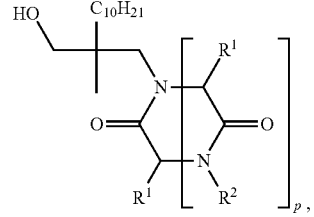

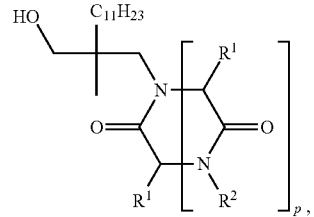

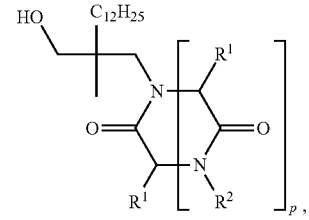

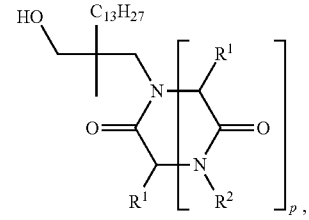

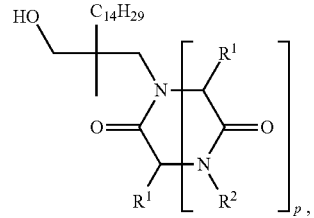

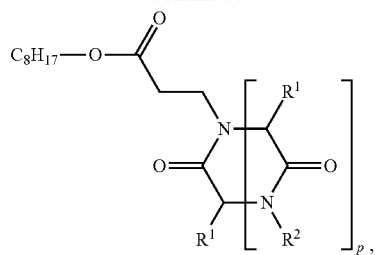
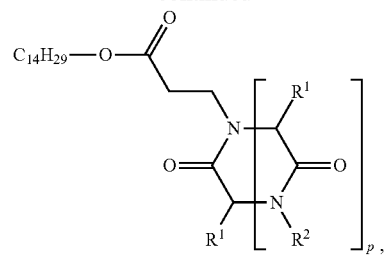
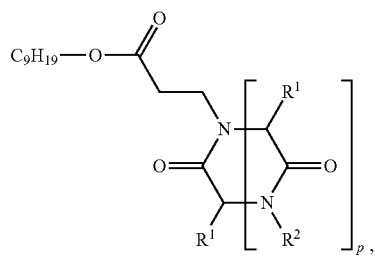
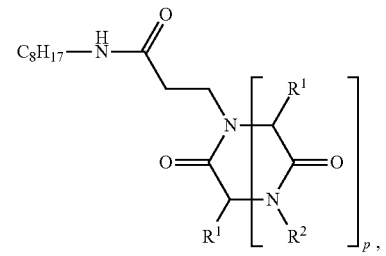
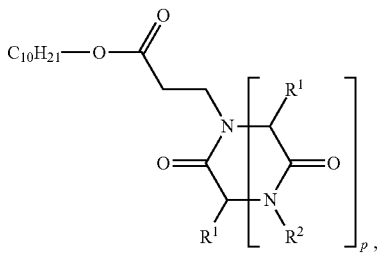
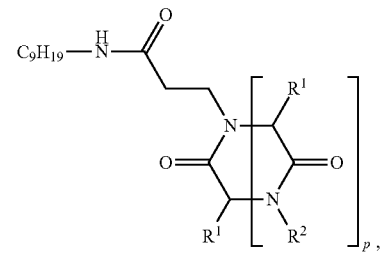
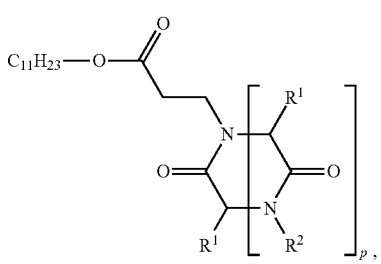
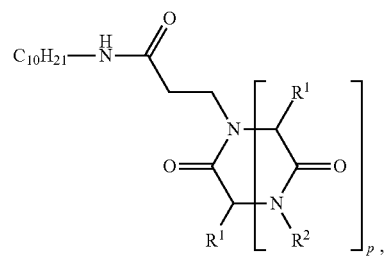
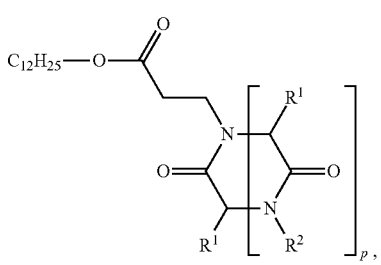
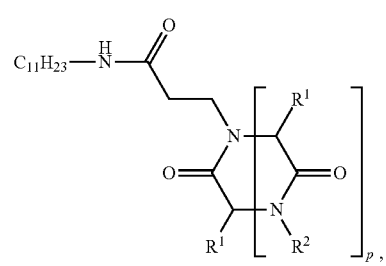
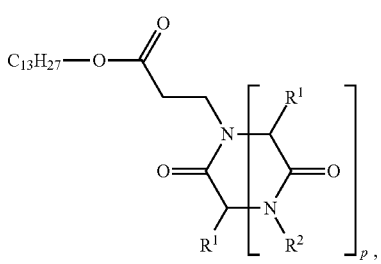
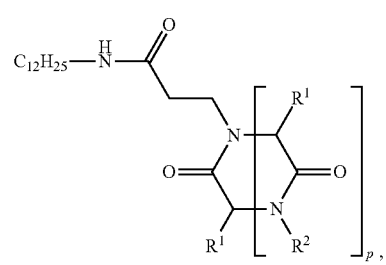

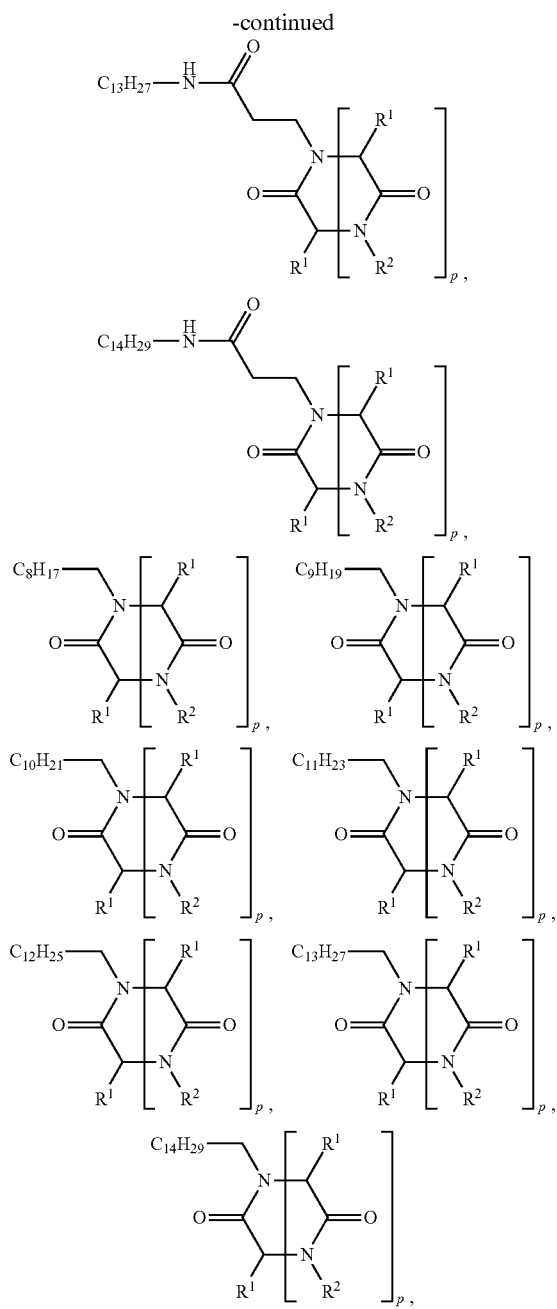
and salts thereof,
wherein:
R¹ is selected from the group consisting of —H, —CH₃, —CH(CH₃)₂, —CH(CH₃)(CH₂CH₃), —CH₂CH(CH₃)₂,
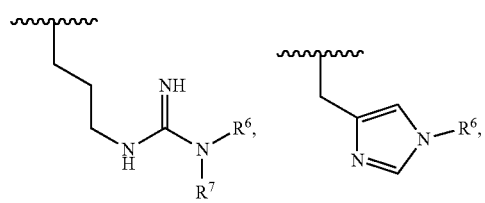
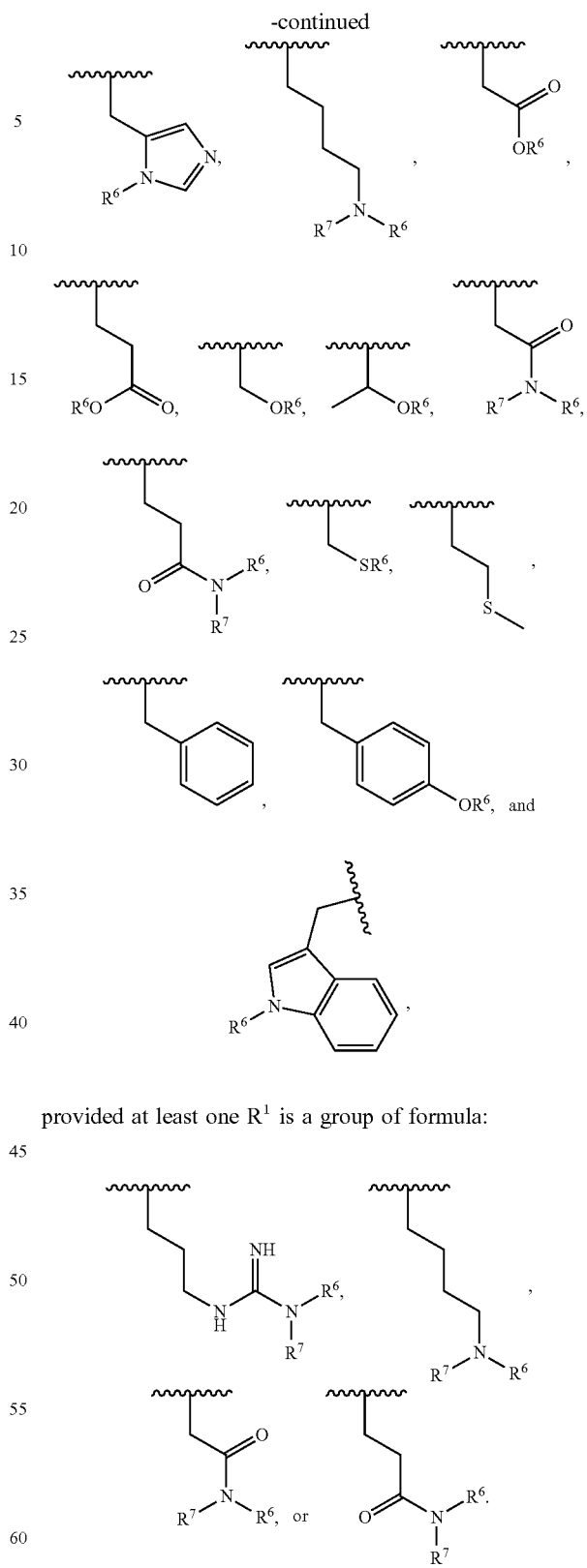
provided at least one R¹ is a group of formula:
8. The method of claim 7, wherein at least one instance of R⁶ or R⁷ is a group of the formula (i), (ii), or (iii).
9. The method of claim 1, wherein the compound is selected from the group consisting of:

259
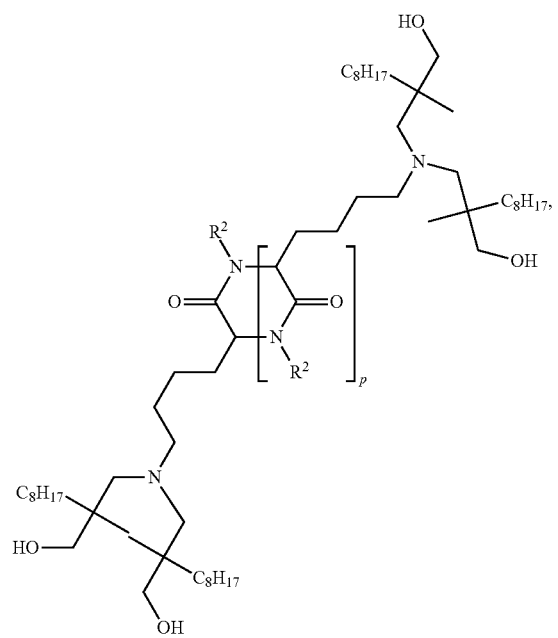
260
-continued
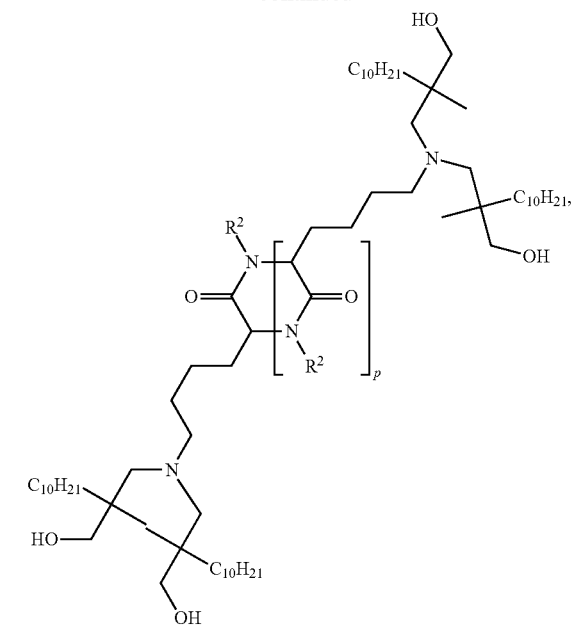
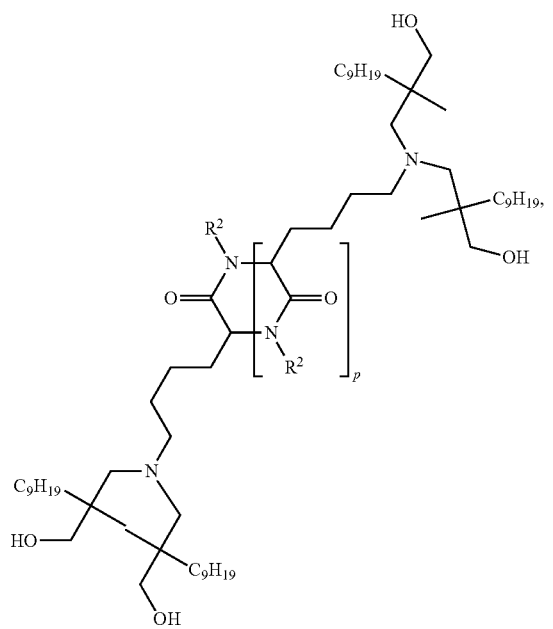
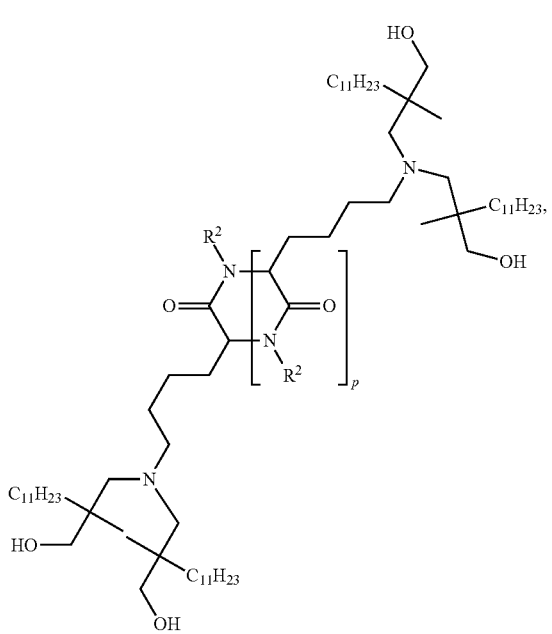

261
-continued
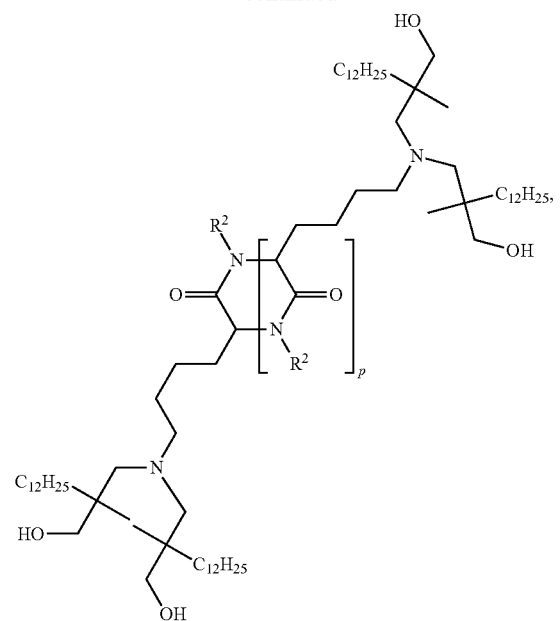
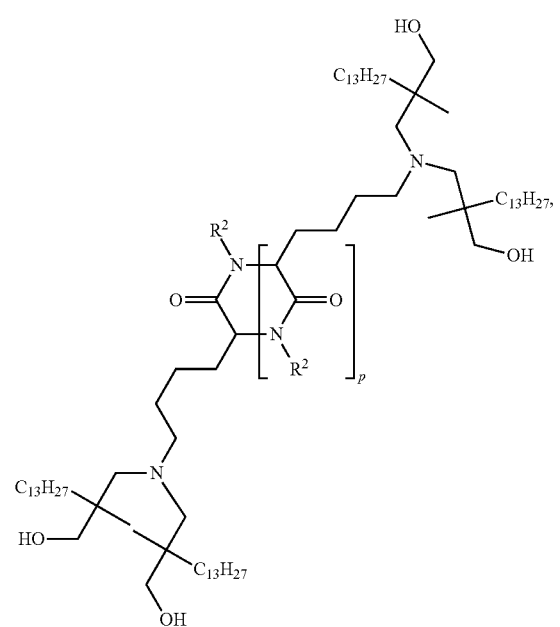
262
-continued
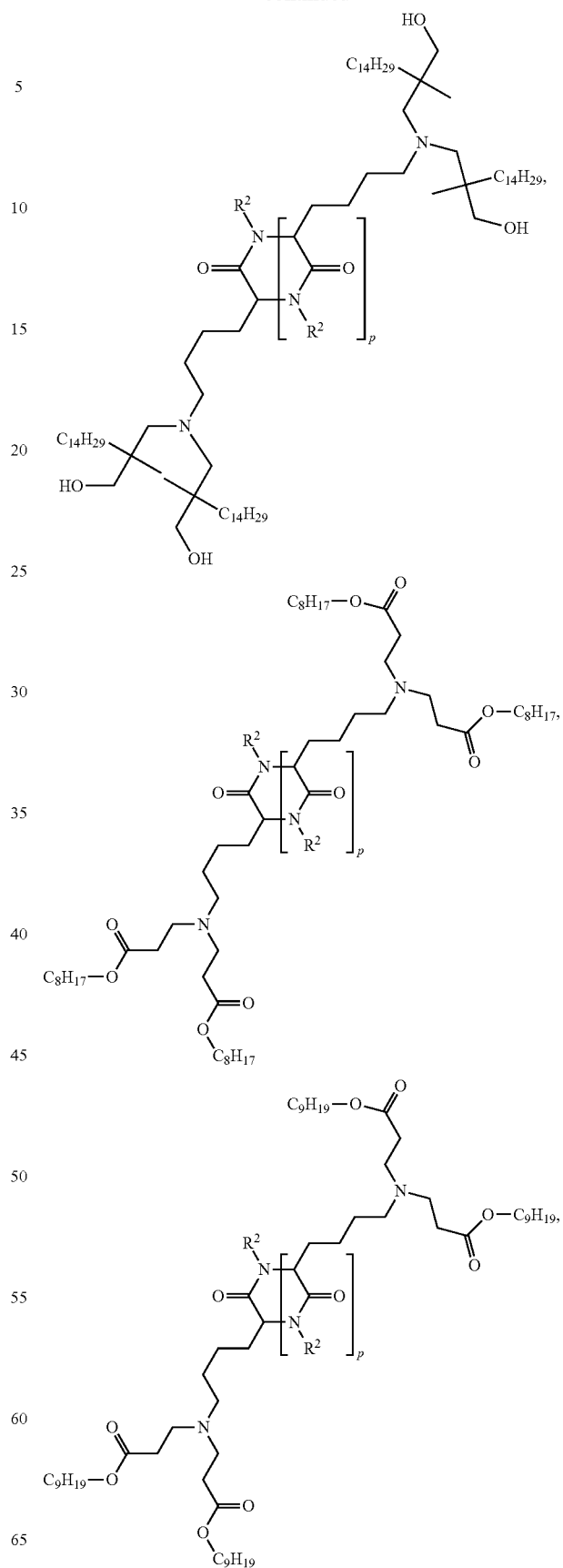

263
-continued
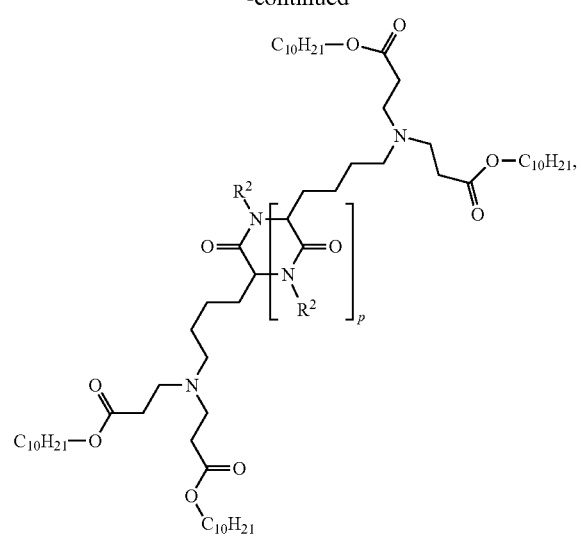
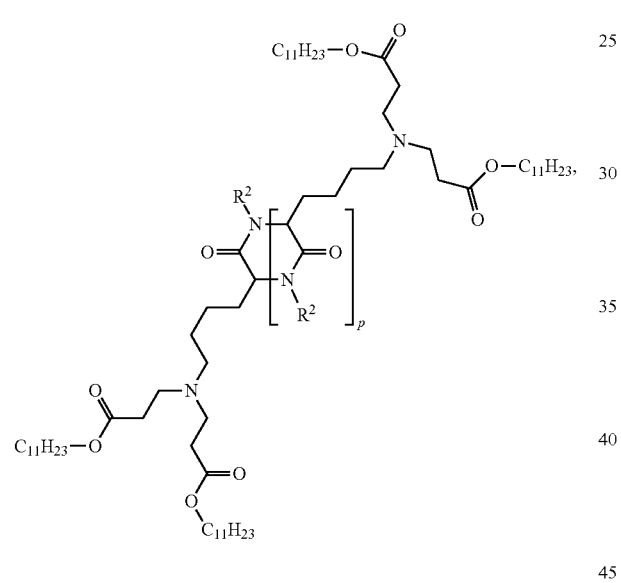
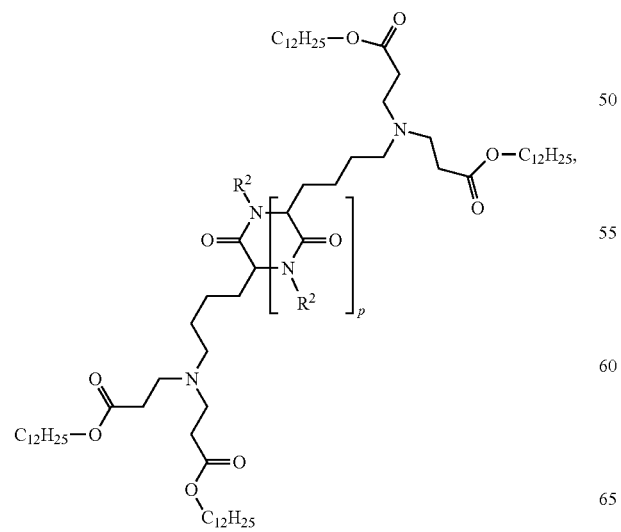
264
-continued
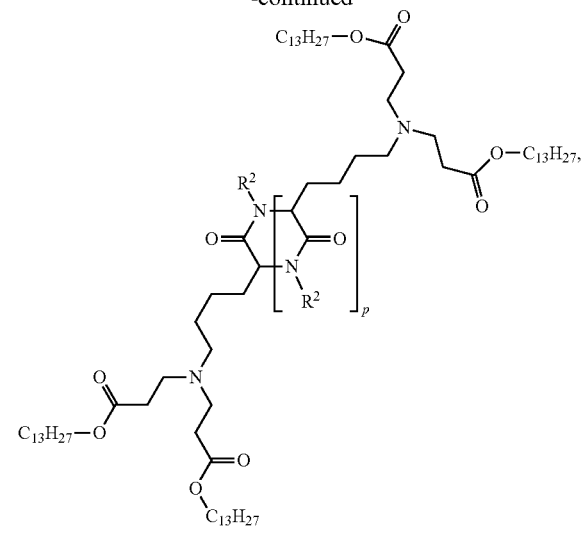
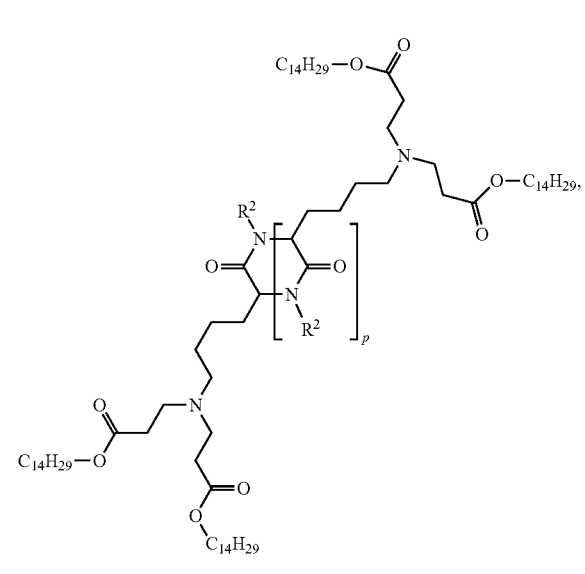
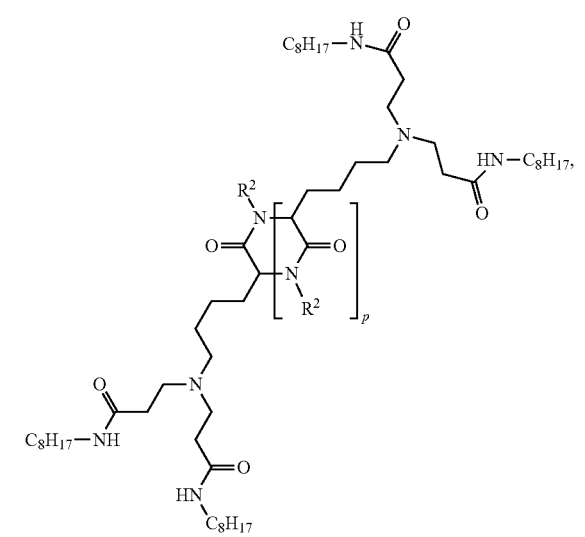

265
-continued
266
-continued
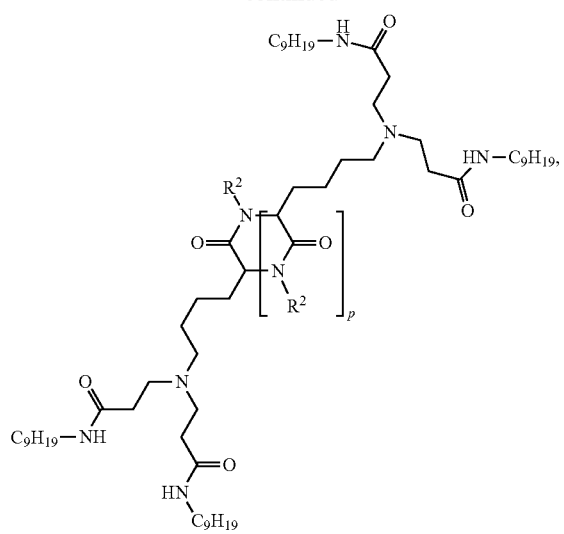
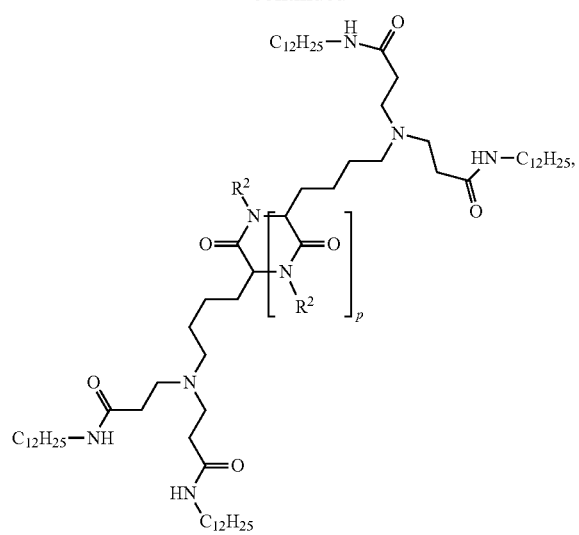
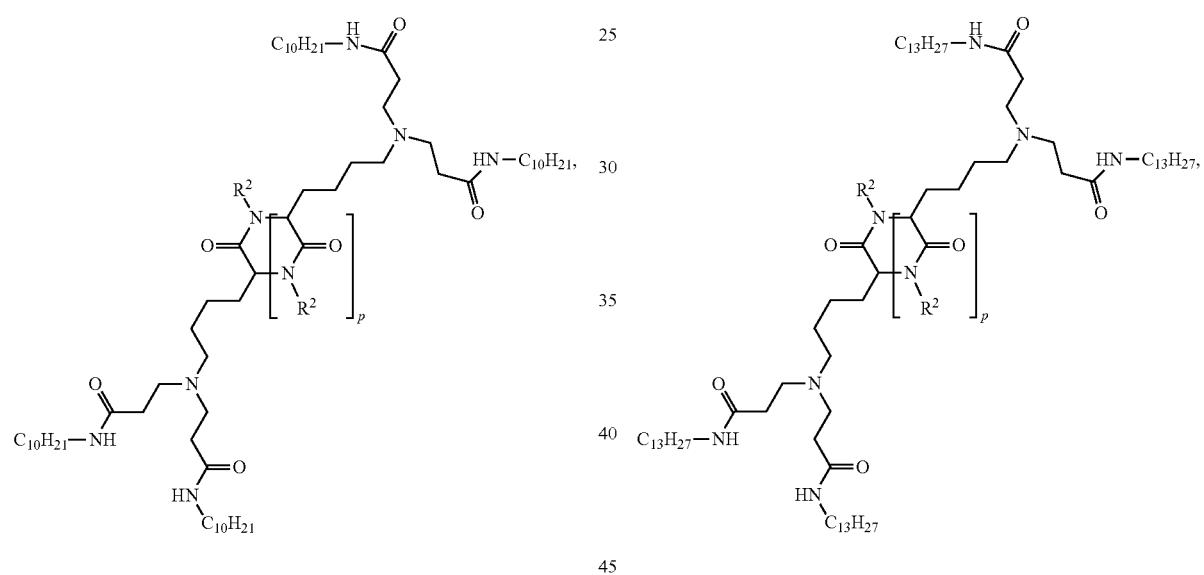
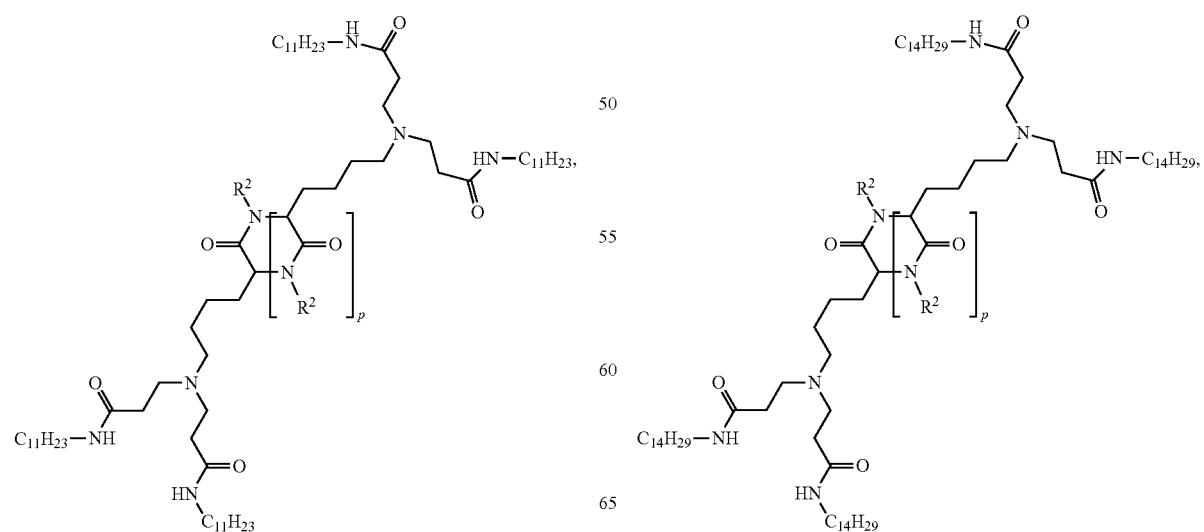

267
-continued
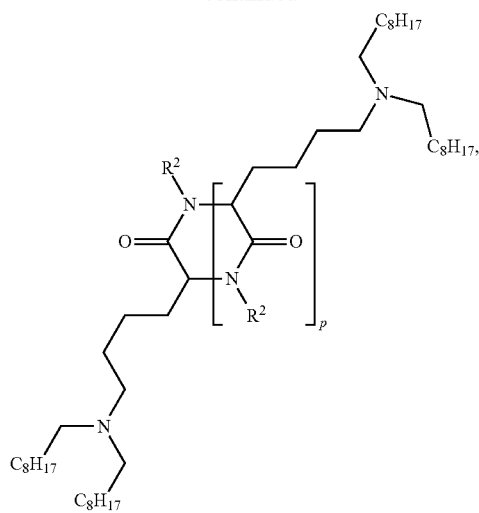
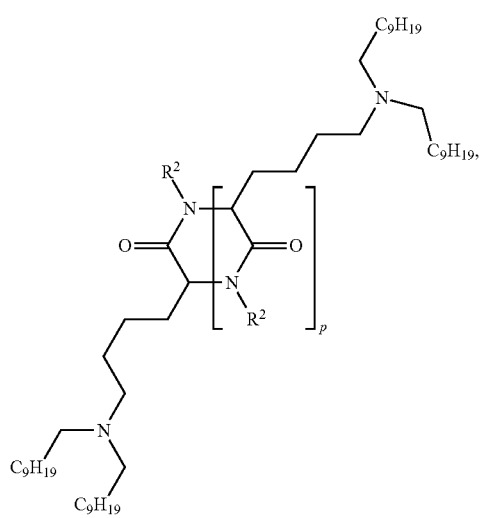
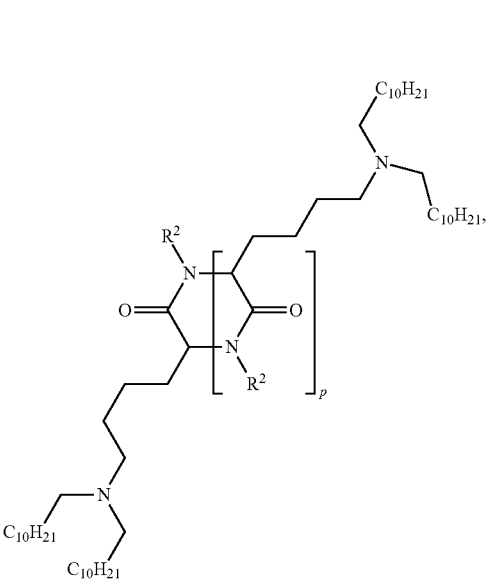
268
-continued
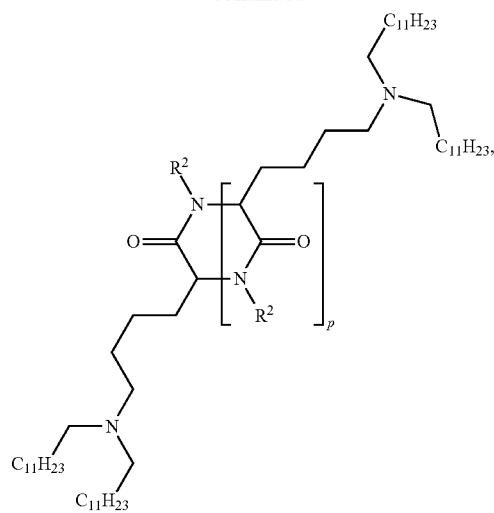
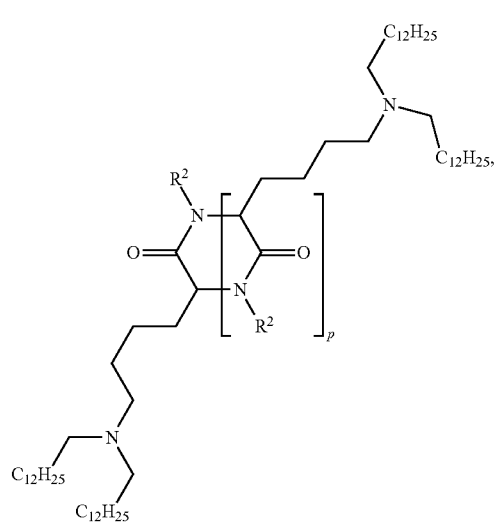
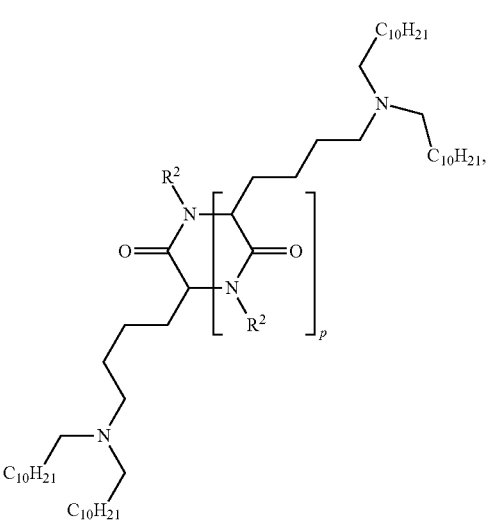

-continued
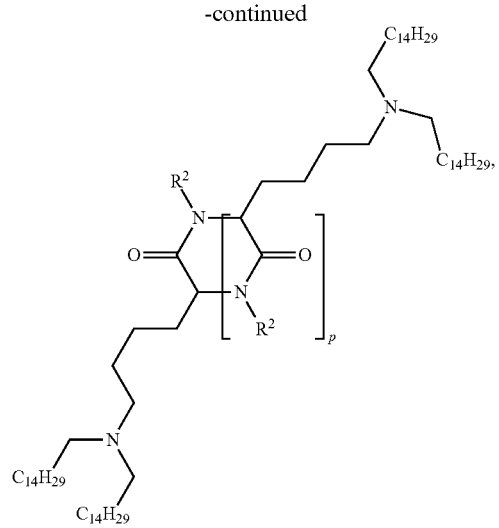
and salts thereof.
10. The method of claim 1, wherein the compound is selected from the group consisting of:
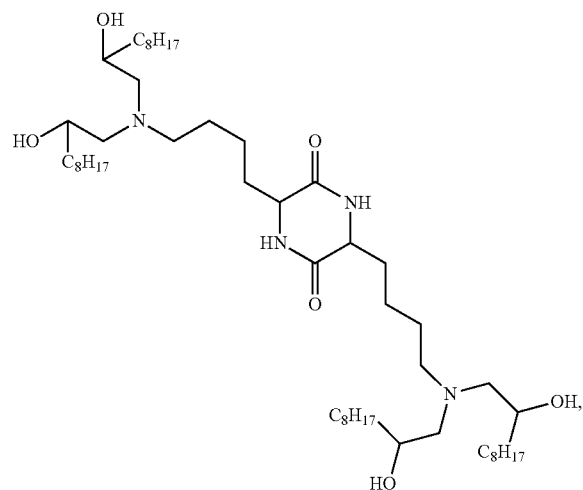
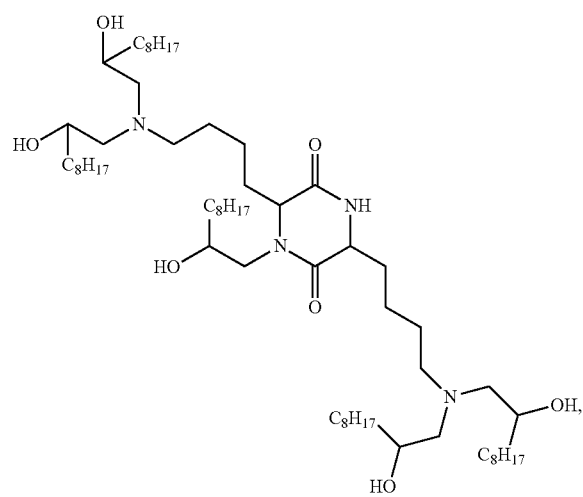
-continued
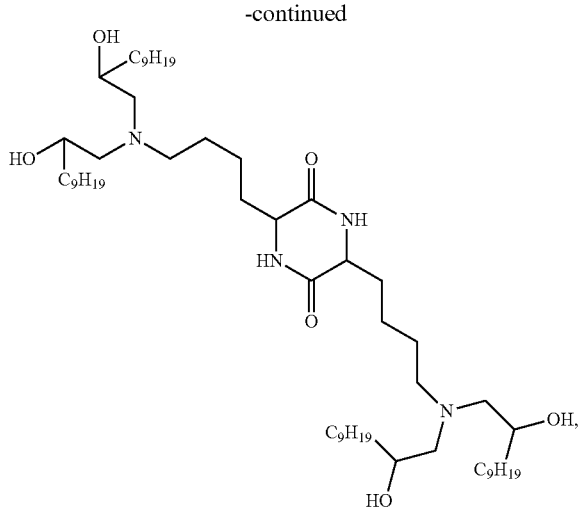
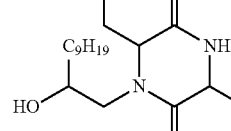
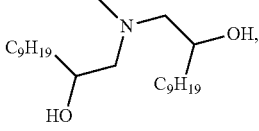

-continued
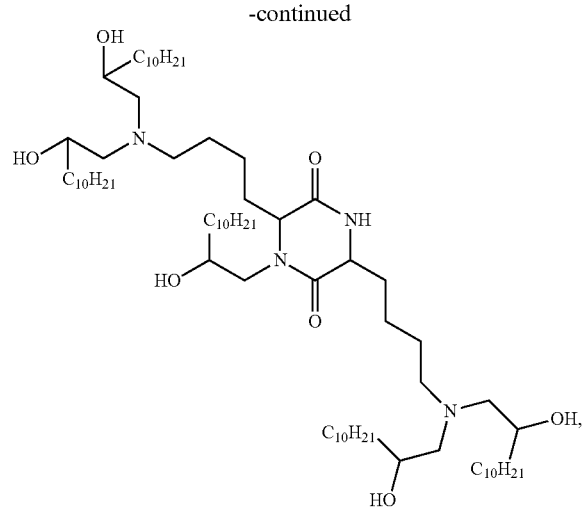
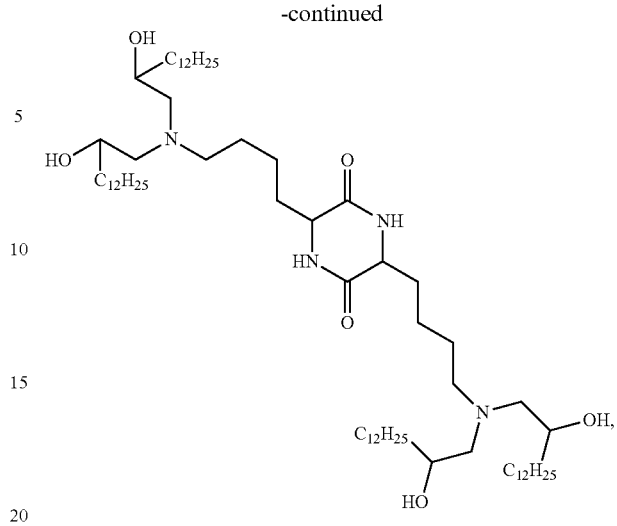
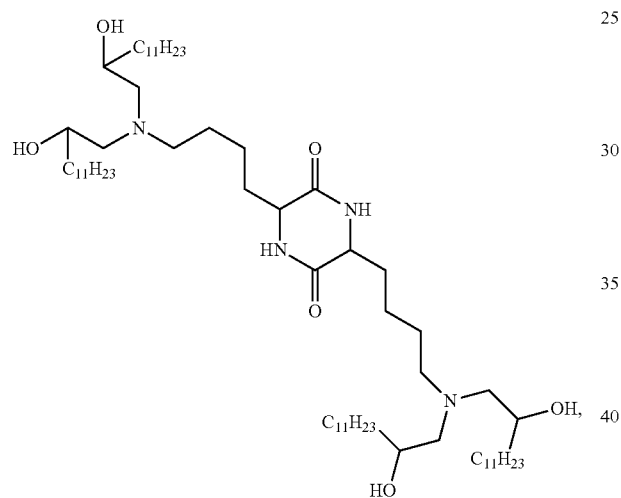
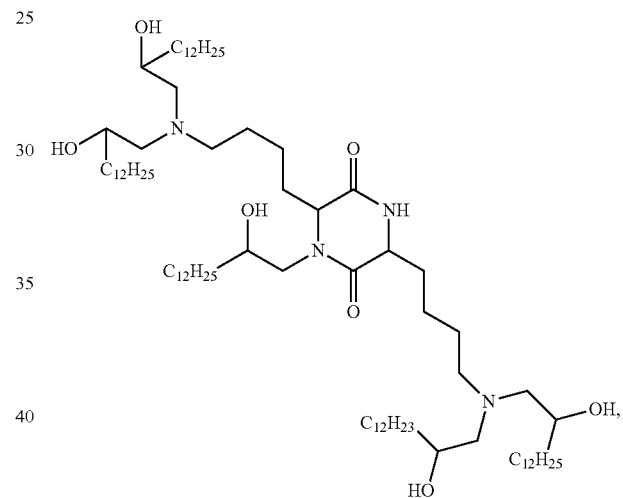
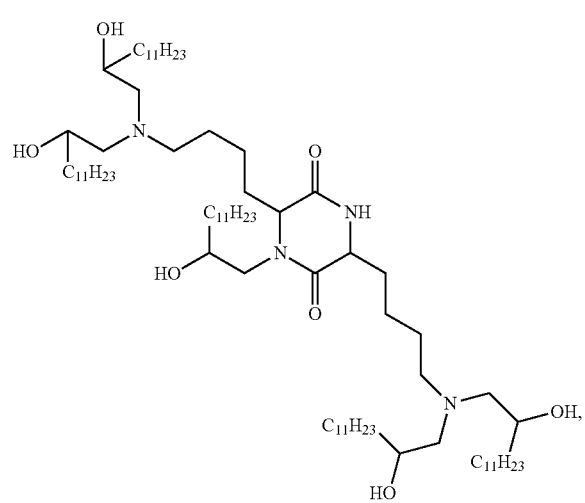
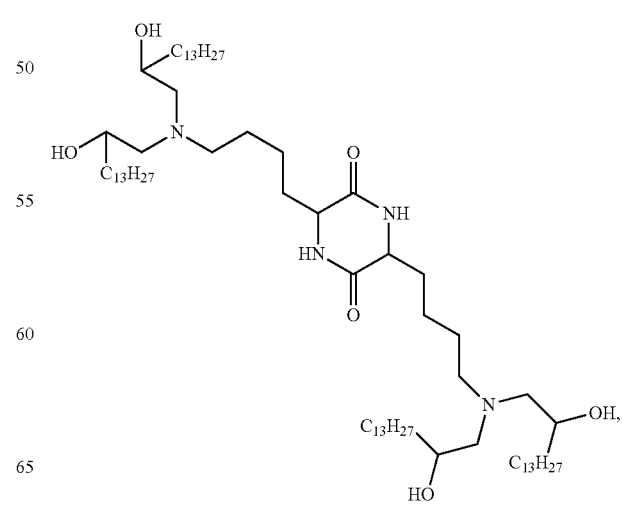

273
-continued
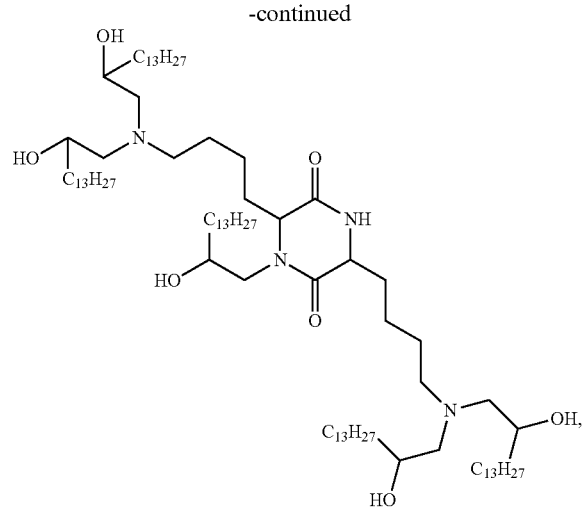
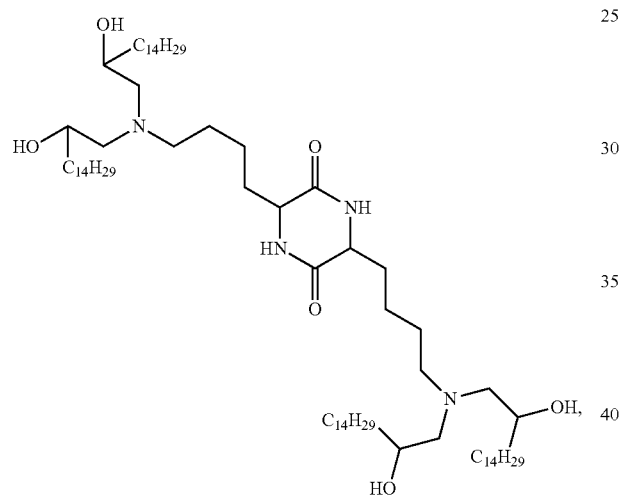
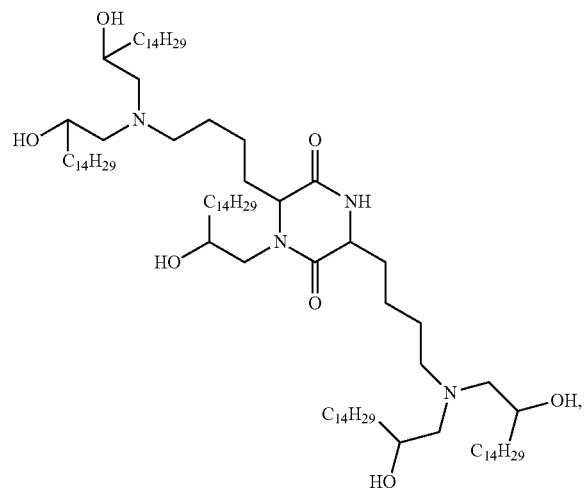
274
-continued
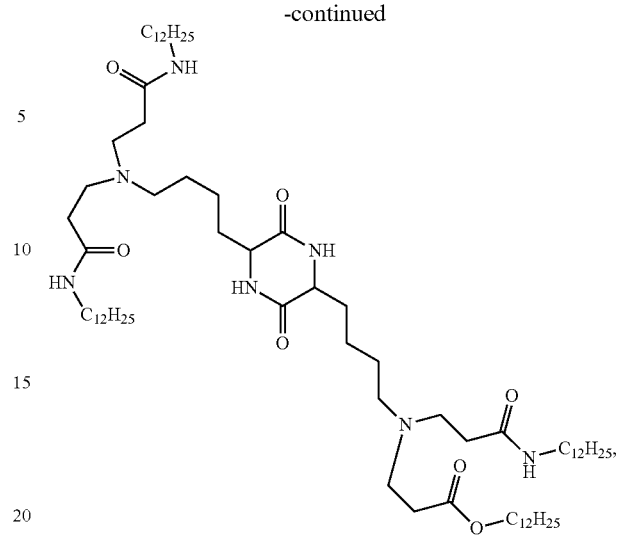
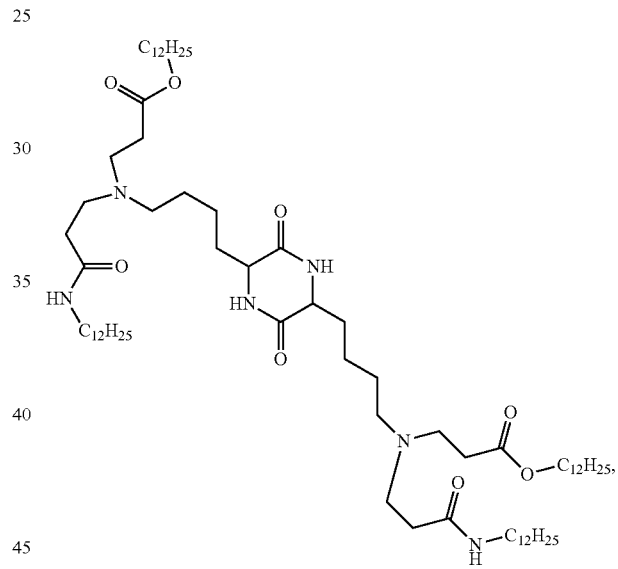
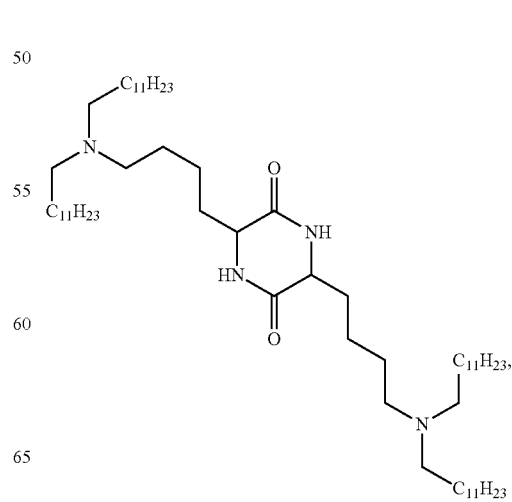

cKG-E12
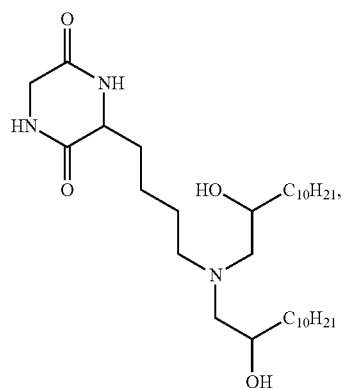
cDK-E12
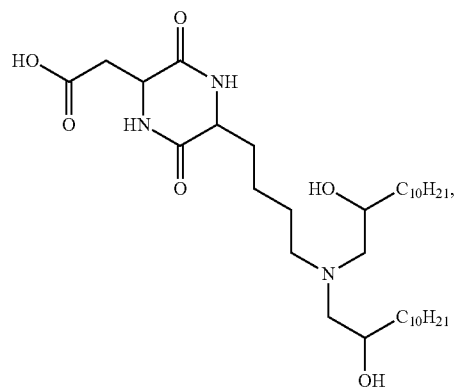
cKT-E12
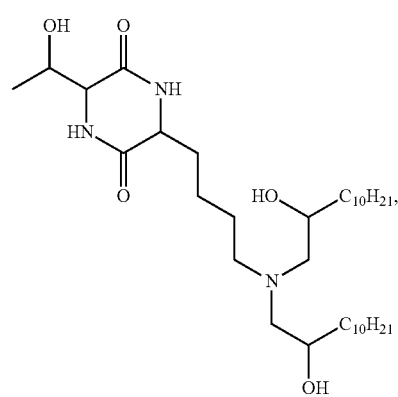
cMK-E12
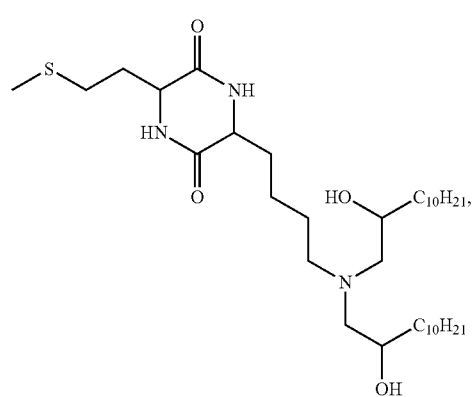
cYK-E12
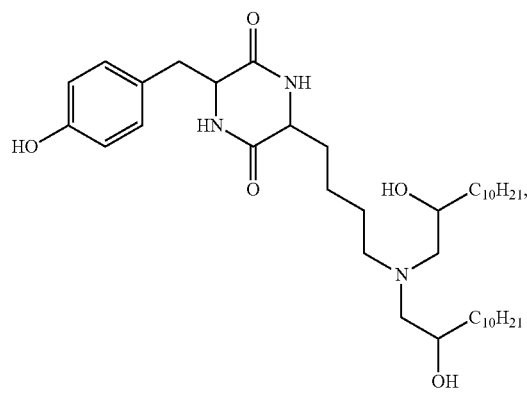
cKV-E12
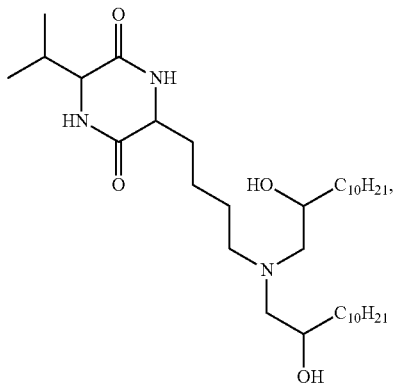
cLK-E12
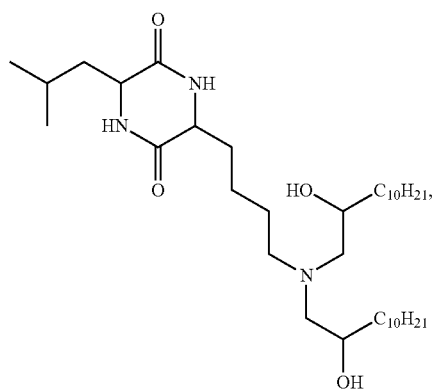
cAK-E12
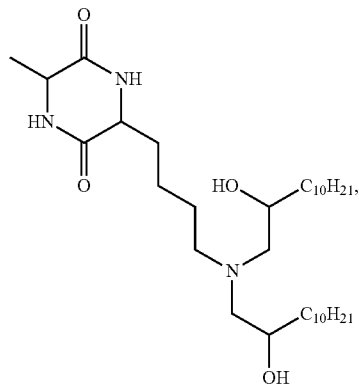

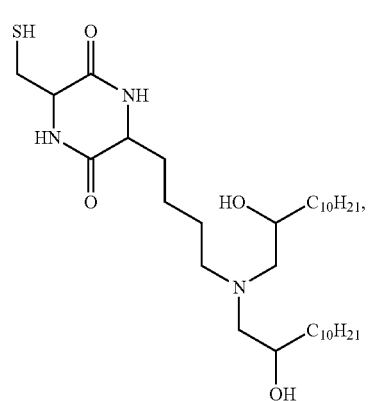
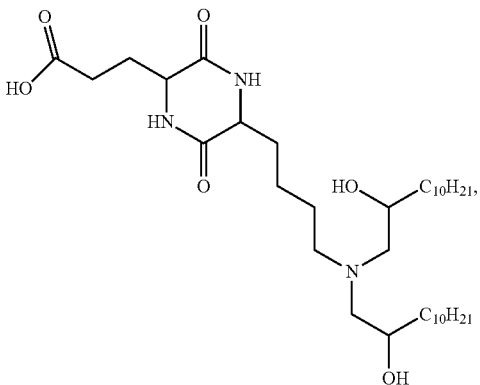
and salts thereof.
11. The method of claim 10, wherein the compound is:
or salt thereof.

12. The method of claim 1, wherein the composition further comprises cholesterol.

13. The method of claim 1, wherein the composition further comprises a PEGylated lipid.

14. The method of claim 1, wherein the composition further comprises a phospholipid.

15. The method of claim 1, wherein the composition further comprises an apolipoprotein.

16. The method of claim 1, wherein the polynucleotide is RNA.

17. The method of claim 16, wherein the RNA is RNAi, dsRNA, siRNA, shRNA, miRNA, or antisense RNA.

18. The method of claim 16, wherein upon delivery of the RNA into the cell, the RNA is able to interfere with the expression of a specific gene in the biological cell.

19. The method of claim 1, wherein the polynucleotide is DNA.

20. The method of claim 1, wherein the polynucleotide encodes a protein or peptide.

21. The method of claim 1, wherein at least one instance of $R^2$, $R^6$, or $R^7$ is a group of the formula (i), and further provided neither $R^2$, $R^6$, nor $R^7$ is a group of the formula (ii) or (iii).

22. The method of claim 1, wherein at least one instance of $R^2$, $R^6$, or $R^7$ is a group of the formula (ii), and further provided neither $R^2$, $R^6$, nor $R^7$ is a group of the formula (i) or (iii).

23. The method of claim 1, wherein at least one instance of $R^2$, $R^6$, or $R^7$ is a group of the formula (iii), and further provided neither $R^2$, $R^6$, nor $R^7$ is a group of the formula (i) or (ii).

24. The method of claim 1, wherein at least one instance of $R^6$ or $R^7$ is a group of the formula (i), (ii), or (iii).

25. The method of claim 1, wherein $R^L$ is $C_{6-20}$ alkyl.

26. The method of claim 1, wherein $R^L$ is unsubstituted $C_{6-20}$ alkyl.

27. The method of claim 1, wherein each instance of $R^2$ is independently hydrogen or a group of the formula (i), (ii), or (iii).

28. The method of claim 1, wherein X is $NR^X$, wherein $R^X$ is hydrogen, alkyl, or a nitrogen protecting group.

29. The method of claim 1, wherein X is O.

30. The method of claim 1, wherein X is S.

31. The method of claim 1, wherein $R^P$ is hydrogen or an oxygen protecting group.

32. The method of claim 1, wherein:
$R^6$ and $R^7$ are each independently hydrogen or a group of formula (i) or (ii), provided at least one instance of $R^6$ and $R^7$ is a group of formula (i) or (ii);
each instance of $R^2$ is independently hydrogen or a group of the formula (i) or (ii);
$R^P$ is hydrogen or an oxygen protecting group; and
$R^L$ is $C_{6-20}$ alkyl.

33. The method of claim 1, wherein the cell is of the pancreas, spleen, liver, fat, kidneys, uterus, ovaries, muscle, heart, lungs, or thymus.

34. The method of claim 1, wherein the cell is a hepatocyte.

* * * * *